(12) United States Patent
Zhang et al.

(10) Patent No.: US 9,663,498 B2
(45) Date of Patent: May 30, 2017

(54) AROMATIC HETEROCYCLIC COMPOUNDS AND THEIR APPLICATION IN PHARMACEUTICALS

(71) Applicant: Sunshine Lake Pharma Co., Ltd., Dongguan, Guangdong (CN)

(72) Inventors: Yingjun Zhang, Dongguan (CN); Chuanfei Jin, Dongguan (CN); Wenhe Zhong, Dongguan (CN); Ji Zhang, Dongguan (CN); Li Gao, Dongguan (CN); Kangzhi Chen, Dongguan (CN)

(73) Assignee: SUNSHINE LAKE PHARMA CO., LTD., Dongguan, Guangdong (CN)

(*) Notice: Subject to any disclaimer, the term of this patent is extended or adjusted under 35 U.S.C. 154(b) by 0 days.

(21) Appl. No.: 15/027,691

(22) PCT Filed: Dec. 19, 2014

(86) PCT No.: PCT/CN2014/094428
§ 371 (c)(1),
(2) Date: Apr. 6, 2016

(87) PCT Pub. No.: WO2015/090233
PCT Pub. Date: Jun. 25, 2016

(65) Prior Publication Data
US 2016/0251339 A1 Sep. 1, 2016

(30) Foreign Application Priority Data
Dec. 20, 2013 (CN) .......................... 2013 1 0712676

(51) Int. Cl.
| | | |
|---|---|---|
| C07D 209/10 | (2006.01) | |
| C07D 401/12 | (2006.01) | |
| C07D 405/12 | (2006.01) | |
| A61K 31/454 | (2006.01) | |
| A61K 31/496 | (2006.01) | |
| A61K 31/5377 | (2006.01) | |
| C07D 403/12 | (2006.01) | |
| C07D 209/08 | (2006.01) | |
| C07D 209/12 | (2006.01) | |
| C07D 209/42 | (2006.01) | |
| A61K 45/06 | (2006.01) | |
| C07D 231/56 | (2006.01) | |
| C07D 413/12 | (2006.01) | |

(52) U.S. Cl.
CPC .......... *C07D 405/12* (2013.01); *A61K 31/454* (2013.01); *A61K 31/496* (2013.01); *A61K 31/5377* (2013.01); *A61K 45/06* (2013.01); *C07D 209/08* (2013.01); *C07D 209/10* (2013.01); *C07D 209/12* (2013.01); *C07D 209/42* (2013.01); *C07D 231/56* (2013.01); *C07D 403/12* (2013.01)

(58) Field of Classification Search
None
See application file for complete search history.

(56) References Cited

U.S. PATENT DOCUMENTS

| | | |
|---|---|---|
| 5,990,105 A | 11/1999 | Bos et al. |
| 6,133,287 A | 10/2000 | Slassi et al. |
| 6,187,805 B1 | 2/2001 | Pineiro et al. |
| 6,316,450 B1 | 11/2001 | Bromidge et al. |
| 6,548,504 B1 | 4/2003 | Bromidge et al. |
| 6,613,781 B2 | 9/2003 | Zhou et al. |
| 6,774,241 B2 | 8/2004 | Clark et al. |
| 6,790,848 B2 | 9/2004 | Briggs et al. |
| 6,825,202 B2 | 11/2004 | Berger et al. |
| 6,855,709 B2 | 2/2005 | Tenbrink et al. |
| 6,906,095 B2 | 6/2005 | Cole et al. |
| 7,022,708 B2 | 4/2006 | Clark et al. |
| 7,247,651 B2 | 7/2007 | Madera et al. |
| 7,381,739 B2 | 6/2008 | Madera et al. |
| 7,498,327 B2 | 3/2009 | Wang et al. |
| 7,678,800 B2 | 3/2010 | Kehler et al. |
| 7,696,229 B2 | 4/2010 | Dunn et al. |
| 7,776,910 B2 | 8/2010 | Lopez-Tapia et al. |
| 7,812,017 B2 | 10/2010 | Angbrant et al. |
| 7,875,605 B2 | 1/2011 | Ramakrishna et al. |
| 7,964,627 B2 | 6/2011 | Ramakrishna et al. |
| 7,998,981 B2 | 8/2011 | Ramakrishna et al. |
| 8,003,670 B2 | 8/2011 | Nirogi et al. |

(Continued)

FOREIGN PATENT DOCUMENTS

| | | |
|---|---|---|
| CN | 104276993 A | 1/2015 |
| CN | 104557726 A | 4/2015 |

(Continued)

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Testa et al. Pure Appl. Chem. vol. 76, pp. 907-914 (2004).*
Eng. translation of the abstract of CN104557726.
Eng. translation of the abstract of CN104276993.
Nirogi et al., Novel and Potent 5-Piperazinyl Methyl-N1-aryl Sulfonyl Indole Derivatives as 5-HT6 Receptor Ligands, ACS Medicinal Chemistry Letters, 2010, 1(7): 340-344.
Ahmed et al., Bicyclic heteroarylpiperazines as selective brain penetrant 5-HT6 receptor antagonists, Bioorganic & Medicinal Chemistry Letters, 2005, 15(21): 4867-4871.
Nirogi et al., Design, synthesis and pharmacological evaluation of 4-(piperazin-1-ylmethyl)-N1-arylsulfonyl indole derivatives as 5-HT6 receptor ligands, Bioorganic & Medicinal Chemistry Letters, 2012, 22(24): 7431-7435.

(Continued)

*Primary Examiner* — Emily Bernhardt
(74) *Attorney, Agent, or Firm* — Kam W. Law; Squire Patton Boggs (US) LLP

(57) ABSTRACT

Provided herein are novel aromatic heterocyclic compounds or a stereoisomer, a geometric isomer, a tautomer, an N-oxide, a hydrate, a solvate, a metabolite, a pharmaceutically acceptable salt or a prodrug thereof, and their uses for treating Alzheimer's disease. Also provided herein are pharmaceutical compositions containing such compounds, and methods for using such compounds or pharmaceutical compositions thereof to treat Alzheimer's disease.

7 Claims, No Drawings

(56) References Cited

U.S. PATENT DOCUMENTS

| | | |
|---|---|---|
| 8,053,463 B2 | 11/2011 | Lin et al. |
| 8,076,326 B2 | 12/2011 | Haupt et al. |
| 8,119,683 B2 | 2/2012 | Liou et al. |
| 8,153,680 B2 | 4/2012 | Chen et al. |
| 8,183,237 B2 | 5/2012 | Haupt et al. |
| 8,318,725 B2 | 11/2012 | Nirogi et al. |
| 8,343,959 B2 | 1/2013 | Haupt et al. |
| 8,362,010 B2 | 1/2013 | Haupt et al. |
| 8,470,830 B2 | 6/2013 | Ramakrishna et al. |
| 8,507,469 B2 | 8/2013 | Schultz et al. |
| 8,710,059 B2 | 4/2014 | Haupt et al. |
| 8,772,313 B2 | 7/2014 | Haupt et al. |
| 9,051,265 B2 | 6/2015 | Kamenecka et al. |
| 2005/0090496 A1 | 4/2005 | Ahmed et al. |
| 2005/0124626 A1 | 6/2005 | Johnson et al. |
| 2005/0176705 A1 | 8/2005 | Bromidge et al. |
| 2006/0035884 A1 | 2/2006 | Neitzel et al. |
| 2006/0148818 A1 | 7/2006 | Johansson et al. |
| 2007/0213326 A1 | 9/2007 | Merce Vidal |
| 2008/0200471 A1 | 8/2008 | Dunn et al. |
| 2008/0318941 A1 | 12/2008 | Dunn et al. |
| 2009/0069337 A1 | 3/2009 | Dunn et al. |
| 2010/0016297 A1 | 1/2010 | Conticello et al. |
| 2010/0022581 A1 | 1/2010 | Danca et al. |
| 2010/0029629 A1 | 2/2010 | Conticello et al. |
| 2010/0041669 A1 | 2/2010 | Ramakrishna et al. |
| 2010/0056491 A1 | 3/2010 | Schumacher et al. |
| 2010/0056531 A1 | 3/2010 | Danca et al. |
| 2010/0075963 A1 | 3/2010 | Lehr et al. |
| 2014/0088094 A1 | 3/2014 | Glick et al. |

FOREIGN PATENT DOCUMENTS

| | | |
|---|---|---|
| EP | 1947085 A1 | 7/2008 |
| WO | 0063203 A1 | 10/2000 |
| WO | 0112629 A1 | 2/2001 |
| WO | 0132660 A1 | 5/2001 |
| WO | 0232863 A1 | 4/2002 |
| WO | 0236562 A2 | 5/2002 |
| WO | 02051837 A2 | 7/2002 |
| WO | 02059088 A1 | 8/2002 |
| WO | 02085853 A2 | 10/2002 |
| WO | 02085892 A1 | 10/2002 |
| WO | 02098857 A1 | 12/2002 |
| WO | 02100822 A1 | 12/2002 |
| WO | 03053433 A1 | 7/2003 |
| WO | 03053970 A1 | 7/2003 |
| WO | 2004000828 A1 | 12/2003 |
| WO | 2004048328 A2 | 6/2004 |
| WO | 2004080986 A1 | 9/2004 |
| WO | 2005066157 A1 | 7/2005 |
| WO | 2007020653 A1 | 2/2007 |
| WO | 2007138611 A1 | 12/2007 |
| WO | 2009034581 A1 | 3/2009 |

OTHER PUBLICATIONS

Nirogi et al., Indole-3-piperazinyl derivatives: Novel chemical class of 5-HT6 receptor antagonists, Bioorganic & Medicinal Chemistry Letters, 2011, 21(1): 346-349.

Glennon et al., Higher-end serotonin receptors: 5-HT5, 5-HT6, and 5-HT7, Journal of Medicinal Chemistry, 2003, 46 (14): 2795-2812.

Doddareddy et al., Hologram quantitative structure activity relationship studies on 5-HT6 antagonists, Bioorganic and Medicinal Chemistry, 2004, 12(14): 3815-3824.

International Search Report of PCT/CN2014/094428.

Written Opinion of PCT/CN2014/094428.

* cited by examiner

AROMATIC HETEROCYCLIC COMPOUNDS AND THEIR APPLICATION IN PHARMACEUTICALS

CROSS-REFERENCE TO RELATED APPLICATIONS

This is a U.S. national stage application of the International Patent Application No. PCT/CN2014/094428, filed 19 Dec. 2014, which claims priority to Chinese Patent Application No. 201310712676.9, filed 20 Dec. 2013, both of which are incorporated herein by reference in their entireties.

FIELD

The invention belongs to the pharmaceutical field, and it relates to the compounds for treating Alzheimer's disease, and to the pharmaceutical compositions containing such compounds and their uses. Especially, these compounds of the invention are aromatic heterocyclic compounds used as 5-$HT_6$ receptor antagonists.

BACKGROUND

Various central nervous system disorders such as anxiety, depression etc., are believed to involve a disturbance of the neurotransmitter 5-hydroxytryptamine (5-HT) or serotonin. The actions of the neurotransmitter 5-hydroxytryptamine (5-HT) as a major modulatory neurotransmitter in the brain, are mediated through a number of receptor families termed 5-$HT_1$, 5-$HT_2$, 5-$HT_3$, 5-$HT_4$, 5-$HT_5$, 5-$HT_6$ and 5-$HT_7$. Based on a high level of 5-$HT_6$ receptor mRNA in the brain, it has been stated that the 5-$HT_6$ receptor may play a role in the pathology and treatment of central nervous system disorders. In particular, 5-$HT_6$ receptor selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. (See for ex. B. L. Roth et al., *J. Pharmacol. Exp. Ther*, 1994, 268, 1403-14120; D. R. Sibley et al., *Mol. Pharmacol*, 1993, 43, 320-327; A. J. Sleight et al., *Neurotransmission*, 1995, 11, 1-5; and A. J. Sleight et al., *Serotonin ID Research Alert.*, 1997, 2 (3), 115-118).

Studies have found that a known 5-$HT_6$ selective antagonist significantly increased glutamate and aspartate levels in the frontal cortex without elevating levels of noradrenaline, dopamine or 5-$HT_6$. This selective elevation of certain neurochemicals is noted during memory and cognition, strongly suggests a role for 5-$HT_6$ ligands in cognition (Dawson, L. A.; Nguyen, H. Q.; Li, P., *British Journal of Pharmacology*, 2000, 130 (1), 23-26). Animal studies of memory and learning with a known selective 5-$HT_6$ antagonist has some positive effects (Rogers, D. C.; Hatcher, P. D.; Hagan, J. J., *Society of Neuroscience*, Abstracts, 2000, 26, 680). A related potential therapeutic use for 5-$HT_6$ ligands is the treatment of attention deficit disorders (ADD, also known as Attention Deficit Hyperactivity Disorder or ADHD) in children as well as adults. As 5-$HT_6$ antagonists appear to enhance the activity of the nigrostriatal dopamine pathway and ADHD has been linked to abnormalities in the caudate (Ernst, M.; Zametkin, A. J.; Matochik, J. H.; Jons, P. A.; Cohen, R. M., *Journal of Neuroscience*, 1998, 18 (15), 5901-5907), 5-$HT_6$ antagonists may attenuate attention deficit disorders. 5-$HT_6$ antagonists have also been identified as potentially useful compounds for treatment of obesity. See for example, Bentley et al., *Br. J Pharmac*. 1999, Suppl 126; Bently et al., *J. Psychopharmacol*. 1997, Suppl A64, 255; Wooley et al., *Neuropharmacology* 2001, 41, 210-129; and WO02098878.

Pulmonary arterial hypertension (PAH) is a kind of progressive malignant disease which is characterized as increasing progressive pulmonary vascular resistance, finally leading to right heart failure and even death. With the development of deepening research in the pathogenesis of PAH, the treatment of PAH has broad prospects. 5-hydroxytryptamine (5-HT) used as a vasoactive substance was first proposed in 1955, which widely exists in animals, especially in the cardiovascular system, and almost all of the 5-HT is inactived by endothelial cells in liver and lungs except that a small part of 5-HT is reabsorbed and stored in platelets. 5-HT binding to its receptor produces a variety of biological effects, and now the widely accepted classification of 5-HT is that 5-HT have been divided into seven receptor classes, wherein 5-$HT_2$ is a member of the G protein receptor super family which contains 5-$HT_{2A}$, 5-$HT_{2B}$, 5-$HT_{2C}$ and distributed in the vessel wall, vascular endothelial cells, platelets, kidneys and other tissues or organs. 5-HT system has been implicated with the pathophysiology of pulmonary arterial hypertension for many years, and some studies indicated that 5-$HT_2$ receptor antagonist can specifically bind with 5-$HT_2$ receptor to inhibit the action of 5-HT and plays a series of biological effects. And specially, the study of 5-HT in vascular endothelial protection, prevention of the proliferation of vascular smooth muscle, coronary heart disease and other aspects has been the concern of the medical workers. Currently, several kinds of serotonin (5-HT) receptor antagonist and serotonin transporters blockers are been studied for treating PAH, although these clinical trials have not yet to be completed and drug hasn't listed, the related new drug research and development is becoming a hotspot for the PAH treatment, which has important clinical and practical significances.

SUMMARY

The invention relates to novel aromatic heterocyclic compounds and methods of treating Alzheimer's disease. The compound or pharmaceutical composition thereof provided herein have a good affinity for 5-$HT_6$, especially have a good therapeutic effect on Alzheimer's disease.

In one aspect, provided herein are compounds having Formula (I)

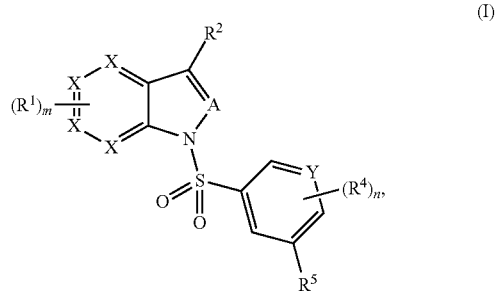

or a stereoisomer, a geometric isomer, a tautomer, an N-oxide, a hydrate, a solvate, a metabolite, a pharmaceutically acceptable salt or a prodrug thereof, wherein:

m is 0, 1, 2 or 3;

n is 1, 2 or 3;

A is $CR^3$ or N;

each X is independently $CR^1$ or N, and at most two X are N;

Y is $CR^4$ or N;

each $R^1$ is independently H, D, F, Cl, Br, I, —CN, —NO$_2$, —OH, —NH$_2$, C$_{1-6}$ alkyl, C$_{2-6}$ alkenyl, C$_{2-6}$ alkynyl, C$_{3-8}$ cycloalkyl, C$_{1-6}$ haloalkyl, C$_{1-6}$ alkoxy, C$_{1-6}$ haloalkoxy, C$_{1-6}$ alkylthio, C$_{1-6}$ alkenylthio, $R^{6a}R^6N$—C$_{1-6}$ alkyl, —C(=O)$R^{6b}$, —C(=O)O$R^{6c}$, —C(=O)N$R^6R^{6a}$, $R^6R^{6a}N$—S(=O)$_2$—, $R^{6b}$S(=O)$_2$—, $R^{6b}$S(=O)—C$_{1-6}$ alkyl, $R^6R^{6a}N$—C(=O)—C$_{1-6}$ alkyl, C$_{6-10}$ aryl, C$_{6-10}$ arylamino, C$_{1-9}$ heteroaryl, C$_{3-8}$ cycloalkyl-C$_{1-6}$-alkyl, C$_{2-10}$ heterocyclyl-C$_{1-6}$-alkyl, C$_{6-10}$ aryl-C$_{1-6}$-alkyl or C$_{1-9}$ heteroaryl-C$_{1-6}$-alkyl, or each $R^1$ is independently the following group,

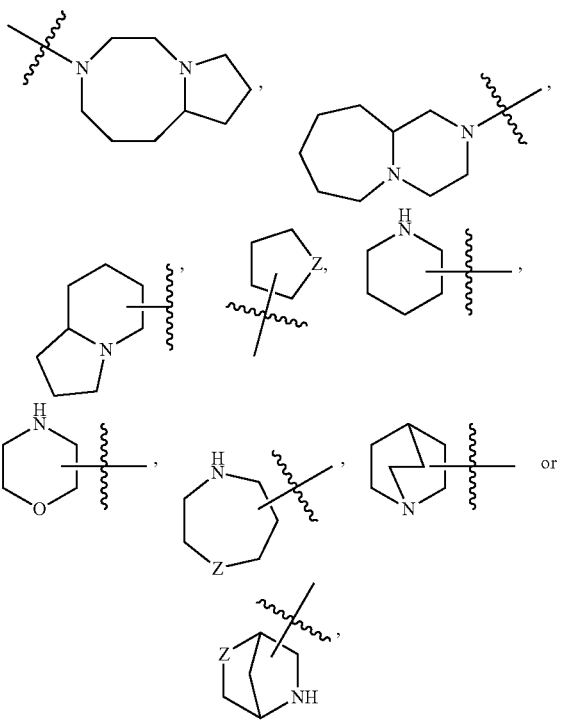

and wherein, Z is —NH—, —O— or —S—;

$R^2$ is H, D, F, Cl, Br, I, —CN, —NO$_2$, —OH, —NH$_2$, —SO$_2$Cl, $R^{6a}R^6N$—, —C(=O)$R^{6b}$, —C(=O)N$R^6R^{6a}$, —OC(=O)N$R^6R^{6a}$, —OC(=O)O$R^{6c}$, —N($R^6$)C(=O)N$R^6R^{6a}$, —N($R^6$)C(=O)O$R^{6c}$, —N($R^6$)C(=O)—$R^{6b}$, $R^6R^{6a}N$—S(=O)$_2$—, $R^{6b}$S(=O)$_2$—, $R^{6b}$S(=O)$_2$N($R^{6a}$)—, hydroxy-substituted C$_{1-6}$ alkyl, hydroxy-substituted C$_{1-6}$ haloalkyl, carboxy-substituted C$_{1-6}$ alkyl, C$_{1-6}$ alkyl-OC(=O)C$_{1-6}$ alkyl, $R^{6b}$S(=O)—C$_{1-6}$ alkyl, $R^6R^{6a}N$—C(=O)—C$_{1-6}$ alkyl, $R^6R^{6a}N$—C$_{1-6}$ alkoxy, $R^{6b}$S(=O)—C$_{1-6}$ alkoxy, $R^6R^{6a}N$—C(=O)—C$_{1-6}$ alkoxy, C$_{6-10}$ aryl, C$_{1-9}$ heteroaryl, C$_{1-6}$ alkoxy, C$_{1-6}$ alkylamino, C$_{1-6}$ alkyl, C$_{1-6}$ alkoxy-C$_{1-6}$-alkyl, C$_{1-6}$ haloalkyl, C$_{2-10}$ heterocyclyl-C$_{1-6}$-alkyl or C$_{6-10}$ aryl-C$_{1-6}$-alkyl, or $R^2$ is the following group,

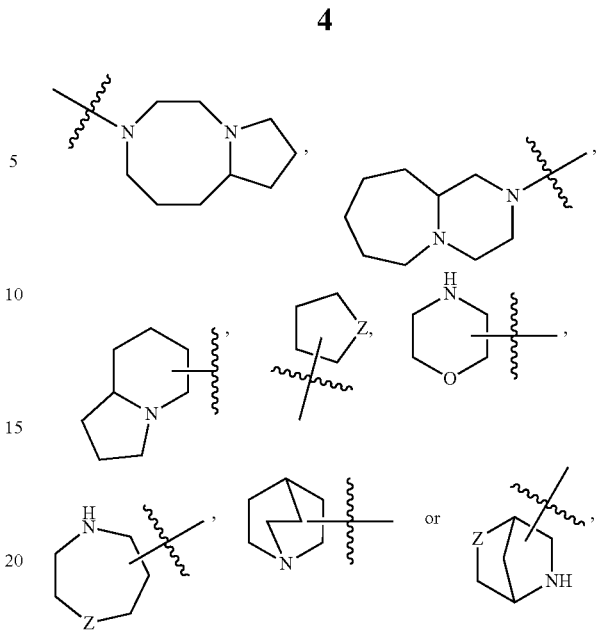

and wherein, Z is —NH—, —O— or —S—;

$R^3$ is H, D, F, Cl, Br, I, —CN, —NO$_2$, —OH, —NH$_2$, C$_{1-6}$ alkyl, C$_{2-6}$ alkenyl, C$_{2-6}$ alkynyl, carboxy-substituted C$_{1-6}$ alkyl, —C(=O)$R^{6b}$, C$_{6-10}$ aryl, C$_{3-8}$ cycloalkyl, C$_{1-6}$ haloalkyl, C$_{1-6}$ haloalkoxy or —C(=O)N$R^6R^{6a}$;

each $R^4$ is independently D, F, Cl, Br, I, —CN, C$_{1-6}$ alkyl, C$_{2-6}$ alkenyl, C$_{2-6}$ alkynyl, C$_{3-8}$ cycloalkyl, C$_{1-6}$ haloalkyl, C$_{1-6}$ alkoxy, C$_{1-6}$ haloalkoxy or C$_{6-10}$ aryl, or two adjacent $R^4$ together with the carbon atom to which they are attached, form an optionally substituted 5- to 7-membered carbon ring, heterocyclic ring, aromatic ring or heteroaromatic ring;

$R^5$ is C$_{2-10}$ heterocyclyl or C$_{5-8}$ cycloalkyl, and wherein optionally each of C$_{2-10}$ heterocyclyl and C$_{5-8}$ cycloalkyl is independently substituted with one, two, three or four substitutents independently selected from D, F, Cl, Br, I, —CN, oxo (=O), —C(=O)$R^{6b}$, —C(=O)O$R^{6c}$, —C(=O)N$R^6R^{6a}$, C$_{1-6}$ alkyl, C$_{3-8}$ cycloalkyl, C$_{2-10}$ heterocyclyl, C$_{1-6}$ haloalkyl, C$_{1-6}$ alkoxy, C$_{1-6}$ haloalkoxy, C$_{6-10}$ aryl-C$_{1-4}$-alkyl and C$_{1-9}$ heteroaryl-C$_{1-6}$-alkyl;

each $R^6$ and $R^{6a}$ is independently H, D, —OH, C$_{1-6}$ alkyl, C$_{1-6}$ haloalkyl, C$_{1-6}$ alkoxy, C$_{6-10}$ aryl, C$_{2-10}$ heterocyclyl, C$_{3-8}$ cycloalkyl, C$_{6-10}$ aryl-C$_{1-6}$-alkyl, C$_{6-10}$ aryloxy, C$_{2-10}$ heterocyclyloxy, C$_{3-8}$ cycloalkoxy, C$_{6-10}$ arylamino, C$_{2-10}$ heterocyclylamino, C$_{3-8}$ cycloalkylamino, C$_{1-9}$ heteroaryl or C$_{3-8}$ carbocyclyl, or $R^6$ and $R^{6a}$ together with the nitrogen atom to which they are attached, form an optionally substituted 3- to 8-membered ring;

each $R^{6b}$ and $R^{6c}$ is independently H, D, —OH, C$_{1-6}$ alkyl, C$_{1-6}$ haloalkyl, C$_{1-6}$ alkoxy, C$_{6-10}$ aryl, C$_{2-10}$ heterocyclyl, C$_{3-8}$ cycloalkyl, C$_{6-10}$ aryl-C$_{1-6}$-alkyl, C$_{6-10}$ aryloxy, C$_{2-10}$ heterocyclyloxy, C$_{3-8}$ cycloalkoxy, C$_{6-10}$ arylamino, C$_{2-10}$ heterocyclylamino, C$_{3-8}$ cycloalkylamino, C$_{1-9}$ heteroaryl or C$_{3-8}$ carbocyclyl; and with the proviso that, the compound of Formula (I) does not include 6-bromo-1-((4-methoxy-3-(piperazin-1-yl)phenyl)sulfonyl)-1H-indole.

In certain embodiments, wherein each $R^1$ and $R^3$ is independently H, D, F, Cl, Br, I, —CN, —NO$_2$, —OH, —NH$_2$, C$_{1-4}$ alkyl, C$_{2-4}$ alkenyl, C$_{2-4}$ alkynyl, C$_{6-10}$ aryl, C$_{3-6}$ cycloalkyl, C$_{1-4}$ haloalkyl or C$_{1-4}$ haloalkoxy.

In other embodiments, wherein $R^2$ is H, D, F, Cl, Br, I, —CN, —C(=O)$R^{6b}$, C$_{1-4}$ alkyl, C$_{1-4}$ haloalkyl, hydroxy-substituted C$_{1-4}$ haloalkyl or C$_{1-4}$ alkoxy-C$_{1-4}$-alkyl, wherein $R^{6b}$ is as defined herein.

In other embodiments, wherein each $R^4$ is independently D, F, Cl, Br, I, —CN, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy or $C_{6-10}$ aryl, or two adjacent $R^4$ together with the carbon atom to which they are attached, form an optionally substituted 5- to 6-membered aromatic ring or heteroaromatic ring.

In other embodiments, wherein $R^5$ is $C_{3-7}$ heterocyclyl, wherein optionally $C_{3-7}$ heterocyclyl is independently substituted with one, two, three or four substitutents independently selected from D, F, Cl, Br, I, —CN, oxo (=O), $C_{1-6}$ alkyl, $C_{3-6}$ cyclalkyl, $C_{2-8}$ heterocyclyl, $C_{1-4}$ haloalkyl, $C_{1-4}$ alkoxy, $C_{1-4}$ haloalkoxy, —C(=O)$R^{6b}$, —C(=O)O$R^{6c}$ and —C(=O)N$R^6R^{6a}$, wherein $R^6$, $R^{6a}$, $R^{6b}$ and $R^{6c}$ are as defined herein.

In other embodiments, wherein each $R^6$, $R^{6a}$, $R^{6b}$ and $R^{6c}$ is independently H, D, —OH or $C_{1-4}$ alkyl.

In other embodiments, provided herein are compounds having Formula (II)

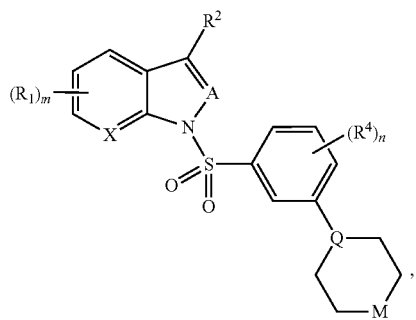

(II)

or a stereoisomer, a geometric isomer, a tautomer, an N-oxide, a hydrate, a solvate, a metabolite, a pharmaceutically acceptable salt or a prodrug thereof, wherein:

m is 0, 1, 2 or 3;
n is 1, 2 or 3;
A is $CR^3$ or N;
X is $CR^1$ or N;
Q is CH or N;
M is —NR' or —O—;
each $R^1$ and $R^3$ is independently H, D, F, Cl, Br, I, —CN, —NO$_2$, —OH, —NH$_2$, $C_{1-4}$ alkyl, $C_{2-4}$ alkenyl, $C_{2-4}$ alkynyl, $C_{6-10}$ aryl, $C_{3-6}$ cycloalkyl, $C_{1-4}$ haloalkyl or $C_{1-4}$ haloalkoxy;
$R^2$ is H, D, F, Cl, Br, I, —CN, —C(=O)$R^{6b}$, $C_{1-4}$ alkyl, $C_{1-4}$ haloalkyl, hydroxy-substituted $C_{1-4}$ haloalkyl or $C_{1-4}$ alkoxy-$C_{1-4}$-alkyl;
each $R^4$ is independently D, F, Cl, Br, I, —CN, $C_{1-4}$ alkyl, $C_{2-4}$ alkenyl, $C_{2-4}$ alkynyl, $C_{3-6}$ cycloalkyl, $C_{1-4}$ haloalkyl, $C_{1-4}$ alkoxy, $C_{1-4}$ haloalkoxy or $C_{6-10}$ aryl, or two adjacent $R^4$ together with the carbon atom to which they are attached, form an optionally substituted 5- to 6-membered aromatic ring or heteroaromatic ring;
$R^{6b}$ is H, D, —OH or $C_{1-4}$ alkyl;
$R^7$ is H, D, $C_{1-6}$ alkyl, $C_{3-6}$ cycloalkyl, $C_{2-8}$ heterocyclyl or $C_{1-4}$ haloalkyl; and
with the proviso that, the compound of Formula (II) does not include 6-bromo-1-((4-methoxy-3-(piperazin-1-yl)phenyl)sulfonyl)-1H-indole.

In other embodiments, wherein each $R^1$ and $R^3$ is independently H, D, F, Cl, Br, I, —CN, —NO$_2$, —OH, —NH$_2$, —CHF$_2$, —CF$_3$, —CH$_2$CF$_3$, —CF$_2$CHF$_2$, —CHFCF$_3$, —CF$_2$CF$_3$, —CH$_2$CF$_2$CF$_3$, —CH$_2$CF$_2$CHF$_2$, methyl, ethyl, n-propyl, iso-propyl, n-butyl, iso-butyl or tert-butyl.

In other embodiments, wherein $R^2$ is H, D, F, Cl, Br, I, —CN, —C(=O)CH$_3$, —C(=O)CH$_2$CH$_3$, —C(=O)CH$_2$CH$_2$CH$_3$, —CF$_3$, —CH$_2$CF$_3$, —CF$_2$CHF$_2$, —CHFCF$_3$, —CF$_2$CF$_3$, —CH$_2$CF$_2$CF$_3$, —CH$_2$CF$_2$CHF$_2$, —CH(OH)CF$_3$, —CH(OH)CHF$_2$, —CH$_2$CH(OH)CF$_3$, —CH$_2$CH(OH)CHF$_2$, —CH(OH)CH$_2$CHF$_2$, —CH(OH)CH$_2$CF$_3$, —CH$_2$OCH$_3$, —CH$_2$OCH$_2$CH$_3$, —CH$_2$OCH(CH$_3$)$_2$, —CH$_2$OCH$_2$CH$_2$CH$_3$, —CH$_2$CH$_2$OCH$_3$, —CH$_2$CH$_2$OCH$_2$CH$_3$, —CH$_2$CH$_2$OCH(CH$_3$)$_2$, —CH$_2$CH$_2$OCH$_2$CH$_2$CH$_3$, methyl, ethyl, n-propyl, iso-propyl, n-butyl, iso-butyl or tert-butyl.

In other embodiments, wherein each $R^4$ is independently D, F, Cl, Br, I, —CN, methyl, ethyl, n-propyl, iso-propyl, —CF$_3$, —CH$_2$CF$_3$, —CF$_2$CHF$_2$, —CHFCF$_3$, —CF$_2$CF$_3$, —CH$_2$CF$_2$CF$_3$, —CH$_2$CF$_2$CHF$_2$, methoxy, ethoxy, n-propoxy, iso-propoxy, n-butoxy, iso-butoxy, tert-butoxy, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$ or —OCH$_2$CF$_2$CHF$_2$, or two adjacent $R^4$ together with the carbon atom to which they are attached, form a substituted or unsubstituted benzene ring.

In other embodiments, wherein $R^7$ is H, D, methyl, ethyl, n-propyl, iso-propyl, n-butyl, iso-butyl, tert-butyl, —CH$_2$CH$_2$CH(CH$_3$)$_2$, —CH$_2$C(CH$_3$)$_3$, cyclopropyl, cyclobutyl, cyclopentyl, azetidinyl, oxetanyl, thietanyl, pyrrolidyl or tetrahydrofuryl.

In another aspect, provided herein is a pharmaceutical composition comprising the compound disclosed herein.

In certain embodiments, the pharmaceutical composition disclosed herein further comprising a pharmaceutically acceptable carrier, excipient, diluent, adjuvant, vehicle or a combination thereof.

In other embodiments, the pharmaceutical composition disclosed herein further comprising an additional therapeutic agent used for treating Alzheimer's disease, neuropathy or a combination thereof.

In other embodiments, the pharmaceutical composition disclosed herein, wherein the additional therapeutic agent is donepezil, nalmefene, risperidone, Vitamin E, SAM-760, AVN-211, AVN-101, RP-5063, tozadenant, PRX-3140, PRX-8066, SB-742457, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

In another aspect, provided herein is use of the compound or the pharmaceutical composition disclosed herein in the manufacture of a medicament for preventing, treating or lessening a 5-HT$_6$- or 5-HT$_2$-mediated disease.

In certain embodiments, the use disclosed herein, wherein the 5-HT$_6$ mediated disease is a CNS disorder, a gastrointestinal disorder or obesity; the 5-HT$_2$-mediated disease is a cardiovascular disease.

In other embodiments, wherein the CNS disorder mediated by 5-HT$_6$ is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In other embodiments, wherein the cardiovascular disease is pulmonary hypertension, thrombosis, heart failure or cardiac hypertrophy.

In another aspect, provided herein is a method for preventing, treating or lessening the 5-HT$_6$- or 5-HT$_2$-mediated disease, comprising administering to a subject a therapeutically effective amount of the compound or the pharmaceutical composition disclosed herein.

In certain embodiments, the method disclosed herein, wherein the 5-HT$_6$-mediated disease is a CNS disorder, a gastrointestinal disorder or obesity; the 5-HT$_2$-mediated disease is a cardiovascular disease.

In other embodiments, the method disclosed herein, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In other embodiments, the method disclosed herein, wherein the cardiovascular disease is pulmonary hypertension, thrombosis, heart failure or cardiac hypertrophy.

In another aspect, provided herein is the compound or the pharmaceutical composition disclosed herein for use in preventing, treating or lessening the 5-HT$_6$- or 5-HT$_2$-mediated disease.

In certain embodiments, the compound or the composition disclosed herein, wherein the 5-HT$_6$-mediated disease is a CNS disorder, a gastrointestinal disorder or obesity; the 5-HT$_2$-mediated disease is a cardiovascular disease.

In other embodiments, the compound or the composition disclosed herein, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In other embodiments, the compound or the composition disclosed herein, wherein the cardiovascular disease is pulmonary hypertension, thrombosis, heart failure or cardiac hypertrophy.

In another aspect, provided herein are methods for preparing, separating, and purifying of the compounds represented by Formula (I) or (II).

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

DETAILED DESCRIPTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and the *Handbook of Chemistry and Physics*, 75$^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Racemate" or "racemic mixture" refers to a 50:50 mixture of enantiomers which lacks optical activity.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur when there has been no stereoselectivity or stereospecificity in a chemical reaction or process.

Any asymmetric atom (e.g., carbon or the like) of the compound disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (*Wiley Interscience*, New York, 1981); *Principles of Asymmetric Synthesis* (2$^{nd}$ Ed. Robert E. Gawley, Jeffrey Aubé, Elsevier, Oxford, UK, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972); *Chiral Separation Techniques: A Practical Approach* (Subramanian, G Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

The term "unsaturated" refers to a moiety having one or more units of unsaturation.

As described herein, compounds disclosed herein may optionally be substituted with one or more substituents, such as the compound(s) illustrated by general formula above, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Substituents described herein include, but are not limited to, deuterium, hydroxy, amino, F, Cl, Br, I, cyano, azido, aryl, heteroaryl, alkoxy, alkylamino, alkylthio, alkyl, alkenyl, alkynyl, cycloalkyl, heterocyclyl, mercapto, nitro, aryloxy, heteroaryloxy, oxo (=O), carboxy, haloalkyl, haloalkoxy, hydroxy-substituted alkyl, hydroxy-substituted haloalkyl, hydroxy-substituted alkoxy, hydroxy-substituted alkyl-C (=O), alkyl-C(=O), alkyl-S(=O), alkyl-S(=O)$_2$—, hydroxy-substituted alkyl-S(=O), hydroxy-substituted alkyl —S(=O)$_2$, carboxyalkoxy, and the like.

Unless otherwise defined herein, for a variable that occurs more than one time in any substituent or in the compound of the invention or any other formulae herein, its definition on each occurrence is independent of its definition at every other occurrence. Combinations of substituents are permissible only if such combinations result in stable compound. Stable compounds are compounds which can be isolated in a useful degree of purity from a reaction mixture.

In addition, the description of "each . . . is independently", "each (of) . . . and . . . is independently" and " . . . is independently" in the invention can be used interchangeably herein, unless otherwise specified. It should have a general understanding that it can be expressed both in different groups in which same symbols expressed specific options do not affect each other and the same groups in which same symbols expressed specific options do not affect each other. Taking $R^6$ as a example, the specific options of $R^6$ in Formula "—N($R^6$)C(=O)N$R^6R^{6a}$" and Formula "—N($R^6$)C(=O)O$R^{6c}$" are not affected with each other and at the same time, the specific options of several $R^6$ in Formula "—N($R^6$)C(=O)N$R^6R^{6a}$" are not affected with each other.

At various places in the present specification, substituents of compounds disclosed herein are disclosed in groups or in ranges. It is specifically intended that the invention includes each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted with one or more substituents described herein. Unless otherwise specified, the alkyl group contains 1-20 carbon atoms. In some embodiments, the alkyl group contains 1-12 carbon atoms. In other embodiments, the alkyl group contains 1-6 carbon atoms. In still other embodiments, the alkyl group contains 1-4 carbon atoms, and in yet other embodiments, the alkyl group contains 1-3 carbon atoms.

Some non-limiting examples of the alkyl group include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In other embodiments, the alkylene group contains 1-3 carbon atoms. In still other embodiments, the alkylene group contains 1-2 carbon atoms. And the alkylene group is exemplified by methylene (—CH$_2$—), ethylene (—CH$_2$CH$_2$—), isopropylene (—CH(CH$_3$)CH$_2$—), and the like. The alkylene group may be optionally substituted with one or more substituents described herein.

The term "alkenyl" refers to a linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted with one or more substituents described herein, and includes radicals having "cis" and "trans" orientations, or alternatively, "E" and "Z" orientations. In some embodiments, the alkenyl group contains 2 to 8 carbon atoms. In other embodiments, the alkenyl group contains 2 to 6 carbon atoms, and in still other embodiments, the alkenyl group contains 2 to 4 carbon atoms. Examples of the alkenyl group include, but are not limited to, ethylenyl or vinyl (—CH=CH$_2$), allyl (—CH$_2$CH=CH$_2$), and the like.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted with one or more substituents described herein. In some embodiments, the alkynyl group contains 2 to 8 carbon atoms; in other embodiments, the alkynyl group contains 2 to 6 carbon atoms; and in still other embodiments, the alkynyl group contains 2 to 4 carbon atoms. Examples of the alkynyl group include, but are not limited to, ethynyl (—C≡CH), propargyl (—CH$_2$C≡CH), 1-propynyl (—C≡C—CH$_3$), and the like.

The term "carboxy" or "carboxyl", whether used alone or with other terms, such as "carboxyalkyl", refers to —CO$_2$H; the term "carbonyl", whether used alone or with other terms, such as "aminocarbonyl" or "carbonyloxy", refers to —(C=O)—.

The term "H" refers to a single hydrogen atom. This radical may be attached to other groups, for example, to an oxygen atom to form hydroxy radical.

The term "D" or "$^2$H" refers to a single deuterium atom. This radical may be attached to a methylene to form one deuterium substituted methyl (CDH$_2$); two deuterium atoms are attached to a methylidyne to form two deuteriums substituted methyl (CD$_2$H); and three deuterium atoms are attached to a carbon atom having four valences to form three deuteriums substituted methyl (CD$_3$);

The term "azido" or "N$_3$" refers to an azide moiety. This radical may be attached, for example, to a methyl group to form azidomethane (methyl azide, MeN$_3$); or attached to a phenyl group to form phenyl azide (PhN$_3$).

The term "heteroalkyl" refers to an alkyl chain contains one or more heteroatoms, wherein the alkyl radical and heteroatom are defined as described herein. Unless otherwise specified, the heteroalkyl group contains 1-10 carbon atoms. In certain embodiments, the heteroalkyl group contains 1-5 carbon atoms; in other embodiments, the heteroalkyl group contains 1-4 carbon atoms; in still other embodiments, the heteroalkyl group contains 1-3 carbon atoms. Some non-limiting examples include, CH$_3$OCH$_2$—, CH$_3$CH$_2$OCH$_2$—, CH$_3$SCH$_2$—, (CH$_3$)$_2$NCH$_2$—, (CH$_3$)$_2$CH$_2$OCH$_2$—, CH$_3$OCH$_2$CH$_2$—, CH$_3$CH$_2$OCH$_2$CH$_2$—, and the like. The heteroalkyl group may be optionally substituted with one or more substituents described herein.

The term "heteroatom" refers to one or more of oxygen (O), sulfur (S), nitrogen (N), phosphorus (P), or silicon (Si), including any oxidized form of nitrogen (N), sulfur (S) and phosphorus (P); the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" or "halo" refers to Fluoro (F), Chloro (Cl), Bromo (Br) or Iodo (I).

The term "hydroxy-substituted alkyl" refers to an alkyl group substituted with one or more hydroxy radicals, wherein the alkyl group is defined as described herein. Examples of the hydroxy-substituted alkyl include, but are not limited to, hydroxymethyl, hydroxyethyl, 1,2-dihydroxyethyl, and the like.

The term "hydroxy-substituted haloalkyl" refers to a haloalkyl group substituted with one or more hydroxy radicals, wherein the haloalkyl group is defined as described herein. Examples of the hydroxy-substituted haloalkyl include, but are not limited to, 1-hydroxy-2,2,2-trifluoroethyl, 1-hydroxy-2,2-difluoroethyl, and the like. The hydroxy-substituted haloalkyl group may be optionally substituted with one or more substituents described herein.

The term "carboxy-substituted alkyl" refers to an alkyl group substituted with one or more carboxy radicals, wherein the alkyl group is defined as described herein. Examples of the carboxy-substituted alkyl include, but are not limited to, carboxymethyl, 1-carboxyethyl, and the like.

The term "haloalkyl", "haloalkenyl" or "haloalkoxy" respectively refers to an alkyl, alkenyl, or alkoxy group, as the case may be, substituted with one or more halogen atoms, and wherein each of the alkyl, alkenyl or alkoxy is defined as described herein. Examples of such groups include, but are not limited to, difluromethyl, trifluoromethyl, trifluoromethoxy, 2,2,2-trifluoroethoxy, 2,2,3,3-tetrafluoropropoxy, and the like. And wherein optionally each of the haloalkyl, haloalkenyl or haloalkoxy may be optionally substituted with one or more substituents described herein.

The term "alkoxy" refers to an alkyl group, as previously defined, attached to the parent molecular moiety through an oxygen atom. Unless otherwise specified, the alkoxy group contains 1-12 carbon atoms. In some embodiments, the alkoxy group contains 1-6 carbon atoms. In other embodiments, the alkoxy group contains 1-4 carbon atoms. In still other embodiments, the alkoxy group contains 1-3 carbon atoms. The alkoxy group is optionally substituted with one or more substituents described herein.

Some non-limiting examples of the alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "alkoxyalkyl" refers to an alkyl group substituted with one or more alkoxy radicals, wherein the alkyl and alkoxy are as defined herein. Examples of such groups include, but are not limited to, methoxymethyl, ethoxymethyl, and the like. The alkoxyalkyl group is optionally substituted with one or more substituents described herein.

The term "alkylthio" refers to a linear or branched-alkyl radical of one to six carbon atoms, attached to a divalent sulfur atom. In some embodiments, the alkylthio radical is a lower alkylthio radical having one to four carbon atoms. Some non-limiting examples of the alkylthio group include methylthio (CH$_3$S—). And wherein the alkylthio group is optionally substituted with one or more substituents described herein.

The term "alkenylthio" refers to a linear or branched-alkenyl radical of one to six carbon atoms, attached to a divalent sulfur atom. In some embodiments, the alkenylthio radical is a lower alkenylthio radical having one to four carbon atoms. Some non-limiting examples of the alkenylthio group include allylthio (CH$_2$=CHCH$_2$S—). And wherein the alkenylthio group is optionally substituted with one or more substituents described herein.

The term "alkylamino" embraces "N-alkylamino" and "N,N-dialkylamino", that is an amino group independently substituted with one or two alkyl radicals and wherein the alkyl group is as defined herein. In some embodiments, the alkylamino radical is "lower alkylamino" radical having one or two $C_{1-6}$ alkyl radicals attached to a nitrogen atom. In other embodiments, the alkylamino radical is "lower alkylamino" radical having one to three carbon atoms. Suitable alkylamino radical may be monoalkylamino or dialkylamino. Examples of the alkylamino radical include, but are not limited to, N-methylamino, N-ethylamino, N,N-dimethylamino, N,N-diethylamino, and the like. And wherein the alkylamino radical is optionally substituted with one or more substituents described herein.

The term "aminoalkyl" refers to a linear or branched alkyl radical having one to ten carbon atoms substituted with one or more amino radicals. More preferred aminoalkyl radical is "lower aminoalkyl" radical having one to six carbon atoms. Non-limiting examples of such radical include aminomethyl, aminoethyl, aminopropyl, and the like. And wherein the aminoalkyl radical is optionally substituted with one or more substituents described herein.

The term "x membered", wherein x is an integer which typically describes the number of ring-forming atoms in a moiety and the number of ring-forming atoms herein is x. For example, piperidinyl is an example of a 6-membered heterocycloalkyl.

The term "ring" refers to "carbocyclic", heterocyclic", "aromatic", "heteroaromatic", "spirocyclic", "fused cyclic", and the like, and wherein "carbocyclic", heterocyclic", "aromatic", "heteroaromatic", "spirocyclic" and "fused cyclic" are defined as described herein.

The term "fused bicyclic ring", "fused cyclic", "fused bicyclyl" or "fused cyclyl" as used interchangeably herein refers to a monovalent or multivalent saturated or partially unsaturated bridged-ring system, which refers to a bicyclic ring system that is not aromatic. For example, as depicted below in Figure a, Figure b and Figure c, two five-membered rings (Figure a), two six-membered rings (Figure b), and a five-membered ring and a six-membered ring (Figure c) are independently a bridged ring system shared a common C—C bond. Such a ring system may contain isolated or conjugated unsaturation, but not aromatic or heteroaromatic rings in its core structure (but may have aromatic substitution thereon). Each ring in the fused bicyclic ring system is independently carbocyclic ring or heterocyclic ring.

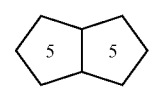

a

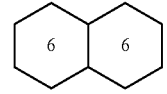

b

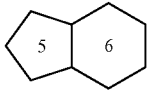

Some non-limiting examples of the fused bicyclyl group include hexahydrofuro[2,3-b]furan-3-yl, hexahydrofuro[3,2-b]furan-3-yl, octahydrocyclopenta[c]pyrrol-5-yl, octahydropentalen-2-yl, octahydro-1H-isoindol-5-yl, and the like. The fused bicyclyl group is optionally substituted with one or more substituents described herein.

The term "spirocyclyl", "spirocyclic", "spiro bicyclyl" or "spiro bicyclic" as used interchangeably herein refers to a monovalent or multivalent, saturated or partially unsaturated ring system wherein a ring originating from a particular annular carbon of another ring. For example, as depicted below in Figure d and Figure e, ring A and ring B share a carbon atom between the two saturated ring systems, which terms as a "spirocyclyl" or "spiro bicyclyl". Each ring in the spiro bicyclyl can be either a carbocyclyl or a heterocyclyl. Some non-limiting examples of the spiro bicyclyl group include 4-oxaspiro[2.4]hept-6-yl, and (R)-4-azaspiro[2.4]hept-6-yl. The spiro bicyclyl group is optionally substituted with one or more substituents described herein.

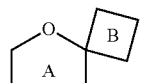

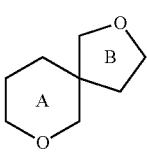

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen, and wherein the heterocycloalkyl group is optionally substituted with one or more substituents described herein.

The term "carbocycle", "carbocyclyl", "carbocyclic" or "carbocyclic ring" refers to a monovalent or multivalent non-aromatic, saturated or partially unsaturated ring having 3 to 12 carbon atoms as a monocyclic, bicyclic or tricyclic ring system. A carbobicyclic ring system includes a spiro carbobicyclyl or a fused carbobicyclyl. Suitable carbocyclyl groups include, but are not limited to, cycloalkyl, cycloalkenyl, and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The carbocyclyl group is optionally substituted with one or more substituents described herein.

The term "cycloalkyl" refers to a monovalent or multivalent saturated ring having 3 to 12 carbon atoms as a monocyclic, bicyclic, or tricyclic ring system, and wherein the bicyclic, or tricyclic ring system may include fused ring, bridged ring and spiro ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. The cycloalkyl radicals are optionally substituted with one or more substituents described herein.

The term "cycloalkylalkyl" refers to an alkyl group substituted with one or more cycloalkyl radicals, wherein the cycloalkyl and alkyl group are as defined herein. Examples of such groups include, but are not limited to, cyclopropylethyl, cyclopentylethyl, cyclohexylethyl, cyclohexylmethyl, and the like. The cycloalkylalkyl group is optionally substituted with one or more substituents described herein.

The term "cycloalkoxy" or "cycloalkyloxy", or "carbocycloxy" refers to an optionally substituted cycloalkyl group or carbocyclyl group described herein attached to the parent molecular via an oxygen atom, wherein the cycloalkyl and carbocyclyl group are as defined herein. Examples of such groups include, but are not limited to, cyclopropoxy, cyclopentoxy, cyclohexoxy, hydroxy-substituted cyclopropoxy, and the like. And wherein optionally each of the cycloalkoxy or carbocycloxy is independently substituted with one or more substitutents described herein.

The term "cycloalkylamino" refers to an amino group substituted with one or two optionally substituted cycloalkyl radicals described herein. Examples of the cycloalkylamino group include, but are not limited to, cyclopropylamino, cyclopentylamino, cyclohexylamino, hydroxy-substituted cyclopropylamino, dicyclohexylamino, dicyclopropylamino, and the like. The cycloalkylamino group is optionally substituted with one or more substituents described herein.

The term "cycloalkyl alkoxy", "cycloalkyl-alkoxy" or "cycloalkylalkoxy" refers to an alkoxy group substituted with one or more cycloalkyl groups, wherein cycloalkyl and alkoxy group are as defined herein. Examples of cycloalkylalkoxy group include, but are not limited to, cyclopropylmethoxy, cyclopropylethoxy, cyclopentylethoxy, cyclohexylethoxy, cyclohexylmethoxy, cyclopropylpropoxy, and the like. The cycloalkylalkoxy group is optionally substituted with one or more substituents described herein.

The term "carbocyclylalkoxy" refers to an alkoxy group substituted with one or more carbocyclyl groups, wherein carbocyclyl group and alkoxy group are as defined herein. Examples of carbocyclylalkoxy group include, but are not limited to, cyclopropylmethoxy, cyclohexenylethoxy, and the like. The carbocyclylalkoxy group is optionally substituted with one or more substituents described herein.

The term "heterocycle", "heterocyclic", "heterocyclyl", or "heterocyclic ring" as used interchangeably herein refers to a saturated or partially unsaturated monocyclic, bicyclic or tricyclic ring containing 3 to 12 ring atoms of which one or more ring members are independently selected hetero atom as defined herein and that is completely saturated or that contains one or more units of unsaturation, but which is not aromatic. In one embodiment, the "heterocycle", "heterocyclic", "heterocyclyl" or "heterocyclic ring" group is a monocycle having 3 to 8 ring members (e.g., 2 to 6 carbon atoms and 1 to 3 heteroatoms selected from N, O, P and S, wherein the S or P is optionally substituted with one or more oxo to provide the group SO or $SO_2$, or PO or $PO_2$, with the proviso that when the ring is a 3-membered ring, there is only one heteroatom) or a bicycle having 7 to 12 ring members (e.g., 4 to 9 carbon atoms and 1 to 3 heteroatoms selected from N, O, P and S, wherein the S or P is optionally substituted with one or more oxo to provide the group SO or SO$_2$, or PO or PO$_2$). The heterocyclyl group is optionally substituted with one or more substituents described herein.

The heterocyclyl group may be a carbon radical or a heteroatom radical, of which a —CH$_2$— group can optionally be replaced by a —C(=O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl (oxetan-2-yl, oxetan-3-yl), thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of the heterocyclyl group of which the —CH$_2$— group is replaced by —C(=O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, 1,1-dioxo-thiomorpholinyl, and the like. The heterocyclyl group is optionally substituted with one or more substituents described herein.

In one embodiment, the heterocyclyl group may be a 4-7 membered heterocyclyl, which refers to a saturated or partially unsaturated monocyclic ring containing 4 to 7 ring atoms, of which at least one ring atom is selected from nitrogen, sulfur and oxygen. Some non-limiting examples of the 4-7 membered heterocyclyl group include azetidinyl, oxetanyl (oxetan-2-yl, oxetan-3-yl), thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, and the like. Some non-limiting examples of the heterocyclyl group of which the —CH$_2$— group is replaced by —C(=O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, 1,1-dioxo-thiomorpholinyl, and the like. The 4-7 membered heterocyclyl group is optionally substituted with one or more substituents described herein.

In another embodiment, heterocyclyl may be a 4-membered heterocyclyl, which refers to a saturated or partially unsaturated monocyclic ring containing 4 ring atoms, of which at least one ring atom is selected from nitrogen, sulfur and oxygen. Examples of 4-membered heterocyclyl include, but are not limited to, azetidinyl, oxetanyl (oxetan-2-yl, oxetan-3-yl), thietanyl, and the like. The 4-membered heterocyclyl group is optionally substituted with one or more substituents described herein.

In another embodiment, heterocyclyl may be a 5-membered heterocyclyl, which refers to a saturated or partially unsaturated monocyclic ring containing 5 ring atoms, of which at least one ring atom is selected from nitrogen, sulfur and oxygen. Examples of 5-membered heterocyclyl include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, and the like. Some non-limiting examples of heterocyclyl wherein —CH$_2$— group is replaced by —C(O)— moiety are 2-oxopyrrolidinyl, oxo-1,3-thiazolidinyl, and the like. A non-limited example of heterocyclyl wherein the ring sulfur atom is oxidized is sulfolanyl, and the like. The 5-membered heterocyclyl group is optionally substituted with one or more substituents described herein.

In still another embodiment, heterocyclyl may be a 6-membered heterocyclyl, which refers to a saturated or partially unsaturated monocyclic ring containing 6 ring atoms, of which at least one ring atom is selected from nitrogen, sulfur and oxygen. Examples of 6-membered heterocyclyl include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, and the like. Some non-limiting examples of heterocyclyl wherein —CH$_2$— group is replaced by —C(O)— moiety are 2-piperidinonyl, 3,5-dixoxpiperidinyl, pyrimidinedionyl, and the like. A non-limited example of heterocyclyl wherein the ring sulfur atom is oxidized is 1,1-dioxo-thiomorpholinyl, and the like. The 6-membered heterocyclyl group is optionally substituted with one or more substituents described herein.

In yet another embodiment, heterocyclyl refers to a 7-12 membered heterocyclyl. Examples of 7-12 membered heterocyclyl include, but are not limited to, 2-oxa-5-azabicyclo [2.2.1]hept-5-yl, and the like. The 7-12 membered heterocyclyl group is optionally substituted with one or more substituents described herein.

The term "heterocyclylalkyl" refers to an alkyl group substituted with one or more heterocyclyl radicals; the term "heterocyclylalkoxy" refers to a heterocycyl substituted alkoxy, wherein oxygen atom is attached to the rest group of molecule; the term "heterocyclylalkylamino" refers to a heterocycyl substituted alkylamino, wherein nitrogen atom is attached to the rest group of molecule. Wherein the heterocyclyl, alkyl, alkoxy and alkylamino are defined as the invention described herein. Examples of such groups include, but are not limited to, pyrrol-2-ylmethyl, morpholin-4-ylethyl, morpholin-4-ylethoxy, piperazin-4-ylethoxy, piperidin-4-ylethylamino, and the like. Wherein optionally each of the heterocyclylalkyl, heterocyclylalkoxy and heterocyclylalkylamino is independently substituted with one or more substitutents described herein.

The term "heterocyclyloxy" refers to an optionally substituted heterocyclyl described herein attached to an oxygen atom, and wherein the oxygen atom is attached to the rest group of molecule. Examples of heterocyclyloxy group include, but are not limited to, pyrrol-2-oxy, pyrrol-3-oxy, piperidin-2-oxy, piperidin-3-oxy, piperazin-2-oxy, piperidin-4-oxy, and the like. The heterocyclyloxy group is optionally substituted with one or more substituents described herein.

The term "heterocyclylamino" refers to an amino substituted with one or two heterocyclyl radicals, wherein heterocyclyl is defined as the invention described herein. Examples of heterocyclylamino group include, but are not limited to, pyrrol-2-amino, pyrrol-3-amino, piperidin-2-amino, piperidin-3-amino, piperidin-4-amino, piperazin-2-amino, dipyrrol-2-amino, and the like. The heterocyclylamino group is optionally substituted with one or more substituents described herein.

The term "aryl" refers to a monocyclic, bicyclic, or tricyclic carbocyclic ring system having a total of 6 to 14 ring members, preferably, 6 to 12 ring members, and more preferably 6 to 10 ring members, wherein at least one ring in the system is aromatic, and wherein each ring in the system contains 3 to 7 ring members. The aryl group is generally, but not necessarily bonded to the parent molecule through an aromatic ring of the aryl group. The term "aryl" may be used interchangeably with the term "aryl ring" or "aromatic." Examples of aryl ring may include phenyl, naphthyl and anthracene. The aryl radical is optionally substituted with one or more substituents described herein.

The term "aralkyl" or "arylalkyl" refers to aryl-substituted alkyl radicals. In some embodiments, aralkyl radical or arylalkyl radical is "lower aralkyl" radical having aryl radical attached to alkyl radical having one to six carbon atoms. In other embodiments, aralkyl radical or arylalkyl radical is a "phenylalkyl", alkyl portion of which having one to four carbon atoms. Some non-limiting examples of such radical include benzyl, diphenylmethyl, phenylethyl, and the like. The aryl group of arylalkyl radical is further substituted with halo, alkyl, alkoxy, haloalkyl or haloalkoxy. The aralkyl group is optionally substituted with one or more substituents described herein.

The term "aryloxy" refers to an optionally substituted aryl group attached to the oxygen atom described herein, which is attached to the rest group of molecule via oxygen atom, and wherein the aryl group is as defined herein. Examples of aryloxy group include, but are not limited to, phenoxy, tolyloxy, ethylphenoxy, and the like. The aryloxy group is optionally substituted with one or more substituents described herein.

The term "arylthio" refers to an optionally substituted aryl group attached to the sulfur atom, and the sulfur atom is attached to the rest group of molecule, wherein the aryl group is as defined herein. Examples of arylthio group include, but are not limited to, phenylthio, tolylthio, ethylphenylthio, and the like. The arylthio group is optionally substituted with one or more substituents described herein.

The term "arylamino" refers to an amino group substituted with one or two aryl radicals. Examples of arylamino group include, but are not limited to, N-phenylamino. In some embodiments, the aryl ring of arylamino radical can be further substituted. The arylamino group is optionally substituted with one or more substituents described herein.

The term "heteroaryl" refers to a monocyclic, bicyclic or tricyclic ring systems having a total of 5 to 12 ring members, preferably, 5 to 10 ring members, and more preferably 5 to 6 ring members, wherein at least one ring in the system is aromatic, and at least one ring in the system contains one or more heteroatoms, and wherein each ring in the system contains 5 to 7 ring members. The heteroaryl group is generally, but not necessarily bonded to the parent molecule through an aromatic ring of the heteroaryl group. The term "heteroaryl" may be used interchangeably with the term "heteroaryl ring", "aromatic heterocyclic" or the term "heteroaromatic compound". The heteroaryl radical is optionally substituted with one or more substituents described herein. In one embodiment, a 5-10 membered heteroaryl comprises 1, 2, 3 or 4 heteroatoms independently selected from O, S and N.

Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles, but are not limited to: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, triazolo[4,3-b]pyridazinyl, [1,2,4]triazolo[1,5-a]pyrimidinyl, or [1,2,4]triazolo[1,5-a]pyridyl, and the like.

As described herein, a bond drawn from a substituent R to the center of one ring within a ring system (as shown in Figure f) represents substitution of the substituent R at any substitutable position on the ring A. For example, Figure f represents possible substitution in any of the positions on the A ring, as shown in Figure $f^1$-$f^4$.

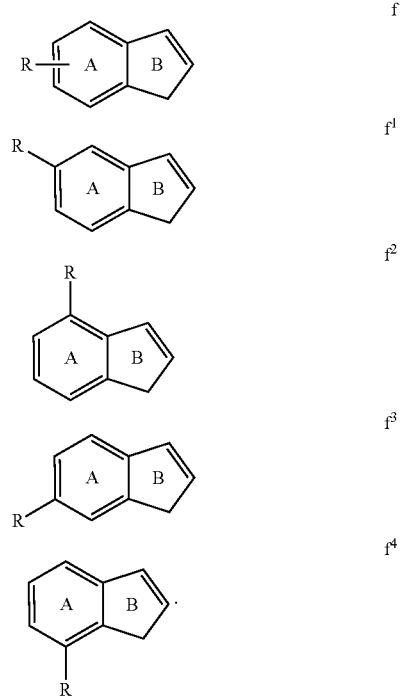

The term "heteroarylamino" refers to an amino group substituted with one or two optionally substituted heteroaryl radicals, wherein the heteroaryl is as defined herein. Examples of heteroarylamino group include, but are not limited to, N-thienylamino, pyridin-4-ylamino, m-fluoropyridylamino, dipyridylamino, and the like. The heteroarylamino group is optionally substituted with one or more substituents described herein.

The term "heteroaryloxy" refers to an optionally substituted heteroaryl group, attached to an oxygen atom, and the oxygen atom is attached to the rest group of molecule, wherein the aryl is as defined herein. Examples of heteroaryloxy group include, but are not limited to, pyridyloxy, pyrimidyloxy, and the like. The heteroaryloxy group is optionally substituted with one or more substituents described herein.

The term "heteroarylalkyl" refers to an alkyl group substituted with one or more heteroaryl radicals, wherein the heteroaryl and alkyl are defined as the invention described herein. Examples of heteroarylalkyl include, but are not limited to, imdazolyl-2-methyl, furyl-2-ethyl, indolyl-3-methyl, and the like. The heteroarylalkyl group is optionally substituted with one or more substituents described herein.

The term "prodrug" refers to a compound that is transformed in vivo into a compound of formula (I) or (I-A). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates and amino acid esters. For example, a compound disclosed herein that contains an OH group may be acylated at this position to form its prodrug. Other prodrug forms include phosphates, such as, those phosphates resulting from the phosphonation of an OH group on the parent compound. A thorough discussion of prodrugs is provided in: Higuchi et al., Pro-drugs as Novel Delivery Systems, Vol. 14 of the *A.C.S. Symposium Series*; Roche et al., ed., Bioreversible Carriers in Drug Design, *American Pharmaceutical Association and Pergamon Press*, 1987; Rautio et al., Prodrugs: Design and Clinical Applications, *Nature Review Drug Discovery*, 2008, 7, 255-270; and Hecker et al., Prodrugs of Phosphates and Phosphonates, *Journal of Medicinal Chemistry*, 2008, 51, 2328-2345, each of which is incorporated herein by reference.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmacol Sci*, 1977, 66, 1-19, which is incorporated herein by reference. Some non-limiting examples of pharmaceutically acceptable non-toxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC, Boc), benzyloxycarbonyl (CBZ, Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include trialkylsilyl, acetyl, benzoyl, and benzyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "ADHD" is an abbreviation of "Attention-deficit hyperactivity disorder", which is a mental disorder commonly appeared in childhood. This disease is called "Hyperkinetic Disorder" according to the World Health Organization's "The General Classification of Disease Manual" $10^{th}$ edit (ICD-10, WHO, 1992), and classification number is F90. "ADHD" is also commonly known as "hyperactive child", The term "schizophrenia" is refers to Schizophrenia, Schizophrenia disorders, schizoaffective disorders and psychiatric disorders. Wherein the term "psychosis" refers to the action of delusions, obvious hallucinations, disorganized language or behavior, or stiff behavior, according to "*Diagnostic and Statistical Manual of Mental Disorder*" $4^{th}$ edit, American Psychiatric Association, Washington, D.C.

The term "PAH" is an abbreviation of "Pulmonary Arterial Hypertension", which is a extremely malignant progressive disease, and defined as a pulmonary artery pressure sustained high level which is greater than 25 mm Hg at rest time and more than 30 mm during exercise, and at the same time, mean pulmonary capillary wedge pressure and left ventricular end-diastolic pressure are below 15 mm Hg. And "PAH" is characterized as progressive increasement of pulmonary vascular resistance, which can finally lead to right heart failure and even death.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, p-toluenesulfonic acid, sulfosalicylic acid, and the like.

Pharmaceutically acceptable base addition salts can be formed with inorganic or organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine and chlorine, such as $^{2}H$ (deuterium, D), $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, $^{125}I$, respectively.

In another aspect, the compounds of the invention include isotopically enriched compounds as defined herein, for example those into which radioactive isotopes, such as $^{3}H$, $^{14}C$ and $^{18}F$, or those into which non-radioactive isotopes, such as $^{2}H$ and $^{13}C$ are present. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) or (I-A) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I) or (I-A). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, DMSO-$d_6$.

DESCRIPTION OF COMPOUNDS OF THE INVENTION

Provided herein are aromatic heterocyclic compounds, pharmaceutically acceptable salts and pharmaceutical preparations thereof which are useful as $5\text{-HT}_6$ antagonistic agents, especially have a potent effect on treating Alzheimer's disease.

In one aspect, provided herein are compounds having Formula (I) or Formula (I-A)

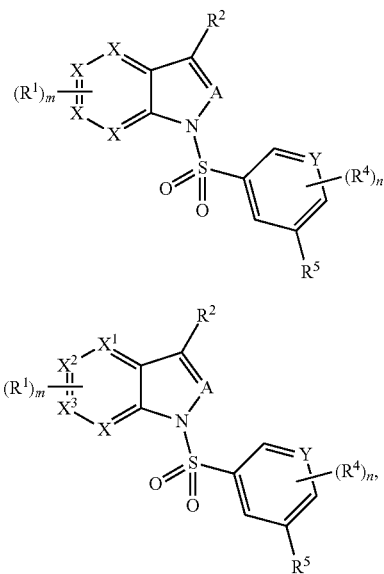

or a stereoisomer, a geometric isomer, a tautomer, an N-oxide, a hydrate, a solvate, a metabolite, a pharmaceutically acceptable salt or a prodrug thereof, wherein:
each m is independently 0, 1, 2 or 3;
each n is independently 1, 2 or 3;
each A is independently $CR^3$ or N;
each X of Formula (I) is independently $CR^1$ or N, and at most two X are N; or
each X of Formula (I) is independently CH or N, and at most two X are N;
each of $X^1$, $X^2$, $X^3$ and X of Formula (I-A) is independently $CR^1$ or N, and at most two of $X^1$, $X^2$, $X^3$ and X of Formula (I-A) are N; or each of $X^1$, $X^2$, $X^3$ and X of Formula (I-A) is independently CH or N, and at most two of $X^1$, $X^2$, $X^3$ and X are N;
each Y is independently $CR^4$ or N;
each $R^1$ is independently H, D, F, Cl, Br, I, —CN, —$NO_2$, —OH, —$NH_2$, $C_{1-6}$ alkyl, $C_{2-6}$ alkenyl, $C_{2-6}$ alkynyl, $C_{3-8}$ cycloalkyl, $C_{1-6}$ haloalkyl, $C_{1-6}$ alkoxy, $C_{1-6}$ haloalkoxy, $C_{1-6}$ alkylthio, $C_{1-6}$ alkenylthio, $R^{6a}R^6N$—$C_{1-6}$ alkyl, —C(=O)$R^{6b}$, —C(=O)O$R^{6c}$, —C(=O)N$R^6R^{6a}$, $R^6R^{6a}N$—S(=O)$_2$—, $R^{6b}S$(=O)$_2$—, $R^{6b}S$(=O)—$C_{1-6}$ alkyl, $R^6R^{6a}N$—C(=O)—$C_{1-6}$ alkyl, $C_{6-10}$ aryl, $C_{6-10}$ arylamino, $C_{1-9}$ heteroaryl, $C_{3-8}$ cycloalkyl-$C_{1-6}$-alkyl, $C_{2-10}$ heterocyclyl-$C_{1-6}$-alkyl, $C_{6-10}$ aryl-$C_{1-6}$-alkyl or $C_{1-9}$ heteroaryl-$C_{1-6}$-alkyl, or each $R^1$ is independently the following group,

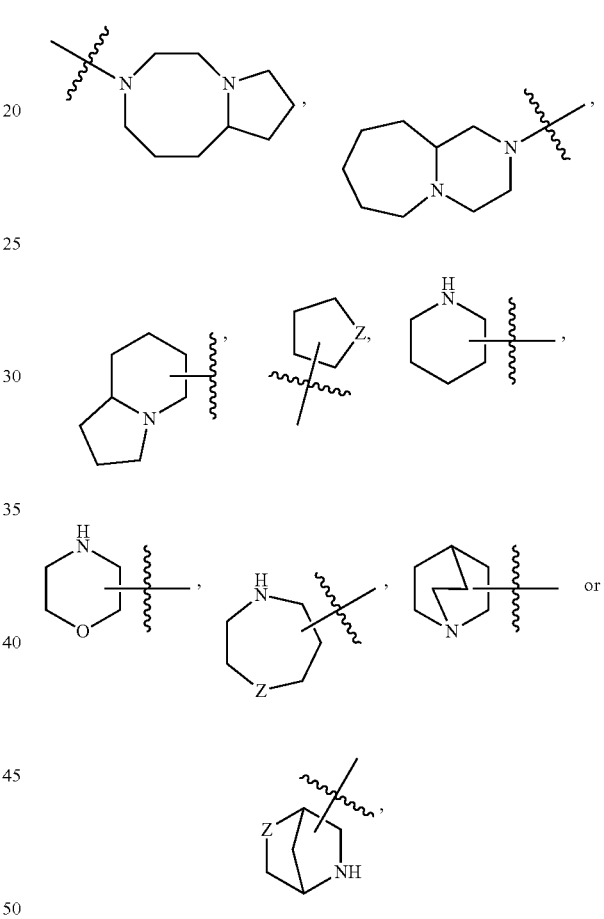

and wherein, Z is —NH—, —O— or —S—;
each $R^2$ is independently H, D, F, Cl, Br, I, —CN, —$NO_2$, —OH, —$NH_2$, —$SO_2Cl$, $R^{6a}R^6N$—, —C(=O)$R^{6b}$, —C(=O)N$R^6R^{6a}$, —OC(=O)N$R^6R^{6a}$, —OC(=O)O$R^{6c}$, —N($R^6$)C(=O)N$R^6R^{6a}$, —N($R^6$)C(=O)O$R^{6c}$, —N($R^6$)C(=O)—$R^{6b}$, $R^6R^{6a}N$—S(=O)$_2$—, $R^{6b}S$(=O)$_2$—, $R^{6b}S$(=O)$_2N(R^{6a})$—, hydroxy-substituted $C_{1-6}$ alkyl, hydroxy-substituted $C_{1-6}$ haloalkyl, carboxy-substituted $C_{1-6}$ alkyl, $C_{1-6}$ alkyl-OC(=O)$C_{1-6}$ alkyl, $R^{6b}S$(=O)—$C_{1-6}$ alkyl, $R^6R^{6a}N$—C(=O)—$C_{1-6}$ alkyl, $R^{6a}R^6N$—$C_{1-6}$ alkoxy, $R^{6b}S$(=O)—$C_{1-6}$ alkoxy, $R^6R^{6a}N$—C(=O)—$C_{1-6}$ alkoxy, $C_{6-10}$ aryl, $C_{1-9}$ heteroaryl, $C_{1-6}$ alkoxy, $C_{1-6}$ alkylamino, $C_{1-6}$ alkyl, $C_{1-6}$ alkoxy-$C_{1-6}$-alkyl, $C_{1-6}$ haloalkyl, $C_{2-10}$ heterocyclyl-$C_{1-6}$-alkyl or $C_{6-10}$ aryl-$C_{1-6}$-alkyl, or $R^2$ is the following group,

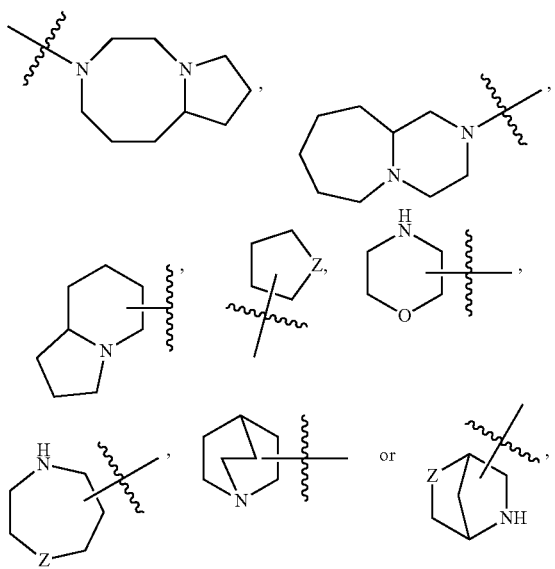

and wherein, Z is —NH—, —O— or —S—;

each $R^3$ independently is H, D, F, Cl, Br, I, —CN, —NO$_2$, —OH, —NH$_2$, C$_{1-6}$ alkyl, C$_{2-6}$ alkenyl, C$_{2-6}$ alkynyl, carboxy-substituted C$_{1-6}$ alkyl, —C(=O)R$^{6b}$, C$_{6-10}$ aryl, C$_{3-8}$ cycloalkyl, C$_{1-6}$ haloalkyl, C$_{1-6}$ haloalkoxy or —C(=O)NR$^6$R$^{6a}$;

each $R^4$ is independently D, F, Cl, Br, I, —CN, C$_{1-6}$ alkyl, C$_{2-6}$ alkenyl, C$_{2-6}$ alkynyl, C$_{3-8}$ cycloalkyl, C$_{1-6}$ haloalkyl, C$_{1-6}$ alkoxy, C$_{1-6}$ haloalkoxy or C$_{6-10}$ aryl, or two adjacent $R^4$ together with the carbon atom to which they are attached, form an optionally substituted 5- to 7-membered carbon ring, heterocyclic ring, aromatic ring or heteroaromatic ring;

each $R^5$ is independently C$_{2-10}$ heterocyclyl or C$_{5-8}$ cycloalkyl, and wherein optionally each of C$_{2-10}$ heterocyclyl and C$_{5-8}$ cycloalkyl is independently substituted with one, two, three or four substitutents independently selected from D, F, Cl, Br, I, —CN, oxo (=O), —C(=O)R$^{6b}$, —C(=O)OR$^{6c}$, —C(=O)NR$^6$R$^{6a}$, C$_{1-6}$ alkyl, C$_{3-8}$ cycloalkyl, C$_{2-10}$ heterocyclyl, C$_{1-6}$ haloalkyl, C$_{1-6}$ alkoxy, C$_{1-6}$ haloalkoxy, C$_{6-10}$ aryl-C$_{14}$-alkyl and C$_{1-9}$ heteroaryl-C$_{1-6}$-alkyl;

each $R^6$ and $R^{6a}$ is independently H, D, —OH, C$_{1-6}$ alkyl, C$_{1-6}$ haloalkyl, C$_{1-6}$ alkoxy, C$_{6-10}$ aryl, C$_{2-10}$ heterocyclyl, C$_{3-8}$ cycloalkyl, C$_{6-10}$ aryl-C$_{1-6}$-alkyl, C$_{6-10}$ aryloxy, C$_{2-10}$ heterocyclyloxy, C$_{3-8}$ cycloalkoxy, C$_{6-10}$ arylamino, C$_{2-10}$ heterocyclylamino, C$_{3-8}$ cycloalkylamino, C$_{1-9}$ heteroaryl or C$_{3-8}$ carbocyclyl, or $R^6$ and $R^{6a}$ together with the nitrogen atom to which they are attached, form an optionally substituted 3- to 8-membered ring;

each $R^{6b}$ and $R^{6c}$ is independently H, D, —OH, C$_{1-6}$ alkyl, C$_{1-6}$ haloalkyl, C$_{1-6}$ alkoxy, C$_{6-10}$ aryl, C$_{2-10}$ heterocyclyl, C$_{3-8}$ cycloalkyl, C$_{6-10}$ aryl-C$_{1-6}$-alkyl, C$_{6-10}$ aryloxy, C$_{2-10}$ heterocyclyloxy, C$_{3-8}$ cycloalkoxy, C$_{6-10}$ arylamino, C$_{2-10}$ heterocyclylamino, C$_{3-8}$ cycloalkylamino, C$_{1-9}$ heteroaryl or C$_{3-8}$ carbocyclyl; and with the proviso that, the compound of Formula (I) or Formula (I-A) does not include 6-bromo-1-((4-methoxy-3-(piperazin-1-yl)phenyl)sulfonyl)-1H-indole.

In certain embodiments, wherein each $R^1$ and $R^3$ is independently H, D, F, Cl, Br, I, —CN, —NO$_2$, —OH, —NH$_2$, C$_{1-4}$ alkyl, C$_{2-4}$ alkenyl, C$_{2-4}$ alkynyl, C$_{6-10}$ aryl, C$_{3-6}$ cycloalkyl, C$_{1-4}$ haloalkyl or C$_{1-4}$ haloalkoxy.

In other embodiments, wherein each $R^2$ is independently H, D, F, Cl, Br, I, —CN, —C(=O)R$^{6b}$, C$_{1-4}$ alkyl, C$_{1-4}$ haloalkyl, hydroxy-substituted C$_{1-4}$ haloalkyl or C$_{1-4}$ alkoxy-C$_{1-4}$-alkyl, wherein R$^{6b}$ is as defined herein.

In other embodiments, wherein each $R^4$ is independently D, F, Cl, Br, I, —CN, C$_{1-4}$ alkyl, C$_{2-4}$ alkenyl, C$_{2-4}$ alkynyl, C$_{3-6}$ cycloalkyl, C$_{1-4}$ haloalkyl, C$_{1-4}$ alkoxy, C$_{1-4}$ haloalkoxy or C$_{6-10}$ aryl, or two adjacent $R^4$ together with the carbon atom to which they are attached, form an optionally substituted 5- to 6-membered aromatic ring or heteroaromatic ring.

In other embodiments, wherein each $R^5$ is independently C$_{3-7}$ heterocyclyl, wherein optionally C$_{3-7}$ heterocyclyl is independently substituted with one, two, three or four substitutents independently selected from D, F, Cl, Br, I, —CN, oxo (=O), C$_{1-6}$ alkyl, C$_{3-6}$ cyclalkyl, C$_{2-8}$ heterocyclyl, C$_{1-4}$ haloalkyl, C$_{1-4}$ alkoxy, C$_{1-4}$ haloalkoxy, —C(=O)R$^{6b}$, —C(=O)OR$^{6c}$ and —C(=O)NR$^6$R$^{6a}$, wherein R$^6$, R$^{6a}$, R$^{6b}$ and R$^{6c}$ are as defined herein.

In other embodiments, wherein each R$^6$, R$^{6a}$, R$^{6b}$ and R$^{6c}$ is independently H, D, —OH or C$_{1-4}$ alkyl.

In other embodiments, provided herein are compounds having Formula (II)

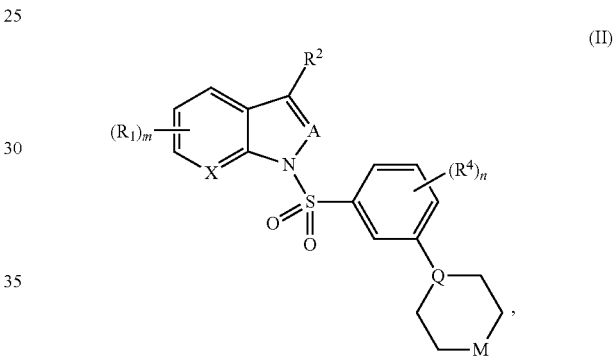

or a stereoisomer, a geometric isomer, a tautomer, an N-oxide, a hydrate, a solvate, a metabolite, a pharmaceutically acceptable salt or a prodrug thereof, wherein:

m is 0, 1, 2 or 3;

n is 1, 2 or 3;

A is CR$^3$ or N;

X is CR$^1$ or N;

Q is CH or N;

M is —NR' or —O—;

each $R^1$ and $R^3$ is independently H, D, F, Cl, Br, I, —CN, —NO$_2$, —OH, —NH$_2$, C$_{1-4}$ alkyl, C$_{2-4}$ alkenyl, C$_{2-4}$ alkynyl, C$_{6-10}$ aryl, C$_{3-6}$ cycloalkyl, C$_{1-4}$ haloalkyl or C$_{1-4}$ haloalkoxy;

$R^2$ is H, D, F, Cl, Br, I, —CN, —C(=O)R$^{6b}$, C$_{1-4}$ alkyl, C$_{1-4}$ haloalkyl, hydroxy-substituted C$_{1-4}$ haloalkyl or C$_{1-4}$ alkoxy-C$_{1-4}$-alkyl;

each $R^4$ is independently D, F, Cl, Br, I, —CN, C$_{1-4}$ alkyl, C$_{2-4}$ alkenyl, C$_{2-4}$ alkynyl, C$_{3-6}$ cycloalkyl, C$_{1-4}$ haloalkyl, C$_{1-4}$ alkoxy, C$_{1-4}$ haloalkoxy or C$_{6-10}$ aryl, or two adjacent $R^4$ together with the carbon atom to which they are attached, form an optionally substituted 5- to 6-membered aromatic ring or heteroaromatic ring;

R$^{6b}$ is H, D, —OH or C$_{1-4}$ alkyl;

R$^7$ is H, D, C$_{1-6}$ alkyl, C$_{3-6}$ cycloalkyl, C$_{2-8}$ heterocyclyl or C$_{1-4}$ haloalkyl; and with the proviso that, the compound of Formula (II) does not include 6-bromo-1-((4-methoxy-3-(piperazin-1-yl)phenyl)sulfonyl)-1H-indole.

In other embodiments, wherein each $R^1$ and $R^3$ is independently H, D, F, Cl, Br, I, —CN, —NO$_2$, —OH, —NH$_2$, —CHF$_2$, —CF$_3$, —CH$_2$CF$_3$, —CF$_2$CHF$_2$, —CHFCF$_3$, —CF$_2$CF$_3$, —CH$_2$CF$_2$CF$_3$, —CH$_2$CF$_2$CHF$_2$, methyl, ethyl, n-propyl, iso-propyl, n-butyl, iso-butyl or tert-butyl.

In other embodiments, wherein $R^2$ is H, D, F, Cl, Br, I, —CN, —C(=O)CH$_3$, —C(=O)CH$_2$CH$_3$, —C(=O)CH$_2$CH$_2$CH$_3$, —CHF$_2$, —CF$_3$, —CH$_2$CF$_3$, —CF$_2$CHF$_2$, —CHFCF$_3$, —CF$_2$CF$_3$, —CH$_2$CF$_2$CF$_3$, —CH$_2$CF$_2$CHF$_2$, —CH(OH)CF$_3$, —CH(OH)CHF$_2$, —CH$_2$CH(OH)CF$_3$, —CH$_2$CH(OH)CHF$_2$, —CH(OH)CH$_2$CHF$_2$, —CH(OH)CH$_2$CF$_3$, —CH$_2$OCH$_3$, —CH$_2$OCH$_2$CH$_3$, —CH$_2$OCH(CH$_3$)$_2$, —CH$_2$OCH$_2$CH$_2$CH$_3$, —CH$_2$CH$_2$OCH$_3$, —CH$_2$CH$_2$OCH$_2$CH$_3$, —CH$_2$CH$_2$OCH(CH$_3$)$_2$, —CH$_2$CH$_2$OCH$_2$CH$_2$CH$_3$, methyl, ethyl, n-propyl, iso-propyl, n-butyl, iso-butyl or tert-butyl.

In other embodiments, wherein each $R^4$ is independently D, F, Cl, Br, I, —CN, methyl, ethyl, n-propyl, iso-propyl, —CF$_3$, —CH$_2$CF$_3$, —CF$_2$CHF$_2$, —CHFCF$_3$, —CF$_2$CF$_3$, —CH$_2$CF$_2$CF$_3$, —CH$_2$CF$_2$CHF$_2$, methoxy, ethoxy, n-propoxy, iso-propoxy, n-butoxy, iso-butoxy, tert-butoxy, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$ or —OCH$_2$CF$_2$CHF$_2$, or two adjacent $R^4$ together with the carbon atom to which they are attached, form a substituted or unsubstituted benzene ring.

In other embodiments, wherein $R^7$ is H, D, methyl, ethyl, n-propyl, iso-propyl, n-butyl, iso-butyl, tert-butyl, —CH$_2$CH$_2$CH(CH$_3$)$_2$, —CH$_2$C(CH$_3$)$_3$, cyclopropyl, cyclobutyl, cyclopentyl, azetidinyl, oxetanyl, thietanyl, pyrrolidyl or tetrahydrofuryl.

In other embodiments, provided herein is one of the compounds as follows,

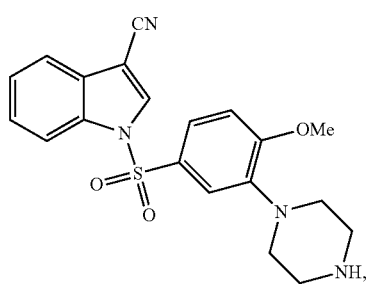

(1)

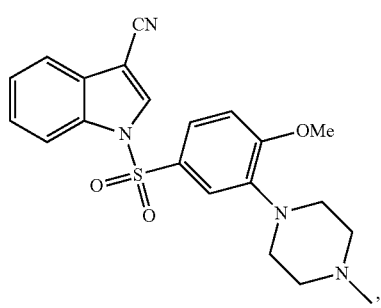

(2)

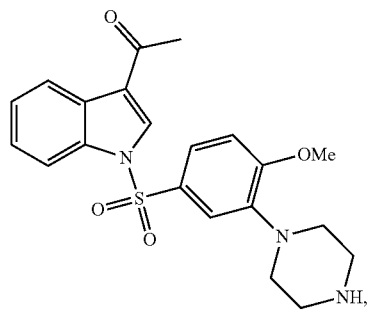

(3)

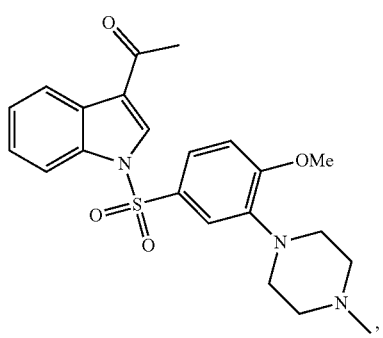

(4)

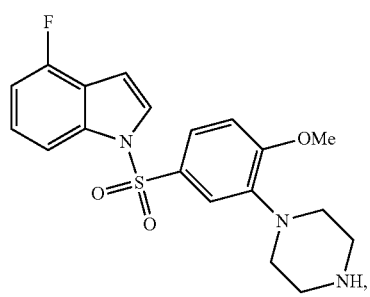

(5)

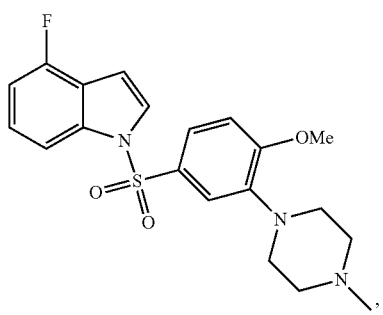

(6)

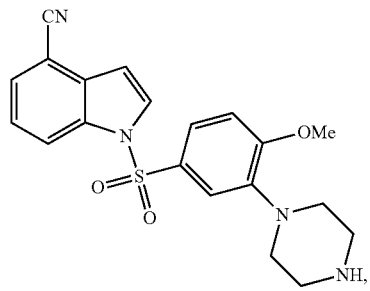

(7)

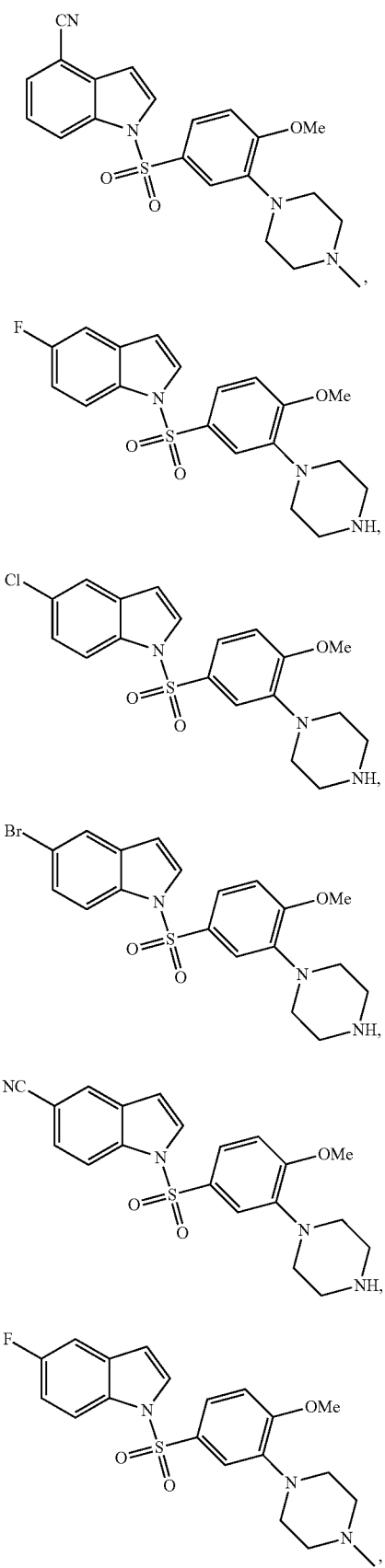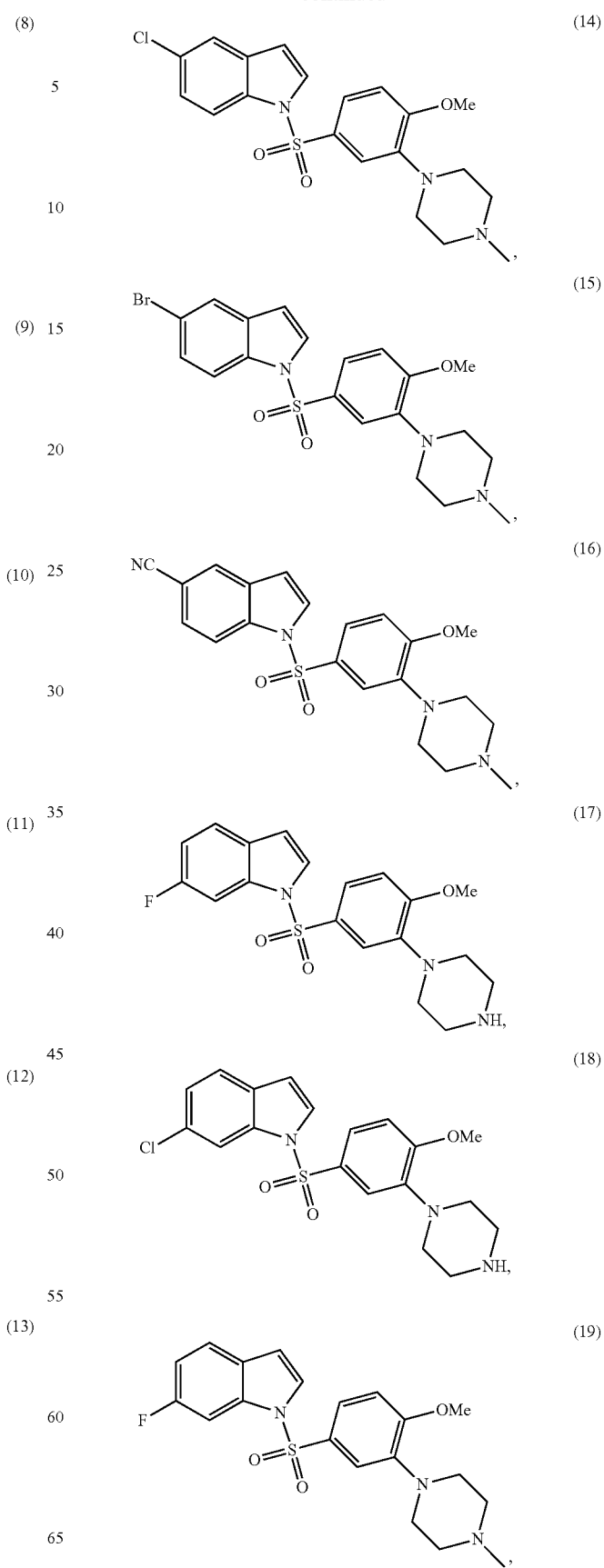

-continued
(20)
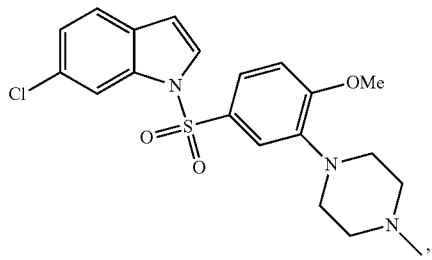
(21)
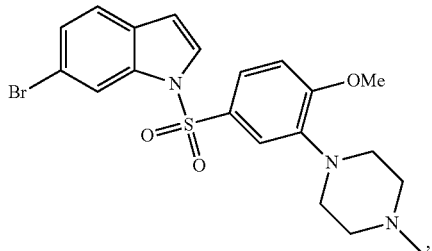
(22)
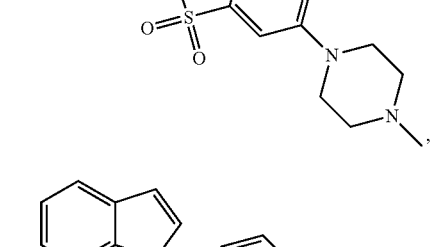
(23)
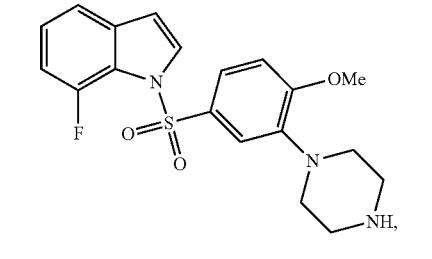
(24)
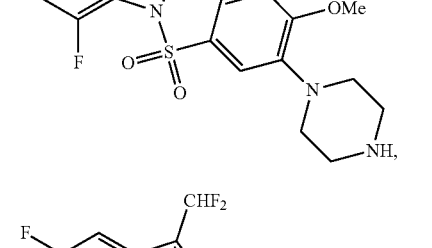
(25)
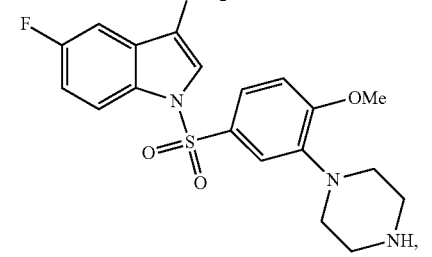
-continued
(26)
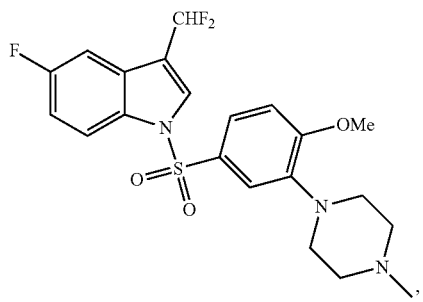
(27)
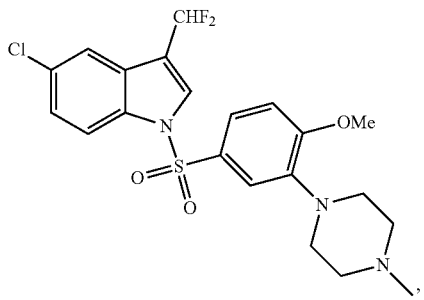
(28)
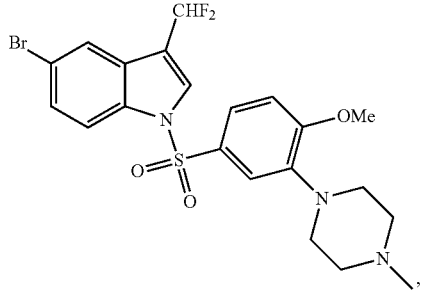
(29)
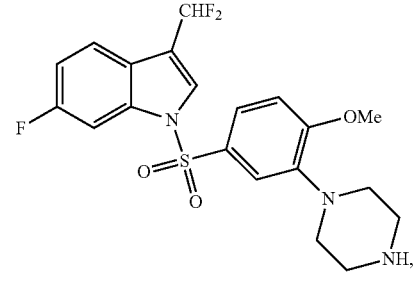
(30)
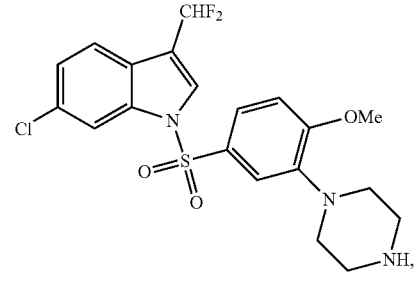

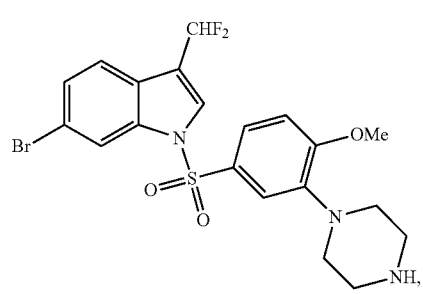
(31)
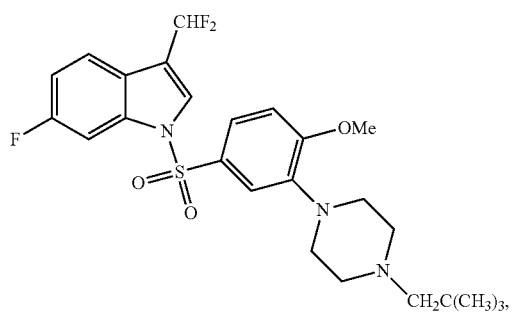
(36)
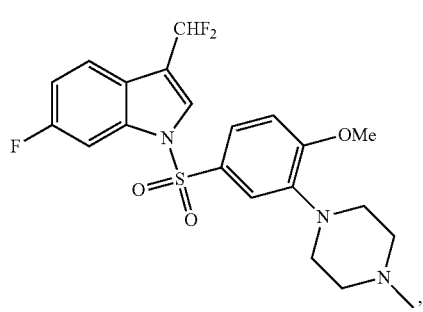
(32)
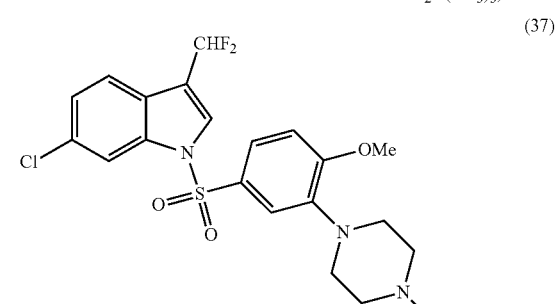
(37)
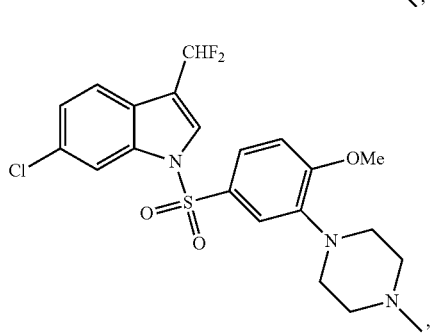
(33)
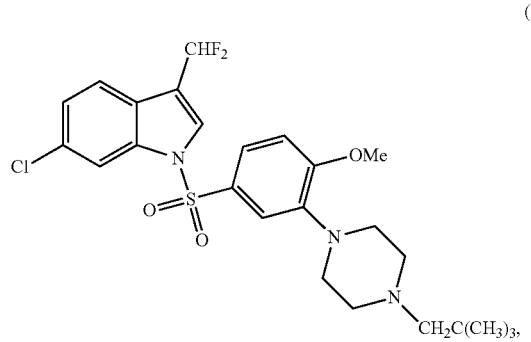
(38)
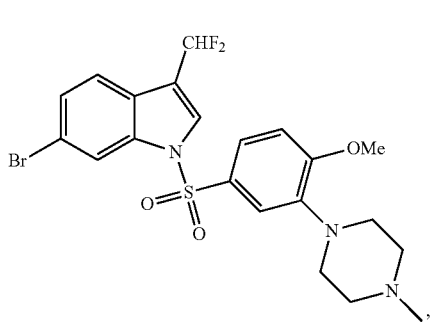
(34)
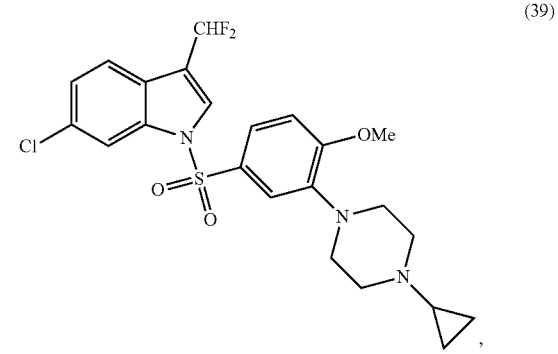
(39)
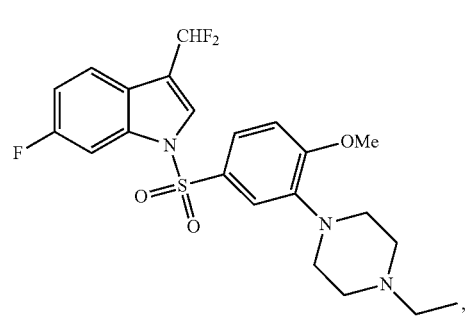
(35)
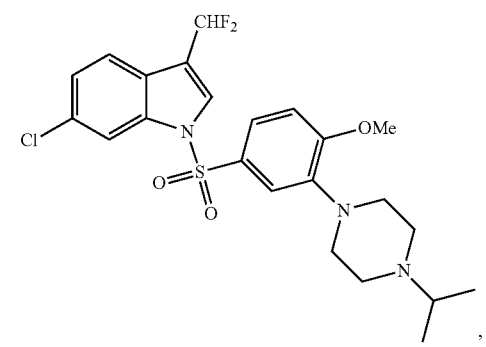
(40)

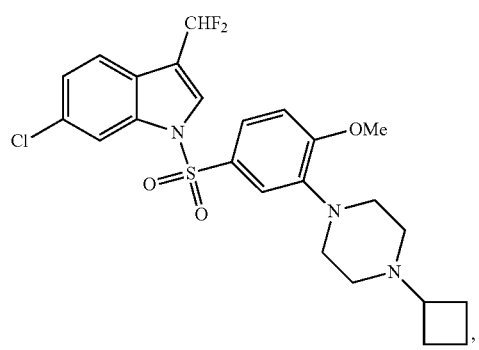
(41)
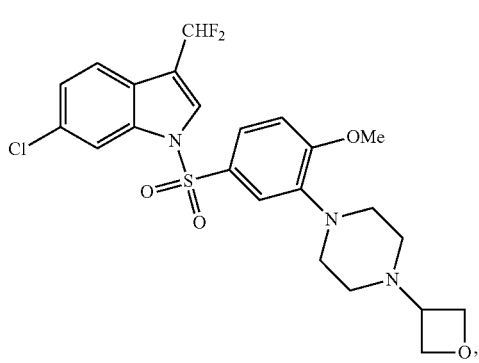
(42)
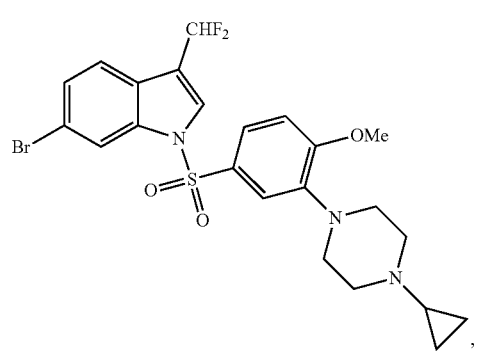
(43)
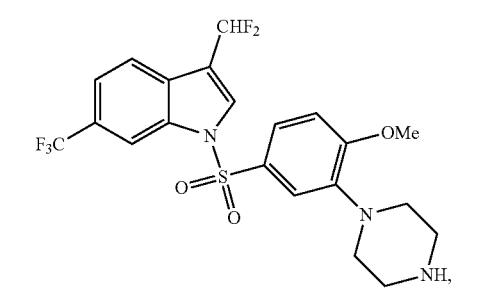
(44)
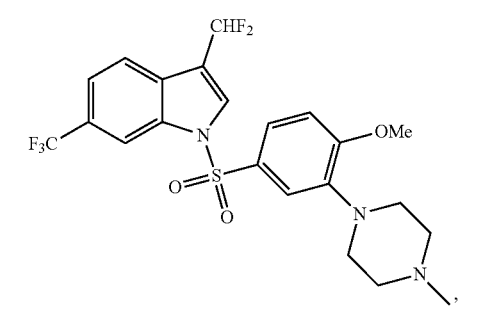
(45)
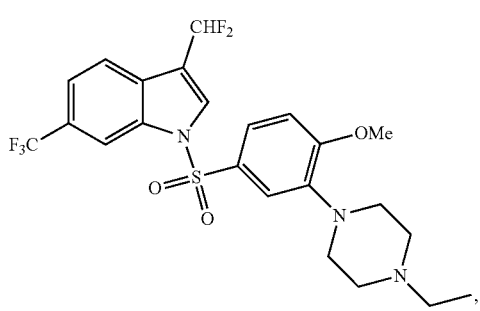
(46)
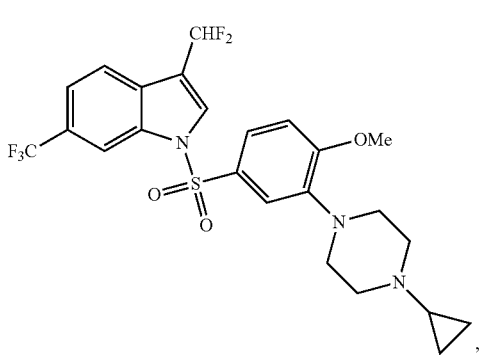
(47)
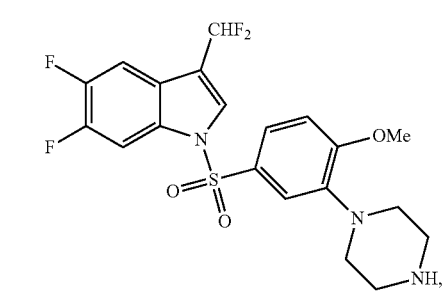
(48)
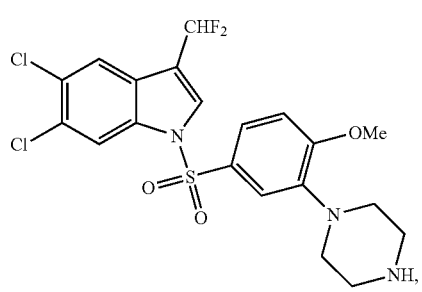
(49)
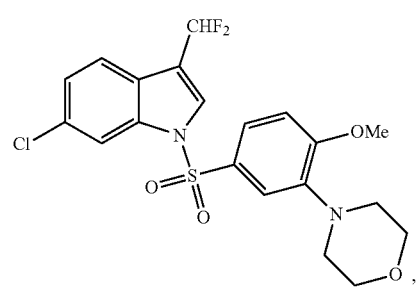
(50)

(51) 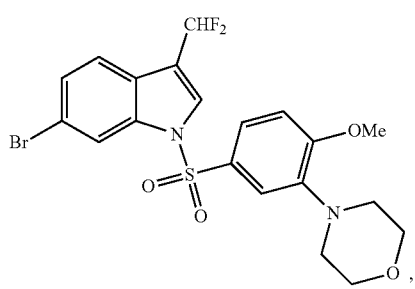
(52) 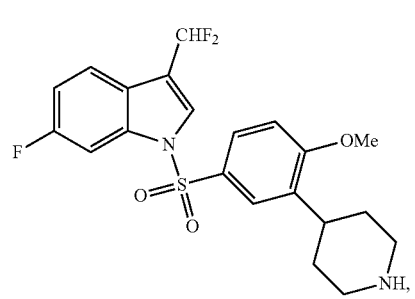
(53) 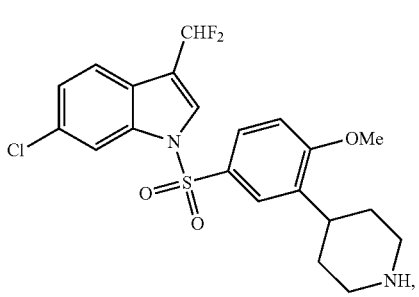
(54) 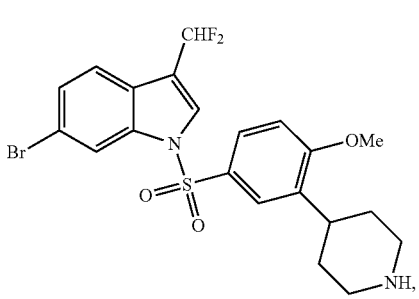
(55) 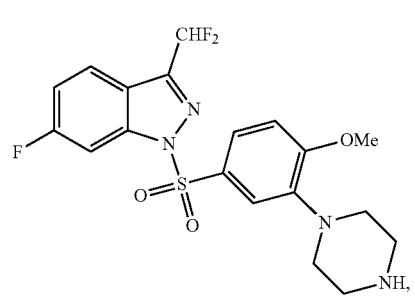
(56) 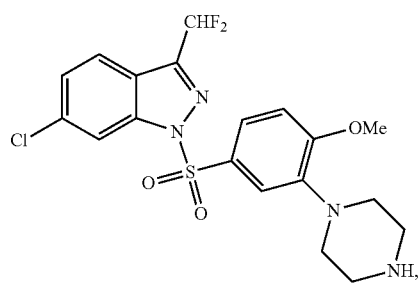
(57) 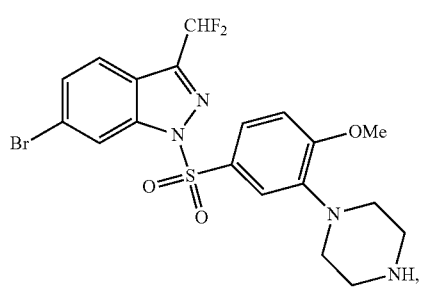
(58) 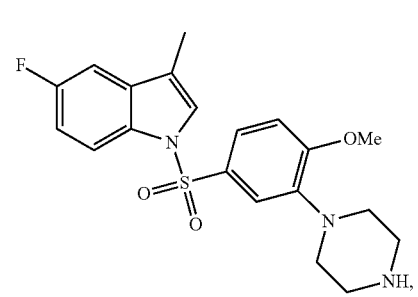
(59) 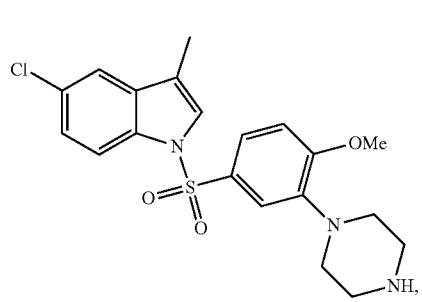
(60) 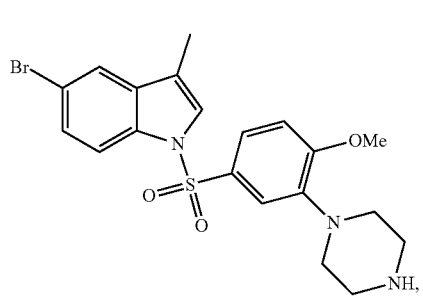

(61)
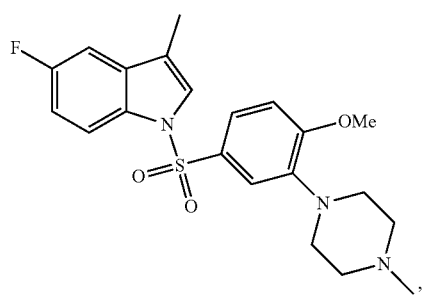
(62)
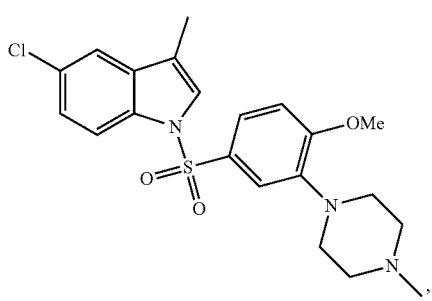
(63)
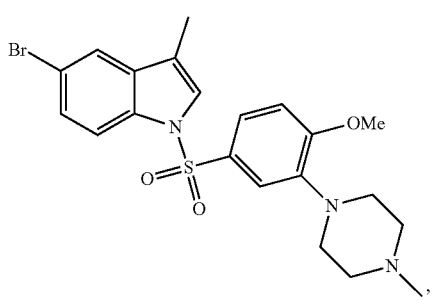
(64)
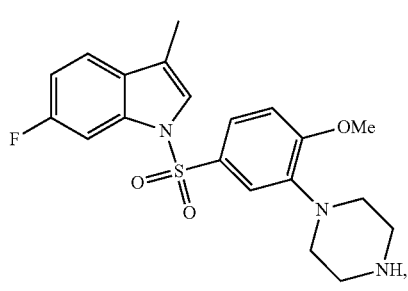
(65)
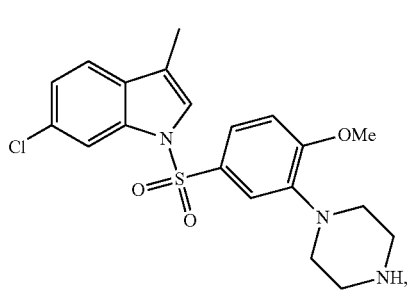
(66)
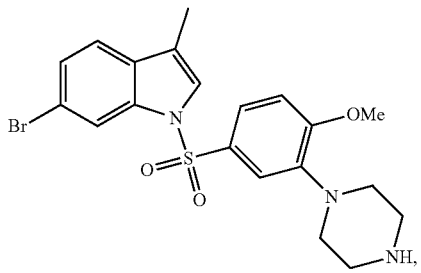
(67)
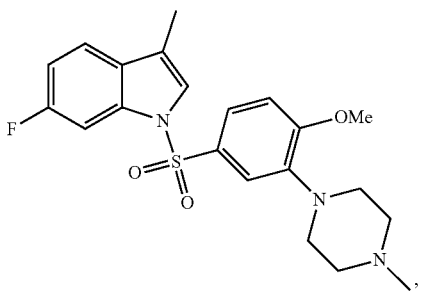
(68)
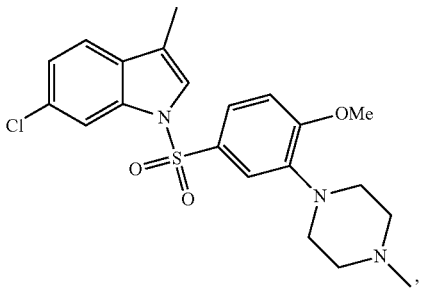
(69)
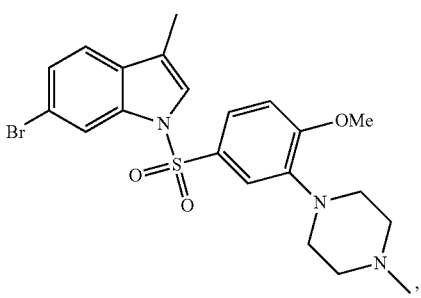
(70)
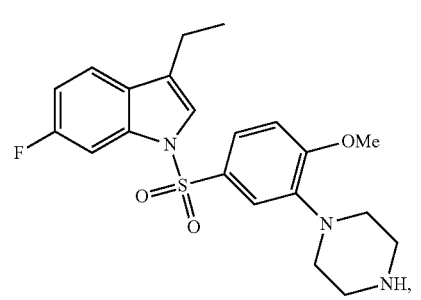

(71)
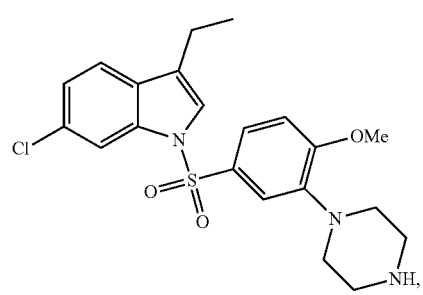
(72)
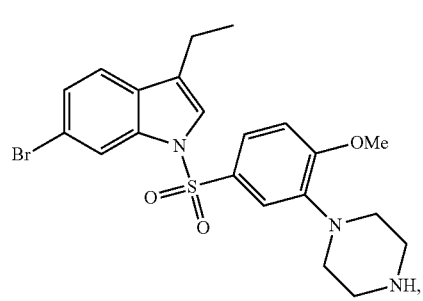
(73)
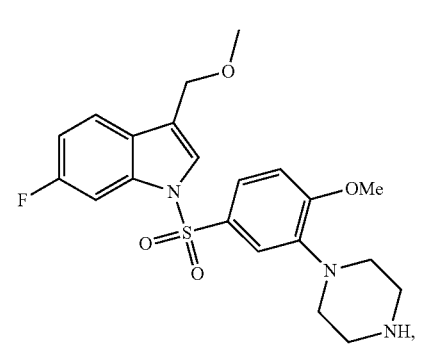
(74)
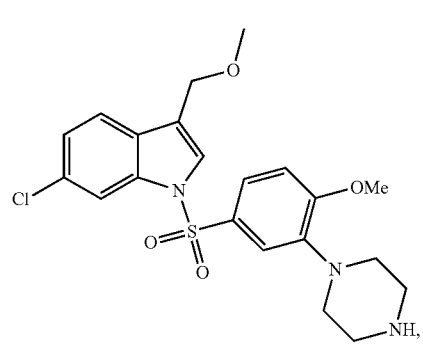
(75)
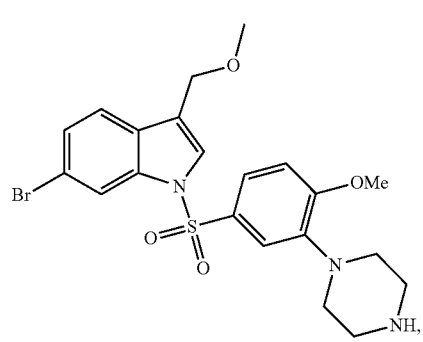
(76)
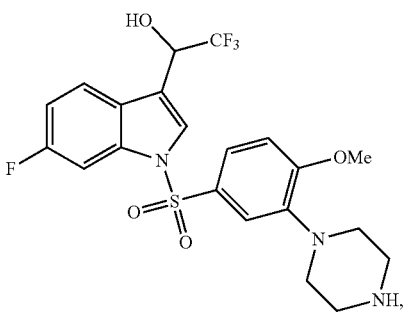
(77)
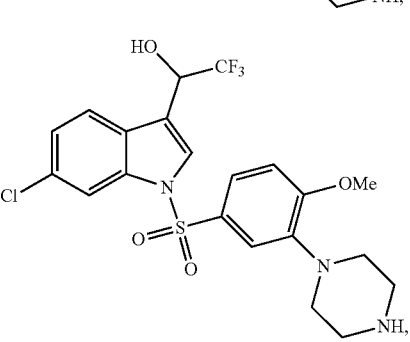
(78)
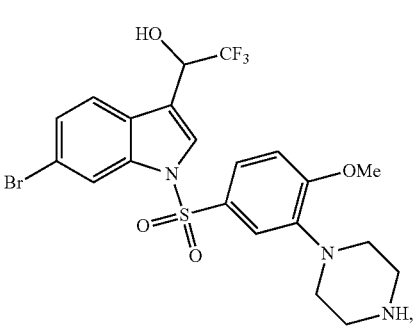
(79)
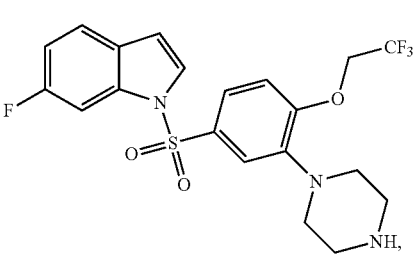
(80)
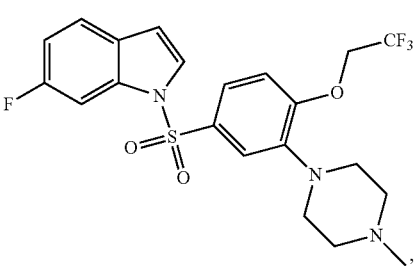

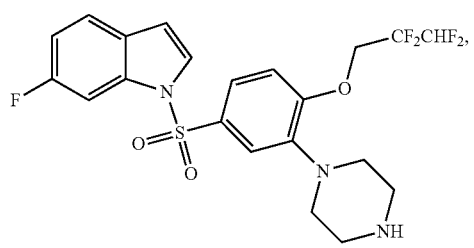 (81)
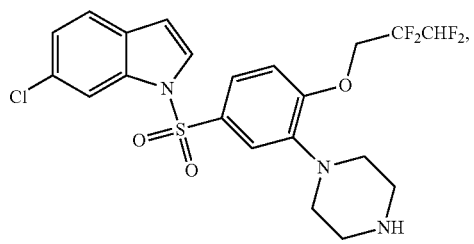 (82)
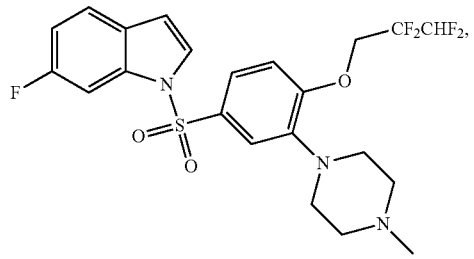 (83)
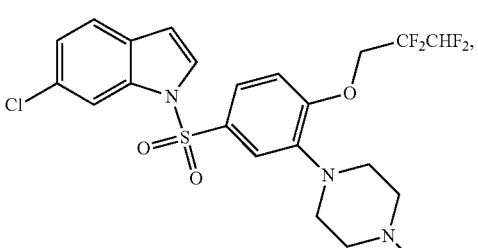 (84)
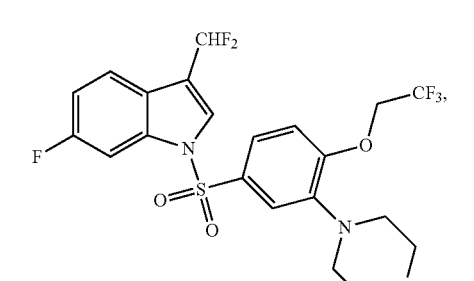 (85)
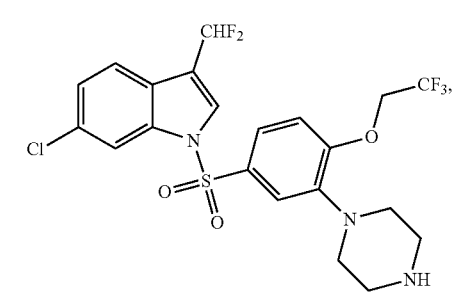 (86)
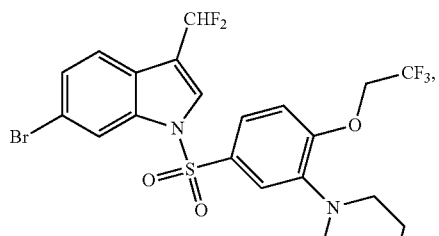 (87)
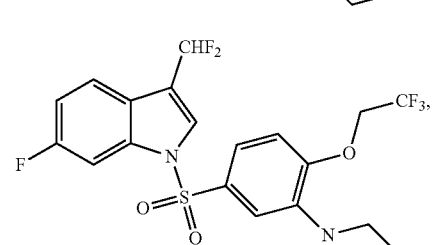 (88)
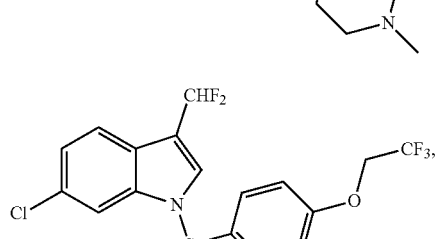 (89)
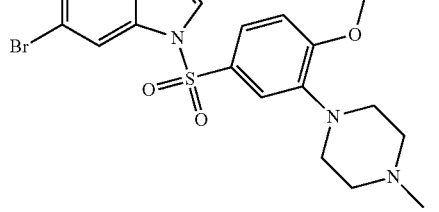 (90)
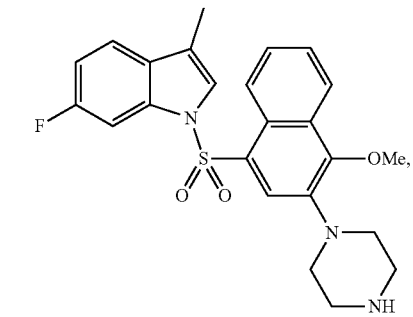 (91)

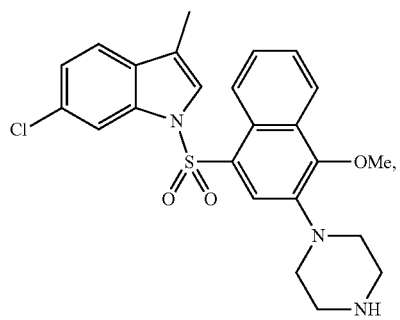
(92)
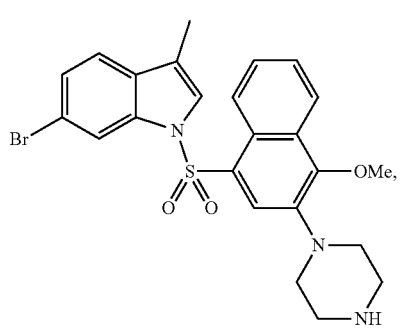
(93)
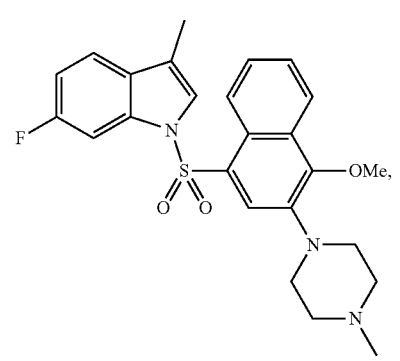
(94)
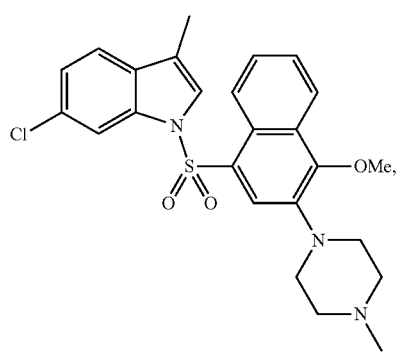
(95)
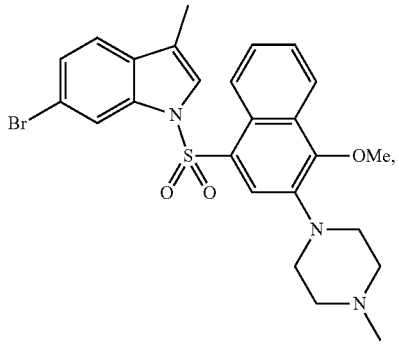
(96)
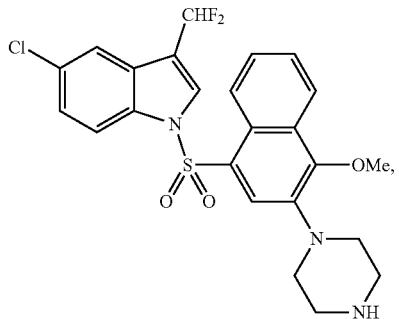
(97)
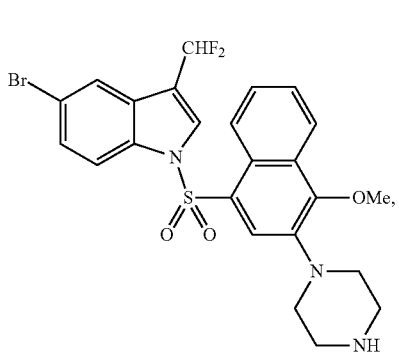
(98)
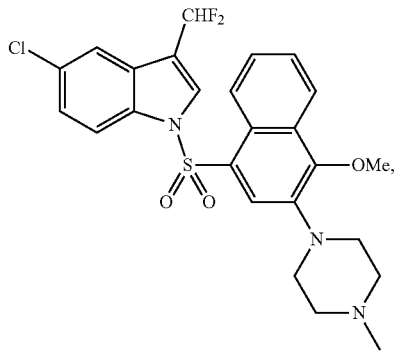
(99)

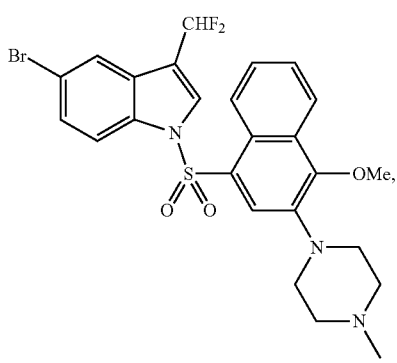

(100)

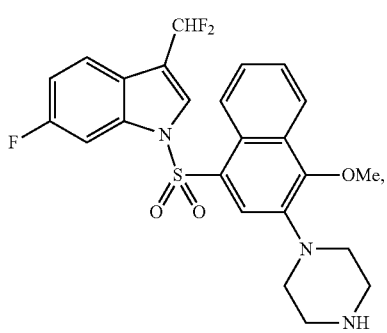

(101)

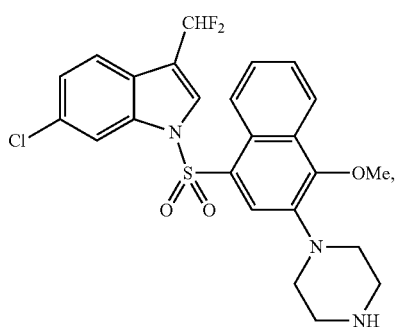

(102)

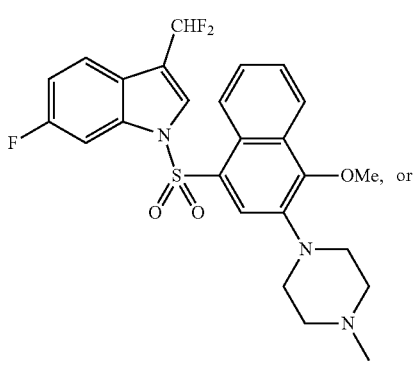

(103)

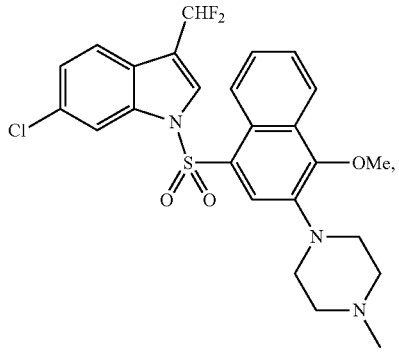

(104)

or a stereoisomer, a geometric isomer, a tautomer, an N-oxide, a hydrate, a solvate, a metabolite, a pharmaceutically acceptable salt or a prodrug thereof.

Also provided herein is the use of a compound disclosed herein, or a pharmaceutically acceptable salts thereof, in the manufacture of a medicament for treating Alzheimer's disease, including those described herein. The compounds disclosed herein are also useful in the manufacture of a medicament to attenuate, prevent, manage or treat 5-HT mediated disease in a patient, especially Alzheimer's disease. Also provided herein is a pharmaceutical composition comprising a therapeutically effective amount of a compound of Formula (I), (I-A) or (II) in association with at least one pharmaceutically acceptable carrier, adjuvant or diluent.

Unless otherwise stated, all suitable isotopic variations, all stereoisomers, geometric isomers, tautomers, N-oxides, hydrates, solvates, metabolites, salts, and pharmaceutically acceptable prodrugs of the compounds disclosed herein are within the scope of the invention.

Unless otherwise stated, structures depicted herein are also meant to include all isomeric (e.g., enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The compounds disclosed herein may contain asymmetric or chiral centers, and therefore exist in different stereoisomeric forms. It is intended that all stereoisomeric forms of the compounds of Formula (I), (I-A) or (II), including but not limited to, diastereomers, enantiomers, atropisomers and geometric (conformational) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

N-oxides of the compounds disclosed herein are also within the scope of the invention and may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

In other aspect, provided herein are intermediates for preparation of the compounds represented by Formula (I), (I-A) or (II).

In other aspect, provided herein are methods for preparation, separation and purification of the compounds represented by Formula (I), (I-A) or (II).

The compounds represented by Formula (I), (I-A) or (II) can be exist in the form of salts. In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith. In another embodiment, the salts are not necessarily pharmaceutically acceptable salts, and which may be useful as intermediates for preparing and/or purifying compounds of Formula (I), (I-A) or (II) and/or for separating enantiomers of compounds of Formula (I), (I-A) or (II).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid, ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or an alkaline earth metal hydroxide, and the like. Some non-limiting examples of suitable salts include organic salts derived from amino acids, such as glycine and arginine, ammonia (primary, secondary, and tertiary amines), and cyclic amines, such as piperidine, morpholine and piperazine, and inorganic salts derived from sodium, calcium, potassium, magnesium, manganese, iron, copper, zinc, aluminum, lithium, and the like.

Compounds, Compositions, Formulations and Administration of Compounds or Compositions of the Invention A therapeutically effective amount of the compounds having Formula (I), (I-A) or Formula (II) and their pharmaceutically acceptable salts can be administered to patients as chemical raw drugs, also can be provided as active ingredients in pharmaceutical compositions. Therefore, also provided herein is a pharmaceutical composition containing the compound having Formula (I), (I-A) or Formula (II), or a stereisomer, or a racemic mixture or non-racemic mixture, or a pharmaceutically acceptable salt, or a solvate thereof. In one embodiment, the pharmaceutical composition further comprises at least one pharmaceutically acceptable carrier, adjuvant or excipient, and optionally other treating and/or preventing ingredients.

Appropriate carriers, adjuvants and exciepients are well known to those of skill in the art and described in, for example, Ansel et al., *Ansel's Pharmaceutical Dosage Forms and Drug Delivery Systems*, 2004, Lippincott, Williams & Wilkins, Philadelphia; Gennaro et al., *Remington: The Science and Practice of Pharmacy*, 2000, Lippincott, Williams & Wilkins, Philadelphia; and Rowe et al., *Handbook of Pharmaceutical Excipients*, 2005, Pharmaceutical Press, Chicago.

Provide herein is the therapeutic method comprising administering the compound or the pharmaceutical composition described herein to a patient, further comprising administering an additional anti-Alzheimer's disease drug (combination therapy). Wherein the additional anti-Alzheimer's disease drug is donepezil, nalmefene, risperidone, Vitamin E, SAM-760, AVN-211, AVN-101, RP-5063, tozadenant, PRX-3140, PRX-8066, SB-742457, naluzaton, idalopirdine, tacrine, rivastigmine, galantamine, memantine, Mirtazapine, venlafaxine, desipramine, nortriptyline, zolpidem, zopiclone, nicergoline, piracetam, selegiline, pentoxifylline or a combination thereof.

The term "therapeutically effective amount" means a total amount of active components which is sufficiently effective for treating the disease. When administering a single active component to a patient, term "therapeutically effective amount" means the amount of this active component. When administering the combination agents, term "therapeutically effective amount" means the total amount of active compositions, which is sufficient to effect the treatment of given disease, no matter that the dose of active composition is combinated, administered simultaneously or sequentially. Compounds having Formula (I), (I-A) or (II) or pharmaceutically acceptable salts thereof are described above. Considering the compatible with other ingredients and harmless to subjects, the carrier, diluent, or excipient must be acceptable. According to another aspect described herein, also provided herein is a method for preparing the pharmaceutical preparation, comprising mixing the compound having formula (I), (I-A) or (II) or a pharmaceutically acceptable salt thereof with one or more pharmaceutically acceptable carriers, diluents or excipients uniformly. The term "pharmaceutically acceptable" refers to a compound, material, composition and/or dose form, which are in the reasonable scope of medical judgment, must be compatible with the tissue of patent, and without excessive toxicity, irritation, allergic reaction, or other problems related to reasonable benefit/risk and complications, and effectively used in the intended application.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, pulmonary, vaginal, or parenteral (including intramuscular, intraarterial, intrathecal, subcutaneous, and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional propostions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one milligram of active ingredient or, more broadly, about 0.01 to about one hundred milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, favouring agents, solubilizers, lubricants, suspending agents, binders, preservatives, tablet disintegrating agents, or an encapsulating material. In powders, the carrier generally is a finely divided solid which is a mixture contained finely divided active component. In tablets, the active component is generally mixed with the carrier having the necessary binding capacity in suitable proportions and compacted in the shape and size desired. The powders and tablets preferably contain the active compound about one to seventy percent. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Liquid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous injection) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomising spray pump.

The compounds of the present invention may be formulated for aerosol administration, particularly to the respiratory tract and including intranasal administration. The compound will generally have a small particle size for example of the order of five microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g, gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or can be the appropriate number of any of these in packaged form.

Other suitable pharmaceutical carriers and their formulations are described in Remington: The Science and Practice of Pharmacy 1995, edited by E. W. Martin, Mack Publishing Company, 19$^{th}$ edition, Easton, Pa.

Uses of the Compounds and Pharmaceutical Compositions

Provided herein are compounds and pharmaceutical compositions used for the manufacture of a medicament for preventing, treating or lessening a 5-$HT_6$- or 5-$HT_2$-mediated disease.

Provided herein are pharmaceutical compositions containing compounds having Formula (I), (I-A) or (II) or the compounds described herein, and a pharmaceutically acceptable carrier, excipient, or adjuvant. The amount of compound in the composition described herein is an effective and detectable amount for treating obesity, a gastrointestinal disease, a CNS disorder, and a cardiovascular disease by inhibiting 5-$HT_6$ or 5-$HT_2$, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease, Huntington's chorea, and the like; the cardiovascular disease is pulmonary hypertension, thrombosis, heart failure, cardiac hypertrophy, and the like.

An "effective amount" or "effective dose" of the compound or pharmaceutically acceptable composition is an amount that is effective in treating or lessening the severity of one or more of the aforementioned disorders or diseases. According to the method of the invention, any dose and any route of administrating the compound or composition to a subject are effective for treating or lessening the severity of the disorder or disease. The accurate dose varies with the relative health of a subject, which depending upon numerous factors such as the race, the age, the general condition of the patient, the severity of the infection, the special factor, the route, and the like. The compound or composition described herein can be administered with one or more additional therapeutic agents to a subject, as the invention discussed.

Besides being useful for human treatment, these compounds and compositions are also useful for veterinary treatment of companion animals, exotic animals and mammals of farm animals. In other embodiments, animals include horses, dogs and cats. As used herein, the compounds disclosed herein include the pharmaceutically acceptable derivatives thereof.

General Synthetic Procedures

In order to describe the invention, the following examples are set forth. It is to be understood that the invention is not limited to these embodiments, but only provides the methods to practice the invention.

Generally, the compounds disclosed herein may be prepared by methods described herein, wherein the substituents are as defined for Formula (I), (I-A) or (II), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated, all temperatures are set forth in degrees Celsius (° C.). Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous tetrahydrofuran was obtained by drying tertrahydrofuran in the refluxing condition with sodium added. Anhydrous dichloromethane and anhydrous chloroform were obtained by drying dichloromethane and chloroform independently in the refluxing condition equipped with hydride calcium. Ethyl acetate, N,N-dimethylacetylamine and petrol ether were dried over anhydrous sodium sulfate before use.

Generally, the following reactions were occurred in nitrogen atmosphere or argon atmosphere or anhydrous solvents equipped with drying tubes (Unless otherwise specified), and reaction flasks were plugged with suitable rubber plugs, substrates were added via syringes. All glassware was dried before use.

Column chromatography was conducted using a silica gel column Silica gel (300-400 mesh) was purchased from Qingdao Ocean Chemical Factory. NMR spectra were obtained as $CDCl_3$, $DMSO-d_6$, $CD_3OD$, or $acetone-d_6$ solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and a G1315B DAD detector were used in the analysis, and an ESI source was used on the LC-MS spectrometer.

Low-resolution mass spectral (MS) data were determined on an Agilent 6120 Series LC-MS spectrometer equipped with G1311A quaternary pumps and a G1316A TCC (Temperature Control of Column, maintained at 30° C.). A G1329A autosampler and a G1315D DAD detector were used in the analysis, and an ESI source was used on the LC-MS spectrometer.

Both Spectrographs were equipped with an Agilent Zorbax SB-C18 (2.1×30 mm, 5 µm). Injection volume was decided by the sample concentration. The flow rate is 0.6 mL/min. The mobile phase was (0.1% formic acid in $CH_3CN$ as mobile phase A) in (0.1% formic acid in $H_2O$ as mobile phase B) with UV detection at 210/254 nm. The conditions of gradient elution were described in Table 1:

TABLE 1

| t (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micron), 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
HOAc acetic acid
MeCN, $CH_3CN$ acetonitrile
$Cl_3CCOCl$ trichloro-acetic chloride
$CHCl_3$ chloroform
$CDCl_3$ chloroform-d
DMSO dimethylsulfoxide
$DMSO-d_6$ deuterated dimethylsulfoxide
DMF N,N-dimethylformamide
$POCl_3$ phosphoryl chloride
$Et_2N$—$SF_3$ diethylaminosulphur trifluoride
$ClSO_2OH$ chlorosulfonic acid
EtOAc, EA ethyl acetate
Et-, $CH_3CH_2$— ethyl
HCl hydrochloric acid
$MgSO_4$ magnesium sulfate
$MgCl_2$ magnesium chloride
MeOH, $CH_3OH$ methanol
HCHO formaldehyde
$CH_2Cl_2$, DCM dichloromethane
mL, ml milliliter
PE petrol ether (60-90° C.)
$Na_2CO_3$ sodium carbonate
$NaHCO_3$ sodium bicarbonate
M mol/L
$K_2CO_3$ potassium carbonate
KOH potassium hydroxide
RT room temperature
Rt retention time
h, hr hour(s)
$NaBH_3CN$ sodium cyanoborohydride
NaCl sodium chloride
NaH sodium hydride
$Na_2SO_4$ sodium sulfate
THF tetrahydrofuran
$Et_3N$, TEA triethylamine
$H_2O$ water
EDTA ethylenediaminetetraacetic acid
PEI polyethyleneimine
Pargyline Pargyline
Tris-HCl Tris(hydroxymethyl)aminomethane-hydrochloric acid
$Pd_2(dba)_3$ Tris(dibenzylideneacetone)dipalladium
DPEphos Bis[2-(diphenylphosphino)phenyl]ether
$PdCl_2(dppf)$ [1,1'-Bis(diphenylphosphino)ferrocene]dichloropalladium(II)
$NaNO_2$ sodium nitrite
NADPH nicotinamide adenine dinucleotide phosphate The following synthesis schemes describe the preparation of the compounds disclosed herein, unless otherwise indicated, each m, n, $R^1$, $R^2$, $R^4$, A, X, Q and $R^7$ is as defined herein.

Scheme 1

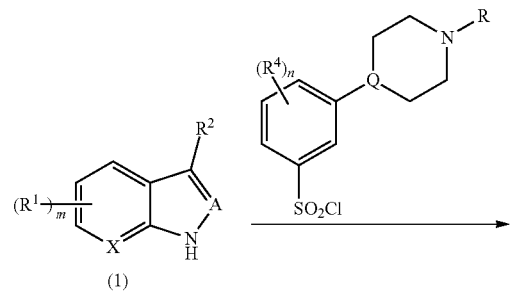

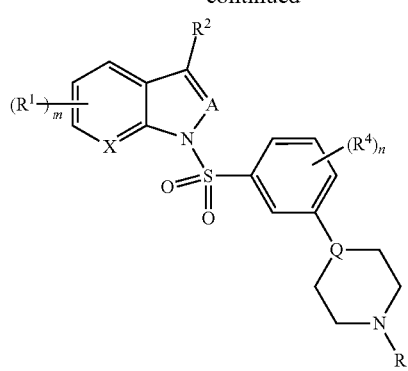

(2)

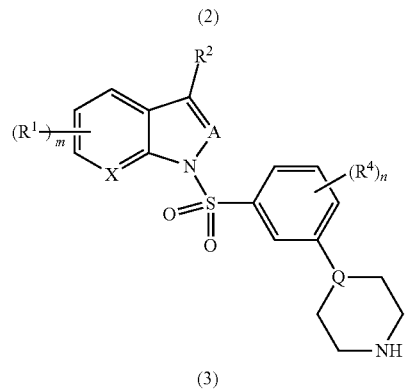

(3)

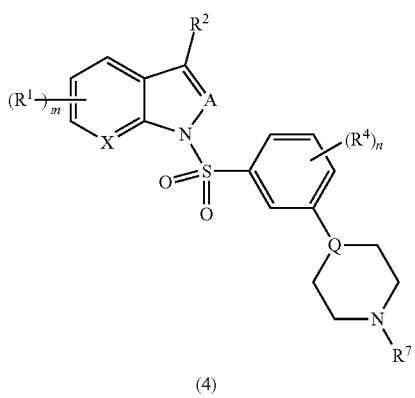

(4)

The compound disclosed herein can be prepared by the procedure illustrated in scheme 1, and the specific synthetic steps can reference the examples, and wherein R is a protecting group, such as —C(═O)CCl₃ or —C(═O)CF₃. Firstly, compound (1) can react with a substituted benzenesulfonyl chloride in the presence of a base to give compound (2), followed by deprotection of compound (2) to give compound (3). Then the desired compound (4) can be obtained from compound (3) by alkylation reaction.

Scheme 2

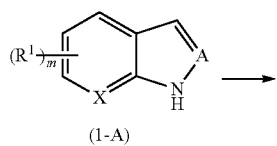

(1-A)

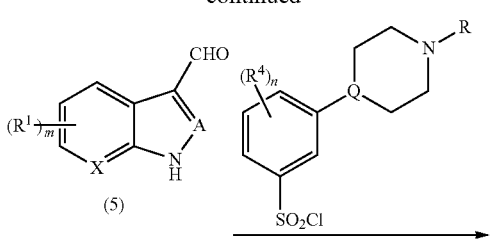

(5)

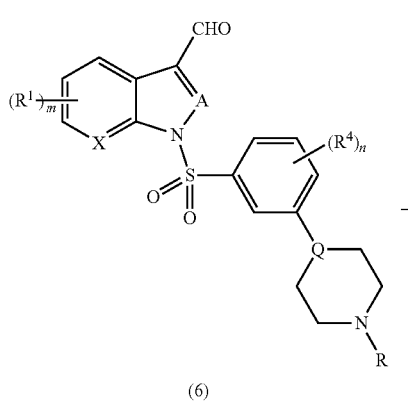

(6)

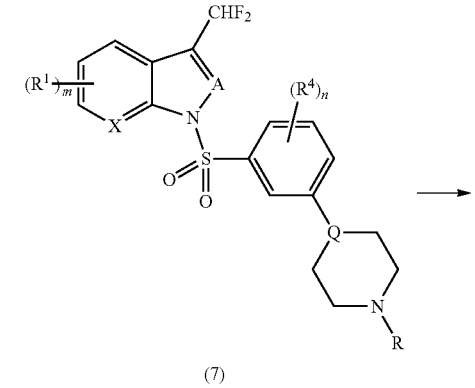

(7)

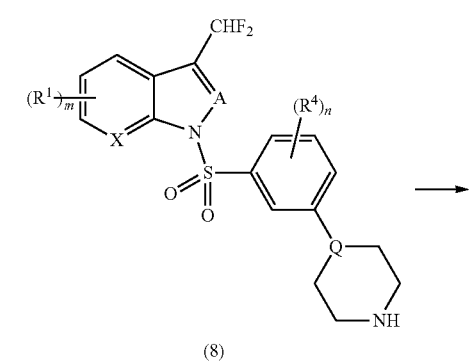

(8)

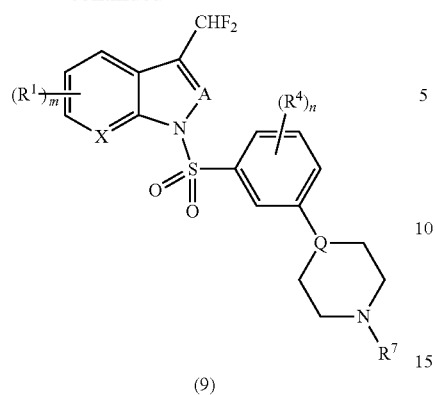

(9)

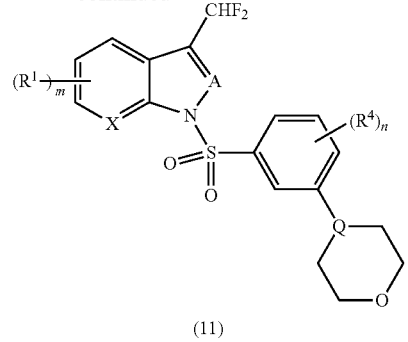

(11)

The compound disclosed herein can be prepared by the procedure illustrated in scheme 2, and the specific synthetic steps can reference the examples, and wherein R is a protecting group, such as —C(=O)CCl₃ or —C(=O)CF₃. Firstly, compound (1-A) can react with POCl₃ or NaNO₂ in a suitable solvent, such as DMF or THF, to give compound (5). Then compound (5) can react with a substituted benzenesulfonyl chloride in the presence of a base to give compound (6), and compound (6) can react with a fluorinated reagent to give compound (2). The compound (8) can be obtained by deprotection of compound (7), and compound (8) can be alkylated to give the desired compound (9).

The compound disclosed herein can be prepared by the procedure illustrated in scheme 3, and the specific synthetic steps can reference the examples. Firstly, compound (1-A) can react with POCl₃ or NaNO₂ in a suitable solvent, such as DMF or THF, to give compound (5). Then compound (5) can react with a substituted benzenesulfonyl chloride in the presence of a base to give compound (10), and the compound (11) can react with a fluorinated reagent to give the desired compound (11).

Scheme 3

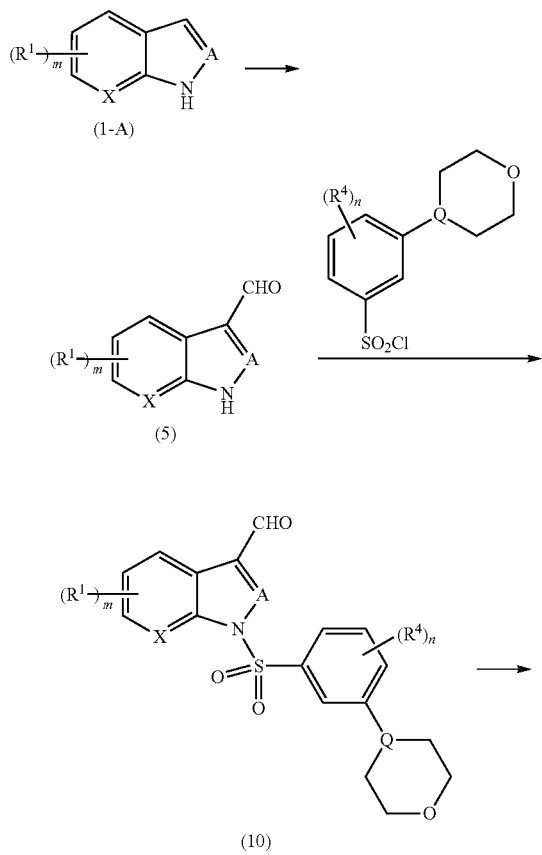

Scheme 4

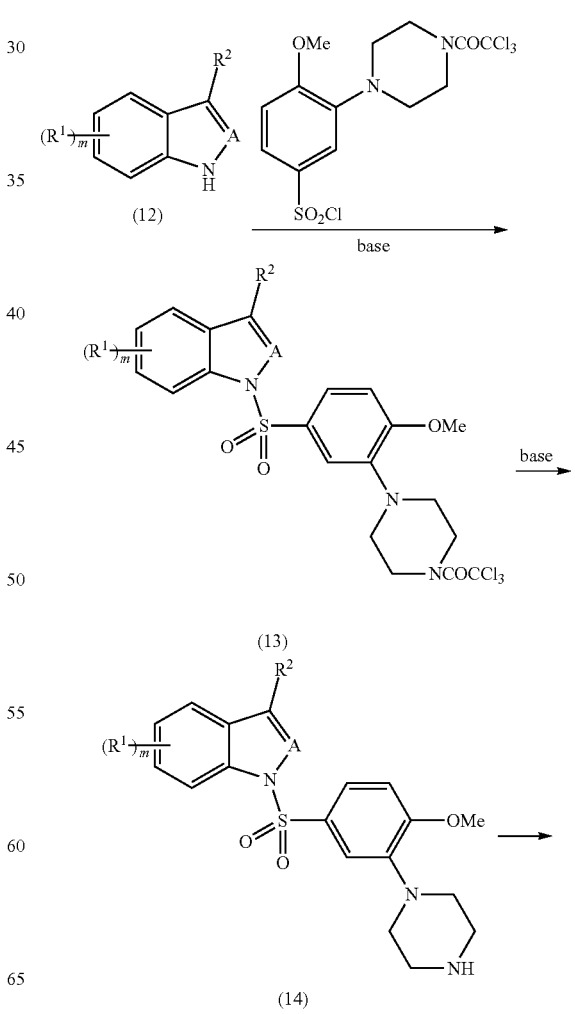

-continued

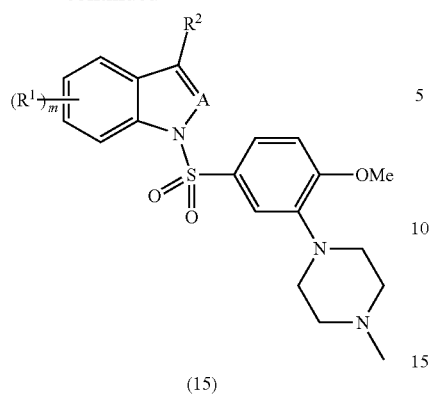

(15)

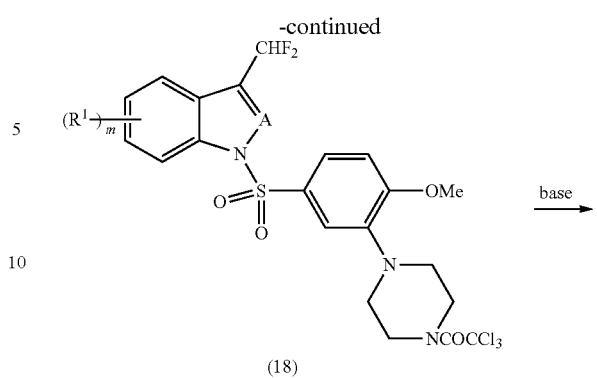

(18)

The compound disclosed herein can be prepared by the procedure illustrated in scheme 4, and the specific synthetic steps can reference the examples. Firstly, compound (12) can react with 4-methoxy-3-(4-(2,2,2-trichloroacetyl)piperazin-1-yl)benzene-1-sulfonyl chloridechloride in the presence of a base to give compound (13), followed by deprotection of compound (13) in the presence of a base to give compound (14). Then compound (14) can react with an aldehyde or a halohydrocarbon to give the desired compound (15).

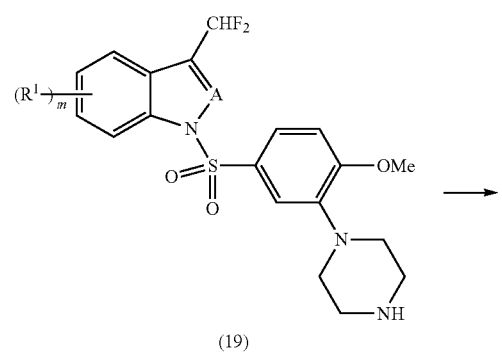

(19)

Scheme 5

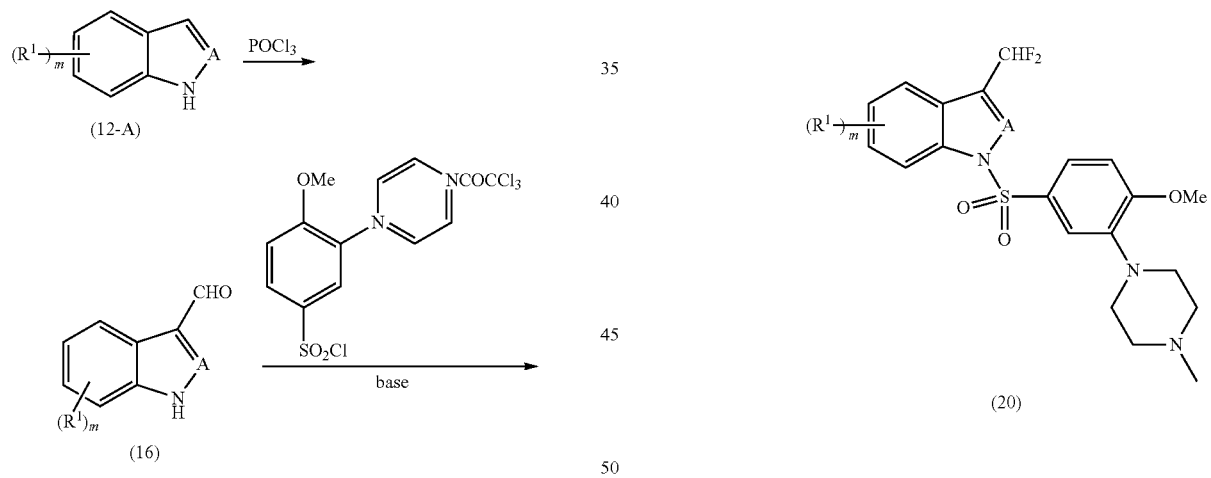

(20)

The compound disclosed herein can be prepared by the procedure illustrated in scheme 5, and the specific synthetic steps can reference the examples. Firstly, compound (12-A) can react with POCl₃ or NaNO₂ in a suitable solvent to give compound (16), and compound (16) can react with 4-methoxy-3-(4-(2,2,2-trichloroacetyl)piperazin-1-yl)benzene-1-sulfonyl chloride in the presence of a base to give compound (17). Compound (17) can react with a fluorinated reagent to give compound (18), followed by deprotection of compound (18) in the presence of a base to give compound (19). Then compound (1) can react with an aldehyde or a halohydrocarbon to give the desired compound (20).

Compounds, pharmaceutical compositions and uses thereof described herein are further illustrated by the following examples.

EXAMPLES

Example 1 Synthesis of 1-((4-methoxy-3-(piperazin-1-yl)phenyl)sulfonyl)-1H-indole-3-carbonitrile

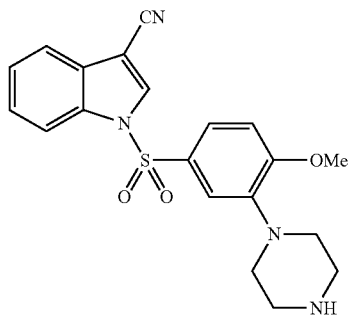 [SMILES: COc1ccc(S(=O)(=O)n2cc(C#N)c3ccccc32)cc1N1CCNCC1]

Step 1) Synthesis of 2,2,2-trichloro-1-(4-(2-methoxyphenyl)piperazin-1-yl)ethanone To a solution of 1-(2-methoxyphenyl)piperazine hydrochloride (1.0 g, 4.39 mmol) and triethylamine (2.5 mL, 17.70 mmol) in dichloromethane (15 mL) was added dropwise trichloroacetyl chloride (1.0 mL, 8.96 mmol) at 0° C. At the end of the addition, the mixture was warmed to 25° C. and reacted for 24 hours. To the reaction mixture was added 50 mL of dichloromethane, and the mixture was washed with 40 mL of saturated aqueous sodium bicarbonate. The organic layer was dried over anhydrous sodium sulfate and filtered. The filtrate was concentrated in vacuo and the residue was purified by silica gel chromatography eluted with PE/EtOAc(V/V)=10/1 to give the title compound as a light yellow solid (763 mg, 52%). The compound was characterized by the following spectroscopic data: MS (ESI, pos. ion) m/z: 337.0 [M+H]$^+$; and $^1$H NMR (400 MHz, CDCl$_3$): δ 7.09-7.06 (m, 1H), 6.96-6.91 (m, 3H), 4.03 (brs, 4H), 3.91 (s, 3H), 3.18 (t, J=4.4 Hz, 4H).

Step 2) Synthesis of 4-methoxy-3-(4-(2,2,2-trichloroacetyl)piperazin-1-yl)benzene-1-sulfonyl chloride To 3 mL of chlorosulfonic acid was added dropwise a solution of 2,2,2-trichloro-1-(4-(2-methoxyphenyl)piperazin-1-yl)ethanone (550 mg, 1.63 mmol) in dichromethane (5 mL) at 0° C. in a low temperature bath, the resulting mixture was stirred for 1 hour. The reaction mixture was poured into a mixture of ice water (30 mL) and dichromethane (50 mL), then the mixture was stirred vigorously and separated. The organic layer was dried over anhydrous magnesium sulfate and filtered. The filtrate was concentrated in vacuo to give the title compound as a light yellow solid (548 mg, 78.5%). The compound was characterized by the following spectroscopic data: MS (ESI, pos. ion) m/z: 435.0 [M+H]$^+$; and $^1$H NMR (400 MHz, CDCl$_3$): δ 7.75 (dd, J=8.8, 2.4 Hz, 1H), 7.47 (d, J=2.4 Hz, 1H), 7.01 (d, J=8.8 Hz, 1H), 4.00 (brs, 7H), 3.21 (t, J=4.8 Hz, 4H).

Step 3) Synthesis of 1-((4-methoxy-3-(4-(2,2,2-trichloro acetyl)piperazin-1-yl)phenyl)sulfonyl)-1H-indole-3-carbonitrile To 10 mL of tetrahydrofuran was added 3-carbonitrile indole (284 mg, 2.0 mmol) and sodium hydride (96 mg, 2.4 mmol, 60%) at 0° C., then the mixture was reacted for 1 hour at 25° C. The mixture was cooled to 5° C., and a solution of 4-methoxy-3-(4-(2,2,2-trichloroacetyl)piperazin-1-yl)benzene-1-sulfonyl chloride (1.05 g, 2.4 mmol) in tetrahydrofuran (4 mL) was added slowly. The mixture was reacted for 2 hours, then 100 mL of dichloromethane was added and the resulting mixture was washed with saturated aqueous sodium bicarbonate (60 mL). The organic layer was separated and dried over anhydrous magnesium sulfate, then filtered. The filtrate was concentrated in vacuo and the residue was purified by silica gel chromatography eluted with PE/EtOAc(V/V)=5/1 to give the title compound as a white solid (965 mg, 89%). The compound was characterized by the following spectroscopic data: MS (ESI, pos. ion) m/z: 541.0 [M+H]$^+$; and $^1$H NMR (400 MHz, CDCl$_3$): δ 8.08 (s, 1H), 8.00 (d, J=8.3 Hz, 1H), 7.69 (t, J=7.5 Hz, 1H), 7.65 (t, J=6.3 Hz, 1H), 7.45 (t, J=6.2 Hz, 1H), 7.33-7.26 (m, 2H), 6.92 (d, J=8.7 Hz, 1H), 3.96 (brs, 4H), 3.91 (s, 3H), 3.11 (t, J=5.0 Hz, 4H).

Step 4) Synthesis of 1-((4-methoxy-3-(piperazin-1-yl)phenyl)sulfonyl)-1H-indole-3-carbonitrile To a solution of 1-((4-methoxy-3-(4-(2,2,2-trichloroacetyl)piperazin-1-yl)phenyl)sulfonyl)-1H-indole-3-carbonitrile (434 mg, 0.8 mmol) in tetrahydrofuran (20 mL) was added potassium hydroxide solution (134 mg of potassium hydroxide solid, 2.4 mmol, 1 mmol/mL in water) slowly at 25° C. The mixture was stirred for 24 hours and 60 mL of dichloromethane was added. The organic layer was separated and washed with saturated aqueous sodium chloride (30 mL×3), then dried over anhydrous sodium sulfate and filtered. The filtrate was concentrated in vacuo and the residue was purified by silica gel chromatography eluted with DCM/methanol(V/V)=30/1 to give the title compound as a light yellow solid (162 mg, 51%). The compound was characterized by the following spectroscopic data: MS (ESI, pos. ion) m/z: 397.1 [M+H]$^+$; and $^1$H NMR (400 MHz, CDCl$_3$): δ 7.75 (d, J=3.7 Hz, 1H), 7.67-7.61 (m, 1H), 7.48 (d, J=1.1 Hz, 1H), 7.35-7.29 (m, 1H), 7.13 (td, J=7.9, 4.2 Hz, 1H), 6.95 (dd, J=12.4, 8.0 Hz, 1H), 6.90 (d, J=8.7 Hz, 1H), 6.66 (dd, J=3.6, 2.3 Hz, 1H), 3.91 (brs, 7H), 3.18-3.08 (m, 4H).

Example 2 Synthesis of 1-((4-methoxy-3-(4-methylpiperazin-1-yl)phenyl)sulfonyl)-1H-indole-3-carbonitrile

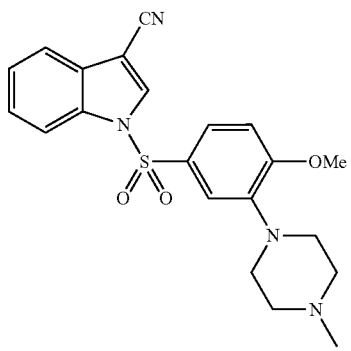 [SMILES: COc1ccc(S(=O)(=O)n2cc(C#N)c3ccccc32)cc1N1CCN(C)CC1]

To a solution of 1-((4-methoxy-3-(piperazin-1-yl)phenyl)sulfonyl)-1H-indole-3-carbonitrile (198 mg, 0.5 mmol) in methanol (10 mL) was added two drops of acetic acid. Then sodium cyanoborohydride (85 mg, 1.35 mmol) and formaldehyde (40%, 0.112 mL, 1.617 mmol) was added slowly to the mixture in turn at 0° C. The mixture was reacted for 10 min, then warmed to 25° C. and reacted for an additional 5 hours. The reaction mixture was quenched with 10 mL of water and sodium carbonate (370 mg, 3.5 mmol), then extracted with dichloromethane (20 mL×2). The combined organic layers were dried over anhydrous sodium sulfate and filtered. The filtrate was concentrated in vacuo and the residue was purified by silica gel chromatography eluted with DCM/methanol(V/V)=15/1 to give the title compound as a white solid (100 mg, 49%). The compound was characterized by the following spectroscopic data: MS (ESI, pos. ion) m/z: 411.1 [M+H]$^+$; $^1$H NMR (400 MHz, CDCl$_3$): δ 8.10 (s, 1H), 8.01 (d, J=8.3 Hz, 1H), 7.69 (d, J=7.8 Hz, 1H), 7.61 (dd, J=8.7, 2.3 Hz, 1H), 7.47-7.34 (m, 3H), 6.88 (d, J=8.7 Hz, 1H), 3.89 (s, 3H), 3.08 (brs, 4H), 2.62 (brs, 4H), 2.37 (s, 3H); and $^{13}$C NMR (100 MHz, CDCl$_3$): δ 157.3, 142.2, 133.7, 133.2, 128.5, 128.4, 126.4, 124.7, 122.9, 120.3, 116.5, 113.8, 113.6, 111.2, 93.3, 56.1, 54.8, 49.9, 45.9.

Example 3 Synthesis of 1-(1-((4-methoxy-3-(piperazin-1-yl)phenyl)sulfonyl)-1H-indol-3-yl) ethanone

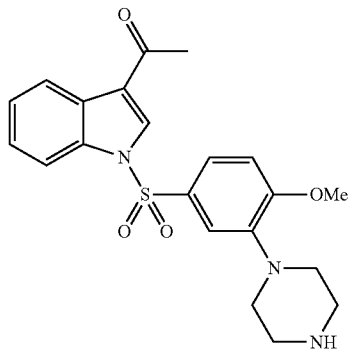 [SMILES: COc1ccc(S(=O)(=O)n2cc(C(C)=O)c3ccccc32)cc1N1CCNCC1]

Step 1) Synthesis of 1-(4-(5-((3-acetyl-1H-indol-1-yl)sulfonyl)-2-methoxyphenyl)piperazin-1-yl)-2,2,2-trichloroethanone The title compound was prepared according to the procedure as described in step 3 of example 1 using 1-(1H-indol-3-yl)ethanone (318 mg, 2.0 mmol), sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL), and the crude product was purified by silica gel chromatography eluted with PE/EtOAc(V/V)=5/1 to give the title compound as a white solid (1.03 g, 92%). The compound was characterized by the following spectroscopic data: MS (ESI, pos. ion) m/z: 558.0 [M+H]$^+$; and $^1$H NMR (400 MHz, CDCl$_3$): δ 8.33 (dd, J=6.7, 2.0 Hz, 1H), 8.19 (s, 1H), 7.93 (dd, J=7.0, 1.7 Hz, 1H), 7.65 (dd, J=8.7, 2.3 Hz, 1H), 7.42-7.31 (m, 3H), 6.90 (d, J=8.7 Hz, 1H), 3.89 (brs, 7H), 3.15-3.05 (m, 4H), 2.57 (s, 3H).

Step 2) Synthesis of 1-(1-((4-methoxy-3-(piperazin-1-yl)phenyl)sulfonyl)-1H-indol-3-yl)ethanone 1-(4-(5-((3-Acetyl-1H-indol-1-yl)sulfonyl)-2-methoxyphenyl)piperazine-1-yl)-2,2,2-trichloroethanone (447 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (248 mg, 75%). The compound was characterized by the following spectroscopic data: MS (ESI, pos. ion) m/z: 414.1 [M+H]$^+$; $^1$H NMR (400 MHz, CDCl$_3$): δ 8.34 (dd, J=6.8, 1.7 Hz, 1H), 8.22 (s, 1H), 7.95 (dd, J=7.1, 1.3 Hz, 1H), 7.63 (dd, J=8.7, 2.3 Hz, 1H), 7.46-7.32 (m, 3H), 6.88 (d, J=8.7 Hz, 1H), 3.89 (s, 3H), 3.12-2.98 (m, 8H), 2.59 (s, 3H); and $^{13}$C NMR (100 MHz, CDCl$_3$): δ 193.4, 157.1, 142.4, 134.9, 132.3, 129.1, 127.5, 125.6, 124.7, 123.1, 122.9, 121.5, 116.6, 113.1, 111.2, 56.0, 51.0, 45.7, 27.8.

Example 4 Synthesis of 1-(1-((4-methoxy-3-(4-methylpiperazin-1-yl)phenyl)sulfonyl)-1H-indol-3-yl)ethanone

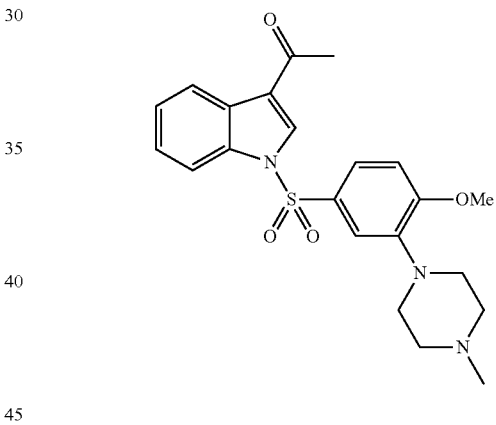

1-(1-((4-Methoxy-3-(piperazin-1-yl)phenyl)sulfonyl)-1H-indol-3-yl)ethanone (206 mg, 0.5 mmol) was reacted with sodium cyanoborohydride (85 mg, 1.35 mmol) and formaldehyde (40%, 0.112 mL, 1.617 mmol) in methanol (10 mL) according to the procedure as described in example 2, and the crude product was purified by silica gel chromatography eluted with DCM/methanol(V/V)=50/1 to give the title compound as a white solid (184 mg, 86%). The compound was characterized by the following spectroscopic data: MS (ESI, pos. ion) m/z: 428.2 [M+H]+; $^1$H NMR (400 MHz, CDCl$_3$): δ 8.36-8.29 (m, 1H), 8.19 (s, 1H), 7.96-7.89 (m, 1H), 7.59 (dd, J=8.6, 2.4 Hz, 1H), 7.40 (d, J=2.4 Hz, 1H), 7.39-7.29 (m, 2H), 6.85 (d, J=8.7 Hz, 1H), 3.86 (s, 3H), 3.04 (brs, 4H), 2.56 (brs, 7H), 2.34 (s, 3H); and $^{13}$C NMR (100 MHz, CDCl$_3$): δ 193.6, 157.3, 142.4, 135.2, 132.5, 129.3, 127.7, 125.8, 124.9, 123.3, 122.9, 121.7, 116.8, 113.3, 111.3, 56.2, 55.2, 50.3, 46.2, 27.9.

Example 5 Synthesis of 4-fluoro-1-((4-methoxy-3-(piperazin-1-yl)phenyl)sulfonyl)-1H-indole

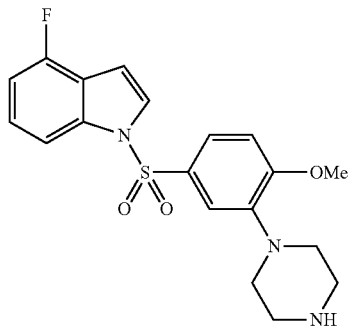 [SMILES: COc1ccc(S(=O)(=O)n2ccc3c(F)cccc32)cc1N1CCNCC1]

Step 1) Synthesis of 2,2,2-trichloro-1-(4-(5-((4-fluoro-1H-indol-1-yl)sulfonyl)-2-methoxyphenyl)piperazin-1-yl)ethanone 4-Fluoroindole (270 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (10 mL) according to the procedure as described in step 3 of example 1, and the crude product was purified by silica gel chromatography eluted with PE/EtOAc(V/V)=5/1 to give the title compound as a white solid (621 mg, 58%). The compound was characterized by the following spectroscopic data: MS (ESI, pos. ion) m/z: 533.9 [M+H]$^+$; $^1$H NMR (400 MHz, CDCl$_3$): δ 7.70 (d, J=8.4 Hz, 1H), 7.52 (dd, J=8.6, 2.3 Hz, 1H), 7.45 (d, J=3.7 Hz, 1H), 7.24 (d, J=2.3 Hz, 1H), 7.17 (td, J=8.1, 3.4 Hz, 1H), 6.84 (dd, J=9.5, 8.4 Hz, 1H), 6.79 (d, J=8.7 Hz, 1H), 6.67 (dd, J=3.7, 0.6 Hz, 1H), 3.89 (brs, 4H), 3.81 (s, 3H), 3.01 (t, J=4.9 Hz, 4H).

Step 2) Synthesis of 4-fluoro-1-((4-methoxy-3-(piperazin-1-yl)phenyl)sulfonyl)-1H-indole 2,2,2-Trichloro-1-(4-(5 ((4-fluoro-1H-indol-1-yl)sulfonyl)-2-methoxyphenyl)piperazin-1-yl)ethanone (428 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (302 mg, 97%). The compound was characterized by the following spectroscopic data: MS (ESI, pos. ion) m/z: 390.1 [M+H]+; $^1$H NMR (400 MHz, CDCl$_3$): δ 7.78 (d, J=8.0 Hz, 1H), 7.60-7.54 (m, 2H), 7.36-7.34 (m, 1H), 7.28-7.22 (m, 1H), 6.91 (dd, J=9.3, 8.2 Hz, 1H), 6.84 (dd, J=8.7, 5.2 Hz, 1H), 6.75 (dd, J=3.7, 0.7 Hz, 1H), 3.87 (s, 3H), 3.20 (t, J=5.3 Hz, 4H), 3.15 (t, J=5.0 Hz, 4H); and $^{13}$C NMR (100 MHz, CDCl$_3$): δ 157.0, 156.6, 154.6, 141.2, 136.9, 129.7, 126.3, 125.3, 123.1, 116.7, 111.1, 109.5, 108.5, 104.5, 56.0, 49.3, 44.7.

Example 6 Synthesis of 4-fluoro-1-((4-methoxy-3-(4-methylpiperazin-1-yl)phenyl)sulfonyl)-1H-indole

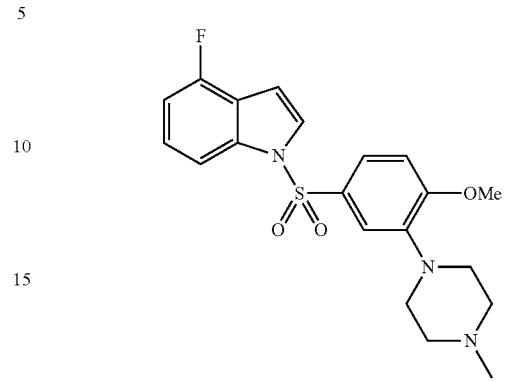

4-Fluoro-1-((4-methoxy-3-(piperazin-1-yl)phenyl)sulfonyl)-1H-indole (194 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (145 mg, 72%). The compound was characterized by the following spectroscopic data: MS (ESI, pos. ion) m/z: 404.2 [M+H]$^+$; $^1$H NMR (400 MHz, CDCl$_3$): δ 7.79 (d, J=8.3 Hz, 1H), 7.58-7.54 (m, 2H), 7.35 (d, J=2.0 Hz, 1H), 7.28-7.22 (m, 1H), 6.91 (t, J=8.8 Hz, 1H), 6.84 (d, J=8.6 Hz, 1H), 6.75 (d, J=3.4 Hz, 1H), 3.87 (s, 3H), 3.08 (brs, 4H), 2.65 (brs, 4H), 2.40 (s, 3H); and $^{13}$C NMR (100 MHz, CDCl$_3$): δ 157.1, 156.6, 154.6, 141.7, 137.0, 129.6, 126.3, 125.2, 122.5, 116.4, 110.8, 109.5, 108.4, 104.4, 55.9, 54.8, 49.8, 45.8.

Example 7 Synthesis of 1-((4-methoxy-3-(piperazin-1-yl)phenyl)sulfonyl)-1H-indole-4-carbonitrile

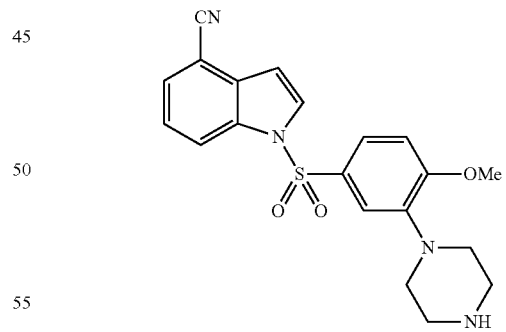

Step 1) Synthesis of 1-((4-methoxy-3-(4-(2,2,2-trichloroacetyl)piperazin-1-yl)phenyl)sulfonyl)-1H-indole-4-carbonitrile 4-Cyanoindole (284 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a white solid (455 mg, 42%). The compound was characterized by the following spectroscopic data: MS (ESI, pos. ion) m/z: 540.9 [M+H]+; and 1H NMR (400 MHz, CDCl3): δ 8.21 (d, J=8.4 Hz, 1H), 7.73 (d, J=3.7 Hz, 1H), 7.60-7.56 (m, 2H), 7.38 (t, J=8.0 Hz, 1H), 7.30 (d, J=2.4 Hz, 1H), 6.89-6.87 (m, 2H), 3.89 (brs, 4H), 3.81 (s, 3H), 3.08 (t, J=4.9 Hz, 4H).

Step 2) Synthesis of 1-((4-methoxy-3-(piperazin-1-yl)phenyl)sulfonyl)-1H-indole-4-carbonitrile 1-((4-Methoxy-3-(4-(2,2,2-trichloro acetyl)piperazin-1-yl)phenyl)sulfonyl)-1H-indole-4-carbonitrile (455 mg, 0.84 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (230 mg, 69%). The compound was characterized by the following spectroscopic data: MS (ESI, pos. ion) m/z: 397.1 [M+H]+; 1H NMR (400 MHz, CDCl3): δ 8.21 (d, J=8.4 Hz, 1H), 7.73 (d, J=3.7 Hz, 1H), 7.55-7.53 (m, 2H), 7.36 (t, J=8.0 Hz, 1H), 7.31 (d, J=2.4 Hz, 1H), 6.86-6.82 (m, 2H), 3.85 (s, 3H), 3.06 (brs, 4H), 3.03 (brs, 4H); and 13C NMR (100 MHz, CDCl3): δ 156.9, 142.2, 134.5, 132.3, 129.2, 128.9, 127.8, 124.2, 122.6, 117.9, 117.3, 116.3, 111.0, 106.8, 104.3, 55.9, 50.9, 45.6.

Example 8 Synthesis of 1-((4-methoxy-3-(4-methyl-piperazin-1-yl)phenyl)sulfonyl)-1H-indole-4-carbonitrile

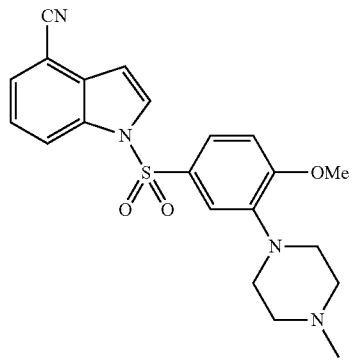 [SMILES: COc1ccc(S(=O)(=O)n2ccc3c(C#N)cccc32)cc1N1CCN(C)CC1]

1-((4-Methoxy-3-(piperazin-1-yl)phenyl)sulfonyl)-1H-indole-4-carbonitrile (198 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (182 mg, 89%). The compound was characterized by the following spectroscopic data: MS (ESI, pos. ion) m/z: 411.2 [M+H]+; 1H NMR (400 MHz, CDCl3): δ 8.21 (d, J=8.4 Hz, 1H), 7.73 (d, J=3.7 Hz, 1H), 7.55-7.52 (m, 2H), 7.36 (t, J=8.0 Hz, 1H), 7.31 (d, J=2.4 Hz, 1H), 6.86-6.82 (m, 2H), 3.85 (s, 3H), 3.04 (brs, 4H), 2.61 (brs, 4H), 2.37 (s, 3H); and 13C NMR (100 MHz, CDCl3): δ 156.8, 141.9, 134.5, 132.3, 129.3, 128.9, 127.8, 124.3, 122.5, 117.9, 117.3, 116.3, 111.0, 106.8, 104.4, 55.9, 54.8, 49.8, 45.8.

Example 9 Synthesis of 5-fluoro-1-((4-methoxy-3-(piperazin-1-yl)phenyl)sulfonyl)-1H-indole

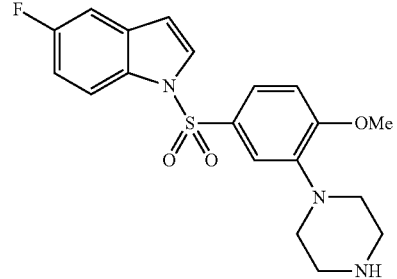 [SMILES: COc1ccc(S(=O)(=O)n2ccc3cc(F)ccc32)cc1N1CCNCC1]

Step 1) Synthesis of 2,2,2-trichloro-1-(4-(5-((5-fluoro-1H-indol-1-yl)sulfonyl)-2-methoxyphenyl)piperazin-1-yl)ethanone 5-Fluoroindole (270 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a white solid (717 mg, 67%). The compound was characterized by the following spectroscopic data: MS (ESI, pos. ion) m/z: 534.0 [M+H]+; and 1H (400 MHz, CDCl3): δ 7.91 (dd, J=9.0, 4.4 Hz, 1H), 7.58-7.55 (m, 2H), 7.27 (d, J=2.3 Hz, 1H), 7.17 (dd, J=8.8, 2.5 Hz, 1H), 7.06-7.01 (m, 1H), 6.85 (d, J=8.7 Hz, 1H), 6.61 (dd, J=3.6, 0.4 Hz, 1H), 4.01-3.94 (m, 4H), 3.88 (s, 3H), 3.07 (t, J=4.96 Hz, 4H).

Step 2) Synthesis of 5-fluoro-1-((4-methoxy-3-(piperazin-1-yl)phenyl)sulfonyl)-1H-indole 2,2,2-Trichloro-1-(4-(5-((5-fluoro-1H-indol-1-yl)sulfonyl)-2-methoxyphenyl)piperazin-1-yl)ethanone (428 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (258 mg, 83%). The compound was characterized by the following spectroscopic data: MS (ESI, pos. ion) m/z: 390.1 [M+H]+; 1H (400 MHz, CDCl3): δ 7.91 (dd, J=9.0, 4.4 Hz, 1H), 7.57 (d, J=3.6 Hz, 1H), 7.51 (dd, J=2.4, 8.6 Hz, 1H), 7.30 (d, J=2.4 Hz, 1H), 7.16 (dd, J=2.5, 8.8 Hz, 1H), 7.02 (td, J=2.5, 9.0 Hz, 1H), 6.80 (d, J=8.7 Hz, 1H), 6.59 (dd, J=0.5, 3.6 Hz, 1H), 3.84 (s, 3H), 3.03-3.01 (m, 4H), 2.96-2.94 (m, 4H); and 13C NMR (100 MHz, CDCl3): δ 159.5 (d, J=238.5 Hz), 156.6, 142.2, 131.7 (d, J=10.1 Hz), 131.2, 129.7, 128.1, 122.4, 116.3, 114.5 (d, J=9.4 Hz), 112.4 (d, J=25.5 Hz), 110.8, 108.7 (d, J=4.1 Hz), 106.8 (d, J=23.7 Hz), 55.8, 51.3, 45.9.

Example 10 Synthesis of 5-fluoro-1-((4-methoxy-3-(4-methylpiperazin-1-yl) phenyl)sulfonyl)-1H-indole

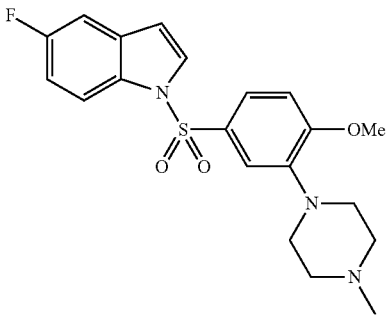 [SMILES: COc1ccc(S(=O)(=O)n2ccc3cc(F)ccc32)cc1N1CCN(C)CC1]

5-Fluoro-1-((4-methoxy-3-(piperazin-1-yl)phenyl)sulfonyl)-1H-indole (192 mg, 0.49 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (60 mg, 30%). The compound was characterized by the following spectroscopic data: MS (ESI, pos. ion) m/z: 404.1 [M+H]$^+$; $^1$H NMR (400 MHz, CDCl$_3$): δ 7.91 (dd, J=9.0, 4.4 Hz, 1H), 7.56 (d, J=3.7 Hz, 1H), 7.50 (dd, J=8.6, 2.3 Hz, 1H), 7.28 (d, J=2.4 Hz, 1H), 7.15 (dd, J=8.8, 2.5 Hz, 1H), 7.01 (td, J=9.1, 2.6 Hz, 1H), 6.79 (d, J=8.6 Hz, 1H), 6.57 (dd, J=3.7, 0.4 Hz, 1H), 3.83 (s, 3H), 3.02 (brs, 4H), 2.59 (brs, 4H), 2.34 (s, 3H); and $^{13}$C NMR (100 MHz, CDCl$_3$): δ 159.5 (d, J=238.5 Hz), 156.5, 141.7, 131.7 (d, J=10.2 Hz), 131.2, 129.6, 128.1, 122.3, 116.2, 114.5 (d, J=9.4 Hz), 112.4 (d, J=25.5 Hz), 110.7, 108.7 (d, J=3.9 Hz), 106.7 (d, J=23.8 Hz), 55.8, 54.7, 49.8, 45.7.

Example 11 Synthesis of 5-chloro-1-((4-methoxy-3-(piperazin-1-yl)phenyl)sulfonyl)-1H-indole

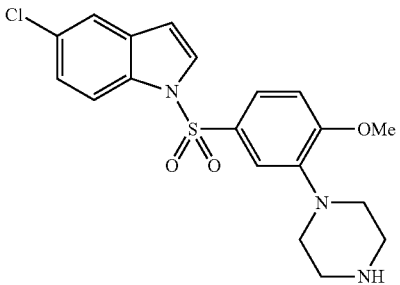 [SMILES: COc1ccc(S(=O)(=O)n2ccc3cc(Cl)ccc32)cc1N1CCNCC1]

Step 1) Synthesis of 2,2,2-trichloro-1-(4-(5-((5-chloro-1H-indol-1-yl)sulfonyl)-2-methoxyphenyl)piperazin-1-yl)ethanone 5-Chloroindole (303 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (793 mg, 72%). The compound was characterized by the following spectroscopic data: MS (ESI, pos. ion) m/z: 550.1 [M+H]$^+$; and $^1$H (400 MHz, CDCl$_3$): δ 7.89 (d, J=8.8 Hz, 1H), 7.58-7.55 (m, 2H), 7.50 (d, J=2.0 Hz, 1H), 7.27-7.25 (m, 2H), 6.85 (d, J=8.7 Hz, 1H), 6.59 (dd, J=3.6, 0.4 Hz, 1H), 3.94 (brs, 4H), 3.88 (s, 3H), 3.07 (t, J=5.0 Hz, 4H).

Step 2) Synthesis of 5-chloro-1-((4-methoxy-3-(piperazin-1-yl)phenyl)sulfonyl)-1H-indole 2,2,2-Trichloro-1-(4-(5-((5-chloro-1H-indol-1-yl)sulfonyl)-2-methoxyphenyl)piperazin-1-yl)ethanone (441 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (272 mg, 84%). The compound was characterized by the following spectroscopic data: MS (ESI, pos. ion) m/z: 406.2 [M+H]$^+$; $^1$H (400 MHz, CDCl$_3$): δ 7.89 (d, J=8.8 Hz, 1H), 7.56 (d, J=3.7 Hz, 1H), 7.51 (dd, J=2.4, 8.6 Hz, 1H), 7.47 (d, J=2.0 Hz, 1H), 7.28 (d, J=2.4 Hz, 1H), 7.24 (dd, J=2.0, 8.8 Hz, 1H), 6.80 (d, J=8.7 Hz, 1H), 6.56 (dd, J=0.5, 3.6 Hz, 1H), 3.83 (s, 3H), 3.02-3.01 (m, 4H), 2.96-2.94 (m, 4H); and $^{13}$C NMR (100 MHz, CDCl$_3$): δ 156.6, 142.2, 133.2, 131.9, 129.5, 129.0, 127.7, 124.6, 122.4, 120.9, 116.2, 114.5, 110.8, 108.2, 55.8, 51.2, 45.8.

Example 12 Synthesis of 5-chloro-1-((4-methoxy-3-(4-methylpiperazin-1-yl)phenyl)sulfonyl)-1H-indole

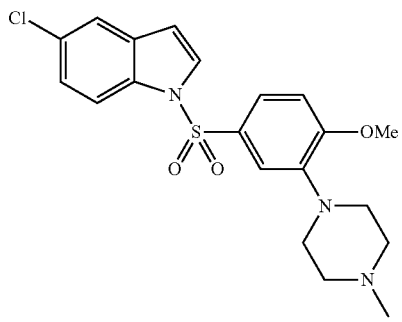 [SMILES: COc1ccc(S(=O)(=O)n2ccc3cc(Cl)ccc32)cc1N1CCN(C)CC1]

5-Chloro-1-((4-methoxy-3-(piperazin-1-yl)phenyl)sulfonyl)-1H-indole (203 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (195 mg, 93%). The compound was characterized by the following spectroscopic data: MS (ESI, pos. ion) m/z: 420.0 [M+H]$^+$; $^1$H (400 MHz, CDCl$_3$): δ 7.89 (d, J=8.8 Hz, 1H), 7.55 (d, J=3.7 Hz, 1H), 7.50 (dd, J=2.4, 8.6 Hz, 1H), 7.47 (d, J=2.0 Hz, 1H), 7.28 (d, J=2.4 Hz, 1H), 7.23 (dd, J=2.0, 8.8 Hz, 1H), 6.80 (d, J=8.7 Hz, 1H), 6.56 (dd, J=0.6, 3.7 Hz, 1H), 3.84 (s, 3H), 3.01 (brs, 4H), 2.56 (brs, 4H), 2.34 (s, 3H); and $^{13}$C NMR (100 MHz, CDCl$_3$): δ 156.6, 141.8, 133.2, 131.9, 129.6, 129.0, 127.7, 124.6, 122.3, 120.9, 116.2, 114.5, 110.8, 108.2, 55.9, 54.9, 50.0, 46.0.

Example 13 Synthesis of 5-bromo-1-((4-methoxy-3-(piperazin-1-yl)phenyl)sulfonyl)-1H-indole

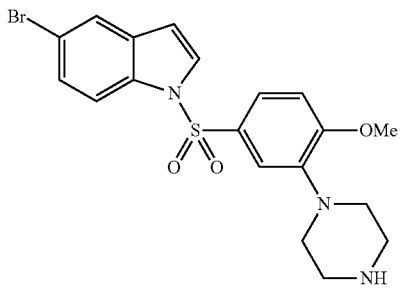

Step 1) Synthesis of 2,2,2-trichloro-1-(4-(5-((5-bromo-1H-indol-1-yl)sulfonyl)-2-methoxy phenyl) piperazin-1-yl)-ethanone 5-Bromoindole (392 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (679 mg, 57%). The compound was characterized by the following spectroscopic data: MS (ESI, pos. ion) m/z: 593.9 [M+H]$^+$; and $^1$H NMR (400 MHz, CDCl$_3$): δ 7.78 (d, J=8.8 Hz, 1H), 7.59 (d, J=1.8 Hz, 1H), 7.51-7.47 (m, 2H), 7.32 (dd, J=8.8, 1.9 Hz, 1H), 7.20 (s, 1H), 6.78 (d, J=8.7 Hz, 1H), 6.51 (d, J=3.4 Hz, 1H), 3.94 (brs, 4H), 3.81 (s, 3H), 3.00 (t, J=5.0 Hz, 4H).

Step 2) Synthesis of 5-bromo-1-((4-methoxy-3-(piperazin-1-yl)phenyl)sulfonyl)-1H-indole 2,2,2-Trichloro-1-(4-(5-((5-bromo-1H-indol-1-yl)sulfonyl)-2-methoxyphenyl)piperazin-1-yl)-ethanone (477 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (338 mg, 94%). The compound was characterized by the following spectroscopic data: MS (ESI, pos. ion) m/z: 450.0 [M+H]$^+$; $^1$H NMR (400 MHz, CDCl$_3$): δ 7.85 (d, J=8.8 Hz, 1H), 7.65 (d, J=1.8 Hz, 1H), 7.57-7.50 (m, 2H), 7.39 (dd, J=8.8, 1.9 Hz, 1H), 7.29 (d, J=2.3 Hz, 1H), 6.82 (d, J=8.7 Hz, 1H), 6.58 (dd, J=3.7, 0.6 Hz, 1H), 3.85 (s, 3H), 3.13-3.04 (m, 8H); and $^{13}$C NMR (100 MHz, CDCl$_3$): δ 156.9, 141.9, 133.8, 132.7, 129.9, 127.9, 127.5, 124.3, 122.9, 116.9, 116.7, 115.1, 111.2, 108.4, 56.2, 50.5, 45.6.

Example 14 Synthesis of 5-bromo-1-((4-methoxy-3-(4-methylpiperazin-1-yl)phenyl) sulfonyl)-1H-indole

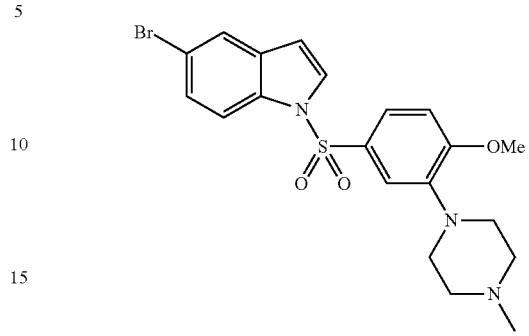

5-Bromo-1-((4-methoxy-3-(piperazin-1-yl)phenyl)sulfonyl)-1H-indole (225 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (158 mg, 68%). The compound was characterized by the following spectroscopic data: MS (ESI, pos. ion) m/z: 464.1 [M+H]$^+$; $^1$H NMR (600 MHz, CDCl$_3$): δ 7.87 (d, J=8.6 Hz, 1H), 7.66 (s, 1H), 7.55 (dd, J=19.9, 5.1 Hz, 2H), 7.40 (d, J=8.4 Hz, 1H), 7.31 (s, 1H), 6.82 (d, J=8.5 Hz, 1H), 6.58 (s, 1H), 3.87 (s, 3H), 3.04 (brs, 4H), 2.59 (brs, 4H), 2.36 (s, 3H); and $^{13}$C NMR (150 MHz, CDCl$_3$): δ 156.6, 141.9, 133.6, 132.5, 129.6, 127.6, 127.3, 124.0, 122.4, 116.7, 116.3, 114.9, 110.8, 108.1, 55.9, 54.9, 50.1, 46.0.

Example 15 Synthesis of 1-((4-methoxy-3-(piperazin-1-yl)phenyl)sulfonyl)-1H-indole-5-carbonitrile

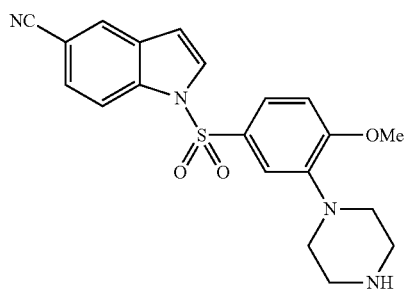 [SMILES: COc1ccc(S(=O)(=O)n2ccc3cc(Br)ccc32)cc1N1CCNCC1]

Step 1) Synthesis of 1-((4-methoxy-3-(4-(2,2,2-trichloroacetyl)piperazin-1-yl)phenyl)sulfonyl)-1H-indole-5-carbonitrile 5-Cyanoindole (284 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (1.0 g, 93%). The compound was characterized by the following spectroscopic data: MS (ESI, pos. ion) m/z: 541.1 [M+H]⁺; and ¹H (400 MHz, CDCl₃): δ 8.06 (d, J=8.6 Hz, 1H), 7.88 (d, J=1.0 Hz, 1H), 7.68 (d, J=3.7 Hz, 1H), 7.60 (dd, J=8.7, 2.4 Hz, 1H), 7.56 (dd, J=8.6, 1.5 Hz, 1H), 7.29 (d, J=2.4 Hz, 1H), 6.88 (d, J=8.7 Hz, 1H), 6.72 (dd, J=3.7, 0.6 Hz, 1H), 4.08-3.91 (m, 4H), 3.89 (s, 3H), 3.09 (t, J=5.2 Hz, 4H).

Step 2) Synthesis of 1-((4-methoxy-3-(piperazin-1-yl)phenyl)sulfonyl)-1H-indole-5-carbonitrile 1-((4-Methoxy-3-(4-(2,2,2-trichloroacetyl)piperazin-1-yl)phenyl)sulfonyl)-1H-indole-5-carbonitrile (434 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (272 mg, 86%). The compound was characterized by the following spectroscopic data: MS (ESI, pos. ion) m/z: 397.1 [M+H]⁺; ¹H NMR (400 MHz, DMSO-d₆): δ 8.16 (d, J=1.1 Hz, 1H), 8.11 (d, J=8.7 Hz, 1H), 8.05 (d, J=3.7 Hz, 1H), 7.73 (dd, J=8.7, 1.6 Hz, 1H), 7.66 (dd, J=8.7, 2.4 Hz, 1H), 7.31 (d, J=2.4 Hz, 1H), 7.09 (d, J=8.8 Hz, 1H), 6.91 (d, J=3.2 Hz, 1H), 3.81 (s, 3H), 2.91 (brs, 4H), 2.90 (brs, 4H); and ¹³C NMR (100 MHz, DMSO-d₆): δ 156.8, 141.9, 135.8, 130.5, 129.3, 128.0, 127.5, 126.8, 122.4, 119.2, 115.5, 114.2, 112.1, 108.8, 105.8, 56.1, 49.8, 44.8.

Example 16 Synthesis of 1-((4-methoxy-3-(4-methylpiperazin-1-yl)phenyl)sulfonyl)-1H-indole-5-carbonitrile

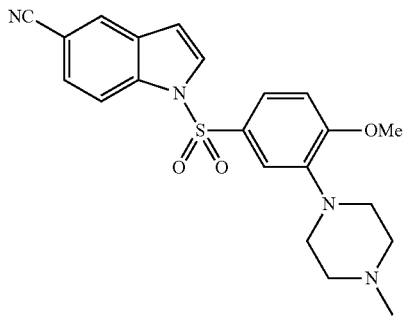 [SMILES: COc1ccc(S(=O)(=O)n2ccc3cc(C#N)ccc32)cc1N1CCN(C)CC1]

1-((4-Methoxy-3-(piperazin-1-yl)phenyl)sulfonyl)-1H-indole-5-carbonitrile (198 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (145 mg, 71%). The compound was characterized by the following spectroscopic data: MS (ESI, pos. ion) m/z: 411.0 [M+H]⁺; ¹H (400 MHz, CDCl₃): δ 8.06 (d, J=8.6 Hz, 1H), 7.86 (d, J=1.0 Hz, 1H), 7.67 (d, J=3.7 Hz, 1H), 7.56-7.52 (m, 2H), 7.30 (d, J=2.3 Hz, 1H), 6.83 (d, J=8.7 Hz, 1H), 6.69 (d, J=3.5 Hz, 1H), 3.85 (s, 3H), 3.03 (brs, 4H), 2.60 (brs, 4H), 2.34 (s, 3H); and ¹³C NMR (100 MHz, CDCl₃): δ 156.9, 142.0, 136.4, 130.6, 129.3, 128.5, 127.3, 126.3, 122.5, 119.3, 116.2, 114.2, 110.9, 108.2, 106.7, 55.9, 54.7, 49.8, 45.7.

Example 17 Synthesis of 6-fluoro-1-((4-methoxy-3-(piperazin-1-yl)phenyl)sulfonyl)-1H-indole

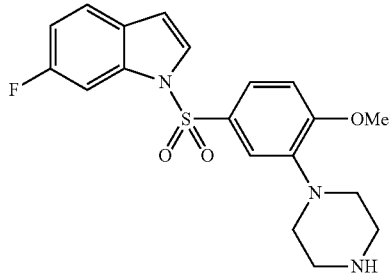 [SMILES: COc1ccc(S(=O)(=O)n2ccc3ccc(F)cc32)cc1N1CCNCC1]

Step 1) Synthesis of 2,2,2-trichloro-1-(4-(5-((6-fluoro-1H-indol-1-yl)sulfonyl)-2-methoxyphenyl)piperazin-1-yl)ethanone 6-Fluoroindole (270 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (589 mg, 55%). The compound was characterized by the following spectroscopic data: MS (ESI, pos. ion) m/z: 534.0 [M+H]⁺; and ¹H (400 MHz, CDCl₃): δ 7.70 (dd, J=9.6, 2.3 Hz, 1H), 7.59 (dd, J=8.6, 2.3 Hz, 1H), 7.52 (d, J=3.6 Hz, 1H), 7.44 (dd, J=8.7, 5.3 Hz, 1H), 7.29 (d, J=2.3 Hz, 1H), 6.98 (td, J=9.1, 2.4 Hz, 1H), 6.87 (d, J=8.7 Hz, 1H), 6.62 (dd, J=3.7, 0.7 Hz, 1H), 3.96 (brs, 4H), 3.88 (s, 3H), 3.09 (t, J=5.0 Hz, 4H).

Step 2) Synthesis of 6-fluoro-1-((4-methoxy-3-(piperazin-1-yl)phenyl)sulfonyl)-1H-indole 2,2,2-Trichloro-1-(4-(5-((6-fluoro-1H-indol-1-yl)sulfonyl)-2-methoxyphenyl)piperazin-1-yl)ethanone (428 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a light yellow solid (280 mg, 90%). The compound was characterized by the following spectroscopic data: MS (ESI, pos. ion) m/z: 390.1 [M+H]⁺; ¹H NMR (400 MHz, CDCl₃): δ 7.70 (dd, J=9.7, 2.3 Hz, 1H), 7.55-7.51 (m, 2H), 7.42 (dd, J=8.6, 5.3 Hz, 1H), 7.29 (d, J=2.4 Hz, 1H), 6.96 (td, J=9.1, 2.4 Hz, 1H), 6.82 (d, J=8.7 Hz, 1H), 6.59 (dd, J=3.7, 0.7 Hz, 1H), 3.85 (s, 3H), 3.03-2.97 (m, 8H); and ¹³C NMR (100 MHz, CDCl₃): δ 160.9 (d, J=240.0 Hz), 156.8, 142.4, 135.2 (d, J=12.0 Hz), 129.8, 127.2, 126.9 (d, J=4.0 Hz), 122.7, 122.2 (d, J=9.0 Hz), 116.5, 111.8 (d, J=24 Hz), 111.1, 108.8, 101.1 (d, J=28 Hz), 56.1, 51.5, 46.0.

Example 18 Synthesis of 6-fluoro-1-((4-methoxy-3-(4-methylpiperazin-1-yl)phenyl)sulfonyl)-1H-indole

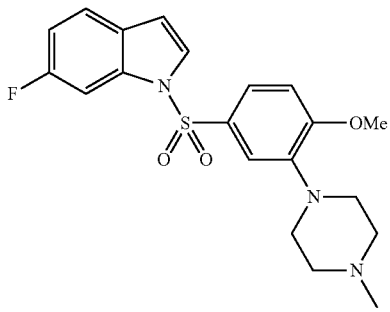 [SMILES: COc1ccc(S(=O)(=O)n2ccc3ccc(F)cc32)cc1N1CCN(C)CC1]

6-Fluoro-1-((4-methoxy-3-(piperazin-1-yl)phenyl)sulfonyl)-1H-indole (195 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (155 mg, 77%). The compound was characterized by the following spectroscopic data: MS (ESI, pos. ion) m/z: 404.1 [M+H]$^+$; $^1$H NMR (600 MHz, CDCl$_3$): δ 7.76-7.69 (m, 1H), 7.60-7.52 (m, 2H), 7.45 (dd, J=8.5, 5.3 Hz, 1H), 7.32 (d, J=1.9 Hz, 1H), 6.99 (td, J=9.0, 2.0 Hz, 1H), 6.84 (d, J=8.7 Hz, 1H), 6.62 (d, J=3.4 Hz, 1H), 3.88 (s, 3H), 3.05 (brs, 4H), 2.59 (brs, 4H), 2.36 (s, 3H); and $^{13}$C NMR (150 MHz, CDCl$_3$): δ 160.8 (d, J=240.2 Hz), 156.6, 141.9, 135.0 (d, J=12.4 Hz), 129.6, 126.9, 126.7 (d, J=3.9 Hz), 122.4, 122.0 (d, J=9.9 Hz), 116.3, 111.7 (d, J=24.2 Hz), 110.8, 108.6, 100.9 (d, J=28.2 Hz), 55.9, 54.9, 50.1, 46.1.

Example 19 Synthesis of 6-chloro-1-((4-methoxy-3-(piperazin-1-yl)phenyl)sulfonyl)-1H-indole

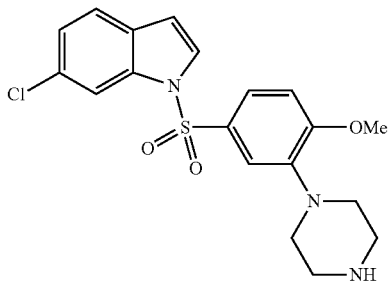 [SMILES: COc1ccc(S(=O)(=O)n2ccc3ccc(Cl)cc32)cc1N1CCNCC1]

Step 1) Synthesis of 2,2,2-trichloro-1-(4-(5-((6-chloro-1H-indol-1-yl)sulfonyl)-2-methoxy phenyl)piperazin-1-yl)ethanone 6-Chloroindole (303 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (573 mg, 52%). The compound was characterized by the following spectroscopic data: MS (ESI, pos. ion) m/z: 550.0 [M+H]$^+$; and $^1$H NMR (400 MHz, CDCl$_3$): δ 8.03 (s, 1H), 7.60 (dd, J=8.6, 2.0 Hz, 1H), 7.54 (d, J=3.6 Hz, 1H), 7.45 (d, J=8.4 Hz, 1H), 7.34 (d, J=2.0 Hz, 1H), 7.22 (d, J=8.4 Hz, 1H), 6.89 (d, J=8.7 Hz, 1H), 6.63 (d, J=3.6 Hz, 1H), 3.98 (brs, 4H), 3.90 (s, 3H), 3.19-3.00 (m, 4H).

Step 2) Synthesis of 6-chloro-1-((4-methoxy-3-(piperazin-1-yl)phenyl)sulfonyl)-1H-indole 2,2,2-Trichloro-1-(4-(5-((6-chloro-1H-indol-1-yl)sulfonyl)-2-methoxyphenyl)piperazin-1-yl)ethanone (441 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (182 mg, 56%). The compound was characterized by the following spectroscopic data: MS (ESI, pos. ion) m/z: 406.1 [M+H]$^+$; $^1$H (400 MHz, CDCl$_3$): δ 8.00 (d, J=1.8 Hz, 1H), 7.55-7.51 (m, 2H), 7.41 (d, J=8.4 Hz, 1H), 7.33 (d, J=2.4 Hz, 1H), 7.18 (dd, J=8.4, 1.8 Hz, 1H), 6.82 (d, J=8.7 Hz, 1H), 6.59 (dd, J=3.6, 0.4 Hz, 1H), 3.85 (s, 3H), 3.08-3.02 (m, 8H); and $^{13}$C NMR (100 MHz, CDCl$_3$): δ 156.7, 141.9, 135.1, 130.4, 129.5, 129.2, 127.0, 123.8, 122.6, 122.1, 116.5, 113.8, 110.9, 108.6, 55.9, 50.7, 45.5.

Example 20 Synthesis of 6-chloro-1-((4-methoxy-3-(4-methylpiperazin-1-yl)phenyl)sulfonyl)-1H-indole

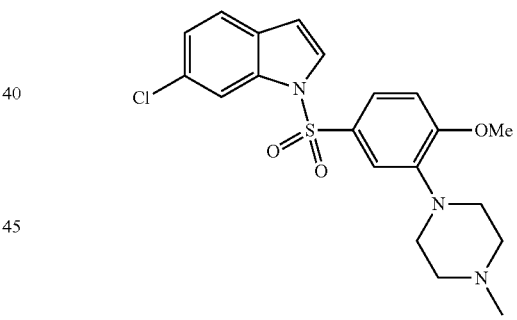

6-Chloro-1-((4-methoxy-3-(piperazin-1-yl)phenyl)sulfonyl)-1H-indole (203 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (124 mg, 59%). The compound was characterized by the following spectroscopic data: MS (ESI, pos. ion) m/z: 420.1 [M+H]$^+$; $^1$H NMR (400 MHz, CDCl$_3$): δ 8.00 (d, J=0.8 Hz, 1H), 7.54-7.52 (m, 2H), 7.41 (d, J=8.4 Hz, 1H), 7.32 (d, J=2.3 Hz, 1H), 7.17 (dd, J=8.4, 1.8 Hz, 1H), 6.82 (d, J=8.6 Hz, 1H), 6.59 (d, J=3.6 Hz, 1H), 3.85 (s, 3H), 3.06 (brs, 4H), 2.63 (brs, 4H), 2.37 (s, 3H); and $^{13}$C NMR (100 MHz, CDCl$_3$): δ 156.6, 141.7, 135.2, 130.4, 129.6, 129.2, 127.0, 123.8, 122.4, 122.0, 116.4, 113.8, 110.9, 108.5, 55.9, 54.7, 49.7, 45.7.

Example 21 Synthesis of 6-bromo-1-((4-methoxy-3-(4-methylpiperazin-1-yl)phenyl) sulfonyl)-1H-indole

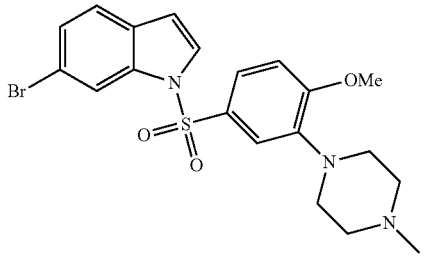 [SMILES: COc1ccc(S(=O)(=O)n2ccc3ccc(Br)cc32)cc1N1CCN(C)CC1]

Step 1) Synthesis of 2,2,2-trichloro-1-(4-(5-((6-bromo-1H-indol-1-yl)sulfonyl)-2-methoxy phenyl) piperazin-1-yl)-ethanone 6-Bromoindole (392 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (668 mg, 56%). The compound was characterized by the following spectroscopic data: MS (ESI, pos. ion) m/z: 594.0 [M+H]$^+$; and $^1$H (400 MHz, CDCl$_3$): δ 8.18 (t, J=0.8 Hz, 1H), 7.57 (dd, J=8.6, 2.3 Hz, 1H), 7.50 (d, J=3.7 Hz, 1H), 7.39-7.32 (m, 3H), 6.87 (d, J=8.7 Hz, 1H), 6.60 (dd, J=3.7, 0.6 Hz, 1H), 3.96 (brs, 4H), 3.88 (s, 3H), 3.10 (t, J=5.0 Hz, 4H).

Step 2) Synthesis of 6-bromo-1-((4-methoxy-3-(piperazin-1-yl)phenyl)sulfonyl)-1H-indole 2,2,2-Trichloro-1-(4-(5-((6-bromo-1H-indol-1-yl)sulfonyl)-2-methoxyphenyl)piperazin-1-yl)-ethanone (477 mg, 0.8 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (353 mg, 98%). The compound was characterized by the following spectroscopic data: MS (ESI, pos. ion) m/z: 450.0 [M+H]$^+$; $^1$H NMR (400 MHz, CDCl$_3$): δ 8.17 (t, J=0.8 Hz, 1H), 7.53-7.50 (m, 2H), 7.37-7.30 (m, 3H), 6.82 (d, J=8.8 Hz, 1H), 6.58 (dd, J=3.6, 0.8 Hz, 1H), 3.85 (s, 3H), 3.05-3.00 (m, 8H); and $^{13}$C NMR (100 MHz, CDCl$_3$) δ 156.7, 142.0, 135.4, 129.6, 129.4, 126.9, 126.5, 122.5, 122.4, 118.0, 116.7, 116.5, 110.9, 108.6, 55.9, 51.1, 45.7.

Step 3) Synthesis of 6-bromo-1-((4-methoxy-3-(4-methylpiperazin-1-yl)phenyl)sulfonyl)-1H-indole 6-Bromo-1-((4-methoxy-3-(piperazin-1-yl)phenyl)sulfonyl)-1H-indole (225 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (114 mg, 49%). The compound was characterized by the following spectroscopic data: MS (ESI, pos. ion) m/z: 464.0 [M+H]$^+$; $^1$H NMR (400 MHz, CDCl$_3$): δ 8.17 (t, J=0.8 Hz, 1H), 7.53-7.50 (m, 2H), 7.37-7.29 (m, 3H), 6.82 (d, J=8.8 Hz, 1H), 6.58 (dd, J=3.6, 0.4 Hz, 1H), 3.85 (s, 3H), 3.05 (brs, 4H), 2.58 (brs, 4H), 2.35 (s, 3H); and $^{13}$C NMR (100 MHz, CDCl$_3$): δ 156.6, 141.8, 135.5, 129.5, 129.4, 126.9, 126.5, 122.4, 122.3, 118.0, 116.7, 116.4, 110.9, 108.6, 55.9, 54.9, 50.0, 46.0.

Example 22 Synthesis of 7-fluoro-1-((4-methoxy-3-(piperazin-1-yl)phenyl)sulfonyl)-1H-indole

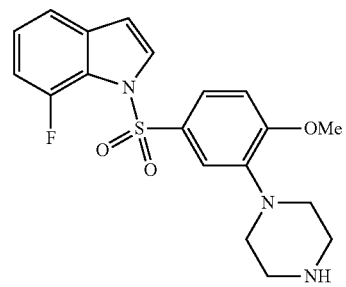 [SMILES: COc1ccc(S(=O)(=O)n2ccc3cccc(F)c32)cc1N1CCNCC1]

Step 1) Synthesis of 2,2,2-trichloro-1-(4-(5-((7-fluoro-1H-indol-1-yl)sulfonyl)-2-methoxyphenyl) piperazin-1-yl)ethanone 7-Fluoroindole (270 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc(V/V)=5/1 to give the title compound as a light yellow solid (619 mg, 58%). The compound was characterized by the following spectroscopic data: MS (ESI, pos. ion) m/z: 534.0 [M+H]$^+$; and $^1$H NMR (CDCl$_3$, 400 MHz): δ 7.75 (d, J=3.6 Hz, 1H), 7.64 (dt, J=8.0, 1.0 Hz, 1H), 7.48-7.47 (m, 1H), 7.32 (dd, J=7.8, 0.6 Hz, 1H), 7.13 (td, J=7.9, 4.2 Hz, 1H), 6.95 (dd, J=12.7, 8.0 Hz, 1H), 6.90 (d, J=14.9 Hz, 1H), 6.66 (dd, J=5.9, 2.3 Hz, 1H), 3.98 (brs, 4H), 3.91 (s, 3H), 3.13 (t, J=4.8 Hz, 4H).

Step 2) Synthesis of 7-fluoro-1-((4-methoxy-3-(piperazin-1-yl)phenyl)sulfonyl)-1H-indole 2,2,2-Trichloro-1-(4-(5-((7-fluoro-1H-indol-1-yl)sulfonyl)-2-methoxyphenyl)piperazin-1-yl)ethanone (600 mg, 1.12 mmol) was reacted with potassium hydroxide solution (189 mg of potassium hydroxide solid, 3.37 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (332 mg, 76%). The compound was characterized by the following spectroscopic data: MS (ESI, pos. ion) m/z: 390.2 [M+H]$^+$; and $^1$H NMR (400 MHz, CDCl$_3$): δ 7.76 (s, 1H), 7.60 (d, J=6.6 Hz, 1H), 7.47 (s, 1H), 7.31 (s, 1H), 7.12 (s, 1H), 6.95 (s, 1H), 6.87 (d, J=7.2 Hz, 1H), 6.66 (s, 1H), 3.88 (s, 3H), 3.06-3.04 (m, 8H).

Example 23 Synthesis of 3-(difluoromethyl)-5-fluoro-1-((4-methoxy-3-(piperazin-1-yl) phenyl) sulfonyl)-1H-indole

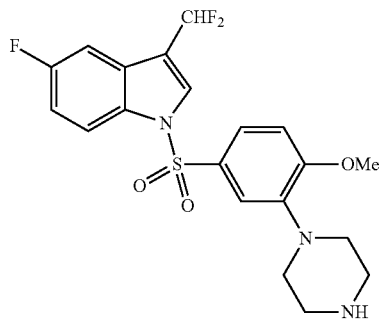 [SMILES: COc1ccc(S(=O)(=O)n2cc(C(F)F)c3cc(F)ccc32)cc1N1CCNCC1]

Step 1) Synthesis of 5-fluoro-1H-indole-3-carbaldehyde

To 3 mL of DMF was added phosphoryl chloride (2.04 g, 13.3 mmol) dropwise at 0° C. The mixture was stirred for half an hour, then a solution of 5-fluoroindole (1.5 g, 11.1 mmol) in 2 mL of DMF was added dropwise into the mixture. The resulting mixture was heated to 25° C. and reacted for 24 hours. The reaction mixture was quenched with 30 mL of water and neutralized with sodium carbonate solid to the pH=8-9. The mixture was filtered and the filter cake was dried in vacuo to give the title compound as a yellow solid (1.56 g, 86%). The compound was characterized by the following spectroscopic data: MS (ESI, pos. ion) m/z: 164.1 [M+H]$^+$; and $^1$H NMR (400 MHz, DMSO-$d_6$): δ 9.93 (s, 1H), 8.35 (s, 1H), 7.77 (dd, J=9.6, 2.6 Hz, 1H), 7.54 (dd, J=8.9, 4.6 Hz, 1H), 7.12 (td, J=9.2, 2.6 Hz, 1H).

Step 2) Synthesis of 5-fluoro-1-((4-methoxy-3-(4-(2,2,2-trichloroacetyl)piperazin-1-yl)phenyl) sulfonyl)-1H-indole-3-carbaldehyde 5-Fluoro-1H-indole-3-carbaldehyde (326 mg, 2.0 mmol) was reacted with sodium hydride (96 mg, 2.4 mmol, 60%) and 4-methoxy-3-(4-(2,2,2-trichloroacetyl)piperazin-1-yl) benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (552 mg, 49%). The compound was characterized by the following spectroscopic data: MS (ESI, pos. ion) m/z: 562.1 [M+H]$^+$; and $^1$H NMR (400 MHz, CDCl$_3$): δ 10.08 (s, 1H), 8.26 (s, 1H), 7.96-7.88 (m, 2H), 7.69 (dd, J=8.7, 2.3 Hz, 1H), 7.41 (d, J=2.1 Hz, 1H), 7.16 (td, J=9.0, 2.6 Hz, 1H), 6.95 (d, J=8.7 Hz, 1H), 4.00 (brs, 4H), 3.93 (s, 3H), 3.19-3.07 (m, 4H).

Step 3) Synthesis of 2,2,2-trichloro-1-(4-(5-((3-(difluoromethyl)-5-fluoro-1H-indol-1-yl) sulfonyl)-2-methoxyphenyl)piperazin-1-yl)ethanone To 10 mL of anhydrous dichloromethane were added 5-fluoro-1-((4-methoxy-3-(4-(2,2,2-trichloroacetyl) piperazin-1-yl)phenyl)sulfonyl)-1H-indole-3-carbaldehyde (552 mg, 0.98 mmol) and diethylaminosulphur trifluoride (335 μL, 2.5 mmol) at 25° C., the mixture was stirred for 26 hours. To the mixture was added 50 mL of dichloromethane and the mixture was washed with saturated sodium bicarbonate (40 mL×2). The organic layer was dried over anhydrous sodium sulfate and filtered. The filtrate was concentrated in vacuo and the residue was purified by silica gel chromatography eluted with PE/DCM(V/V)=1/1 to give the title compound as a light yellow solid (441 mg, 77%). The compound was characterized by the following spectroscopic data: MS (ESI, pos. ion) m/z: 584.1 [M+H]$^+$; and $^1$H NMR (400 MHz, CDCl$_3$): δ 7.95 (dd, J=9.1, 4.3 Hz, 1H), 7.82 (t, J=2.2 Hz, 1H), 7.63 (dd, J=8.7, 2.3 Hz, 1H), 7.40-7.32 (m, 2H), 7.14 (td, J=9.0, 2.5 Hz, 1H), 6.92 (d, J=8.7 Hz, 1H), 6.85 (t, J=55.2 Hz, 1H), 4.00 (brs, 4H), 3.92 (s, 3H), 3.19-3.06 (m, 4H).

Step 4) Synthesis of 3-(difluoromethyl)-5-fluoro-1-((4-methoxy-3-(piperazin-1-yl)phenyl) sulfonyl)-1H-indole 2,2,2-Trichloro-1-(4-(5-((3-(difluoromethyl)-5-fluoro-1H-indol-1-yl)sulfonyl)-2-methoxyphenyl)piperazin-1-yl) ethanone (430 mg, 0.74 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (253 mg, 78%). The compound was characterized by the following spectroscopic data: MS (ESI, pos. ion) m/z: 440.2 [M+H]$^+$; $^1$H NMR (400 MHz, CDCl$_3$): δ 7.95 (dd, J=9.1, 4.3 Hz, 1H), 7.82 (t, J=2.2 Hz, 1H), 7.57 (dd, J=8.6, 2.3 Hz, 1H), 7.35 (dd, J=6.6, 2.3 Hz, 2H), 7.12 (td, J=9.0, 2.5 Hz, 1H), 6.87 (d, J=8.7 Hz, 1H), 6.84 (t, J=55.6 Hz, 1H), 3.89 (s, 3H), 3.06-3.00 (m, 8H); and $^{13}$C NMR (100 MHz, CDCl$_3$) δ 159.7 (d, J=240.3 Hz), 157.0, 142.5, 131.4, 129.1, 127.5 (d, J=10.2 Hz), 127.2 (t, J=9.4 Hz), 122.6, 116.4, 114.8 (d, J=9.4 Hz), 113.7 (d, J=26.0 Hz), 111.6 (t, J=233.4 Hz), 111.08, 106.2 (d, J=24.7 Hz), 55.9, 51.3, 45.9.

Example 24 Synthesis of 3-(difluoromethyl)-5-fluoro-1-((4-methoxy-3-(4-methylpiperazin-1-yl) phenyl)sulfonyl)-1H-indole

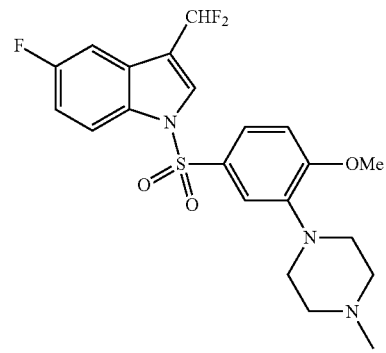 [SMILES: COc1ccc(S(=O)(=O)n2cc(C(F)F)c3cc(F)ccc32)cc1N1CCN(C)CC1]

3-(Difluoromethyl)-5-fluoro-1-((4-methoxy-3-(piperazin-1-yl)phenyl)sulfonyl)-1H-indole (220 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a pale yellow solid (193 mg, 88%). The compound was characterized by the following spectroscopic data: MS (ESI, pos. ion) in/z: 454.0 [M+H]+; $^1$H NMR (400 MHz, CDCl$_3$): δ 7.95 (dd, J=9.1, 4.3 Hz, 1H), 7.82 (t, J=2.2 Hz, 1H), 7.56 (dd, J=8.6, 2.4 Hz, 1H), 7.34 (dt, J=6.0, 3.1 Hz, 2H), 7.12 (td, J=9.0, 2.5 Hz, 1H), 6.83 (t, J=55.6 Hz, 1H), 6.86 (d, J=8.7 Hz, 1H), 3.89 (s, 3H), 3.07 (brs, 4H), 2.61 (brs, 4H), 2.37 (s, 3H); and $^{13}$C NMR (100 MHz, CDCl$_3$): δ 159.7 (d, J=240.4 Hz), 156.9, 142.1, 131.4, 129.1, 127.5 (d, J=10.3 Hz), 127.2 (t, J=9.5 Hz), 122.6, 116.3, 114.8 (d, J=9.3 Hz), 113.7 (d, J=25.6 Hz), 111.6 (t, J=233.5 Hz), 111.0, 106.2 (d, J=24.8 Hz), 55.9, 54.9, 50.0, 45.9.

Example 25 Synthesis of 5-chloro-3-(difluoromethyl)-1-((4-methoxy-3-(piperazin-1-yl) phenyl) sulfonyl)-1H-indole

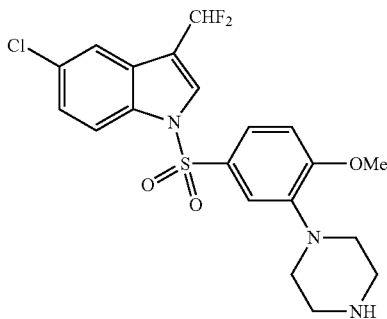 [SMILES: COc1ccc(S(=O)(=O)n2cc(C(F)F)c3cc(Cl)ccc32)cc1N1CCNCC1]

Step 1) Synthesis of 5-chloro-1H-indole-3-carbaldehyde

5-Chloroindole (1.5 g, 9.9 mmol) was reacted with phosphoryl chloride (0.998 mL, 10.9 mmol) in DMF (12 mL) according to the procedure as described in step 1 of example 23 to afford the title compound as a yellow solid (1.76 mg, 99%). The compound was characterized by the following spectroscopic data: MS (ESI, pos. ion) m/z: 180.0 [M+H]$^+$; and $^1$H NMR (400 MHz, DMSO-d$_6$): δ 9.94 (s, 1H), 8.36 (s, 1H), 8.07 (d, J=2.0 Hz, 1H), 7.54 (d, J=8.6 Hz, 1H), 7.28 (dd, J=8.6, 2.1 Hz, 1H).

Step 2) Synthesis of 5-chloro-1-((4-methoxy-3-(4-(2,2,2-trichloroacetyl)piperazin-1-yl)phenyl) sulfonyl)-1H-indole-3-carbaldehyde 5-Chloro-1H-indole-3-carbaldehyde (359 mg, 2.0 mmol) was reacted with sodium hydride (96 mg, 2.4 mmol, 60%) and 4-methoxy-3-(4-(2,2,2-trichloroacetyl)piperazin-1-yl) benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (892 mg, 77%). The compound was characterized by the following spectroscopic data: MS (ESI, pos. ion) m/z: 577.9 [M+H]$^+$; and $^1$H NMR (400 MHz, CDCl$_3$): δ 10.08 (s, 1H), 8.28 (d, J=2.0 Hz, 1H), 8.24 (s, 1H), 7.89 (d, J=8.9 Hz, 1H), 7.68 (dd, J=8.7, 2.3 Hz, 1H), 7.39 (dd, J=10.6, 2.1 Hz, 2H), 6.95 (d, J=8.7 Hz, 1H), 4.03 (brs, 4H), 3.93 (s, 3H), 3.18-3.08 (m, 4H).

Step 3) Synthesis of 2,2,2-trichloro-1-(4-(5-((5-chloro-3-(difluoromethyl)-1H-indol-1-yl) sulfonyl)-2-methoxyphenyl)piperazin-1-yl)ethanone 5-Chloro-1-((4-methoxy-3-(4-(2,2,2-trichloro acetyl)piperazin-1-yl)phenyl)sulfonyl)-1H-indole-3-carbaldehyde (579 mg, 1.0 mmol) was reacted with diethylaminosulphur trifluoride (335 μL, 2.5 mmol) in DCM (12 mL) according to the procedure as described in step 3 of example 23, and the crude product was purified by silica gel chromatography eluted with PE/DCM(V/V)=1/1 to give the title compound as a light yellow solid (487 mg, 81%). The compound was characterized by the following spectroscopic data: MS (ESI, pos. ion) m/z: 600.0 [M+H]$^+$; and $^1$H NMR (400 MHz, CDCl$_3$): δ 7.93 (d, J=8.9 Hz, 1H), 7.81 (t, J=2.3 Hz, 1H), 7.69 (d, J=1.6 Hz, 1H), 7.65 (dd, J=8.7, 2.3 Hz, 1H), 7.44 (s, 1H), 7.38 (dd, J=8.9, 2.0 Hz, 1H), 6.94 (d, J=8.7 Hz, 1H), 6.85 (t, J=55.2 Hz, 1H), 4.03 (brs, 4H), 3.93 (s, 3H), 3.21-3.10 (m, 4H).

Step 4) Synthesis of 5-chloro-3-(difluoromethyl)-1-((4-methoxy-3-(piperazin-1-yl)phenyl) sulfonyl)-1H-indole 2,2,2-Trichloro-1-(4-(5-((5-chloro-3-(difluoromethyl)-1H-indol-1-yl)sulfonyl)-2-methoxyphenyl)piperazin-1-yl) ethanone (470 mg, 0.78 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a light yellow solid (274 mg, 77%). The compound was characterized by the following spectroscopic data: MS (ESI, pos. ion) m/z: 456.0 [M+H]$^+$; $^1$H NMR (400 MHz, CDCl$_3$): δ 7.92 (d, J=8.9 Hz, 1H), 7.81 (t, J=2.3 Hz, 1H), 7.67 (d, J=1.6 Hz, 1H), 7.57 (dd, J=8.7, 2.4 Hz, 1H), 7.35 (dd, J=7.4, 2.1 Hz, 2H), 6.87 (d, J=8.7 Hz, 1H), 6.84 (t, J=55.2 Hz, 1H), 3.88 (s, 3H), 3.08-3.02 (m, 8H); and $^{13}$C NMR (100 MHz, CDCl$_3$): δ 157.1, 142.4, 133.4, 129.8, 129.0, 127.7, 126.9 (t, J=9.4 Hz), 125.8, 122.8, 120.2, 116.4, 115.8 (t, J=26.3 Hz), 114.7, 111.5 (t, J=233.6 Hz), 111.1, 56.0, 51.0, 45.7.

Example 26 Synthesis of 5-chloro-3-(difluoromethyl)-1-((4-methoxy-3-(4-methylpiperazin-1-yl) phenyl)sulfonyl)-1H-indole

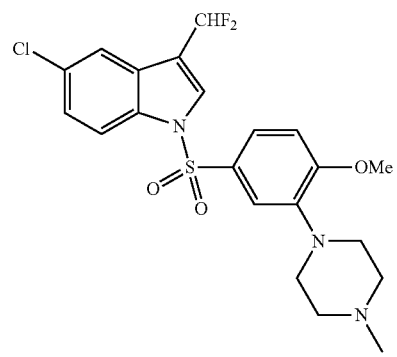

5-Chloro-3-(difluoromethyl)-1-((4-methoxy-3-(piperazin-1-yl)phenyl)sulfonyl)-1H-indole (228 mg, 0.5 mmol)

was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (216 mg, 92%). The compound was characterized by the following spectroscopic data: MS (ESI, pos. ion) m/z: 470.2 [M+H]$^+$; $^1$H NMR (400 MHz, CDCl$_3$): δ 7.93 (d, J=8.9 Hz, 1H), 7.80 (t, J=2.3 Hz, 1H), 7.67 (d, J=1.5 Hz, 1H), 7.57 (dd, J=8.6, 2.4 Hz, 1H), 7.37-7.32 (m, 2H), 6.87 (d, J=8.7 Hz, 1H), 6.83 (t, J=55.2 Hz, 1H), 3.89 (s, 3H), 3.07 (brs, 4H), 2.61 (brs, 4H), 2.38 (s, 3H); and $^{13}$C NMR (100 MHz, CDCl$_3$): δ 157.0, 142.1, 133.4, 129.8, 129.1, 127.7, 126.9 (t, J=9.5 Hz), 125.8, 122.6, 120.1, 116.3, 114.7, 111.5 (t, J=233.6 Hz), 111.1, 56.0, 54.9, 50.0, 45.9.

Example 27 Synthesis of 5-bromo-3-(difluoromethyl)-1-((4-methoxy-3-(piperazin-1-yl) phenyl) sulfonyl)-1H-indole

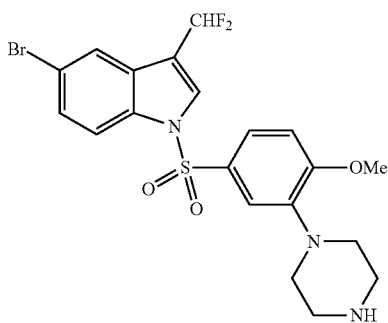

Step 1) Synthesis of 5-bromo-1H-indole-3-carbaldehyde

5-Bromoindole (1.5 g, 7.6 mmol) was reacted with phosphoryl chloride (0.998 mL, 10.9 mmol) in DMF (12 mL) according to the procedure as described in step 1 of example 23 to afford the title compound as a yellow solid (1.63 g, 96%). The compound was characterized by the following spectroscopic data: MS (ESI, pos. ion) m/z: 224.0 [M+H]$^+$; and $^1$H NMR (400 MHz, DMSO-d$_6$): δ 9.93 (s, 1H), 8.33 (s, 1H), 8.22 (d, J=1.8 Hz, 1H), 7.50 (d, J=8.6 Hz, 1H), 7.38 (dd, J=8.6, 1.9 Hz, 1H).

Step 2) Synthesis of 5-bromo-1-((4-methoxy-3-(4-(2,2,2-trichloroacetyl)piperazin-1-yl)phenyl) sulfonyl)-1H-indole-3-carbaldehyde 5-Bromo-1H-indole-3-carbaldehyde (448 mg, 2.0 mmol) was reacted with sodium hydride (96 mg, 2.4 mmol, 60%) and 4-methoxy-3-(4-(2,2,2-trichloroacetyl)piperazin-1-yl) benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (1.02 g, 82%). The compound was characterized by the following spectroscopic data: MS (ESI, pos. ion) m/z: 622.1 [M+H]$^+$; and $^1$H NMR (400 MHz, DMSO-d$_6$): δ 10.03 (s, 1H), 8.94 (s, 1H), 8.23 (d, J=1.9 Hz, 1H), 7.97 (d, J=8.9 Hz, 1H), 7.79 (dd, J=8.7, 2.3 Hz, 1H), 7.62 (dd, J=8.9, 2.0 Hz, 1H), 7.46 (d, J=2.3 Hz, 1H), 7.18 (d, J=8.8 Hz, 1H), 3.86 (brs, 7H), 3.11 (brs, 4H).

Step 3) Synthesis of 2,2,2-trichloro-1-(4-(5-((3-(difluoromethyl)-5-bromo-1H-indol-1-yl) sulfonyl)-2-methoxyphenyl)piperazin-1-yl)-ethanone 5-Bromo-1-((4-methoxy-3-(4-(2,2,2-trichloroacetyl)piperazin-1-yl)phenyl)sulfonyl)-1H-indole-3-carbaldehyde (624 mg, 1.0 mmol) was reacted with diethylaminosulphur trifluoride (335 μL, 2.5 mmol) in DCM (12 mL) according to the procedure as described in step 3 of example 23, and the crude product was purified by silica gel chromatography eluted with PE/DCM(V/V)=1/1 to give the title compound as a light yellow solid (510 mg, 79%). The compound was characterized by the following spectroscopic data: MS (ESI, pos. ion) m/z: 644.0 [M+H]$^+$; and $^1$H NMR (400 MHz, CDCl$_3$): δ 7.85 (d, J=8.9 Hz, 1H), 7.81 (s, 1H), 7.77 (t, J=2.1 Hz, 1H), 7.59 (dd, J=8.7, 2.3 Hz, 1H), 7.47 (dd, J=8.9, 1.8 Hz, 1H), 7.30 (d, J=2.3 Hz, 1H), 6.89 (d, J=8.7 Hz, 1H), 6.82 (t, J=55.4 Hz, 1H), 3.97-3.89 (m, 7H), 3.10 (t, J=4.9 Hz, 4H).

Step 4) Synthesis of 3-(difluoromethyl)-5-bromo-1-((4-methoxy-3-(piperazin-1-yl)phenyl) sulfonyl)-1H-indole 2,2,2-Trichloro-1-(4-(5-((3-(difluoromethyl)-5-bromo-1H-indol-1-yl)sulfonyl)-2-methoxyphenyl)piperazin-1-yl) ethanone (510 mg, 0.79 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (276 mg, 70%). The compound was characterized by the following spectroscopic data: MS (ESI, pos. ion) m/z: 500.0 [M+H]$^+$; $^1$H NMR (400 MHz, CDCl$_3$): δ 7.85 (d, J=8.9 Hz, 1H), 7.81 (d, J=1.2 Hz, 1H), 7.76 (t, J=2.2 Hz, 1H), 7.54 (dd, J=8.6, 2.4 Hz, 1H), 7.46 (dd, J=8.9, 1.9 Hz, 1H), 7.31 (d, J=2.4 Hz, 1H), 6.84 (d, J=8.7 Hz, 1H), 6.81 (t, J=55.4 Hz, 1H), 3.86 (s, 3H), 3.03-3.01 (m, 4H), 2.98-2.97 (m, 4H); and $^{13}$C NMR (100 MHz, CDCl$_3$): δ 157.1, 142.6, 133.8, 129.0, 128.5, 128.2, 126.7 (t, J=9.5 Hz), 123.2, 122.6, 117.4, 116.3, 115.7 (t, J=26.4 Hz), 115.1, 111.5 (t, J=233.6 Hz), 111.1, 56.0, 51.4, 45.9.

Example 28 Synthesis of 3-(difluoromethyl)-5-bromo-1-((4-methoxy-3-(4-methylpiperazin-1-yl) phenyl)sulfonyl)-1H-indole

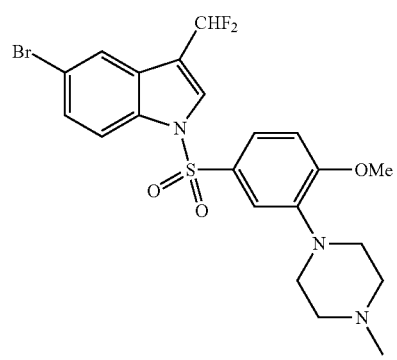 [SMILES: COc1ccc(S(=O)(=O)n2cc(C(F)F)c3cc(Cl)ccc32)cc1N1CCN(C)CC1]

3-(Difluoromethyl)-5-bromo-1-((4-methoxy-3-(piperazin-1-yl)phenyl)sulfonyl)-1H-indole (250 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (226 mg, 88%). The compound was characterized by the following spectroscopic data: MS (ESI, pos. ion) m/z: 514.1 [M+H]+; 1H NMR (400 MHz, CDCl3): δ 7.85 (d, J=8.9 Hz, 1H), 7.81 (s, 1H), 7.76 (t, J=2.1 Hz, 1H), 7.53 (dd, J=8.6, 2.3 Hz, 1H), 7.46 (dd, J=8.9, 1.8 Hz, 1H), 7.32 (d, J=2.3 Hz, 1H), 6.84 (d, J=8.7 Hz, 1H), 6.81 (t, J=55.4 Hz, 1H), 3.87 (s, 3H), 3.04 (brs, 4H), 2.57 (brs, 4H), 2.34 (s, 3H); and 13C NMR (100 MHz, CDCl3): δ 157.0, 142.2, 133.8, 129.0, 128.5, 128.2, 126.7 (t, J=9.4 Hz), 123.2, 122.6, 117.4, 116.3, 115.7 (t, J=26.3 Hz), 115.1, 111.4 (t, J=233.9 Hz), 111.1, 56.0, 54.9, 50.1, 46.0.

Example 29 Synthesis of 3-(difluoromethyl)-6-fluoro-1-((4-methoxy-3-(piperazin-1-yl) phenyl)sulfonyl)-1H-indole

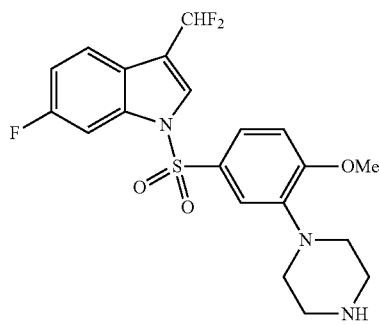 [SMILES: COc1ccc(S(=O)(=O)n2cc(C(F)F)c3ccc(F)cc32)cc1N1CCNCC1]

Step 1) Synthesis of 6-fluoro-1H-indole-3-carbaldehyde

6-Fluoroindole (1.5 g, 11.1 mmol) was reacted with phosphoryl chloride (0.998 mL, 10.9 mmol) in DMF (10 mL) according to the procedure as described in step 1 of example 23 to afford the title compound as a yellow solid (1.38 g, 76%). The compound was characterized by the following spectroscopic data: MS (ESI, pos. ion) m/z: 164.0 [M+H]+; and 1H NMR (400 MHz, DMSO-d6): δ 9.92 (s, 1H), 8.29 (s, 1H), 8.07 (dd, J=8.7, 5.6 Hz, 1H), 7.31 (dd, J=9.7, 2.3 Hz, 1H), 7.11-7.05 (m, 1H).

Step 2) Synthesis of 6-fluoro-1-((4-methoxy-3-(4-(2,2,2-trichloroacetyl)piperazin-1-yl)phenyl) sulfonyl)-1H-indole-3-carbaldehyde 6-Fluoro-1H-indole-3-carbaldehyde (326 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (923 mg, 82%). The compound was characterized by the following spectroscopic data: MS (ESI, pos. ion) m/z: 562.0 [M+H]+; and 1H NMR (400 MHz, CDCl3): δ 10.08 (s, 1H), 8.23 (dd, J=8.8, 5.2 Hz, 1H), 8.21 (s, 1H), 7.73-7.64 (m, 2H), 7.39 (d, J=2.4 Hz, 1H), 7.15 (td, J=9.2, 2.4 Hz, 1H), 6.96 (d, J=8.8 Hz, 1H), 3.99 (brs, 4H), 3.94 (s, 3H), 3.15 (t, J=4.8 Hz, 4H).

Step 3) Synthesis of 2,2,2-trichloro-1-(4-(5-((3-(difluoromethyl)-6-fluoro-1H-indol-1-yl) sulfonyl)-2-methoxyphenyl)piperazin-1-yl)ethanone 6-Fluoro-1-((4-methoxy-3-(4-(2,2,2-trichloro acetyl)piperazin-1-yl)phenyl)sulfonyl)-1H-indole-3-carbaldehyde (720 mg, 1.28 mmol) was reacted with diethylaminosulphur trifluoride (335 µL, 2.5 mmol) in DCM (12 mL) according to the procedure as described in step 3 of example 23, and the crude product was purified by silica gel chromatography eluted with PE/DCM(V/V)=1/1 to give the title compound as a light yellow solid (554 mg, 74%). The compound was characterized by the following spectroscopic data: MS (ESI, pos. ion) m/z: 583.9 [M+H]+; and 1H NMR (400 MHz, CDCl3): δ 7.77 (t, J=2.4 Hz, 1H), 7.72 (dd, J=9.6, 2.4 Hz, 1H), 7.66 (d, J=2.4 Hz, 1H), 7.63 (d, J=2.4 Hz, 1H), 7.34 (d, J=2.4 Hz, 1H), 7.09 (td, J=8.8, 2.4 Hz, 1H), 6.93 (d, J=8.8 Hz, 1H), 6.85 (t, J=55.2 Hz, 1H), 4.03-3.96 (br, 4H), 3.93 (s, 3H), 3.13 (t, J=4.2 Hz, 4H).

Step 4) Synthesis of 3-(difluoromethyl)-6-fluoro-1-((4-methoxy-3-(piperazin-1-yl) phenyl)sulfonyl)-1H-indole 2,2,2-Trichloro-1-(4-(5-((3-(difluoromethyl)-6-fluoro-1H-indol-1-yl)sulfonyl)-2-methoxyphenyl)piperazin-1-yl)ethanone (554 mg, 0.95 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (363 mg, 87%). The compound was characterized by the following spectroscopic data: MS (ESI, pos. ion) m/z: 440.0 [M+H]+; 1H NMR (600 MHz, CDCl3): δ 7.77 (s, 1H), 7.72 (dd, J=9.5, 2.0 Hz, 1H), 7.63 (dd, J=8.6, 5.2 Hz, 1H), 7.59 (dd, J=8.7, 2.2 Hz, 1H), 7.35 (d, J=2.2 Hz, 1H), 7.06 (td, J=9.0, 2.1 Hz, 1H), 6.88 (d, J=8.7 Hz, 1H), 6.85 (t, J=55.8 Hz, 1H), 3.89 (s, 3H), 3.08-2.98 (m, 8H); and 13C NMR (150 MHz, CDCl3): δ 161.2 (d, J=242.1 Hz), 157.1, 142.5, 135.3 (d, J=12.5 Hz), 128.9, 125.9 (td, J=13.4, 3.8 Hz), 122.9, 122.7, 121.4 (d, J=9.9 Hz), 116.4, 116.2 (t, J=26.1 Hz), 112.5 (d, J=24.2 Hz), 111.7 (t, J=233.2 Hz), 111.1, 101.0 (d, J=28.4 Hz), 56.0, 51.3, 45.9.

Example 30 Synthesis of 3-(difluoromethyl)-6-fluoro-1-((4-methoxy-3-(4-methylpiperazin-1-yl) phenyl)sulfonyl)-1H-indole

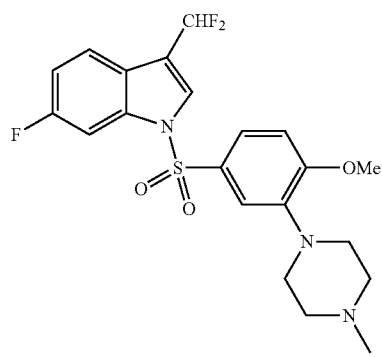 [SMILES: COc1ccc(S(=O)(=O)n2cc(C(F)F)c3ccc(F)cc32)cc1N1CCN(C)CC1]

3-(Difluoromethyl)-6-fluoro-1-((4-methoxy-3-(piperazin-1-yl)phenyl)sulfonyl)-1H-indole (220 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (140 mg, 62%). The compound was characterized by the following spectroscopic data: MS (ESI, pos. ion) m/z: 454.1 [M+H]$^+$; $^1$H NMR (400 MHz, CDCl$_3$): δ 7.77 (t, J=2.4 Hz, 1H), 7.72 (dd, J=9.6, 2.2 Hz, 1H), 7.65-7.55 (m, 2H), 7.35 (d, J=2.4 Hz, 1H), 7.05 (td, J=9.0, 2.3 Hz, 1H), 6.87 (d, J=8.7 Hz, 1H), 6.84 (t, J=55.2 Hz, 1H), 3.89 (s, 3H), 3.08 (brs, 4H), 2.61 (brs, 4H), 2.37 (s, 3H); and $^{13}$C NMR (100 MHz, CDCl$_3$): δ 161.2 (d, J=242.2 Hz), 157.0, 142.1, 135.3 (d, J=12.4 Hz), 129.0, 125.9 (td, J=9.7, 3.7 Hz), 122.9, 122.7, 121.4 (d, J=9.9 Hz), 116.3, 112.5 (d, J=24.3 Hz), 111.6 (t, J=233.2 Hz), 111.1, 101.0 (d, J=28.3 Hz), 56.0, 54.9, 49.9, 45.9.

Example 31 Synthesis of 6-chloro-3-(difluoromethyl)-1-((4-methoxy-3-(piperazin-1-yl) phenyl)sulfonyl)-1H-indole

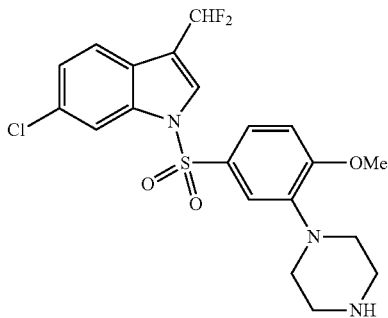 [SMILES: COc1ccc(S(=O)(=O)n2cc(C(F)F)c3ccc(Cl)cc32)cc1N1CCNCC1]

Step 1) Synthesis of 6-chloro-1H-indole-3-carbaldehyde

6-Chloroindole (1.5 g, 9.9 mmol) was reacted with phosphoryl chloride (0.998 mL, 10.9 mmol) in DMF (12 mL) according to the procedure as described in step 1 of example 23 to afford the title compound as a yellow solid (1.62 g, 91%). The compound was characterized by the following spectroscopic data: MS (ESI, pos. ion) m/z: 180.0 [M+H]$^+$; and $^1$H NMR (400 MHz, DMSO-d$_6$): δ 9.93 (s, 1H), 8.33 (s, 1H), 8.07 (d, J=8.4 Hz, 1H), 7.58 (d, J=1.7 Hz, 1H), 7.25 (dd, J=8.4, 1.8 Hz, 1H).

Step 2) Synthesis of 6-chloro-1-((4-methoxy-3-(4-(2,2,2-trichloroacetyl)piperazin-1-yl) phenyl)sulfonyl)-1H-indole-3-carbaldehyde 6-Chloro-1H-indole-3-carbaldehyde (359 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (1.01 g, 87%). The compound was characterized by the following spectroscopic data: MS (ESI, pos. ion) m/z: 579.9 [M+H]$^+$; and $^1$H NMR (400 MHz, CDCl$_3$): δ 10.08 (s, 1H), 8.21 (t, J=6 Hz, 2H), 8.00 (d, J=1.2 Hz, 1H), 7.70 (dd, J=8.8, 2.4 Hz, 1H), 7.46 (d, J=1.6 Hz, 1H), 7.37 (dd, J=8.8, 1.6 Hz, 1H), 6.97 (d, J=8.8 Hz, 1H), 3.98 (brs, 4H), 3.94 (s, 3H), 3.16 (t, J=4.8 Hz, 4H).

Step 3) Synthesis of 2,2,2-trichloro-1-(4-(5-((3-(difluoromethyl)-6-chloro-1H-indol-1-yl) sulfonyl)-2-methoxyphenyl)piperazin-1-yl)ethanone 6-Chloro-1-((4-methoxy-3-(4-(2,2,2-trichloro acetyl)piperazin-1-yl)sulfonyl)-1H-indole-3-carbaldehyde (579 mg, 1.0 mmol) was reacted with diethylaminosulphur trifluoride (335 μL, 2.5 mmol) in DCM (12 mL) according to the procedure as described in step 3 of example 23, and the crude product was purified by silica gel chromatography eluted with PE/DCM(V/V)=1/1 to give the title compound as a light yellow solid (457 mg, 76%). The compound was characterized by the following spectroscopic data: MS (ESI, pos. ion) m/z: 600.7 [M+H]$^+$; and $^1$H NMR (400 MHz, CDCl$_3$): δ 8.04 (d, J=1.6 Hz, 1H), 7.77 (t, J=2.2 Hz, 1H), 7.65-7.61 (m, 2H), 7.39 (d, J=2.4 Hz, 1H), 7.30 (dd, J=8.4, 1.6 Hz, 1H), 6.94 (d, J=8.4 Hz, 1H), 6.85 (t, J=55.6 Hz, 1H), 4.01-4.02 (m, 4H), 3.93 (s, 3H), 3.14 (t, J=5.0 Hz, 4H).

Step 4) Synthesis of 3-(difluoromethyl)-6-chloro-1-((4-methoxy-3-(piperazin-1-yl)phenyl) sulfonyl)-1H-indole 2,2,2-Trichloro-1-(4-(5-((3-(difluoromethyl)-6-chloro-1H-indol-1-yl)sulfonyl)-2-methoxyphenyl)piperazin-1-yl)ethanone (440 mg, 0.73 mmol) was reacted with potassium hydroxide solution (134 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (273 mg, 82%). The compound was characterized by the following spectroscopic data: MS (ESI, pos. ion) m/z: 456.0 [M+H]$^+$; $^1$H NMR (600 MHz, CDCl$_3$): δ 8.03 (s, 1H), 7.77 (s, 1H), 7.61-7.57 (m, 2H), 7.38 (d, J=2.0 Hz, 1H), 7.28 (s, 1H), 6.89 (d, J=8.7 Hz, 1H), 6.84 (t, J=55.2 Hz, 1H), 3.90 (s, 3H), 3.11-3.01 (m, 8H); and $^{13}$C NMR (150 MHz, CDCl$_3$) δ 157.1, 142.4, 135.3, 131.6, 128.9, 126.1 (t, J=9.6 Hz), 125.1, 124.6, 122.7, 121.3, 116.5, 116.2 (t, J=26.3 Hz), 113.9, 111.6 (t, J=233.4 Hz), 111.2, 56.0, 51.2, 45.8.

Example 32 Synthesis of 3-(difluoromethyl)-6-chloro-1-((4-methoxy-3-(4-methylpiperazin-1-yl) phenyl)sulfonyl)-1H-indole

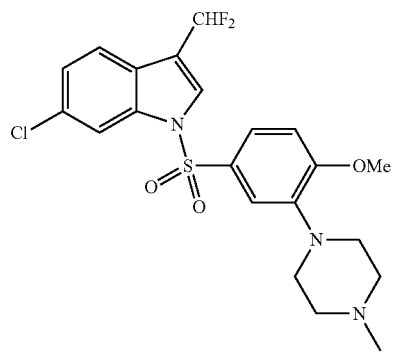 [SMILES: COc1ccc(S(=O)(=O)n2cc(C(F)F)c3ccc(Cl)cc32)cc1N1CCN(C)CC1]

3-(Difluoromethyl)-6-chloro-1-((4-methoxy-3-(piperazin-1-yl)phenyl)sulfonyl)-1H-indole (228 mg, 0.5 mmol) was reacted with sodium cyanoborohydride (85 mg, 1.35 mmol) and formaldehyde (40%, 0.112 mL, 1.6 mmol) in methanol (10 mL) according to the procedure as described in example 2, and the crude product was purified by silica gel chromatography eluted with DCM/methanol(V/V)=50/1 to give the title compound as a white solid (181 mg, 77%). The compound was characterized by the following spectroscopic data: MS (ESI, pos. ion) m/z: 470.2 [M+H]$^+$; $^1$H NMR (600 MHz, CDCl$_3$): δ 8.03 (s, 1H), 7.77 (s, 1H), 7.59 (dd, J=13.0, 8.7 Hz, 2H), 7.38 (s, 1H), 7.28 (s, 1H), 6.88 (d, J=8.6 Hz, 1H), 6.84 (t, J=55.2 Hz, 1H), 3.90 (s, 3H), 3.09 (brs, 4H), 2.60 (brs, 4H), 2.37 (s, 3H); and $^{13}$C NMR (150 MHz, CDCl$_3$): δ 157.0, 142.1, 135.4, 131.7, 128.9, 126.1 (t, J=9.6 Hz), 125.1, 124.6, 122.6, 121.3, 116.4, 116.2 (t, J=26.3 Hz), 113.9, 111.6 (t, J=233.4 Hz), 111.1, 56.0, 54.9, 50.1, 46.1.

Example 33 Synthesis of 3-(difluoromethyl)-6-bromo-1-((4-methoxy-3-(piperazin-1-yl) phenyl) sulfonyl)-1H-indole

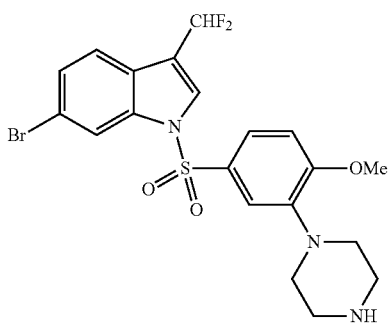

Step 1) Synthesis of 6-bromo-1H-indole-3-carbaldehyde

6-Bromoindole (1.5 g, 7.65 mmol) was reacted with phosphoryl chloride (0.998 mL, 10.9 mmol) in DMF (12 mL) according to the procedure as described in step 1 of example 23 to afford the title compound as a yellow solid (1.47 g, 86%). The compound was characterized by the following spectroscopic data: MS (ESI, pos. ion) m/z: 224.0 [M+H]$^+$; and $^1$H NMR (400 MHz, DMSO-d$_6$): δ 9.93 (s, 1H), 8.31 (s, 1H), 8.02 (d, J=8.4 Hz, 1H), 7.71 (d, J=1.5 Hz, 1H), 7.36 (dd, J=8.4, 1.6 Hz, 1H).

Step 2) Synthesis of 6-bromo-1-((4-methoxy-3-(4-(2,2,2-trichloroacetyl)piperazin-1-yl)phenyl) sulfonyl)-1H-indole-3-carbaldehyde 6-Bromo-1H-indole-3-carbaldehyde (448 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.05 g, 2.4 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (1.01 g, 81%). The compound was characterized by the following spectroscopic data: MS (ESI, pos. ion) m/z: 621.9 [M+H]$^+$; and $^1$H NMR (400 MHz, DMSO-d$_6$): δ 10.04 (s, 1H), 8.91 (s, 1H), 8.14 (d, J=1.6 Hz, 1H), 8.05 (d, J=8.5 Hz, 1H), 7.82 (dd, J=8.7, 2.4 Hz, 1H), 7.58 (dd, J=8.5, 1.7 Hz, 1H), 7.50 (d, J=2.4 Hz, 1H), 7.21 (d, J=8.9 Hz, 1H), 3.88 (brs, 7H), 3.12 (s, 4H).

Step 3) Synthesis of 2,2,2-trichloro-1-(4-(5-((3-(difluoromethyl)-6-bromo-1H-indol-1-yl)sulfonyl)-2-methoxyphenyl)piperazin-1-yl)-ethanone 6-Bromo-1-((4-methoxy-3-(4-(2,2,2-trichloro acetyl)piperazin-1-yl)phenyl)sulfonyl)-1H-indole-3-carbaldehyde (624 mg, 1.0 mmol) was reacted with diethylaminosulphur trifluoride (335 µL, 2.5 mmol) in DCM (12 mL) according to the procedure as described in step 3 of example 23, and the crude product was purified by silica gel chromatography eluted with PE/DCM(V/V)=1/1 to give the title compound as a light yellow solid (420 mg, 65%). The compound was characterized by the following spectroscopic data: MS (ESI, pos. ion) m/z: 644.0 [M+H]$^+$; and $^1$H NMR (400 MHz, CDCl$_3$): δ 8.21 (d, J=1.4 Hz, 1H), 7.75 (t, J=2.2 Hz, 1H), 7.62 (dd, J=8.7, 2.3 Hz, 1H), 7.56 (d, J=8.4 Hz, 1H), 7.43 (dd, J=8.5, 1.6 Hz, 1H), 7.39 (d, J=2.3 Hz, 1H), 6.93 (d, J=8.7 Hz, 1H), 6.85 (t, J=55.2 Hz, 1H), 3.93 (brs, 7H), 3.19-3.07 (m, 4H).

Step 4) Synthesis of 3-(difluoromethyl)-6-bromo-1-((4-methoxy-3-(piperazin-1-yl)phenyl) sulfonyl)-1H-indole 2,2,2-Trichloro-1-(4-(5-((3-(difluoromethyl)-6-bromo-1H-indol-1-yl)sulfonyl)-2-methoxyphenyl)piperazin-1-yl) ethanone (440 mg, 0.62 mmol) was reacted with potassium hydroxide solution (112 mg of potassium hydroxide solid, 2.0 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (183 mg, 59%). The compound was characterized by the following spectroscopic data: MS (ESI, pos. ion) m/z: 500.2 [M+H]$^+$; $^1$H NMR (400 MHz, CDCl$_3$): δ 8.21 (d, J=1.4 Hz, 1H), 7.76 (t, J=2.3 Hz, 1H), 7.57 (dd, J=12.3, 5.7 Hz, 2H), 7.46-7.36 (m, 2H), 6.89 (d, J=8.7 Hz, 1H), 6.84 (t, J=55.6 Hz, 1H), 3.90 (s, 3H), 3.06-3.04 (m, 8H); and $^{13}$C NMR (100 MHz, CDCl$_3$): δ 157.1, 142.5, 135.7, 128.9, 127.2, 126.1 (t, J=9.5 Hz), 125.5, 122.6, 121.6, 119.2, 116.9, 116.6, 111.5 (t, J=233.5 Hz), 111.2, 56.0, 51.3, 45.9.

Example 34 Synthesis of 3-(difluoromethyl)-6-bromo-1-((4-methoxy-3-(4-methylpiperazin-1-yl) phenyl)sulfonyl)-1H-indole

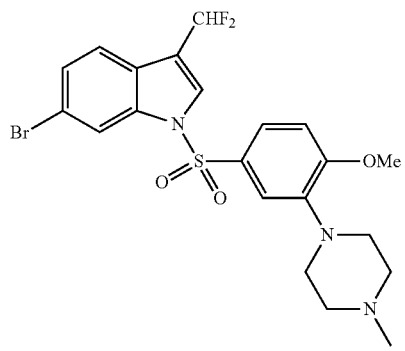 [SMILES: COc1ccc(S(=O)(=O)n2cc(C(F)F)c3ccc(Br)cc32)cc1N1CCN(C)CC1]

3-(Difluoromethyl)-6-bromo-1-((4-methoxy-3-(piperazin-1-yl)phenyl)sulfonyl)-1H-indole (150 mg, 0.3 mmol) was reacted with sodium cyanoborohydride (63 mg, 1.0 mmol) and formaldehyde (40%, 0.112 mL, 1.6 mmol) in methanol (5 mL) according to the procedure as described in example 2, and the crude product was purified by silica gel chromatography eluted with DCM/methanol(V/V)=50/1 to give the title compound as a light yellow solid (139 mg, 90%). The compound was characterized by the following spectroscopic data: MS (ESI, pos. ion) m/z: 514.1 [M+H]$^+$; $^1$H NMR (400 MHz, CDCl$_3$): δ 8.20 (d, J=1.4 Hz, 1H), 7.76 (t, J=2.3 Hz, 1H), 7.60-7.53 (m, 2H), 7.42 (dd, J=8.5, 1.7 Hz, 1H), 7.39 (d, J=2.4 Hz, 1H), 6.89 (d, J=8.7 Hz, 1H), 6.84 (t, J=55.6 Hz, 1H), 3.90 (s, 3H), 3.11 (brs, 4H), 2.64 (brs, 4H), 2.39 (s, 3H); and $^{13}$C NMR (100 MHz, CDCl$_3$) δ 157.0, 142.0, 135.7, 128.9, 127.2, 126.1, 122.6, 121.6, 119.3, 116.9, 116.5, 111.5 (t, J=233.5 Hz), 111.2, 56.0, 54.9, 49.9, 45.9.

Example 35 Synthesis of 3-(difluoromethyl)-1-((3-(4-ethylpiperazin-1-yl)-4-methoxyphenyl)sulfonyl)-6-fluoro-1H-indole

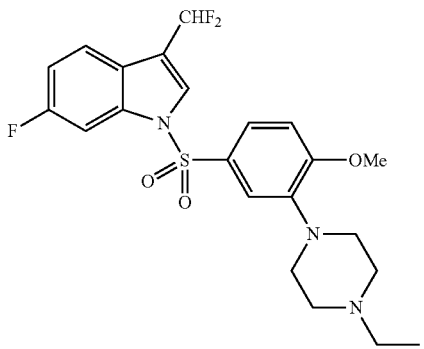 [SMILES: CCN1CCN(c2cc(S(=O)(=O)n3cc(C(F)F)c4ccc(F)cc43)ccc2OC)CC1]

To 10 mL of acetone were added 3-(difluoromethyl)-6-fluoro-1-((4-methoxy-3-(piperazin-1-yl) phenyl)sulfonyl)-1H-indole (193 mg, 0.44 mmol), K$_2$CO$_3$ (121 mg, 0.88 mmol) and bromoethane (100 μL, 1.35 mmol). The mixture was reacted at 25° C. for 20 hours. After the reaction, to the mixture was added dichlormethane (40 mL) and the mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA(V/V)=1/1 to give the title compound as a yellow solid (205 mg, 89%). The compound was characterized by the following spectroscopic data: MS (ESI, pos. ion) m/z: 468.0 [M+H]$^+$; $^1$H NMR (600 MHz, CDCl$_3$): δ 7.77 (s, 1H), 7.72 (dd, J=7.8, 1.8 Hz, 1H), 7.63 (dd, J=9.0, 5.4 Hz, 1H), 7.60 (dd, J=9.0, 2.4 Hz, 1H), 7.35 (d, J=1.8 Hz, 1H), 7.07 (td, J=9.0, 2.4 Hz, 1H), 6.89 (d, J=9.0 Hz, 1H), 6.85 (d, J=55.8 Hz, 1H), 3.90 (s, 3H), 3.11 (brs, 4H), 2.66 (brs, 4H), 2.53 (q, J=7.2 Hz, 2H), 1.16 (t, J=7.2 Hz, 3H); and $^{13}$C NMR (CDCl$_3$, 150 MHz): δ 161.2 (d, J=242.1 Hz), 157.0, 142.1, 135.3 (d, J=12.45 Hz), 129.0, 125.9 (td, J=3.75 Hz), 122.9 (d, J=1.8 Hz), 122.8, 121.5 (d, J=9.9 Hz), 116.3, 116.3 (t, J=26.1 Hz), 112.5 (d, J=24.3 Hz), 111.7 (t, J=233.1 Hz), 111.1, 101.1 (d, J=28.2 Hz), 56.0, 52.6, 52.3, 50.0, 11.8.

Example 36 Synthesis of 3-(difluoromethyl)-6-fluoro-1-((4-methoxy-3-(4-neopentylpiperazin-1-yl)phenyl)sulfonyl)-1H-indole

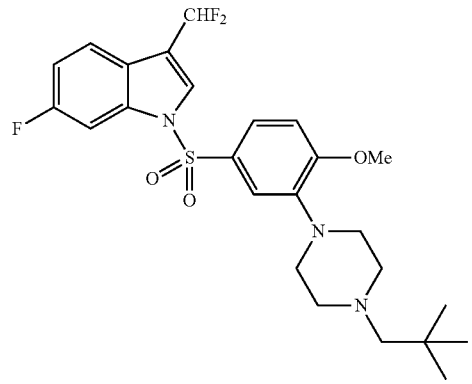 [SMILES: COc1ccc(S(=O)(=O)n2cc(C(F)F)c3ccc(F)cc32)cc1N1CCN(CC(C)(C)C)CC1]

3-(Difluoromethyl)-6-fluoro-1-((4-methoxy-3-(piperazin-1-yl)phenyl)sulfonyl)-1H-indole (219 mg, 0.5 mmol) was reacted with sodium cyanoborohydride (126 mg, 2.0 mmol) and pivalaldehyde (172 mg, 2.0 mmol) in methanol (10 mL) according to the procedure as described in example 2, and the crude product was purified by silica gel chromatography eluted with PE/EA(V/V)=3/1 to give the title compound as a white solid (221 mg, 87%). The compound was characterized by the following spectroscopic data: MS (ESI, pos. ion) m/z: 510.0 [M+H]$^+$; $^1$H NMR (600 MHz, CDCl$_3$): δ 7.75 (s, 1H), 7.70 (dd, J=9.6, 1.8 Hz, 1H), 7.61 (m, 1H), 7.56-7.54 (m, 1H), 7.34 (d, J=1.8 Hz, 1H), 7.05 (td, J=9.0, 1.8 Hz, 1H), 6.85 (d, J=9.0 Hz, 1H), 6.83 (t, J=55.2 Hz, 1H), 3.87 (s, 3H), 3.01 (brs, 4H), 2.67 (brs, 4H), 2.11 (s, 2H), 0.90 (s, 9H); and $^{13}$C NMR (150 MHz, CDCl$_3$): 161.3 (d, J=241.8 Hz), 157.1, 142.5, 135.3 (d, J=12.45 Hz), 128.9, 125.9 (td, J=3.6 Hz), 122.9, 122.5, 121.4 (d, J=9.9 Hz), 116.4, 116.2 (t, J=26.4 Hz), 112.4 (d, J=24.15 Hz), 111.7 (t, J=233.1 Hz), 111.1, 101.1 (d, J=28.35 Hz), 70.0, 56.0, 55.6, 50.6, 33.2, 27.9.

Example 37 Synthesis of 6-chloro-3-(difluoromethyl)-1-((3-(4-ethylpiperazin-1-yl)-4-methoxyphenyl)sulfonyl)-1H-indole

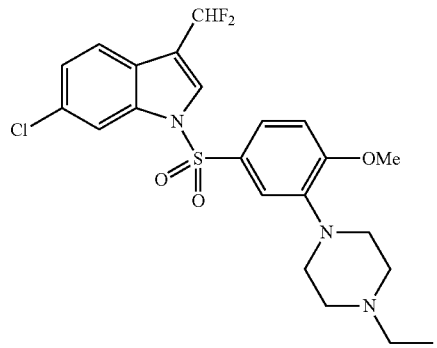 [SMILES: CCN1CCN(c2cc(S(=O)(=O)n3cc(C(F)F)c4ccc(Cl)cc43)ccc2OC)CC1]

6-Chloro-3-(difluoromethyl)-1-((4-methoxy-3-(piperazin-1-yl)phenyl)sulfonyl)-1H-indole (201 mg, 0.44 mmol) was reacted with K$_2$CO$_3$ (121 mg, 0.88 mmol) and bromoethane (100 μL, 1.35 mmol) in acetone (10 mL) according to the procedure as described in example 35, and the crude product was purified by silica gel chromatography eluted with DCM/MeOH(V/V)=50/1 to give the title compound as a light yellow solid (168 mg, 78.8%). The compound was characterized by the following spectroscopic data: MS (ESI, pos. ion) m/z: 484.0 [M+H]$^+$; $^1$H NMR (600 MHz, CDCl$_3$): δ 8.02 (d, J=1.8 Hz, 1H), 7.77 (t, J=2.4 Hz, 1H), 7.59 (m, 2H), 7.37 (d, J=2.4 Hz, 1H), 7.28 (dd, J=6.6, 1.8 Hz, 1H), 6.88 (d, J=8.4 Hz, 1H), 6.84 (t, J=55.2 Hz, 1H), 3.89 (s, 3H), 3.10 (brs, 4H), 2.64 (brs, 4H), 2.50 (q, J=7.2 Hz, 2H), 1.14 (t, J=7.2 Hz, 3H); and $^{13}$C NMR (CDCl$_3$, 150 MHz): δ 157.1, 142.1, 135.4, 131.6, 128.8, 126.1 (t, J=9.6 Hz), 125.1 (t, J=21.0 Hz), 124.6, 122.7 121.3, 116.4, 116.2 (t, J=26.4 Hz), 113.9, 111.6 (t, J=233.4 Hz), 111.1, 56.0, 52.6, 52.3, 50.6, 11.9.

Example 38 Synthesis of 6-chloro-3-(difluoromethyl)-1-((4-methoxy-3-(4-neopentylpiperazin-1-yl)phenyl)sulfonyl)-1H-indole

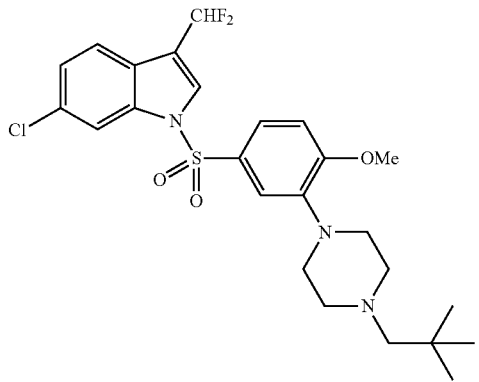 [SMILES: COc1ccc(S(=O)(=O)n2cc(C(F)F)c3ccc(Cl)cc32)cc1N1CCN(CC(C)(C)C)CC1]

3-(Difluoromethyl)-6-chloro-1-((4-methoxy-3-(piperazin-1-yl)phenyl)sulfonyl)-1H-indole (227 mg, 0.5 mmol) was reacted with sodium cyanoborohydride (126 mg, 2.0 mmol) and pivalaldehyde (172 mg, 2.0 mmol) in methanol (10 mL) according to the procedure as described in example 2, and the crude product was purified by silica gel chromatography eluted with PE/EA(V/V)=3/1 to give the title compound as a white solid (185 mg, 70.2%). The compound was characterized by the following spectroscopic data: MS (ESI, pos. ion) m/z: 525.9 [M+H]$^+$; $^1$H NMR (600 MHz, CDCl$_3$): δ 8.03 (d, J=1.2 Hz, 1H), 7.78 (t, J=2.4 Hz, 1H), 7.60 (d, J=8.4 Hz, 1H), 7.57 (dd, J=8.4, 2.1 Hz, 1H), 7.40 (d, J=2.3 Hz, 1H), 7.29 (dd, J=8.4, 1.8 Hz, 1H), 6.88 (d, J=8.7 Hz, 1H), 6.85 (t, J=55.2 Hz, 1H), 3.89 (s, 3H), 3.05 (brs, 4H), 2.70 (brs, 4H), 2.14 (s, 2H), 0.92 (s, 9H); and $^{13}$C NMR (150 MHz, CDCl$_3$): δ157.1, 142.5, 135.4, 131.6, 128.8, 126.2 (t, J=9.6 Hz), 125.1, 124.6, 122.5 120.2, 116.5, 116.12 (t, J=26.4 Hz), 113.9, 111.6 (t, J=233.4 Hz), 111.1, 70.0, 56.0, 55.6, 50.7, 33.2, 27.9.

Example 39 Synthesis of 6-chloro-1-((3-(4-cyclopropylpiperazin-1-yl)-4-methoxyphenyl) sulfonyl)-3-(difluoromethyl)-1H-indole

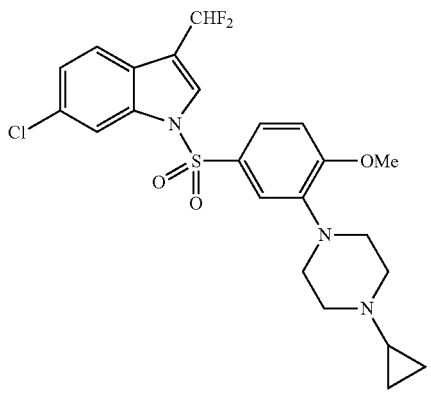 [SMILES: COc1ccc(S(=O)(=O)n2cc(C(F)F)c3ccc(Cl)cc32)cc1N1CCN(C2CC2)CC1]

3-(Difluoromethyl)-6-chloro-1-((4-methoxy-3-(piperazin-1-yl)phenyl)sulfonyl)-1H-indole (227 mg, 0.5 mmol) was dissolved in 10 mL of methanol at 25° C., and acetic acid (1.5 mmol, 90 μL) was added to the solution. Then sodium cyanoborohydride (95 mg, 1.5 mmol) and 1-ethoxy-1-trimethylsiloxylcyclopropane (2 mmol, 432 μL) were added to the mixture slowly. The resulting mixture was reacted for 12 hours, and then quenched with water (10 mL) and sodium carbonate (370 mg, 3.5 mmol). The resulting mixture was extracted with dichloromethane (50 mL×3). The combined organic layers were dried over anhydrous sodium sulfate and filtered. The filtrate was concentrated in vacuo and the residue was purified by silica gel chromatography eluted with PE/EA(V/V)=5/1 to give the title compound as a white solid (129 mg, 51.9%). The compound was characterized by the following spectroscopic data: MS (ESI, pos. ion) m/z: 495.9 [M+H]$^+$; $^1$H NMR (600 MHz, CDCl$_3$): δ 8.02 (d, J=1.2 Hz, 1H), 7.76 (d, J=1.8 Hz, 1H), 7.59 (m, 2H), 7.36 (d, J=1.8 Hz, 1H), 7.28 (d, J=6.6, 1.8 Hz, 1H), 6.89 (d, J=8.4 Hz, 1H), 6.84 (t, J=55.2 Hz, 1H), 3.91 (s, 3H), 3.05 (brs, 4H), 2.81 (brs, 4H), 0.90 (t, J=7.2 Hz, 1H), 0.51 (d, J=6.6 Hz, 4H); and $^{13}$C NMR (150 MHz, CDCl$_3$): δ 157.1, 142.3, 135.4, 131.7, 129.1, 128.9, 126.1 (t, J=9.0 Hz), 125.1, 124.6, 122.7 121.3, 116.4 (t, J=27.0 Hz), 113.9, 111.6 (t, J=232.50 Hz), 111.1, 56.0, 53.2, 50.0, 38.5, 15.7.

Example 40 Synthesis of 6-chloro-3-(difluoromethyl)-1-((3-(4-isopropylpiperazin-1-yl)-4-methoxyphenyl)sulfonyl)-1H-indole

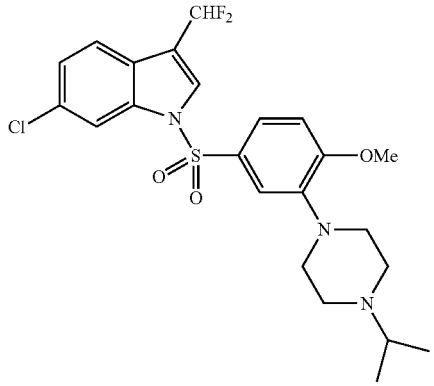 [SMILES: COc1ccc(S(=O)(=O)n2cc(C(F)F)c3ccc(Cl)cc32)cc1N1CCN(C(C)C)CC1]

3-(Difluoromethyl)-6-chloro-1-((4-methoxy-3-(piperazin-1-yl)phenyl)sulfonyl)-1H-indole (456 mg, 1.0 mmol) was reacted with sodium cyanoborohydride (189 mg, 3.0 mmol), acetic acid (180 μL, 3.0 mmol) and acetone (0.59 mL, 3.0 mmol) in methanol (20 mL) according to the procedure as described in example 2, and the crude product was purified by silica gel chromatography eluted with DCM/MeOH(V/V)=50/1 to give the title compound as a white solid (440 mg, 88.3%). The compound was characterized by the following spectroscopic data: MS (ESI, pos. ion) m/z: 498.3 [M+H]$^+$; $^1$H NMR (400 MHz, CDCl$_3$): δ 8.02 (d, J=1.4 Hz, 1H), 7.76 (t, J=2.3 Hz, 1H), 7.63-7.55 (m, 2H), 7.37 (d, J=2.3 Hz, 1H), 7.28 (dd, J=8.2, 2.0 Hz, 1H), 6.88 (d, J=8.7 Hz, 1H), 6.84 (t, J=55.2 Hz, 1H), 3.90 (s, 3H), 3.08-3.07 (m, 4H), 2.77-2.73 (m, 1H), 2.72-2.66 (m, 4H), 1.10 (d, J=6.5 Hz, 6H); and $^{13}$C NMR (100 MHz, CDCl$_3$): δ 157.1, 142.3, 135.4, 131.6, 128.9, 126.1 (t, J=9.5 Hz), 125.1 (t, J=2.2 Hz), 124.5, 122.5, 121.2, 116.3, 116.2 (t, J=26.3 Hz), 113.9, 111.5 (t, J=233.5 Hz), 111.1, 55.9, 54.5, 50.5, 48.6, 18.5.

Example 41 Synthesis of 6-chloro-1-((3-(4-cyclobutylpiperazin-1-yl)-4-methoxyphenyl) sulfonyl)-3-(difluoromethyl)-1H-indole

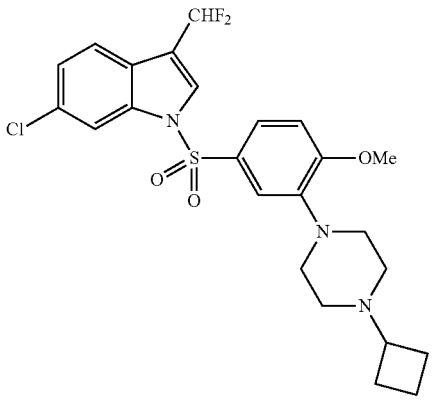 [SMILES: COc1ccc(S(=O)(=O)n2cc(C(F)F)c3ccc(Cl)cc32)cc1N1CCN(C2CCC2)CC1]

3-(Difluoromethyl)-6-chloro-1-((4-methoxy-3-(piperazin-1-yl)phenyl)sulfonyl)-1H-indole (456 mg, 1.0 mmol) was reacted with sodium cyanoborohydride (189 mg, 3.0 mmol), acetic acid (180 μL, 3.0 mmol) and cyclobutanone (223 μL, 3.0 mmol) in methanol (10 mL) according to the procedure as described in example 2, and the crude product was purified by silica gel chromatography eluted with DCM/MeOH(V/V)=50/1 to give the title compound as a white solid (404 mg, 79.2%). The compound was characterized by the following spectroscopic data: MS (ESI, pos. ion) m/z: 509.9 [M+H]+; 1H NMR (600 MHz, CDCl3): δ 8.02 (d, J=1.5 Hz, 1H), 7.76 (t, J=2.0 Hz, 1H), 7.62-7.55 (m, 2H), 7.36 (d, J=2.3 Hz, 1H), 7.28-7.26 (m, 1H), 6.88 (d, J=8.7 Hz, 1H), 6.84 (t, J=55.2 Hz, 1H), 3.89 (s, 3H), 3.08 (brs, 4H), 2.87-2.76 (m, 1H), 2.51 (brs, 4H), 2.11-2.03 (m, 2H), 1.96-1.90 (m, 2H), 1.79-1.68 (m, 2H); and 13C NMR (150 MHz, CDCl3): δ 157.1, 142.3, 135.4, 131.7, 128.9, 126.1 (t, J=9.6 Hz), 125.1, 124.5, 122.6, 121.2, 116.4, 116.2 (t, J=26.1 Hz), 113.9, 111.5 (t, J=233.5 Hz), 111.1, 60.2, 55.9, 49.9, 49.3, 26.9, 14.3.

Example 42 Synthesis of 6-chloro-3-(difluoromethyl)-1-((4-methoxy-3-(4-(oxetan-3-yl) piperazin-1-yl)phenyl)sulfonyl)-1H-indole

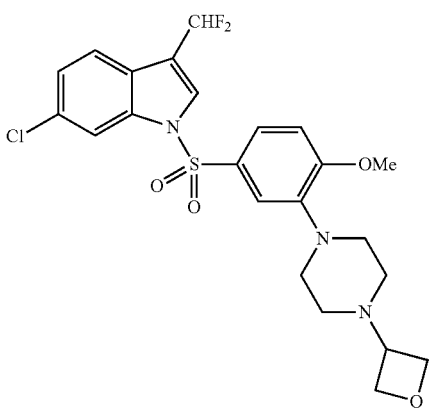 [SMILES: COc1ccc(S(=O)(=O)n2cc(C(F)F)c3ccc(Cl)cc32)cc1N1CCN(C2COC2)CC1]

3-(Difluoromethyl)-6-chloro-1-((4-methoxy-3-(piperazin-1-yl)phenyl)sulfonyl)-1H-indole (456 mg, 1.0 mmol) was reacted with sodium cyanoborohydride (189 mg, 3.0 mmol), acetic acid (180 μL, 3.0 mmol) and 3-oxetanone (216 mg, 3.0 mmol) in methanol (10 mL) according to the procedure as described in example 2, and the crude product was purified by silica gel chromatography eluted with DCM/MeOH(V/V)=50/1 to give the title compound as a white solid (482 mg, 94.1%). The compound was characterized by the following spectroscopic data: MS (ESI, pos. ion) m/z: 511.9 [M+H]+; 1H NMR (400 MHz, CDCl3): δ 8.03 (d, J=1.5 Hz, 1H), 7.77 (t, J=2.3 Hz, 1H), 7.62-7.56 (m, 2H), 7.38 (d, J=2.3 Hz, 1H), 7.30-7.26 (m, 1H), 6.89 (d, J=8.7 Hz, 1H), 6.84 (t, J=55.2 Hz, 1H), 4.72-4.65 (m, 4H), 3.89 (s, 3H), 3.58 (p, J=6.4 Hz, 1H), 3.11 (brs, 4H), 2.52 (brs, 4H); and 13C NMR (100 MHz, CDCl3): δ 157.1, 142.0, 135.4, 131.6, 129.01, 126.1 (t, J=9.5 Hz), 125.1, 124.6, 122.7, 121.3, 116.5, 116.3 (t, J=26.3 Hz), 113.9, 111.5 (t, J=233.5 Hz), 111.2, 75.3, 59.2, 56.0, 49.8, 49.5.

Example 43 Synthesis of 6-bromo-1-((3-(4-cyclopropylpiperazin-1-yl)-4-methoxyphenyl) sulfonyl)-3-(difluoromethyl)-1H-indole

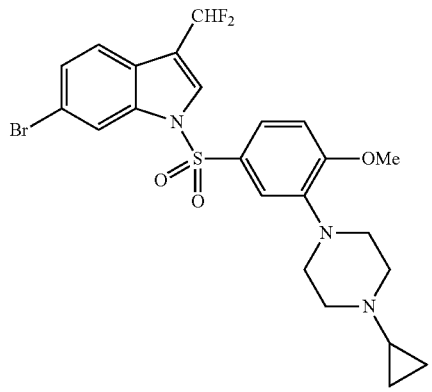

6-Bromo-3-(difluoromethyl)-1-((4-methoxy-3-(piperazin-1-yl)phenyl)sulfonyl)-1H-indole (200 mg, 0.4 mmol) was reacted with sodium cyanoborohydride (76 mg, 1.2 mmol), acetic acid (2.0 mmol, 120 μL) and 1-ethoxy-1-trimethylsiloxylcyclopropane (0.97 mmol, 209 μL) in methanol (10 mL) according to the procedure as described in example 39, and the crude product was purified by silica gel chromatography eluted with PE/EA(V/V)=3/1 to give the title compound as a white solid (86 mg, 40%). The compound was characterized by the following spectroscopic data: MS (ESI, pos. ion) m/z: 540.0 [M+H]+; 1H NMR (600 MHz, CDCl3): δ 8.17 (d, J=1.8 Hz, 1H), 7.73 (t, J=2.4 Hz, 1H), 7.57 (dd, J=9.0, 2.4 Hz, 1H), 7.53 (d, J=8.4 Hz, 1H), 7.40 (dd, J=8.4, 1.2 Hz, 1H), 7.35 (d, J=2.4 Hz, 1H), 6.87 (d, J=9.0 Hz, 1H), 6.82 (t, J=55.2 Hz, 1H), 3.89 (s, 3H), 3.10 (brs, 4H), 2.88 (brs, 4H), 0.88 (t, J=7.2 Hz, 1H), 0.55 (brs, 4H); and 13C NMR (150 MHz, CDCl3): δ157.1, 135.6, 129.0, 127.2, 126.1 (t, J=9.6 Hz), 125.5, 122.9, 121.6, 119.3, 116.8, 116.7, 116.3 (t, J=26.1 Hz), 113.7, 111.5 (t, J=233.4 Hz), 111.2, 56.1, 53.2, 49.4, 38.8, 14.1.

Example 44 Synthesis of 3-(difluoromethyl)-1-((4-methoxy-3-(piperazin-1-yl)phenyl) sulfonyl)-6-(trifluoromethyl)-1H-indole

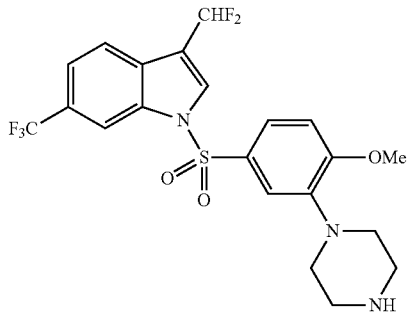 [SMILES: COc1ccc(S(=O)(=O)n2cc(C(F)F)c3ccc(C(F)(F)F)cc32)cc1N1CCNCC1]

Step 1) Synthesis of 1-((4-methoxy-3-(4-(2,2,2-trichloro acetyl)piperazin-1-yl)phenyl)sulfonyl)-6-(trifluoromethyl)-1H-indole-3-carbaldehyde 6-Trifluoromethyl-1H-indole-3-carbaldehyde (300 mg, 1.4 mmol) was reacted with sodium hydride (60 mg, 1.5 mmol, 60%) and 4-methoxy-3-(4-(2,2,2-trichloroacetyl)piperazin-1-yl)benzene-1-sulfonyl chloride (672 mg, 1.5 mmol, dissolved in THF (4 mL)) in THF (12 mL) according to the procedure as described in step 3 of example 1, and the crude product was purified by silica gel chromatography eluted with PE/DCM(V/V)=1/3 to give the title compound as a white solid (718 mg, 83.8%). The compound was characterized by the following spectroscopic data: MS (ESI, pos. ion) m/z: 611.8 [M+H]$^+$; and $^1$H NMR (600 MHz, CDCl$_3$): δ 10.12 (s, 1H), 8.39 (d, J=8.4 Hz, 1H), 8.37 (s, 1H), 8.24 (s, 1H), 7.82-7.78 (m, 2H), 7.62 (d, J=7.8 Hz, 1H), 7.00 (d, J=9.0 Hz, 1H), 3.94 (brs, 7H), 3.24 (s, 4H).

Step 2) Synthesis of 2,2,2-trichloro-1-(4-(5-((3-(difluoromethyl)-6-(trifluoromethyl)-1H-indol-1-yl)sulfonyl)-2-methoxyphenyl)piperazin-1-yl)ethanone 1-((4-Methoxy-3-(4-(2,2,2-trichloro acetyl)piperazin-1-yl)phenyl)sulfonyl)-6-(trifluoromethyl)-1H-indole-3-carbaldehyde (710 mg, 1.16 mmol) was reacted with diethylaminosulphur trifluoride (335 μL, 2.5 mmol) in DCM (12 mL) according to the procedure as described in step 3 of example 23, and the crude product was purified by silica gel chromatography eluted with PE/DCM(V/V)=1/1 to give the title compound as a white solid (608 mg, 82.7%). The compound was characterized by the following spectroscopic data: MS (ESI, pos. ion) m/z: 633.7 [M+H]$^+$; and $^1$H NMR (600 MHz, CDCl$_3$): δ 8.29 (s, 1H), 7.90 (s, 1H), 7.80 (d, J=8.4 Hz, 1H), 7.64 (dd, J=8.4, 1.8 Hz, 1H), 7.55 (d, J=8.4 Hz, 1H), 7.45 (s, 1H), 6.92 (d, J=9.0 Hz, 1H), 6.88 (t, J=55.8 Hz, 1H), 3.91 (br, 7H), 3.12 (t, J=4.8 Hz, 4H).

Step 3) Synthesis of 3-(difluoromethyl)-1-((4-methoxy-3-(piperazin-1-yl)phenyl)sulfonyl)-6-(trifluoromethyl)-1H-indole 2,2,2-Trichloro-1-(4-(5-((3-(difluoromethyl)-6-(trifluoromethyl)-1H-indol-1-yl)sulfonyl)-2-methoxyphenyl) piperazin-1-yl)ethanone (600 mg, 0.95 mmol) was reacted with potassium hydroxide solution (112 mg of potassium hydroxide solid, 2.0 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (293 mg, 63.0%). The compound was characterized by the following spectroscopic data: MS (ESI, pos. ion) m/z: 489.9 [M+H]$^+$; $^1$H NMR (600 MHz, DMSO-d$_6$): δ 8.51 (s, 1H), 8.22 (s, 1H), 7.90 (d, J=8.4 Hz, 1H), 7.68 (d, J=8.4 Hz, 1H), 7.64 (dd, J=9.0, 2.4 Hz, 1H), 7.33 (d, J=2.4 Hz, 1H), 7.26 (t, J=54 Hz, 1H), 7.10 (d, J=9.0 Hz, 1H), 3.80 (s, 3H), 3.29 (br, NH), 2.81 (brs, 4H), 2.76 (brs, 4H); and $^{13}$C NMR (150 MHz, DMSO-d$_6$): δ 157.6, 142.9, 133.8, 131.1 (t, J=9.9 Hz), 129.4, 127.7, 126.4 (q, J=31.8 Hz), 124.8 (q, J=270.45 Hz), 122.8, 122.2, 121.2 (d, J=3.3 Hz), 116.1 (d, J=26.4 Hz), 115.9, 112.8, 112.4 (t, J=229.8 Hz), 110.8, 56.6, 51.4, 45.9.

Example 45 Synthesis of 3-(difluoromethyl)-1-((4-methoxy-3-(4-methylpiperazin-1-yl) phenyl)sulfonyl)-6-(trifluoromethyl)-1H-indole

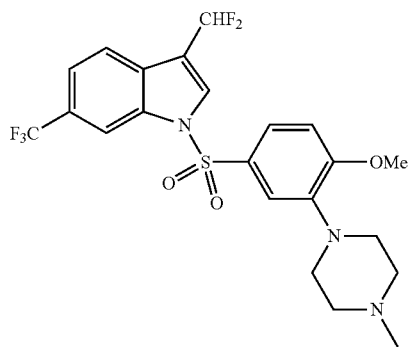 [SMILES: COc1ccc(S(=O)(=O)n2cc(C(F)F)c3ccc(C(F)(F)F)cc32)cc1N1CCN(C)CC1]

3-(Difluoromethyl)-1-((4-methoxy-3-(piperazin-1-yl)phenyl)sulfonyl)-6-(trifluoromethyl)-1H-indole (170 mg, 0.34 mmol) was reacted with sodium cyanoborohydride (63 mg, 1.0 mmol) and formaldehyde (40%, 0.11 mL, 1.6 mmol) in methanol (5 mL) according to the procedure as described in example 2, and the crude product was purified by silica gel chromatography eluted with DCM/methanol(V/V)=50/1 to give the title compound as a white solid (164 mg, 96.0%). The compound was characterized by the following spectroscopic data: MS (ESI, pos. ion) m/z: 504.1 [M+H]$^+$; $^1$H NMR (400 MHz, CDCl$_3$): δ 8.30 (s, 1H), 7.90 (t, J=2.4 Hz, 1H), 7.78 (d, J=8.4 Hz, 1H), 7.57 (dd, J=8.4, 2.4 Hz, 1H), 7.53 (d, J=8.0 Hz, 1H), 7.38 (d, J=2.4 Hz, 1H), 6.87 (d, J=3.6 Hz, 1H), 6.85 (t, J=50 Hz, 1H), 3.87 (s, 3H), 3.07 (brs, 4H), 2.60 (brs, 4H), 2.36 (s, 3H); and $^{13}$C NMR (100 MHz, CDCl$_3$): δ 157.2, 142.1, 134.2, 129.1, 128.8, 128.0, 127.7 (q, J=3.23 Hz), 124.3 (q, J=270.6 Hz), 122.6, 121.2, 120.6 (q, J=3.5 Hz), 116.5, 116.2 (t, J=26.4 Hz), 111.4 (t, J=233.8 Hz), 111.3 (t, J=4.2 Hz), 111.2, 56.0, 54.9, 49.9, 45.9.

Example 46 Synthesis of 3-(difluoromethyl)-1-((3-(4-ethylpiperazin-1-yl)-4-methoxyphenyl) sulfonyl)-6-(trifluoromethyl)-1H-indole

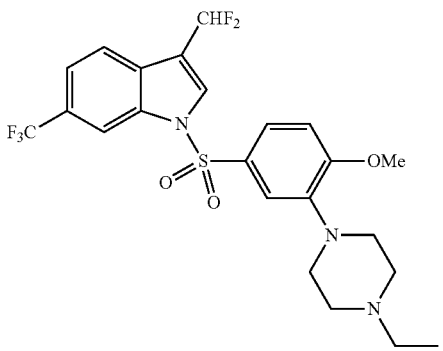 [SMILES: CCN1CCN(c2cc(S(=O)(=O)n3cc(C(F)F)c4ccc(C(F)(F)F)cc43)ccc2OC)CC1]

3-(Difluoromethyl)-1-((4-methoxy-3-(piperazin-1-yl) phenyl)sulfonyl)-6-(trifluoromethyl)-1H-indole (250 mg, 0.51 mmol) was reacted with K$_2$CO$_3$ (76 mg, 0.55 mmol) and bromoethane (114 μL, 1.54 mmol) in acetone (10 mL) according to the procedure as described in example 35, and the crude product was purified by silica gel chromatography eluted with DCM/MeOH(V/V)=50/1 to give the title compound as a light yellow solid (130 mg, 50%). The compound was characterized by the following spectroscopic data: MS (ESI, pos. ion) m/z: 518.1 [M+H]$^+$; $^1$H NMR (600 MHz, CDCl$_3$): δ 8.30 (s, 1H), 7.90 (d, J=2.0 Hz, 1H), 7.78 (d, J=8.4 Hz, 1H), 7.57 (dd, J=9.0, 2.4 Hz, 1H), 7.54 (d, J=8.4 Hz, 1H), 7.37 (d, J=1.8 Hz, 1H), 6.86 (t, J=55.2 Hz, 1H), 6.86 (d, J=8.4 Hz, 1H), 3.87 (s, 3H), 3.06 (brs, 4H), 2.60 (brs, 4H), 2.47 (q, J=7.2 Hz, 2H), 1.12 (t, J=7.2 Hz, 3H); and $^{13}$C NMR (150 MHz, CDCl$_3$): δ 157.2, 142.3, 134.2, 129.1, 128.7, 128.0 (t, J=9.3 Hz), 127.7 (q, J=32.4 Hz), 124.3 (q, J=270.6 Hz), 122.6, 121.1, 120.6 (q, J=3.45 Hz), 116.3, 116.1 (t, J=26.4 Hz), 114.4 (t, J=233.6 Hz), 111.3 (q, J=4.35 Hz), 111.1, 56.0, 52.6, 52.3, 50.1, 11.9.

Example 47 Synthesis of 1-((3-(4-cyclopropylpiperazin-1-yl)-4-methoxyphenyl)sulfonyl)-3-(difluoromethyl)-6-(trifluoromethyl)-1H-indole

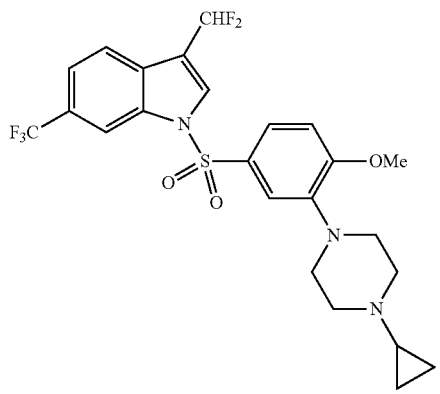 [SMILES: COc1ccc(S(=O)(=O)n2cc(C(F)F)c3ccc(C(F)(F)F)cc32)cc1N1CCN(C2CC2)CC1]

3-(Difluoromethyl)-1-((4-methoxy-3-(piperazin-1-yl) phenyl)sulfonyl)-6-(trifluoromethyl)-1H-indole (400 mg, 0.82 mmol) was reacted with sodium cyanoborohydride (154 mg, 2.44 mmol), acetic acid (4.0 mmol, 245 μL) and 1-ethoxy-1-trimethylsiloxylcyclopropane (530 μL, 2.45 mmol) in methanol (10 mL) according to the procedure as described in example 39, and the crude product was purified by silica gel chromatography eluted with PE/EA(V/V)=3/1 to give the title compound as a white solid (101 mg, 23.1%). The compound was characterized by the following spectroscopic data: MS (ESI, pos. ion) m/z: 530.2 [M+H]$^+$; $^1$H NMR (600 MHz, CDCl$_3$): δ 8.29 (s, 1H), 7.89 (s, 1H), 7.78 (d, J=8.4 Hz, 1H), 7.57 (dd, J=8.4, 1.8 Hz, 1H), 7.54 (d, J=8.4 Hz, 1H), 7.36 (d, J=1.8 Hz, 1H), 6.86 (t, J=55.2 Hz, 1H), 6.86 (d, J=8.4 Hz, 1H), 3.88 (s, 3H), 2.99 (brs, 4H), 2.76 (brs, 4H), 1.69-1.67 (m, 1H), 0.49-0.47 (m, 2H), 0.45 (brs, 2H); and $^{13}$C NMR (150 MHz, CDCl$_3$): δ 157.2, 142.4, 134.2, 129.1, 128.7, 128.0 (t, J=9.3 Hz), 127.7 (q, J=32.4 Hz), 124.3 (q, J=270.6 Hz), 122.6, 121.1, 120.6 (q, J=3.0 Hz), 116.4, 116.1 (t, J=26.6 Hz), 114.4 (t, J=233.7 Hz), 111.3 (q, J=4.35 Hz), 111.1, 56.0, 53.1, 50.1, 38.4, 5.8.

Example 48 Synthesis of 3-(difluoromethyl)-5,6-difluoro-1-((4-methoxy-3-(piperazin-1-yl) phenyl) sulfonyl)-1H-indole

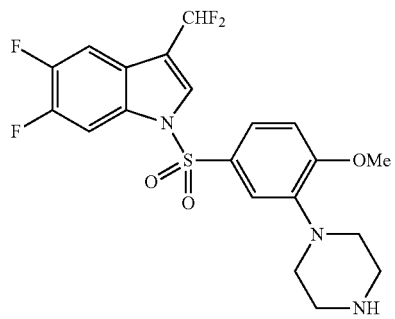 [SMILES: COc1ccc(S(=O)(=O)n2cc(C(F)F)c3cc(F)c(F)cc32)cc1N1CCNCC1]

Step 1) Synthesis of 5,6-difluoro-1-((4-methoxy-3-(4-(2,2,2-trichloroacetyl)piperazin-1-yl)phenyl) sulfonyl)-1H-indole-3-carbaldehyde 5,6-Difluoro-1H-indole-3-carbaldehyde (300 mg, 1.66 mmol) was reacted with sodium hydride (80 mg, 2.0 mmol, 60%) and 4-methoxy-3-(4-(2,2,2-trichloroacetyl)piperazin-1-yl)benzene-1-sulfonyl chloride (741 mg, 1.70 mmol, dissolved in THF (4 mL)) in THF (12 mL) according to the procedure as described in step 3 of example 1, and the crude product was purified by silica gel chromatography eluted with PE/DCM(V/V)=1/3 to give the title compound as a white solid (895 mg, 93%). The compound was characterized by the following spectroscopic data: MS (ESI, pos. ion) m/z: 580.1 [M+H]$^+$; and $^1$H NMR (400 MHz, DMSO-d$_6$): δ 10.02 (s, 1H), 8.98 (s, 1H), 8.09 (dd, J=10.8, 6.8 Hz, 1H), 7.99 (dd, J=10.2, 8.0 Hz, 1H), 7.91 (dd, J=8.7, 2.3 Hz, 1H), 7.50 (d, J=2.4 Hz, 1H), 7.19 (d, J=8.9 Hz, 1H), 3.88 (brs, 7H), 3.12 (brs, 4H).

Step 2) Synthesis of 2,2,2-trichloro-1-(4-(5-((3-(difluoromethyl)-5,6-difluoro-1H-indol-1-yl) sulfonyl)-2-methoxyphenyl)piperazin-1-yl)ethanone 5,6-Difluoro-1-((4-methoxy-3-(4-(2,2,2-trichloro acetyl) piperazin-1-yl)phenyl)sulfonyl)-1H-indole-3-carbaldehyde (800 mg, 1.38 mmol) was reacted with diethylaminosulphur trifluoride (400 μL, 3.0 mmol) in DCM (10 mL) according to the procedure as described in step 3 of example 23, and the crude product was purified by silica gel chromatography eluted with PE/DCM(V/V)=1/1 to give the title compound as a light yellow solid (665 mg, 80%). The compound was characterized by the following spectroscopic data: MS (ESI, pos. ion) m/z: 602.1 [M+H]⁺; and ¹H NMR (600 MHz, DMSO-d₆): δ 8.37 (s, 1H), 8.08 (dd, J=10.8, 6.8 Hz, 1H), 7.82 (dd, J=8.7, 2.3 Hz, 1H), 7.70 (dd, J=9.9, 7.9 Hz, 1H), 7.46 (d, J=2.2 Hz, 1H), 7.20 (t, J=36.4 Hz, 1H), 7.17 (d, J=8.8 Hz, 1H), 3.87 (brs, 7H), 3.10 (brs, 4H).

Step 3) Synthesis of 3-(difluoromethyl)-5,6-difluoro-1-((4-methoxy-3-(piperazin-1-yl)phenyl) sulfonyl)-1H-indole 2,2,2-Trichloro-1-(4-(5-((3-(difluoromethyl)-5,6-difluoro-1H-indol-1-yl)sulfonyl)-2-methoxyphenyl) piperazin-1-yl)ethanone (650 mg, 1.08 mmol) was reacted with potassium hydroxide solution (168 mg of potassium hydroxide solid, 3.0 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (346 mg, 70%). The compound was characterized by the following spectroscopic data: MS (ESI, pos. ion) m/z: 458.2 [M+H]⁺; and ¹H NMR (600 MHz, DMSO-d₆): δ 8.38 (s, 1H), 8.05 (dd, J=10.8, 6.8 Hz, 1H), 7.76 (dd, J=8.7, 2.2 Hz, 1H), 7.70 (dd, J=9.9, 7.9 Hz, 1H), 7.34 (d, J=2.2 Hz, 1H), 7.20 (t, J=36.8 Hz, 1H), 7.12 (d, J=8.7 Hz, 1H), 3.83 (s, 3H), 2.87-2.81 (m, 8H).

Example 49 Synthesis of 5,6-dichloro-3-(difluoromethyl)-1-((4-methoxy-3-(piperazin-1-yl) phenyl) sulfonyl)-1H-indole

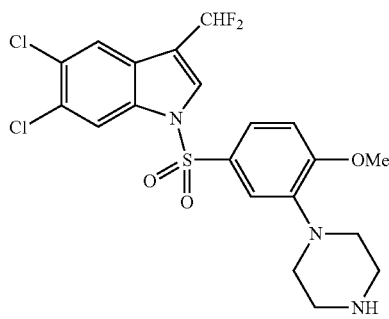 [SMILES: COc1ccc(S(=O)(=O)n2cc(C(F)F)c3cc(Cl)c(Cl)cc32)cc1N1CCNCC1]

Step 1) Synthesis of 5,6-dichloro-1-((4-methoxy-3-(4-(2,2,2-trichloro acetyl)piperazin-1-yl)phenyl) sulfonyl)-1H-indole-3-carbaldehyde 5,6-Dichloro-1H-indole-3-carbaldehyde (300 mg, 1.40 mmol) was reacted with sodium hydride (60 mg, 1.5 mmol, 60%) and 4-methoxy-3-(4-(2,2,2-trichloroacetyl)piperazin-1-yl)benzene-1-sulfonyl chloride (610 mg, 1.40 mmol, dissolved in THF (4 mL)) in THF (12 mL) according to the procedure as described in step 3 of example 1, and the crude product was purified by silica gel chromatography eluted with PE/DCM(V/V)=1/1 to give the title compound as a white solid (625 mg, 73%). The compound was characterized by the following spectroscopic data: MS (ESI, pos. ion) m/z: 611.9 [M+H]⁺; and ¹H NMR (600 MHz, DMSO-d₆): δ 10.02 (s, 1H), 9.01-9.00 (m, 1H), 8.23 (dd, J=8.5, 3.2 Hz, 1H), 8.21-8.19 (m, 1H), 7.88-7.86 (m, 1H), 7.51 (d, J=2.2 Hz, 1H), 7.20 (d, J=8.8 Hz, 1H), 3.87 (brs, 7H), 3.12 (brs, 4H).

Step 2) Synthesis of 2,2,2-trichloro-1-(4-(5-((5,6-dichloro-3-(difluoromethyl)-1H-indol-1-yl) sulfonyl)-2-methoxyphenyl)piperazin-1-yl)ethanone 5,6-Dichloro-1-((4-methoxy-3-(4-(2,2,2-trichloro acetyl) piperazin-1-yl)phenyl)sulfonyl)-1H-indole-3-carbaldehyde (600 mg, 0.98 mmol) was reacted with diethylaminosulphur trifluoride (400 μL, 3.0 mmol) in DCM (10 mL) according to the procedure as described in step 3 of example 23, and the crude product was purified by silica gel chromatography eluted with PE/DCM(V/V)=2/1 to give the title compound as a light yellow solid (485 mg, 78%). The compound was characterized by the following spectroscopic data: MS (ESI, pos. ion) m/z: 633.9 [M+H]⁺; and ¹H NMR (600 MHz, DMSO-d₆): δ 8.40 (s, 1H), 8.22 (s, 1H), 7.91 (s, 1H), 7.79 (dd, J=8.7, 2.3 Hz, 1H), 7.47 (d, J=2.3 Hz, 1H), 7.22 (t, J=36.4 Hz, 1H), 7.18 (d, J=8.8 Hz, 1H), 3.86 (brs, 7H), 3.10 (brs, 4H).

Step 3) Synthesis of 5,6-dichloro-3-(difluoromethyl)-1-((4-methoxy-3-(piperazin-1-yl)phenyl) sulfonyl)-1H-indole 2,2,2-Trichloro-1-(4-(5-((5,6-dichloro-3-(difluoromethyl)-1H-indol-1-yl)sulfonyl)-2-methoxyphenyl) piperazin-1-yl)ethanone (450 mg, 0.71 mmol) was reacted with potassium hydroxide solution (118 mg of potassium hydroxide solid, 2.1 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (230 mg, 66%). The compound was characterized by the following spectroscopic data: MS (ESI, pos. ion) m/z: 490.0 [M+H]⁺; and ¹H NMR (600 MHz, DMSO-d₆): δ 8.42 (s, 1H), 8.18 (s, 1H), 7.91 (s, 1H), 7.72 (dd, J=8.7, 2.2 Hz, 1H), 7.34 (d, J=2.2 Hz, 1H), 7.22 (t, J=39.4 Hz, 1H), 7.13 (d, J=8.8 Hz, 1H), 3.83 (s, 3H), 2.87-2.81 (m, 8H).

Example 50 Synthesis of 4-(5-((6-chloro-3-(difluoromethyl)-1H-indol-1-yl)sulfonyl)-2-methoxyphenyl)morpholine

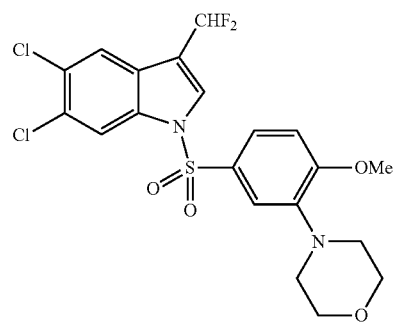 [SMILES: COc1ccc(S(=O)(=O)n2cc(C(F)F)c3cc(Cl)c(Cl)cc32)cc1N1CCOCC1]

Step 1) Synthesis of 4-(2-methoxyphenyl)morpholine

To 60 mL of toluene were added 1-bromo-2-methoxybenzene (5.0 g, 26.8 mmol), morpholine (6.0 g, 67.1 mmol), Pd$_2$(dba)$_3$ (613 mg, 0.67 mmol), DPEphos (583 mg, 1.34 mmol) and sodium tert-butoxide (3.87 g, 40.2 mmol). The mixture was reacted at 115° C. for 20 hours under nitrogen protection, and then the reaction was stopped by cooling to room temperature. To the mixture was added 50 mL of dichloromethane, and the mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA (V/V)=10/1 to give the title compound as red oil (1.75 g, 33.8%). The compound was characterized by the following spectroscopic data: MS (ESI, pos. ion) m/z: 194.2 [M+H]$^+$; and 1H NMR (600 MHz, CDCl$_3$): δ 7.03-7.01 (m, 1H), 6.94 (d, J=4.2 Hz, 2H), 6.88 (d, J=7.8 Hz, 1H), 3.90 (t, J=4.2 Hz, 4H), 3.87 (s, 3H), 3.07 (t, J=4.2 Hz, 4H).

Step 2) Synthesis of
4-methoxy-3-morpholinobenzene-1-sulfonyl
chloride

To 5 mL of dichloromethane was added 4-(2-methoxyphenyl)morpholine (720 mg, 3.73 mmol), then the resulting solution was added dropwise to 2 mL of chlorosulfonic acid at 0° C. The mixture was reacted for 1 hour, and then poured into a mixture of ice water (30 mL) and dichloromethane (30 mL). The resulting mixture was stirred vigorously and separated. The organic layer was dried over anhydrous magnesium sulfate and filtered. The filtrate was concentrated in vacuo to give the title compound as a light yellow solid (1.07 g, 99%). The compound was characterized by the following spectroscopic data: MS (ESI, pos. ion) m/z: 292.0 [M+H]$^+$; and $^1$H NMR (400 MHz, CDCl$_3$): δ 7.74 (dd, J=8.8, 2.4 Hz, 1H), 7.54 (d, J=2.4 Hz, 1H), 7.00 (d, J=8.8 Hz, 1H), 4.00 (s, 3H), 3.92 (t, J=4.4 Hz, 4H), 3.16 (t, J=4.4 Hz, 4H).

Step 3) Synthesis of 6-chloro-1-((4-methoxy-3-morpholinophenyl)sulfonyl)-1H-indole-3-carbaldehyde 6-Chloro-1H-indole-3-carbaldehyde (300 mg, 1.67 mmol) was reacted with sodium hydride (80 mg, 2.0 mmol, 60%) and 4-methoxy-3-morpholinobenzene-1-sulfonyl chloride (540 mg, 1.84 mmol, dissolved in THF (4 mL)) in THF (12 mL) according to the procedure as described in step 3 of example 1, and the crude product was purified by silica gel chromatography eluted with PE/EA(V/V)=5/1 to give the title compound as a white solid (598 mg, 82.6%). The compound was characterized by the following spectroscopic data: MS (ESI, pos. ion) m/z: 435.0 [M+H]$^+$; and $^1$H NMR (600 MHz, CDCl$_3$): δ 10.06 (s, 1H), 8.19 (s, 1H), 8.17 (d, J=9.0 Hz, 1H), 7.98 (s, 1H), 7.63 (dd, J=9.0, 1.8 Hz, 1H), 7.40 (d, J=1.8 Hz, 1H), 7.34 (dd, J=8.4, 0.6 Hz, 1H), 6.91 (d, J=9.0 Hz, 1H), 3.90 (s, 3H), 3.85 (t, J=4.2 Hz, 4H), 3.05 (t, J=4.2 Hz, 4H).

Step 4) Synthesis of 4-(5-((6-chloro-3-(difluoromethyl)-1H-indol-1-yl)sulfonyl)-2-methoxyphenyl)morpholine 6-Chloro-1-((4-methoxy-3-morpholinophenyl)sulfonyl)-1H-indole-3-carbaldehyde (600 mg, 1.38 mmol) was reacted with diethylaminosulphur trifluoride (540 μL, 4.14 mmol) in DCM (12 mL) according to the procedure as described in step 3 of example 23, and the crude product was purified by silica gel chromatography eluted with PE/DCM(V/V)=1/1 to give the title compound as a white solid (219 mg, 34.8%). The compound was characterized by the following spectroscopic data: MS (ESI, pos. ion) m/z: 457.1 [M+H]$^+$; $^1$H NMR (600 MHz, CDCl$_3$): δ 8.01 (d, J=1.2 Hz, 1H), 7.75 (s, 1H), 7.59-7.56 (m, 2H), 7.35 (d, J=1.8 Hz, 1H), 7.26 (dd, J=8.4, 1.8 Hz, 1H), 6.88 (d, J=9.0 Hz, 1H), 6.82 (t, J=55.2 Hz, 1H), 3.88 (s, 3H), 3.84 (t, J=4.8 Hz, 4H), 3.03 (t, J=4.8 Hz, 4H); and $^{13}$C NMR (150 MHz, CDCl$_3$): δ 157.1, 141.9, 135.4, 131.7, 128.9, 126.2 (t, J=9.6 Hz), 125.1 (t, J=1.95 Hz), 124.6, 122.9, 121.3, 116.3 (t, J=26.55 Hz), 116.3, 113.9, 111.6 (t, J=233.4 Hz), 111.3, 66.9, 56.0, 50.6.

Example 51 Synthesis of 4-(5-((6-bromo-3-(difluoromethyl)-1H-indol-1-yl)sulfonyl)-2-methoxyphenyl)morpholine

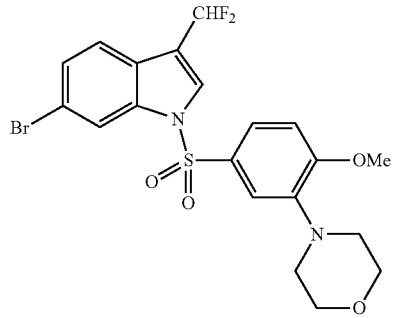

Step 1) Synthesis of 6-bromo-1-((4-methoxy-3-morpholinophenyl)sulfonyl)-1H-indole-3-carbaldehyde 6-Bromo-1H-indole-3-carbaldehyde (400 mg, 1.79 mmol) was reacted with sodium hydride (80 mg, 2.0 mmol, 60%) and 4-methoxy-3-morpholinobenzene-1-sulfonyl chloride (573 mg, 1.96 mmol, dissolved in THF (4 mL)) in THF (12 mL) according to the procedure as described in step 3 of example 1, and the crude product was purified by silica gel chromatography eluted with PE/EA(V/V)=5/1 to give the title compound as a white solid (631 mg, 73.6%). The compound was characterized by the following spectroscopic data: MS (ESI, pos. ion) m/z: 480.0 [M+H]$^+$; and $^1$H NMR (600 MHz, CDCl$_3$): δ 10.08 (s, 1H), 8.20 (s, 1H), 8.17 (d, J=1.2 Hz, 1H), 8.14 (d, J=8.4 Hz, 1H), 7.64 (dd, J=8.4, 1.8 Hz, 1H), 7.50 (dd, J=8.4, 1.2 Hz, 1H), 7.44 (d, J=2.4 Hz, 1H), 6.93 (d, J=9.0 Hz, 1H), 3.92 (s, 3H), 3.8 (t, J=4.2 Hz, 4H), 3.08 (t, J=4.2 Hz, 4H).

Step 2) Synthesis of 4-(5-((6-bromo-3-(difluoromethyl)-1H-indol-1-yl)sulfonyl)-2-methoxyphenyl)morpholine 6-Bromo-1-((4-methoxy-3-morpholinophenyl)sulfonyl)-1H-indole-3-carbaldehyde (625 mg, 1.30 mmol) was reacted with diethylaminosulphur trifluoride (640 μL, 3.98 mmol) in DCM (12 mL) according to the procedure as described in step 3 of example 23, and the crude product was purified by silica gel chromatography eluted with PE/DCM(V/V)=1/1 to give the title compound as a white solid (343 mg, 52.6%). The compound was characterized by the following spectroscopic data: MS (ESI, pos. ion) m/z: 502.0 [M+H]$^+$; $^1$H NMR (600 MHz, CDCl$_3$): δ 8.18 (s, 1H), 7.74 (s, 1H), 7.56 (dd, J=9.0, 2.4 Hz, 1H), 7.53 (d, J=8.4 Hz, 1H), 7.40 (dd, J=8.4, 1.2 Hz, 1H), 7.37 (d, J=1.8 Hz, 1H), 6.88 (d, J=9.0 Hz, 1H), 6.82 (t, J=55.8 Hz, 1H), 3.88 (s, 3H), 3.85 (t, J=4.8 Hz, 4H), 3.03 (t, J=4.8 Hz, 4H); and $^{13}$C NMR (150 MHz, CDCl$_3$): δ 157.1, 141.9, 135.6, 128.9, 127.3, 126.1 (t, J=9.45 Hz), 125.5 (t, J=1.95 Hz), 122.8, 121.6, 119.3, 116.9, 116.3, 116.3 (t, J=26.1 Hz), 111.5 (t, J=233.4 Hz), 111.3, 66.9, 56.0, 50.6.

Example 52 Synthesis of 3-(difluoromethyl)-6-fluoro-1-((4-methoxy-3-(piperidin-4-yl) phenyl)sulfonyl)-1H-indole

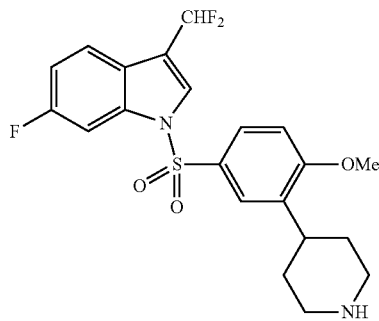 [SMILES: COc1ccc(S(=O)(=O)n2cc(C(F)F)c3ccc(F)cc32)cc1C1CCNCC1]

Step 1) Synthesis of tert-butyl 4-(2-methoxyphenyl)-5,6-dihydropyridine-1(2H)-carboxylate To a mixture of DMF (40 mL) and water (3 mL) were added 1-bromo-2-methoxybenzene (3.0 g, 16 mmol), tert-butyl 4-(4,4,5,5-tetramethyl-1,3,2-dioxaborolan-2-yl)-5,6-dihydropyridine-1 (2H)-carboxylate (5.95 g, 19 mmol), PdCl$_2$(dppf) (650 mg, 0.8 mmol) and sodium acetate (2.36 g, 24 mmol). The mixture was reacted at 95° C. for 24 hours under nitrogen protection, then the reaction was stopped by cooling to room temperature. To the mixture was added 50 mL of dichloromethane, and the mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA (V/V)=30/1 to give the title compound as colourless oil (4.18 g, 90.5%). The compound was characterized by the following spectroscopic data: $^1$H NMR (400 MHz, CDCl$_3$): δ 7.23 (dd, J=7.6, 1.2 Hz, 1H), 7.14 (dd, J=7.2, 1.6 Hz, 1H), 6.92 (td, J=7.2, 0.8 Hz, 1H), 6.87 (d, J=8.4 Hz, 1H), 5.75 (brs, 1H), 4.05 (d, J=2.0 Hz, 2H), 3.81 (s, 3H), 3.59 (t, J=5.2 Hz, 2H), 2.50 (s, 2H), 1.49 (s, 9H).

Step 2) Synthesis of tert-butyl 4-(2-methoxyphenyl)piperidine-1-carboxylate

To 15 mL of methanol were added tert-butyl 4-(2-methoxyphenyl)-5,6-dihydropyridine-1(2H)-carboxylate (4.2 g, 14.5 mmol) and Pd/C (420 mg) in turn. The mixture was reacted at RT for 20 hours under H$_2$ (1 atm). The reaction mixture was filtered and the filtrate was concentrated in vacuo, and the residue was purified by silica gel chromatography eluted with PE/EA(V/V)=30/1 to give the title compound as colourless oil (3.39 g, 80.4%). The compound was characterized by the following spectroscopic data: $^1$H NMR (600 MHz, CDCl$_3$): δ 7.20-7.18 (m, 1H), 7.15-7.14 (m, 1H), 6.93 (t, J=7.2 Hz, 1H), 6.86 (d, J=7.8 Hz, 1H), 4.23 (brs, 2H), 3.83 (s, 3H), 3.09 (tt, J=12.0, 3.6 Hz, 1H), 2.83 (brs, 2H), 1.78 (d, J=12.6 Hz, 2H), 1.61-1.57 (m, 2H), 1.48 (s, 9H).

Step 3) Synthesis of 2,2,2-trichloro-1-(4-(2-methoxyphenyl)piperidin-1-yl)ethanone To 20 mL of ethyl acetate were added tert-butyl 4-(2-methoxyphenyl)piperidine-1-carboxylate (3.4 g, 11.7 mmol) and a solution of hydrogen chloride in ethyl acetate (10 mL, 2 M). The solution was reacted at RT for 2 hours and then concentrated in vacuo to remove the solvent. The residue was dissolved in dichlormethane (30 mL), and triethylamine (4.58 mL, 34.38 mmol) was added. The mixture was cooled to 0° C. in a low temperature bath, and trichloroacetyl chloride (1.92 mL, 17.2 mmol) was added dropwise. After the addition, the mixture was reacted at 25° C. for 24 hours. After the reaction, 20 mL of dichloromethane was added and the mixture was washed with saturated aqueous sodium bicarbonate (40 mL). The organic layer was dried over anhydrous sodium sulfate and filtered. The filtrate was concentrated in vacuo and the residue was purified by silica gel chromatography eluted with PE/EA(V/V)=10/1 to give the title compound as light yellow oil (3.8 g, 96.5%). The compound was characterized by the following spectroscopic data: MS (ESI, pos. ion) m/z: 336.0 [M+H]$^+$; and $^1$H NMR (400 MHz, CDCl$_3$): δ 7.21 (td, J=8.4, 1.6 Hz, 1H), 7.14 (dd, J=7.6, 1.6 Hz, 1H), 6.94 (td, J=7.2, 0.8 Hz, 1H), 6.88 (d, J=8.4 Hz, 1H), 4.70 (d, J=13.2 Hz, 2H), 3.84 (s, 3H), 3.25 (tt, J=12.4, 3.6 Hz, 2H), 2.97 (s, 1H), 1.94 (d, J=12.4 Hz, 2H), 1.82-1.73 (m, 2H).

Step 4) Synthesis of 4-methoxy-3-(1-(2,2,2-trichloro acetyl)piperidin-4-yl)benzene-1-sulfonyl chloride To 5 mL of dichloromethane was added 2,2,2-trichloro-1-(4-(2-methoxyphenyl)piperidin-1-yl)ethanone (3.8 g, 11.3 mmol), then the resulting solution was added dropwise to 6 mL of chlorosulfonic acid at 0° C. The mixture was reacted for 1 hour, and then poured into a mixture of ice water (30 mL) and dichloromethane (30 mL). The resulting mixture was stirred vigorously and separated. The organic layer was dried over anhydrous magnesium sulfate and filtered. The filtrate was concentrated in vacuo to give the title compound as a white solid (4.59 g 93.7%). The compound was characterized by the following spectroscopic data: MS (ESI, pos. ion) m/z: 434.0 [M+H]$^+$; and $^1$H NMR (400 MHz, CDCl$_3$): δ 7.94 (dd, J=8.8, 2.4 Hz, 1H), 7.77 (d, J=2.4 Hz, 1H), 7.02 (d, J=8.8 Hz, 1H), 4.75 (d, J=13.2 Hz, 2H), 3.98 (s, 3H), 3.31-2.94 (m, 3H), 1.98 (d, J=12.4 Hz, 2H), 1.85-1.79 (m, 2H).

Step 5) Synthesis of 6-fluoro-1-((4-methoxy-3-(1-(2,2,2-trichloroacetyl)piperidin-4-yl)phenyl) sulfonyl)-1H-indole-3-carbaldehyde 6-Fluoro-1H-indole-3-carbaldehyde (300 mg, 1.84 mmol) was reacted with sodium hydride (96 mg, 2.4 mmol, 60%) and 4-methoxy-3-(1-(2,2,2-trichloroacetyl)piperidin-4-yl)benzene-1-sulfonyl chloride (1.04 g, 2.39 mmol, dissolved in THF (4 mL)) in THF (12 mL) according to the procedure as described in step 3 of example 1, and the crude product was purified by silica gel chromatography eluted with PE/EA(V/V)=5/1 to give the title compound as a white solid (1.0 g, 97.1%). The compound was characterized by the following spectroscopic data: MS (ESI, pos. ion) m/z: 561.0 [M+H]$^+$; and $^1$H NMR (400 MHz, CDCl$_3$): δ 10.06 (s, 1H), 8.22-8.19 (m, 2H), 7.85 (dd, J=8.8, 2.4 Hz, 1H), 7.69 (d, J=2.4 Hz, 1H), 7.66 (dd, J=9.2, 2.0 Hz, 1H), 7.11 (td, J=9.2, 2.4 Hz, 1H), 6.94 (d, J=8.8 Hz, 1H), 4.72 (d, J=13.2 Hz, 2H), 3.89 (s, 3H), 3.18 (td, J=12.0, 3.6 Hz, 2H), 3.07-2.85 (m, 1H), 1.87 (d, J=12.8 Hz, 2H), 1.73 (td, J=12.8, 3.6 Hz, 2H).

Step 6) Synthesis of 2,2,2-trichloro-1-(4-(5-((3-(difluoromethyl)-6-fluoro-1H-indol-1-yl)sulfonyl)-2-methoxyphenyl)piperidin-1-yl)ethanone 6-Fluoro-1-((4-methoxy-3-(1-(2,2,2-trichloro acetyl)piperidin-4-yl)phenyl)sulfonyl)-1H-indole-3-carbaldehyde (1.0 g, 1.78 mmol) was reacted with diethylaminosulphur trifluoride (700 μL, 5.4 mmol) in DCM (12 mL) according to the procedure as described in step 3 of example 23, and the crude product was purified by silica gel chromatography eluted with PE/DCM(V/V)=1/1 to give the title compound as a light yellow solid (856 mg, 82.3%). The compound was characterized by the following spectroscopic data: ¹H NMR (400 MHz, CDCl₃): δ 7.80 (dd, J=8.8, 2.4 Hz, 1H), 7.75 (t, J=2.4 Hz, 1H), 7.70 (dd, J=9.2, 2.4 Hz, 1H), 7.64-7.60 (m, 2H), 7.05 (td, J=9.2, 2.4 Hz, 1H), 6.91 (d, J=8.8 Hz, 1H), 6.83 (t, J=55.2 Hz, 1H), 4.71 (d, J=13.2 Hz, 2H), 3.87 (s, 3H), 3.17 (td, J=12.4, 3.2 Hz, 2H), 2.95 (brs, 1H), 1.85 (d, J=12.4 Hz, 2H), 1.74-1.66 (m, 2H).

Step 7) Synthesis of 3-(difluoromethyl)-6-fluoro-1-((4-methoxy-3-(piperidin-4-yl)phenyl) sulfonyl)-1H-indole 2,2,2-Trichloro-1-(4-(5-((3-(difluoromethyl)-6-fluoro-1H-indol-1-yl)sulfonyl)-2-methoxyphenyl)piperidin-1-yl)ethanone (856 mg, 1.47 mmol) was reacted with potassium hydroxide solution (247 mg of potassium hydroxide solid, 2.4 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (200 mg, 31.1%). The compound was characterized by the following spectroscopic data: MS (ESI, pos. ion) m/z: 439.2 [M+H]⁺; ¹H NMR (600 MHz, CDCl₃): δ 7.77-7.76 (m, 2H), 7.71-7.69 (m, 2H), 7.61 (dd, J=8.4, 5.4 Hz, 1H), 7.05-7.03 (m, 1H), 6.87 (d, J=8.8 Hz, 1H), 6.83 (t, J=55.2 Hz, 1H), 3.84 (s, 3H), 3.18 (d, J=12.0 Hz, 2H), 3.00 (t, J=12.0 Hz, 1H), 2.74 (t, J=11.4 Hz, 2H), 1.71 (d, J=12.0 Hz, 2H), 1.53 (qd, J=12.6, 3.6 Hz, 2H); and ¹³C NMR (150 MHz, CDCl₃): δ 161.6, 161.2 (d, J=242.1 Hz), 136.6, 135.2 (d, J=12.45 Hz), 128.6, 127.2, 125.9 (td, J=9.75, 3.75 Hz), 125.8, 122.9, 121.4 (d, J=10.95 Hz), 116.2 (d, J=26.1 Hz), 112.4 (d, J=24.3 Hz), 111.70 (t, J=233.1 Hz), 110.6, 101.0 (d, J=28.35 Hz), 55.8, 47.0, 35.6, 32.6.

Example 53 Synthesis of 6-chloro-3-(difluoromethyl)-1-((4-methoxy-3-(piperidin-4-yl) phenyl)sulfonyl)-1H-indole

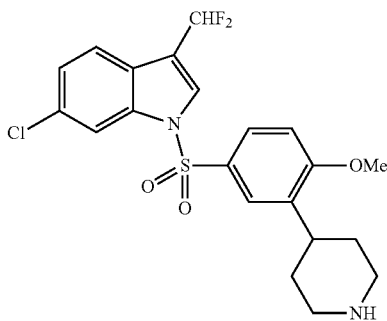

Step 1) Synthesis of 6-chloro-1-((4-methoxy-3-(1-(2,2,2-trichloroacetyl)piperidin-4-yl)phenyl) sulfonyl)-1H-indole-3-carbaldehyde 6-Chloro-1H-indole-3-carbaldehyde (350 mg, 1.95 mmol) was reacted with sodium hydride (96 mg, 2.4 mmol, 60%) and 4-methoxy-3-(1-(2,2,2-trichloroacetyl)piperidin-4-yl)benzene-1-sulfonyl chloride (1.10 g, 2.53 mmol, dissolved in THF (4 mL)) in THF (12 mL) according to the procedure as described in step 3 of example 1, and the crude product was purified by silica gel chromatography eluted with PE/EA(V/V)=5/1 to give the title compound as a white solid (0.69 g, 61.1%). The compound was characterized by the following spectroscopic data: MS (ESI, pos. ion) m/z: 577.1 [M+H]⁺; and ¹H NMR (400 MHz, CDCl₃): δ 10.06 (s, 1H), 8.19 (s, 1H), 8.17 (d, J=8.4 Hz, 1H), 7.96 (d, J=1.6 Hz, 1H), 7.84 (dd, J=8.8, 2.4 Hz, 1H), 7.73 (d, J=2.4 Hz, 1H), 7.34 (dd, J=8.4, 1.6 Hz, 1H), 6.95 (d, J=8.8 Hz, 1H), 4.72 (d, J=13.2 Hz, 2H), 3.89 (s, 3H), 3.19 (td, J=8.0, 3.6 Hz, 2H), 2.95 (brs, 1H), 1.88 (d, J=12.4 Hz, 2H), 1.77-1.68 (m, 2H).

Step 2) Synthesis of 2,2,2-trichloro-1-(4-(5-((6-chloro-3-(difluoromethyl)-1H-indol-1-yl)sulfonyl)-2-methoxyphenyl)piperidin-1-yl)ethanone 6-Chloro-1-((4-methoxy-3-(1-(2,2,2-trichloro acetyl)piperidin-4-yl)phenyl)sulfonyl)-1H-indole-3-carbaldehyde (0.69 g, 1.19 mmol) was reacted with diethylaminosulphur trifluoride (470 μL, 3.58 mmol) in DCM (12 mL) according to the procedure as described in step 3 of example 23, and the crude product was purified by silica gel chromatography eluted with PE/DCM(V/V)=1/1 to give the title compound as a white solid (572 mg, 79.9%). The compound was characterized by the following spectroscopic data: ¹H NMR (400 MHz, CDCl₃): δ 8.00 (d, J=2.0 Hz, 1H), 7.79 (dd, J=8.8, 2.4 Hz, 1H), 7.76 (t, J=2.4 Hz, 1H), 7.67 (d, J=2.4 Hz, 1H), 7.59 (d, J=8.4 Hz, 1H), 7.28 (d, J=2.0 Hz, 1H), 6.92 (d, J=8.8 Hz, 1H), 6.82 (t, J=55.2 Hz, 1H), 4.71 (d, J=12.8 Hz, 2H), 3.87 (s, 3H), 3.18 (td, J=12.0, 3.6 Hz, 2H), 2.96 (brs, 1H), 1.86 (d, J=12.4 Hz, 2H), 1.76-1.67 (m, 2H).

Step 3) Synthesis of 6-chloro-3-(difluoromethyl)-1-((4-methoxy-3-(piperidin-4-yl)phenyl)sulfonyl)-1H-indole 2,2,2-Trichloro-1-(4-(5-((3-(difluoromethyl)-6-chloro-1H-indol-1-yl)sulfonyl)-2-methoxyphenyl)piperidin-1-yl)ethanone (572 mg, 0.95 mmol) was reacted with potassium hydroxide solution (160 mg of potassium hydroxide solid, 2.86 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (180 mg, 41.6%). The compound was characterized by the following spectroscopic data: MS (ESI, pos. ion) m/z: 455.1 [M+H]⁺; ¹H NMR (600 MHz, CDCl₃): δ 8.00 (d, J=1.8 Hz, 1H), 7.77-7.74 (m, 3H), 7.58 (d, J=8.4 Hz, 1H), 7.27-7.25 (m, 1H), 6.88 (d, J=9.0 Hz, 1H), 6.83 (t, J=55.2 Hz, 1H), 3.85 (s, 3H), 3.20 (d, J=12.0 Hz, 2H), 3.01 (td, J=12.0, 2.4 Hz, 1H), 2.77-2.73 (m, 2H), 1.73 (d, J=12.6 Hz, 2H), 1.57 (qd, J=12.0, 3.6 Hz, 2H); and ¹³C NMR (150 MHz, CDCl₃): δ 161.6, 136.5, 135.3, 131.6, 128.5, 127.2, 126.2 (t, J=9.75 Hz), 126.0, 125.1 (t, J=1.8 Hz), 124.5, 121.3, 116.1 (t, J=26.4 Hz), 113.9, 111.6 (t, J=233.3 Hz), 110.7, 55.9, 46.9, 35.5, 32.5.

Example 54 Synthesis of 6-bromo-3-(difluoromethyl)-1-((4-methoxy-3-(piperidin-4-yl) phenyl)sulfonyl)-1H-indole

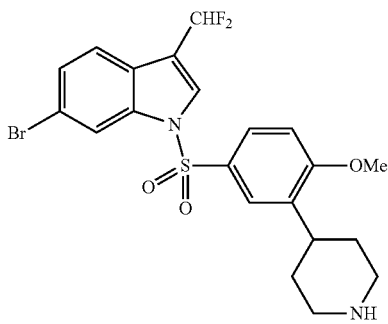 [SMILES: COc1ccc(S(=O)(=O)n2cc(C(F)F)c3ccc(Cl)cc32)cc1C1CCNCC1]

Step 1) Synthesis of 6-bromo-1-((4-methoxy-3-(1-(2,2,2-trichloroacetyl)piperidin-4-yl)phenyl) sulfonyl)-1H-indole-3-carbaldehyde 6-Bromo-1H-indole-3-carbaldehyde (400 mg, 1.79 mmol) was reacted with sodium hydride (96 mg, 2.4 mmol, 60%) and 4-methoxy-3-(1-(2,2,2-trichloroacetyl)piperidin-4-yl)benzene-1-sulfonyl chloride (1.01 g, 2.32 mmol, dissolved in THF (4 mL)) in THF (12 mL) according to the procedure as described in step 3 of example 1, and the crude product was purified by silica gel chromatography eluted with PE/EA(V/V)=5/1 to give the title compound as a white solid (1.05 g, 94.6%). The compound was characterized by the following spectroscopic data: MS (ESI, pos. ion) m/z: 620.9 [M+H]$^+$; and $^1$H NMR (400 MHz, CDCl$_3$): δ 10.06 (s, 1H), 8.18 (s, 1H), 8.3-8.10 (m, 2H), 7.83 (dd, J=8.8, 2.4 Hz, 1H), 7.74 (d, J=2.4 Hz, 1H), 7.47 (dd, J=8.4, 2.0 Hz, 1H), 6.94 (d, J=8.8 Hz, 1H), 4.73 (d, J=13.4 Hz, 2H), 3.89 (s, 3H), 3.19 (td, J=12.0, 3.6 Hz, 2H), 2.95 (brs, 1H), 1.88 (d, J=12.8 Hz, 2H), 1.77-1.68 (m, 2H).

Step 2) Synthesis of 1-(4-(5-(((6-bromo-3-(difluoromethyl)-1H-indol-1-yl)sulfonyl)-2-methoxy phenyl)piperidin-1-yl)-2,2,2-trichloroethanone 6-Bromo-1-((4-methoxy-3-(1-(2,2,2-trichloro acetyl)piperidin-4-yl)phenyl)sulfonyl)-1H-indole-3-carbaldehyde (1.05 g, 1.69 mmol) was reacted with diethylaminosulphur trifluoride (663 μL, 5.06 mmol) in DCM (10 mL) according to the procedure as described in step 3 of example 23, and the crude product was purified by silica gel chromatography eluted with PE/DCM(V/V)=1/1 to give the title compound as a white solid (1.03 g, 94.4%). The compound was characterized by the following spectroscopic data: $^1$H NMR (400 MHz, CDCl$_3$): δ 8.16 (d, J=1.2 Hz, 1H), 7.78 (dd, J=8.8, 2.4 Hz, 1H), 7.74 (t, J=2.4 Hz, 1H), 7.68 (d, J=2.4 Hz, 1H), 7.54 (d, J=8.4 Hz, 1H), 7.41 (dd, J=8.4, 1.6 Hz, 1H), 6.92 (d, J=8.8 Hz, 1H), 6.82 (t, J=55.2 Hz, 1H), 4.72 (d, J=13.6 Hz, 2H), 3.88 (s, 3H), 3.18 (td, J=12.0, 3.6 Hz, 2H), 2.96 (brs, 1H), 1.87 (d, J=11.6 Hz, 2H), 1.76-1.65 (m, 2H).

Step 3) Synthesis of 6-bromo-3-(difluoromethyl)-1-((4-methoxy-3-(piperidin-4-yl)phenyl) sulfonyl)-1H-indole 1-(4-(5-(((6-Bromo-3-(difluoromethyl)-1H-indol-1-yl)sulfonyl)-2-methoxyphenyl)piperidin-1-yl)-2,2,2-trichloroethanone (1.03 g, 1.6 mmol) was reacted with potassium hydroxide solution (270 mg of potassium hydroxide solid, 4.8 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (210 mg, 26.3%). The compound was characterized by the following spectroscopic data: MS (ESI, pos. ion) m/z: 499.0 [M+H]$^+$; $^1$H NMR (600 MHz, CDCl$_3$): δ 8.16 (s, 1H), 7.75-7.74 (d, J=7.2 Hz, 3H), 7.53 (d, J=8.4 Hz, 1H), 7.39 (d, J=8.4 Hz, 1H), 6.88 (d, J=9.0 Hz, 1H), 6.82 (t, J=55.2 Hz, 1H), 3.85 (s, 3H), 3.20 (d, J=12.0 Hz, 2H), 3.01 (td, J=12.0, 3.0 Hz, 1H), 2.75 (t, J=10.8 Hz, 2H), 1.72 (d, J=12.0 Hz, 2H), 1.56 (qd, J=12.6, 3.6 Hz, 2H); and $^{13}$C NMR (150 MHz, CDCl$_3$): δ 161.7, 136.6, 135.6, 128.5, 127.2, 127.1, 126.1 (t, J=9.4 Hz), 126.0, 124.5 (t, J=1.8 Hz), 121.6, 119.3, 116.8, 116.1 (t, J=26.2 Hz), 111.6 (t, J=233.2 Hz), 110.7, 55.9, 47.0, 35.5, 32.7.

Example 55 Synthesis of 3-(difluoromethyl)-6-fluoro-1-((4-methoxy-3-(piperazin-1-yl) phenyl)sulfonyl)-1H-indazole

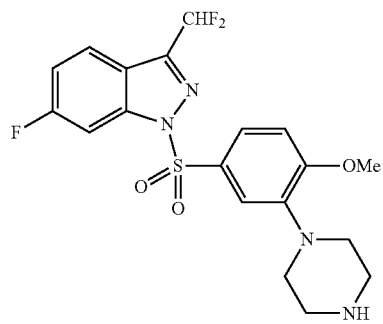 [SMILES: COc1ccc(S(=O)(=O)n2nc(C(F)F)c3ccc(F)cc32)cc1N1CCNCC1]

Step 1) Synthesis of 6-fluoro-1H-indazole-3-carbaldehyde

To a solution of 6-fluoroindole (0.81 g, 6.0 mmol) in tetrahydrofuran (60 mL) were added 500 mL of water, NaNO$_2$ (4.14 g, 60.0 mmol) and diluted hydrochloric acid (12 mL, 1 M) in turn. The mixture was reacted at RT for 4 hours. The reaction mixture was extracted with ethyl acetate (60 mL), and the organic layer was dried over anhydrous sodium sulfate and filtered. The filtrate was concentrated in vacuo. The residue was purified by silica gel chromatography eluted with PE/EA(V/V)=10/1 to give the title compound as a light yellow solid (395.7 mg, 40.1%). The compound was characterized by the following spectroscopic data: MS (ESI, pos. ion) m/z: 165.1 [M+H]$^+$; and $^1$H NMR (600 MHz, DMSO-d$_6$): δ 10.16 (s, 1H), 8.13 (dd, J=8.8, 5.3 Hz, 1H), 7.52 (dd, J=9.2, 2.0 Hz, 1H), 7.25 (td, J=9.1, 2.4 Hz, 1H).

Step 2) Synthesis of 6-fluoro-1-((4-methoxy-3-(4-(2,2,2-trifluoroacetyl)piperazin-1-yl)phenyl) sulfonyl)-1H-indazole-3-carbaldehyde 6-Fluoro-1H-indazole-3-carbaldehyde (330 mg, 2.0 mmol) and triethylamine (0.4 mL, 3.0 mmol) were dissolved in 6 mL of dichloromethane. To the mixture was added dropwise a solution of 4-methoxy-3-(4-(2,2,2-trifluoroacetyl)piperazin-1-yl)benzene-1-sulfonyl chloride (1.16 g, 3.0 mmol) in dichloromethane (4 mL) at 0° C. in a low temperature bath, then the mixture was stirred at RT for 24 hours. To the reaction mixture was added 60 mL of dichloromethane and the mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA(V/V)=6/1 to give the title compound as a light yellow solid (725.2 mg, 70.5%). The compound was characterized by the following spectroscopic data: MS (ESI, pos. ion) m/z: 515.1 [M+H]$^+$; and $^1$H NMR (600 MHz, CDCl$_3$): δ 10.20 (s, 1H), 8.23 (dd, J=8.8, 5.1 Hz, 1H), 7.90 (dd, J=8.9, 2.0 Hz, 1H), 7.79 (dd, J=8.7, 2.2 Hz, 1H), 7.52 (s, 1H), 7.22 (td, J=8.9, 2.2 Hz, 1H), 6.96 (d, J=8.8 Hz, 1H), 3.93 (s, 3H), 3.88-3.86 (m, 2H), 3.80-3.78 (m, 2H), 3.16-3.13 (m, 4H).

Step 3) Synthesis of 1-(4-(5-((3-(difluoromethyl)-6-fluoro-1H-indazol-1-yl)sulfonyl)-2-methoxyphenyl)piperazin-1-yl)-2,2,2-trifluoroethanone 6-Fluoro-1-((4-methoxy-3-(4-(2,2,2-trifluoro acetyl)piperazin-1-yl)phenyl)sulfonyl)-1H-indazole-3-carbaldehyde (500 mg, 0.97 mmol) was reacted with diethylaminosulphur trifluoride (385 μL, 2.92 mmol) in DCM (10 mL) according to the procedure as described in step 3 of example 23, and the crude product was purified by silica gel chromatography eluted with PE/EA(V/V)=5/1 to give the title compound as a white solid (498 mg, 95.6%). The compound was characterized by the following spectroscopic data: MS (ESI, pos. ion) m/z: 537.1 [M+H]$^+$; and $^1$H NMR (600 MHz, CDCl$_3$): δ 7.89 (dd, J=9.0, 1.8 Hz, 1H), 7.86 (dd, J=8.8, 5.0 Hz, 1H), 7.73 (dd, J=8.7, 2.0 Hz, 1H), 7.46 (d, J=1.9 Hz, 1H), 7.17 (td, J=8.8, 1.9 Hz, 1H), 6.93 (d, J=8.7 Hz, 1H), 6.87 (t, J=54.0 Hz, 1H), 3.92 (s, 3H), 3.84 (t, J=4.7 Hz, 2H), 3.76 (t, J=4.3 Hz, 2H), 3.11 (dd, J=9.6, 4.8 Hz, 4H).

Step 4) Synthesis of 3-(difluoromethyl)-6-fluoro-1-((4-methoxy-3-(piperazin-1-yl)phenyl)sulfonyl)-1H-indazole 1-(4-(5-((3-(Difluoromethyl)-6-fluoro-1H-indazol-1-yl)sulfonyl)-2-methoxyphenyl)piperazin-1-yl)-2,2,2-trifluoroethanone (436 mg, 0.81 mmol) was reacted with potassium carbonate (338 mg, 2.44 mmol) in a mixture of THF (4 mL) and tert-butanol (6 mL) according to the procedure as described in step 4 of example 1, and the crude product was purified by silica gel chromatography eluted with DCM/methanol(V/V)=30/1 to give the title compound as a white solid (263 mg, 73.2%). The compound was characterized by the following spectroscopic data: MS (ESI, pos. ion) m/z: 441.1 [M+H]$^+$; $^1$H NMR (600 MHz, CDCl$_3$): δ 7.89 (dd, J=9.0, 2.0 Hz, 1H), 7.85 (dd, J=8.8, 4.9 Hz, 1H), 7.67 (dd, J=8.7, 2.3 Hz, 1H), 7.45 (d, J=2.3 Hz, 1H), 7.15 (td, J=8.8, 2.2 Hz, 1H), 6.89 (t, J=54.0 Hz, 1H), 6.87 (s, 1H), 3.89 (s, 3H), 3.07-3.04 (m, 8H); and $^{13}$C NMR (150 MHz, CDCl$_3$): δ 163.9 (d, J=250.8 Hz), 157.5, 145.1 (t, J=31.3 Hz), 142.4, 141.9 (d, J=13.3 Hz), 128.4, 123.8, 122.9 (d, J=10.8 Hz), 118.4, 117.4, 114.8 (d, J=27.1 Hz), 111.3 (t, J=235.5 Hz), 111.2, 100.2 (d, J=27.2 Hz), 56.2, 51.1, 45.8.

Example 56 Synthesis of 6-chloro-3-(difluoromethyl)-1-((4-methoxy-3-(piperazin-1-yl) phenyl) sulfonyl)-1H-indazole

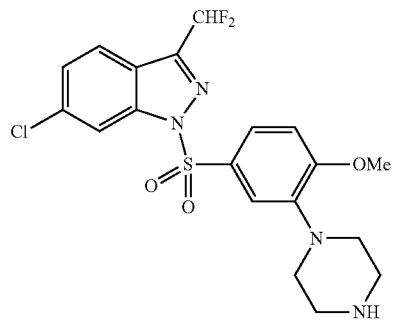

Step 1) Synthesis of 6-chloro-1H-indazole-3-carbaldehyde

6-Chloroindole (906 mg, 6.0 mmol) was reacted with sodium nitrite (4.14 g, 60.0 mmol) in a mixture of THF (60 mL) and water (500 mL) according to the procedure as described in step 1 of example 55, and the crude product was purified by silica gel chromatography eluted with PE/EA (V/V)=10/1 to give the title compound as a yellow solid (367 mg, 34%). The compound was characterized by the following spectroscopic data: MS (ESI, pos. ion) m/z: 181.0 [M+H]$^+$; and $^1$H NMR (600 MHz, DMSO-d$_6$): δ 14.27 (s, 1H), 10.17 (s, 1H), 8.12 (d, J=8.6 Hz, 1H), 7.81 (s, 1H), 7.38 (dd, J=8.5, 1.0 Hz, 1H).

Step 2) Synthesis of 6-chloro-1-((4-methoxy-3-(4-(2,2,2-trifluoroacetyl)piperazin-1-yl)phenyl) sulfonyl)-1H-indazole-3-carbaldehyde 6-Chloro-1H-indazole-3-carbaldehyde (350 mg, 1.94 mmol) was reacted with triethylamine (0.42 mL, 3.0 mmol) and 4-methoxy-3-(4-(2,2,2-trifluoroacetyl)piperazin-1-yl)benzene-1-sulfonyl chloride (0.93 g, 2.4 mmol) in dichloromethane (10 mL) according to the procedure as described in step 2 of example 55, and the crude product was purified by silica gel chromatography eluted with PE/EA(V/V)=6/1 to give the title compound as a light yellow solid (565 mg, 55%). The compound was characterized by the following spectroscopic data: MS (ESI, pos. ion) m/z: 531.0 [M+H]$^+$; and $^1$H NMR (600 MHz, CDCl$_3$): δ 10.20 (s, 1H), 8.25 (s, 1H), 8.19 (d, J=8.6 Hz, 1H), 7.80 (d, J=8.6 Hz, 1H), 7.54 (d, J=2.2 Hz, 1H), 7.43 (dd, J=8.6, 1.0 Hz, 1H), 6.96 (d, J=8.8 Hz, 1H), 3.93 (s, 3H), 3.85 (brs, 2H), 3.78 (brs, 2H), 3.14 (brs, 2H), 3.13 (brs, 2H).

Step 3) Synthesis of 1-(4-(5-((6-chloro-3-(difluoromethyl)-1H-indazol-1-yl)sulfonyl)-2-methoxyphenyl)piperazin-1-yl)-2,2,2-trifluoroethanone 6-Chloro-1-((4-methoxy-3-(4-(2,2,2-trifluoroacetyl)piperazin-1-yl)phenyl)sulfonyl)-1H-indazole-3-carbaldehyde (382 mg, 0.72 mmol) was reacted with diethylaminosulphur trifluoride (277 μL, 2.1 mmol) in DCM (10 mL) according to the procedure as described in step 3 of example 23, and the crude product was purified by silica gel chromatography eluted with PE/EA(V/V)=5/1 to give the title compound as a white solid (367 mg, 92.3%). The compound was characterized by the following spectroscopic data: MS (ESI, pos. ion) m/z: 553.1 [M+H]⁺; and ¹H NMR (600 MHz, CDCl₃): δ 8.24 (d, J=1.0 Hz, 1H), 7.81 (d, J=8.5 Hz, 1H), 7.78 (d, J=8.6 Hz, 1H), 7.62 (d, J=6.2 Hz, 1H), 7.38 (dd, J=8.5, 1.4 Hz, 1H), 6.96 (d, J=8.8 Hz, 1H), 6.87 (t, J=54.0 Hz, 1H), 3.94 (s, 3H), 3.90 (brs, 2H), 3.83 (brs, 2H), 3.17 (brs, 4H).

Step 4) Synthesis of 6-chloro-3-(difluoromethyl)-1-((4-methoxy-3-(piperazin-1-yl)phenyl)sulfonyl)-1H-indazole 1-(4-(5-((6-Chloro-3-(difluoromethyl)-1H-indazol-1-yl)sulfonyl)-2-methoxyphenyl)piperazin-1-yl)-2,2,2-trifluoroethanone (302 mg, 0.55 mmol) was reacted with potassium carbonate (228 mg, 1.65 mmol) in a mixture of THF (4 mL) and tert-butanol (6 mL) according to the procedure as described in step 4 of example 1, and the crude product was purified by silica gel chromatography eluted with DCM/methanol(V/V)=30/1 to give the title compound as a white solid (150 mg, 59%). The compound was characterized by the following spectroscopic data: MS (ESI, pos. ion) m/z: 457.1 [M+H]+; ¹H NMR (400 MHz, CDCl₃): δ 8.23 (d, J=1.3 Hz, 1H), 7.80 (d, J=8.6 Hz, 1H), 7.68 (dd, J=8.6, 2.3 Hz, 1H), 7.46 (d, J=2.3 Hz, 1H), 7.36 (dd, J=8.6, 1.7 Hz, 1H), 6.90 (t, J=54.0 Hz, 1H), 6.88 (s, 1H), 3.89 (s, 3H), 3.09 (brs, 4H), 3.08 (brs, 4H); and ¹³C NMR (100 MHz, CDCl₃): δ 157.6, 145.1 (t, J=31.3 Hz), 142.5, 141.6, 136.7, 128.4, 126.1, 123.8, 122.2, 120.4, 117.5, 113.6, 111.3 (t, J=236.5 Hz), 111.3, 56.2, 51.2, 45.9.

Example 57 Synthesis of 6-bromo-3-(difluoromethyl)-1-((4-methoxy-3-(piperazin-1-yl) phenyl)sulfonyl)-1H-indazole

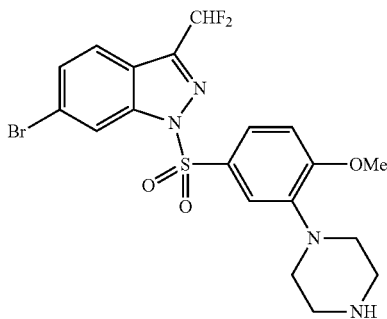 [SMILES: COc1ccc(S(=O)(=O)n2nc(C(F)F)c3ccc(Cl)cc32)cc1N1CCNCC1]

Step 1) Synthesis of 6-bromo-1H-indazole-3-carbaldehyde

6-Bromoindole (1.18 g, 6.0 mmol) was reacted with sodium nitrite (4.14 g, 60.0 mmol) in a mixture of THF (60 mL) and water (500 mL) according to the procedure as described in step 1 of example 55, and the crude product was purified by silica gel chromatography eluted with PE/EA (V/V)=10/1 to give the title compound as a yellow solid (393 mg, 29.1%). The compound was characterized by the following spectroscopic data: MS (ESI, pos. ion) m/z: 224.9 [M+H]⁺; and ¹H NMR (600 MHz, DMSO-d₆): δ 14.27 (s, 1H), 10.17 (s, 1H), 8.06 (d, J=9.7 Hz, 1H), 7.96 (s, 1H), 7.49 (dd, J=8.5, 1.5 Hz, 1H).

Step 2) Synthesis of 6-bromo-1-((4-methoxy-3-(4-(2,2,2-trifluoroacetyl)piperazin-1-yl)phenyl) sulfonyl)-1H-indazole-3-carbaldehyde 6-Bromo-1H-indazole-3-carbaldehyde (350 mg, 1.56 mmol) was reacted with triethylamine (0.42 mL, 3.0 mmol) and 4-methoxy-3-(4-(2,2,2-trifluoroacetyl)piperazin-1-yl)benzene-1-sulfonyl chloride (0.77 g, 2.0 mmol) in dichloromethane (10 mL) according to the procedure as described in step 2 of example 55, and the crude product was purified by silica gel chromatography eluted with PE/EA(V/V)=6/1 to give the title compound as a light yellow solid (641 mg, 71.5%). The compound was characterized by the following spectroscopic data: MS (ESI, pos. ion) m/z: 575.0 [M+H]⁺; and ¹H NMR (600 MHz, CDCl₃): δ 10.20 (s, 1H), 8.43 (d, J=0.9 Hz, 1H), 8.13 (d, J=8.5 Hz, 1H), 7.79 (dd, J=8.7, 2.0 Hz, 1H), 7.57 (dd, J=8.4, 1.4 Hz, 1H), 7.54 (s, 1H), 6.96 (d, J=8.8 Hz, 1H), 3.93 (s, 3H), 3.85 (t, J=4.6 Hz, 2H), 3.77 (t, J=4.0 Hz, 2H), 3.13 (brs, 4H).

Step 3) Synthesis of 1-(4-(5-((6-bromo-3-(difluoromethyl)-1H-indazol-1-yl)sulfonyl)-2-methoxyphenyl)piperazin-1-yl)-2,2,2-trifluoroethanone 6-Bromo-1-((4-methoxy-3-(4-(2,2,2-trifluoroacetyl)piperazin-1-yl)phenyl)sulfonyl)-1H-indazole-3-carbaldehyde (460 mg, 0.8 mmol) was reacted with diethylaminosulphur trifluoride (259 μL, 2.4 mmol) in DCM (10 mL) according to the procedure as described in step 3 of example 23, and the crude product was purified by silica gel chromatography eluted with PE/EA(V/V)=5/1 to give the title compound as a white solid (447 mg, 93.5%). The compound was characterized by the following spectroscopic data: MS (ESI, pos. ion) m/z: 596.9 [M+H]⁺; and ¹H NMR (600 MHz, CDCl₃): δ 8.42 (d, J=0.9 Hz, 1H), 7.77-7.72 (m, 2H), 7.52 (dd, J=8.5, 1.4 Hz, 1H), 7.47 (d, J=2.2 Hz, 1H), 6.94 (d, J=8.8 Hz, 1H), 6.87 (t, J=54.0 Hz, 1H), 3.92 (s, 3H), 3.86 (t, J=4.7 Hz, 2H), 3.77 (t, J=4.3 Hz, 2H), 3.11 (dd, J=9.3, 4.4 Hz, 4H).

Step 4) Synthesis of 6-bromo-3-(difluoromethyl)-1-((4-methoxy-3-(piperazin-1-yl)phenyl)sulfonyl)-1H-indazole 1-(4-(5-((6-Bromo-3-(difluoromethyl)-1H-indazol-1-yl)sulfonyl)-2-methoxyphenyl)piperazin-1-yl)-2,2,2-trifluoroethanone (375 mg, 0.63 mmol) was reacted with potassium carbonate (260 mg, 1.89 mmol) in a mixture of THF (4 mL) and tert-butanol (6 mL) according to the procedure as described in step 4 of example 1, and the crude product was purified by silica gel chromatography eluted with DCM/methanol(V/V)=30/1 to give the title compound as a white solid (154 mg, 48.8%). The compound was characterized by the following spectroscopic data: MS (ESI, pos. ion) m/z: 501.0 [M+H]⁺; ¹H NMR (400 MHz, CDCl₃): δ 8.41 (d, J=1.1 Hz, 1H), 7.74 (d, J=8.6 Hz, 1H), 7.68 (dd, J=8.7, 2.3 Hz, 1H), 7.50 (dd, J=8.6, 1.5 Hz, 1H), 7.46 (d, J=2.3 Hz, 1H), 6.90 (t, J=43.6 Hz, 1H), 6.88 (d, J=1.0 Hz, 1H), 3.89 (s, 3H), 3.09 (brs, 4H), 3.08 (brs, 4H); and ¹³C NMR (100 MHz, CDCl₃): δ 157.4, 145.1 (t, J=31.3 Hz), 142.1, 141.7, 128.6, 128.3, 124.7, 123.8, 122.2, 120.6, 117.4, 116.4, 111.3 (t, J=236.5 Hz), 111.1, 56.0, 50.6, 45.5.

Example 58 Synthesis of 5-fluoro-1-((4-methoxy-3-(piperazin-1-yl)phenyl)sulfonyl)-3-methyl-1H-indole

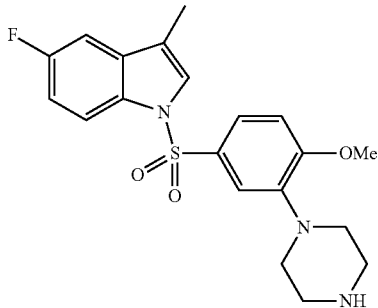 [SMILES: COc1ccc(S(=O)(=O)n2cc(C)c3cc(F)ccc32)cc1N1CCNCC1]

Step 1) Synthesis of 5-fluoro-3-methyl-1H-indole

5-Fluoro-1H-indole-3-carbaldehyde (3.2 g, 19.6 mmol) was dissolved in 10 mL of anhydrous tetrahydrofuran, then lithium aluminium hydride (2.61 g, 68.6 mmol) was added to the solution. The mixture was reacted at 70° C. for 2 hours. After the reaction, the reaction mixture was cooled to RT and quenched with aqueous sodium hydroxide (18 mL, 20%). 60 mL of dichloromethane was added to the mixture and the resulting mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA(V/V)=50/1 to give the title compound as a light yellow solid (2.41 g, 82.3%). The compound was characterized by the following spectroscopic data: MS (ESI, pos. ion) m/z: 150.2 [M+H]$^+$; and $^1$H NMR (400 MHz, CDCl$_3$): δ 7.30-7.23 (m, 2H), 7.04 (s, 1H), 6.97 (td, J=9.0, 2.0 Hz, 1H), 2.33 (s, 3H).

Step 2) Synthesis of 2,2,2-trichloro-1-(4-(5-((5-fluoro-3-methyl-1H-indol-1-yl)sulfonyl)-2-methoxyphenyl)piperazin-1-yl)ethanone 5-Fluoro-3-methyl-1H-indole (493 mg, 3.3 mmol) was reacted with sodium hydride (140 mg, 3.5 mmol, 60%) and 4-methoxy-3-(4-(2,2,2-trichloroacetyl)piperazin-1-yl)benzene-1-sulfonyl chloride (1.2 g, 2.75 mmol, dissolved in THF (4 mL)) in THF (12 mL) according to the procedure as described in step 3 of example 1, and the crude product was purified by silica gel chromatography eluted with PE/EA (V/V)=5/1 to give the title compound as a light yellow solid (710 mg, 47%). The compound was characterized by the following spectroscopic data: MS (ESI, pos. ion) m/z: 548.1 [M+H]$^+$; and $^1$H NMR (400 MHz, CDCl$_3$): δ 7.93 (dd, J=9.0, 4.3 Hz, 1H), 7.55 (dd, J=8.6, 1.6 Hz, 1H), 7.34-7.29 (m, 2H), 7.10 (dd, J=8.6, 2.1 Hz, 1H), 7.05 (td, J=9.0, 1.7 Hz, 1H), 6.86 (d, J=8.7 Hz, 1H), 3.97-3.89 (m, 7H), 3.17-3.02 (m, 4H), 2.21 (s, 3H).

Step 3) Synthesis of 5-fluoro-1-((4-methoxy-3-(piperazin-1-yl)phenyl)sulfonyl)-3-methyl-1H-indole 2,2,2-Trichloro-1-(4-(5-((5-fluoro-3-methyl-1H-indol-1-yl)sulfonyl)-2-methoxyphenyl)piperazin-1-yl) ethanone (700 mg, 1.28 mmol) was reacted with potassium hydroxide solution (202 mg of potassium hydroxide solid, 3.6 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (400 mg, 77.3%). The compound was characterized by the following spectroscopic data: MS (ESI, pos. ion) m/z: 404.1 [M+H]$^+$; $^1$H NMR (400 MHz, CDCl$_3$): δ 7.93 (dd, J=9.0, 4.4 Hz, 1H), 7.50 (dd, J=8.6, 2.3 Hz, 1H), 7.35-7.29 (m, 2H), 7.09 (dd, J=8.7, 2.5 Hz, 1H), 7.04 (td, J=9.0, 2.5 Hz, 1H), 6.81 (d, J=8.7 Hz, 1H), 3.86 (s, 3H), 3.04-3.02 (m, 4H), 2.96-2.94 (m, 4H), 2.21 (d, J=1.1 Hz, 3H); and $^{13}$C NMR (100 MHz, CDCl$_3$): δ 159.6 (d, J=238.0 Hz), 156.5, 142.2, 132.9 (d, J=9.5 Hz), 131.7, 129.9, 124.9, 122.2, 118.4 (d, J=4.1 Hz), 116.3, 114.8 (d, J=9.3 Hz), 112.3 (d, J=26.0 Hz), 110.8, 105.0 (d, J=9.3 Hz), 55.8, 51.6, 46.1, 9.6.

Example 59 Synthesis of 5-fluoro-1-((4-methoxy-3-(4-methylpiperazin-1-yl)phenyl) sulfonyl)-3-methyl-1H-indole

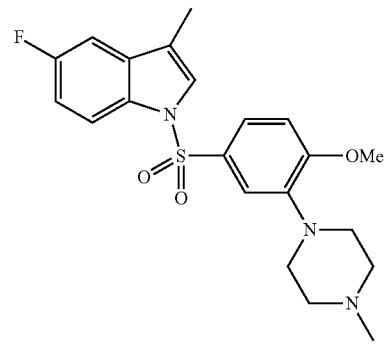 [SMILES: COc1ccc(S(=O)(=O)n2cc(C)c3cc(F)ccc32)cc1N1CCN(C)CC1]

5-Fluoro-1-((4-methoxy-3-(piperazin-1-yl)phenyl)sulfonyl)-3-methyl-1H-indole (370 mg, 0.92 mmol) was reacted with sodium cyanoborohydride (173 mg, 2.75 mmol) and formaldehyde (40%, 0.21 mL, 2.75 mmol) in methanol (10 mL) according to the procedure as described in example 2, and the crude product was purified by silica gel chromatography eluted with DCM/methanol(V/V)=50/1 to give the title compound as a light yellow solid (371 mg, 97.0%). The compound was characterized by the following spectroscopic data: MS (ESI, pos. ion) m/z: 418.1 [M+H]$^+$; $^1$H NMR (600 MHz, CDCl$_3$): δ 7.91 (dd, J=8.9, 4.2 Hz, 1H), 7.47 (d, J=8.6 Hz, 1H), 7.29 (d, J=19.9 Hz, 2H), 7.12-6.94 (m, 2H), 6.78 (d, J=8.6 Hz, 1H), 3.82 (s, 3H), 3.00 (brs, 4H), 2.56 (brs, 4H), 2.33 (s, 3H), 2.17 (s, 3H); and $^{13}$C NMR (150 MHz, CDCl$_3$): δ 159.5 (d, J=238.0 Hz), 156.4, 141.7, 132.9 (d, J=9.5 Hz), 131.7, 129.7, 124.9, 122.3, 118.4 (d, J=4.0 Hz), 116.2, 114.7 (d, J=9.3 Hz), 112.3 (d, J=25.5 Hz), 110.8, 105.1 (d, J=24.0 Hz), 55.9, 55.0, 50.1, 46.0, 9.6.

Example 60 Synthesis of 5-chloro-1-((4-methoxy-3-(piperazin-1-yl)phenyl)sulfonyl)-3-methyl-1H-indole

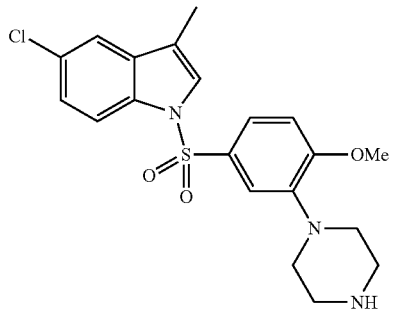 [SMILES: COc1ccc(S(=O)(=O)n2cc(C)c3cc(Cl)ccc32)cc1N1CCNCC1]

Step 1) Synthesis of 5-chloro-3-methyl-1H-indole

5-Chloro-1H-indole-3-carbaldehyde (2.35 g, 13.08 mmol) was reacted with lithium aluminium hydride (1.74 g, 45.8 mmol) in tetrahydrofuran (20 mL) according to the procedure as described in step 1 of example 58, and the crude product was purified by silica gel chromatography eluted with PE/EA(V/V)=50/1 to give the title compound as a yellow solid (1.62 g, 74.7%). The compound was characterized by the following spectroscopic data: MS (ESI, pos. ion) m/z: 166.1 [M+H]⁺; and ¹H NMR (400 MHz, CDCl₃): δ 7.91 (brs, 1H), 7.59 (d, J=1.8 Hz, 1H), 7.27 (dd, J=8.6, 0.4 Hz, 1H), 7.18 (dd, J=8.6, 2.0 Hz, 1H), 7.01 (s, 1H), 2.33 (d, J=1.1 Hz, 3H).

Step 2) Synthesis of 2,2,2-trichloro-1-(4-(5-((5-chloro-3-methyl-1H-indol-1-yl)sulfonyl)-2-methoxyphenyl)piperazin-1-yl)ethanone 5-Chloro-3-methyl-1H-indole (547 mg, 3.3 mmol) was reacted with sodium hydride (140 mg, 3.5 mmol, 60%) and 4-methoxy-3-(4-(2,2,2-trichloroacetyl)piperazin-1-yl)benzene-1-sulfonyl chloride (1.2 g, 2.75 mmol, dissolved in THF (4 mL)) in THF (10 mL) according to the procedure as described in step 3 of example 1, and the crude product was purified by silica gel chromatography eluted with PE/EA (V/V)=5/1 to give the title compound as a light yellow solid (440 mg, 28.2%). The compound was characterized by the following spectroscopic data: MS (ESI, pos. ion) m/z: 564.0 [M+H]⁺; and ¹H NMR (400 MHz, CDCl₃): δ 7.91 (d, J=8.8 Hz, 1H), 7.55 (dd, J=8.6, 2.3 Hz, 1H), 7.43 (d, J=1.9 Hz, 1H), 7.33-7.27 (m, 3H), 6.86 (d, J=8.7 Hz, 1H), 3.98-3.89 (m, 7H), 3.16-3.01 (m, 4H), 2.22 (d, J=1.2 Hz, 3H).

Step 3) Synthesis of 5-chloro-1-((4-methoxy-3-(piperazin-1-yl)phenyl)sulfonyl)-3-methyl-1H-indole 2,2,2-Trichloro-1-(4-(5-((5-chloro-3-methyl-1H-indol-1-yl)sulfonyl)-2-methoxyphenyl)piperazin-1-yl) ethanone (1.1 g, 1.95 mmol) was reacted with potassium hydroxide solution (237 mg of potassium hydroxide solid, 5.84 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (480 mg, 58.8%). The compound was characterized by the following spectroscopic data: MS (ESI, pos. ion) m/z: 420.1 [M+H]⁺; ¹H NMR (400 MHz, CDCl₃): δ 7.91 (d, J=8.8 Hz, 1H), 7.50 (dd, J=8.6, 2.3 Hz, 1H), 7.42 (d, J=1.9 Hz, 1H), 7.32-7.25 (m, 3H), 6.81 (d, J=8.7 Hz, 1H), 3.86 (s, 3H), 2.99 (dt, J=8.6, 4.0 Hz, 8H), 2.22 (d, J=1.2 Hz, 3H); and ¹³C NMR (100 MHz, CDCl₃): δ 156.5, 142.3, 133.7, 133.1, 129.9, 128.9, 124.6, 122.2, 119.2, 117.8, 116.3, 114.7, 110.8, 55.8, 51.6, 46.1, 9.5.

Example 61 Synthesis of 5-chloro-1-((4-methoxy-3-(4-methylpiperazin-1-yl)phenyl) sulfonyl)-3-methyl-1H-indole

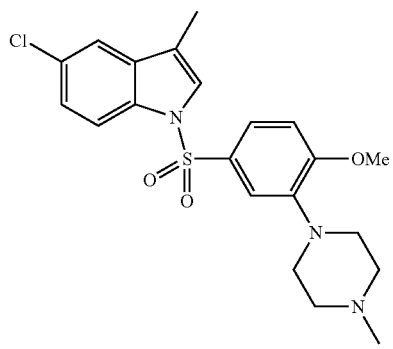 [SMILES: COc1ccc(S(=O)(=O)n2cc(C)c3cc(Cl)ccc32)cc1N1CCN(C)CC1]

5-Chloro-1-((4-methoxy-3-(piperazin-1-yl)phenyl)sulfonyl)-3-methyl-1H-indole (310 mg, 0.74 mmol) was reacted with sodium cyanoborohydride (139 mg, 2.21 mmol) and formaldehyde (40%, 0.16 mL, 2.2 mmol) in methanol (10 mL) according to the procedure as described in example 2, and the crude product was purified by silica gel chromatography eluted with DCM/methanol(V/V)=50/1 to give the title compound as a white solid (298 mg, 93.1%). The compound was characterized by the following spectroscopic data: MS (ESI, pos. ion) m/z: 434.1 [M+H]⁺; ¹H NMR (600 MHz, CDCl₃): δ 7.91 (d, J=8.8 Hz, 1H), 7.50 (dd, J=8.6, 2.0 Hz, 1H), 7.42 (d, J=1.5 Hz, 1H), 7.30 (dd, J=10.6, 8.7 Hz, 2H), 7.27 (dd, J=8.8, 1.6 Hz, 1H), 6.81 (d, J=8.7 Hz, 1H), 3.87 (s, 3H), 3.03 (brs, 4H), 2.59 (brs, 4H), 2.36 (s, 3H), 2.21 (s, 3H); and ¹³C NMR (150 MHz, CDCl₃): δ 156.4, 141.8, 133.7, 133.1, 129.7, 128.8, 124.6, 124.5, 122.3, 119.2, 117.9, 116.3, 114.7, 110.7, 55.9, 55.0, 50.1, 46.1, 9.6.

Example 62 Synthesis of 5-bromo-1-((4-methoxy-3-(piperazin-1-yl)phenyl)sulfonyl)-3-methyl-1H-indole

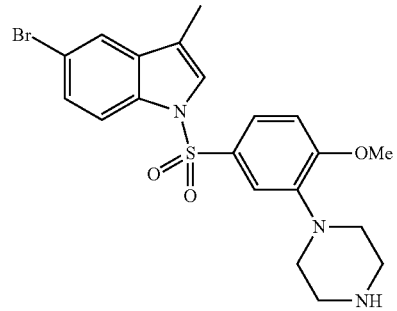

Step 1) Synthesis of 5-bromo-3-methyl-1H-indole

5-Bromo-1H-indole-3-carbaldehyde (2.35 g, 10.49 mmol) was reacted with lithium aluminium hydride (1.74 g, 45.8 mmol) in tetrahydrofuran (20 mL) according to the procedure as described in step 1 of example 58, and the crude product was purified by silica gel chromatography eluted with PE/EA(V/V)=50/1 to give the title compound as a yellow solid (1.54 g, 70.0%). The compound was characterized by the following spectroscopic data: MS (ESI, pos. ion) m/z: 210.1 [M+H]⁺; and ¹H NMR (400 MHz, CDCl₃): δ 7.77 (d, J=1.8 Hz, 1H), 7.32 (dd, J=8.6, 1.9 Hz, 1H), 7.22 (d, J=8.6 Hz, 1H), 6.98 (s, 1H), 2.34 (d, J=1.0 Hz, 3H).

Step 2) Synthesis of 1-(4-(5-((5-bromo-3-methyl-1H-indol-1-yl)sulfonyl)-2-methoxyphenyl) piperazin-1-yl)-2,2,2-trichloroethanone 5-Bromo-3-methyl-1H-indole (578 mg, 2.75 mmol) was reacted with sodium hydride (140 mg, 3.5 mmol, 60%) and 4-methoxy-3-(4-(2,2,2-trichloroacetyl)piperazin-1-yl)benzene-1-sulfonyl chloride (1.0 g, 2.29 mmol, dissolved in THF (4 mL)) in THF (12 mL) according to the procedure as described in step 3 of example 1, and the crude product was purified by silica gel chromatography eluted with PE/EA (V/V)=5/1 to give the title compound as a light yellow solid (669 mg, 47.6%). The compound was characterized by the following spectroscopic data: MS (ESI, pos. ion) m/z: 608.0 [M+H]⁺; and ¹H NMR (400 MHz, CDCl₃): δ 7.86 (d, J=8.8 Hz, 1H), 7.59 (d, J=1.8 Hz, 1H), 7.54 (dd, J=8.6, 2.3 Hz, 1H), 7.41 (dd, J=8.8, 1.9 Hz, 1H), 7.29 (dd, J=5.3, 1.7 Hz, 2H), 6.85 (dd, J=8.6, 4.9 Hz, 1H), 4.14-3.83 (m, 7H), 3.14-3.03 (m, 4H), 2.21 (d, J=1.2 Hz, 3H).

Step 3) Synthesis of 5-bromo-1-((4-methoxy-3-(piperazin-1-yl)phenyl)sulfonyl)-3-methyl-1H-indole 1-(4-(5-((5-Bromo-3-methyl-1H-indol-1-yl)sulfonyl)-2-methoxyphenyl)piperazin-1-yl)-2,2,2-trichloro ethanone (890 mg, 1.46 mmol) was reacted with potassium hydroxide solution (246 mg of potassium hydroxide solid, 4.38 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (460 mg, 67.8%). The compound was characterized by the following spectroscopic data: MS (ESI, pos. ion) m/z: 464.0 [M+H]$^+$; $^1$H NMR (400 MHz, CDCl$_3$): δ 7.87 (d, J=8.8 Hz, 1H), 7.59 (d, J=1.8 Hz, 1H), 7.50 (dd, J=8.6, 2.3 Hz, 1H), 7.41 (dd, J=8.8, 1.9 Hz, 1H), 7.30 (d, J=2.3 Hz, 2H), 6.81 (d, J=8.7 Hz, 1H), 3.87 (s, 3H), 3.05-3.03 (m, 4H), 2.97-2.95 (m, 4H), 2.22 (d, J=1.2 Hz, 3H); and $^{13}$C NMR (100 MHz, CDCl$_3$): δ 156.5, 142.3, 134.1, 133.6, 129.8, 127.2, 124.4, 122.3, 122.2, 117.7, 116.5, 116.3, 115.1, 110.8, 55.8, 51.6, 46.1, 9.5.

Example 63 Synthesis of 5-bromo-1-((4-methoxy-3-(4-methylpiperazin-1-yl)phenyl)sulfonyl)-3-methyl-1H-indole

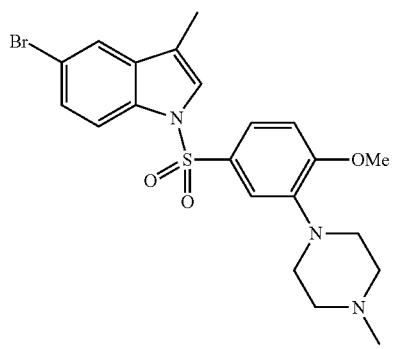

5-Bromo-1-((4-methoxy-3-(piperazin-1-yl)phenyl)sulfonyl)-3-methyl-1H-indole (316 mg, 0.68 mmol) was reacted with sodium cyanoborohydride (129 mg, 2.04 mmol) and formaldehyde (40%, 0.15 mL, 2.06 mmol) in methanol (10 mL) according to the procedure as described in example 2, and the crude product was purified by silica gel chromatography eluted with DCM/methanol(V/V)=50/1 to give the title compound as a white solid (298 mg, 91.8%). The compound was characterized by the following spectroscopic data: MS (ESI, pos. ion) m/z: 478.0 [M+H]$^+$; $^1$H NMR (600 MHz, CDCl$_3$): δ 7.85 (d, J=8.8 Hz, 1H), 7.55 (d, J=1.5 Hz, 1H), 7.48 (dd, J=8.6, 2.1 Hz, 1H), 7.37 (dd, J=8.8, 1.6 Hz, 1H), 7.28 (s, 2H), 6.78 (d, J=8.7 Hz, 1H), 3.82 (s, 3H), 3.01 (brs, 4H), 2.56 (brs, 4H), 2.33 (s, 3H), 2.17 (s, 3H); and $^{13}$C NMR (150 MHz, CDCl$_3$): δ 156.5, 141.8, 134.0, 133.6, 129.6, 127.3, 124.4, 122.3, 117.83, 116.5, 116.2, 115.1, 110.8, 55.9, 55.0, 50.1, 46.1, 9.6.

Example 64 Synthesis of 6-fluoro-1-((4-methoxy-3-(piperazin-1-yl)phenyl)sulfonyl)-3-methyl-1H-indole

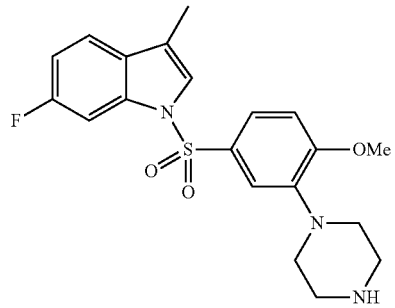 [SMILES: COc1ccc(S(=O)(=O)n2cc(C)c3ccc(F)cc32)cc1N1CCNCC1]

Step 1) Synthesis of 6-fluoro-3-methyl-1H-indole

6-Fluoro-1H-indole-3-carbaldehyde (1.56 g, 9.6 mmol) was reacted with lithium aluminium hydride (1.09 g, 28.8 mmol) in tetrahydrofuran (20 mL) according to the procedure as described in step 1 of example 58, and the crude product was purified by silica gel chromatography eluted with PE/EA(V/V)=50/1 to give the title compound as a yellow solid (1.20 g, 83.8%). The compound was characterized by the following spectroscopic data: MS (ESI, pos. ion) m/z: 150.1 [M+H]$^+$; and $^1$H NMR (400 MHz, CDCl$_3$): δ 7.47 (dd, J=8.8, 5.6 Hz, 1H), 7.01 (dd, J=10.0, 2.4 Hz, 1H), 6.94-6.90 (m, 1H), 6.90-6.84 (m, 1H), 2.31 (d, J=0.8 Hz, 3H).

Step 2) Synthesis of 2,2,2-trichloro-1-(4-(5-((6-fluoro-3-methyl-1H-indol-1-yl)sulfonyl)-2-methoxyphenyl)piperazin-1-yl)ethanone 6-Fluoro-3-methyl-1H-indole (547 mg, 3.67 mmol) was reacted with sodium hydride (140 mg, 3.5 mmol, 60%) and 4-methoxy-3-(4-(2,2,2-trichloroacetyl)piperazin-1-yl)benzene-1-sulfonyl chloride (800 mg, 1.83 mmol, dissolved in THF (4 mL)) in THF (12 mL) according to the procedure as described in step 3 of example 1, and the crude product was purified by silica gel chromatography eluted with PE/EA (V/V)=5/1 to give the title compound as a light yellow solid (579 mg, 57.7%). The compound was characterized by the following spectroscopic data: MS (ESI, pos. ion) m/z: 548.0 [M+H]$^+$; and $^1$H NMR (400 MHz, CDCl$_3$) δ 7.67 (dd, J=10.0, 2.4 Hz, 1H), 7.53 (dd, J=8.8, 2.4 Hz, 1H), 7.34 (dd, J=8.8, 5.6 Hz, 1H), 7.27 (d, J=2.4 Hz, 1H), 7.24-7.21 (m, 1H), 6.97 (td, J=8.8, 2.4 Hz, 1H), 6.83 (d, J=8.4 Hz, 1H), 3.99 (brs, 4H), 3.86 (s, 3H), 3.12-3.01 (m, 4H), 2.20 (d, J=1.2 Hz, 3H).

Step 3) Synthesis of 6-fluoro-1-((4-methoxy-3-(piperazin-1-yl)phenyl)sulfonyl)-3-methyl-1H-indole 2,2,2-Trichloro-1-(4-(5-((6-fluoro-3-methyl-1H-indol-1-yl)sulfonyl)-2-methoxyphenyl)piperazin-1-yl) ethanone (570 mg, 1.04 mmol) was reacted with potassium hydroxide solution (186 mg of potassium hydroxide solid, 3.32 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (335 mg, 79.8%). The compound was characterized by the following spectroscopic data: MS (ESI, pos. ion) m/z: 404.1 [M+H]$^+$; $^1$H NMR (400 MHz, CDCl$_3$): δ 7.68 (dd, J=10.0, 2.4 Hz, 1H), 7.48 (dd, J=8.6, 2.3 Hz, 1H), 7.32 (dd, J=8.6, 5.3 Hz, 1H), 7.27 (d, J=2.3 Hz, 1H), 7.23 (d, J=1.2 Hz, 1H), 6.95 (td, J=9.0, 2.3 Hz, 1H), 6.78 (d, J=8.7 Hz, 1H), 3.83 (s, 3H), 3.05-2.89 (m, 8H), 2.18 (s, 3H); and $^{13}$C NMR (100 MHz, CDCl$_3$): δ 160.9 (d, J=239.9 Hz), 156.5, 142.2, 135.5 (d, J=12.4 Hz), 129.8, 128.1, 123.4 (d, J=3.8 Hz), 122.3, 120.1 (d, J=9.9 Hz), 118.2, 116.3, 111.2 (d, J=24.1 Hz), 110.8, 101.1 (d, J=28.2 Hz), 55.8, 51.5, 46.0, 9.6.

Example 65 Synthesis of 6-fluoro-1-((4-methoxy-3-(4-methylpiperazin-1-yl)phenyl) sulfonyl)-3-methyl-1H-indole

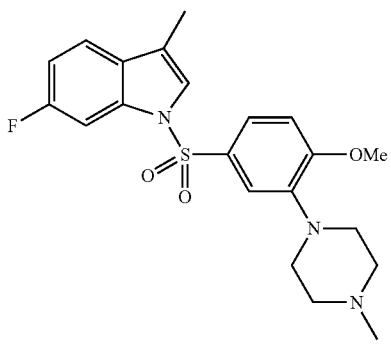 [SMILES: COc1ccc(S(=O)(=O)n2cc(C)c3ccc(F)cc32)cc1N1CCN(C)CC1]

6-Fluoro-1-((4-methoxy-3-(piperazin-1-yl)phenyl)sulfonyl)-3-methyl-1H-indole (312 mg, 0.77 mmol) was reacted with sodium cyanoborohydride (146 mg, 2.32 mmol) and formaldehyde (40%, 0.16 mL, 2.20 mmol) in methanol (10 mL) according to the procedure as described in example 2, and the crude product was purified by silica gel chromatography eluted with DCM/methanol(V/V)=50/1 to give the title compound as a white solid (205 mg, 63.6%). The compound was characterized by the following spectroscopic data: MS (ESI, pos. ion) m/z: 418.1 [M+H]$^+$; $^1$H NMR (600 MHz, CDCl$_3$): δ 7.67 (dd, J=9.8, 2.1 Hz, 1H), 7.48 (dd, J=8.6, 2.1 Hz, 1H), 7.32 (dd, J=8.5, 5.2 Hz, 1H), 7.27 (d, J=2.1 Hz, 1H), 7.23 (s, 1H), 6.94 (td, J=8.9, 2.1 Hz, 1H), 6.78 (d, J=8.6 Hz, 1H), 3.82 (s, 3H), 3.00 (brs, 4H), 2.55 (brs, 4H), 2.30 (s, 3H), 2.18 (s, 3H); and $^{13}$C NMR (150 MHz, CDCl$_3$): δ 161.76, 160.16 (d, J=239.8 Hz), 156.4, 141.7, 135.5 (d, J=12.4 Hz), 129.7, 128.1, 123.3 (d, J=3.9 Hz), 122.3, 120.1 (d, J=9.9 Hz), 118.3, 116.3, 111.3 (d, J=24.1 Hz), 110.8, 101.1 (d, J=28.2 Hz), 55.9, 54.9, 50.1, 46.0, 9.7.

Example 66 Synthesis of 6-chloro-1-((4-methoxy-3-(piperazin-1-yl)phenyl)sulfonyl)-3-methyl-1H-indole

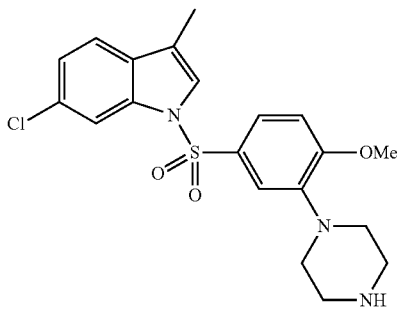 [SMILES: COc1ccc(S(=O)(=O)n2cc(C)c3ccc(Cl)cc32)cc1N1CCNCC1]

Step 1) Synthesis of 6-chloro-3-methyl-1H-indole

6-Chloro-1H-indole-3-carbaldehyde (1.47 g, 8.2 mmol) was reacted with lithium aluminium hydride (932 mg, 24.6 mmol) in tetrahydrofuran (20 mL) according to the procedure as described in step 1 of example 58, and the crude product was purified by silica gel chromatography eluted with PE/EA(V/V)=50/1 to give the title compound as a white solid (1.02 g, 75.1%). The compound was characterized by the following spectroscopic data: MS (ESI, pos. ion) m/z: 166.0 [M+H]$^+$; and $^1$H NMR (400 MHz, CDCl$_3$): δ 7.47 (d, J=8.4 Hz, 1H), 7.30 (d, J=1.7 Hz, 1H), 7.08 (dd, J=8.4, 1.8 Hz, 1H), 6.94-6.91 (m, 1H), 2.30 (d, J=1.2 Hz, 3H).

Step 2) Synthesis of 2,2,2-trichloro-1-(4-(5-((6-chloro-3-methyl-1H-indol-1-yl)sulfonyl)-2-methoxyphenyl)piperazin-1-yl)ethanone 6-Chloro-3-methyl-1H-indole (456 mg, 2.75 mmol) was reacted with sodium hydride (112 mg, 2.8 mmol, 60%) and 4-methoxy-3-(4-(2,2,2-trichloroacetyl)piperazin-1-yl)benzene-1-sulfonyl chloride (800 mg, 1.83 mmol, dissolved in THF (4 mL)) in THF (12 mL) according to the procedure as described in step 3 of example 1, and the crude product was purified by silica gel chromatography eluted with PE/EA (V/V)=5/1 to give the title compound as a light yellow solid (340 mg, 70.2%). The compound was characterized by the following spectroscopic data: MS (ESI, pos. ion) m/z: 564.0 [M+H]$^+$; and $^1$H NMR (400 MHz, CDCl$_3$): δ 7.98 (d, J=1.6 Hz, 1H), 7.52 (dd, J=8.8, 2.4 Hz, 1H), 7.35-7.27 (m, 2H), 7.23 (d, J=1.2 Hz, 1H), 7.19 (dd, J=8.4, 1.6 Hz, 1H), 6.83 (d, J=8.8 Hz, 1H), 4.03-3.89 (m, 4H), 3.85 (s, 3H), 3.09-3.02 (m, 4H), 2.18 (d, J=1.2 Hz, 3H).

Step 3) Synthesis of 6-chloro-1-((4-methoxy-3-(piperazin-1-yl)phenyl)sulfonyl)-3-methyl-1H-indole 2,2,2-Trichloro-1-(4-(5-((6-chloro-3-methyl-1H-indol-1-yl)sulfonyl)-2-methoxyphenyl)piperazin-1-yl) ethanone (620 mg, 1.14 mmol) was reacted with potassium hydroxide solution (186 mg of potassium hydroxide solid, 3.32 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (435 mg, 88.4%). The compound was characterized by the following spectroscopic data: MS (ESI, pos. ion) m/z: 420.1 [M+H]$^+$; $^1$H NMR (400 MHz, CDCl$_3$): δ 7.98 (d, J=1.6 Hz, 1H), 7.47 (dd, J=8.6, 2.3 Hz, 1H), 7.33-7.28 (m, 2H), 7.23 (d, J=1.2 Hz, 1H), 7.16 (dd, J=8.4, 1.8 Hz, 1H), 6.78 (d, J=8.7 Hz, 1H), 3.82 (s, 3H), 3.02-2.91 (m, 8H), 2.17 (d, J=1.2 Hz, 3H); and $^{13}$C NMR (100 MHz, CDCl$_3$): δ 156.7, 142.4, 135.9, 130.7, 130.5, 129.9, 123.9, 123.7, 122.4, 120.4, 118.4, 116.6, 114.2, 111.1, 56.0, 51.8, 46.3, 9.8.

Example 67 Synthesis of 6-chloro-1-((4-methoxy-3-(4-methylpiperazin-1-yl)phenyl)sulfonyl)-3-methyl-1H-indole

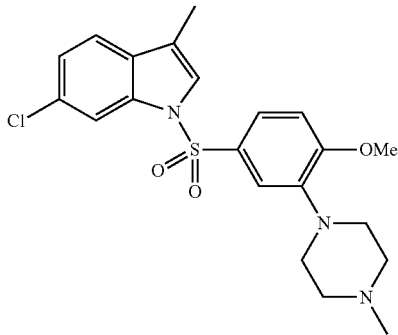 [SMILES: COc1ccc(S(=O)(=O)n2cc(C)c3ccc(Cl)cc32)cc1N1CCN(C)CC1]

6-Chloro-1-((4-methoxy-3-(piperazin-1-yl)phenyl)sulfonyl)-3-methyl-1H-indole (253 mg, 0.6 mmol) was reacted with sodium cyanoborohydride (114 mg, 1.81 mmol) and formaldehyde (40%, 0.13 mL, 1.80 mmol) in methanol (10 mL) according to the procedure as described in example 2, and the crude product was purified by silica gel chromatography eluted with DCM/methanol(V/V)=50/1 to give the title compound as a white solid (236 mg, 90.5%). The compound was characterized by the following spectroscopic data: MS (ESI, pos. ion) m/z: 434.1 [M+H]$^+$; $^1$H NMR (400 MHz, CDCl$_3$): δ 7.97 (d, J=1.6 Hz, 1H), 7.45 (dd, J=8.6, 2.4 Hz, 1H), 7.31-7.26 (m, 2H), 7.22 (d, J=1.2 Hz, 1H), 7.14 (dd, J=8.4, 1.8 Hz, 1H), 6.76 (d, J=8.7 Hz, 1H), 3.79 (s, 3H), 3.00 (brs, 4H), 2.53 (brs, 4H), 2.30 (s, 3H), 2.16 (d, J=1.2 Hz, 3H); and $^{13}$C NMR (100 MHz, CDCl$_3$): δ 156.6, 141.9, 135.8, 130.7, 130.5, 129.9, 123.9, 123.7, 122.3, 120.3, 118.4, 116.5, 114.1, 111.0, 56.0, 55.2, 50.2, 46.2, 9.7.

Example 68 Synthesis of 6-bromo-1-((4-methoxy-3-(piperazin-1-yl)phenyl)sulfonyl)-3-methyl-1H-indole

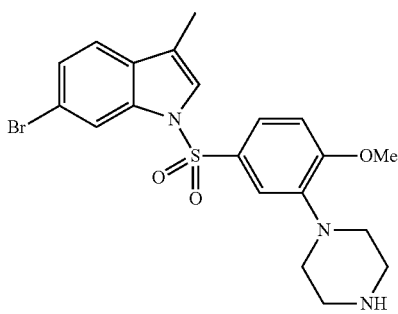

Step 1) Synthesis of 6-bromo-3-methyl-1H-indole

6-Bromo-1H-indole-3-carbaldehyde (1.16 g, 5.2 mmol) was reacted with lithium aluminium hydride (590 mg, 15.5 mmol) in tetrahydrofuran (20 mL) according to the procedure as described in step 1 of example 58, and the crude product was purified by silica gel chromatography eluted with PE/EA(V/V)=50/1 to give the title compound as a white solid (880 mg, 80.5%). The compound was characterized by the following spectroscopic data: MS (ESI, pos. ion) m/z: 210.0 [M+H]$^+$; and $^1$H NMR (400 MHz, CDCl$_3$): δ 7.47 (d, J=1.6 Hz, 1H), 7.41 (d, J=8.4 Hz, 1H), 7.20 (dd, J=8.4, 1.7 Hz, 1H), 6.92 (s, 1H), 2.29 (d, J=1.0 Hz, 3H).

Step 2) Synthesis of 1-(4-(5-((6-bromo-3-methyl-1H-indol-1-yl)sulfonyl)-2-methoxyphenyl)piperazin-1-yl)-2,2,2-trichloroethanone 6-Bromo-3-methyl-1H-indole (265 mg, 1.26 mmol) was reacted with sodium hydride (60 mg, 1.5 mmol, 60%) and 4-methoxy-3-(4-(2,2,2-trichloroacetyl)piperazin-1-yl)benzene-1-sulfonyl chloride (500 mg, 1.15 mmol, dissolved in THF (4 mL)) in THF (12 mL) according to the procedure as described in step 3 of example 1, and the crude product was purified by silica gel chromatography eluted with PE/EA (V/V)=5/1 to give the title compound as a light yellow solid (262 mg, 37.5%). The compound was characterized by the following spectroscopic data: MS (ESI, pos. ion) m/z: 607.9 [M+H]$^+$; and $^1$H NMR (400 MHz, CDCl$_3$): δ 8.15 (t, J=1.6 Hz, 1H), 7.52 (dt, J=5.2, 2.8 Hz, 1H), 7.34-7.30 (m, 2H), 7.27 (d, J=8.4 Hz, 1H), 7.25-7.20 (m, 1H), 6.83 (d, J=8.4 Hz, 1H), 3.97 (brs, 5H), 3.76-3.65 (m, 2H), 3.12-3.01 (m, 4H), 2.17 (d, J=1.0 Hz, 3H).

Step 3) Synthesis of 6-bromo-1-((4-methoxy-3-(piperazin-1-yl)phenyl)sulfonyl)-3-methyl-1H-indole 1-(4-(5-((6-Bromo-3-methyl-1H-indol-1-yl)sulfonyl)-2-methoxyphenyl)piperazin-1-yl)-2,2,2-trichloro ethanone (205 mg, 0.34 mmol) was reacted with potassium hydroxide solution (56 mg of potassium hydroxide solid, 1.0 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (120 mg, 76.4%). The compound was characterized by the following spectroscopic data: MS (ESI, pos. ion) m/z: 464.1 [M+H]$^+$; $^1$H NMR (400 MHz, CDCl$_3$): δ 8.15 (d, J=1.2 Hz, 1H), 7.46 (dd, J=8.4, 2.4 Hz, 1H), 7.33-7.29 (m, 2H), 7.26 (d, J=8.4 Hz, 1H), 7.22 (d, J=1.2 Hz, 1H), 6.79 (d, J=8.8 Hz, 1H), 3.83 (s, 3H), 3.04-2.92 (m, 8H), 2.18 (d, J=1.2 Hz, 3H); and $^{13}$C NMR (100 MHz, CDCl$_3$): δ 156.8, 142.3, 136.2, 130.9, 129.9, 126.4, 123.9, 122.4, 120.7, 118.4, 118.3, 117.1, 116.7, 111.1, 56.1, 51.7, 46.2, 9.5.

Example 69 Synthesis of 6-bromo-1-((4-methoxy-3-(4-methylpiperazin-1-yl)phenyl) sulfonyl)-3-methyl-1H-indole

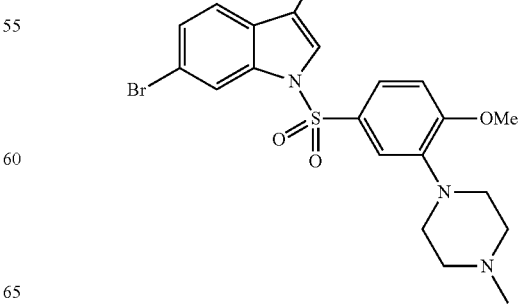

6-Bromo-1-((4-methoxy-3-(piperazin-1-yl)phenyl)sulfonyl)-3-methyl-1H-indole (171 mg, 0.37 mmol) was reacted with sodium cyanoborohydride (70 mg, 1.11 mmol) and formaldehyde (40%, 0.09 mL, 1.20 mmol) in methanol (10 mL) according to the procedure as described in example 2, and the crude product was purified by silica gel chromatography eluted with DCM/methanol(V/V)=50/1 to give the title compound as a white solid (174 mg, 98.5%). The compound was characterized by the following spectroscopic data: MS (ESI, pos. ion) m/z: 478.1 [M+H]$^+$; $^1$H NMR (600 MHz, CDCl$_3$): δ 7.98 (d, J=1.6 Hz, 1H), 7.43 (dd, J=8.4, 2.4 Hz, 1H), 7.31-7.27 (m, 2H), 7.21 (d, J=1.2 Hz, 1H), 7.14 (dd, J=8.4, 2.0 Hz, 1H), 6.77 (d, J=8.5 Hz, 1H), 3.85 (s, 3H), 3.04 (brs, 4H), 2.56 (brs, 4H), 2.34 (s, 3H), 2.19 (s, 3H); and $^{13}$C NMR (150 MHz, CDCl$_3$): δ 156.7, 141.9, 136.1, 130.8, 129.8, 126.4, 123.8, 122.4, 120.8, 118.5, 118.3, 117.0, 116.6, 111.0, 56.1, 55.2, 50.3, 46.3, 9.8.

Example 70 Synthesis of 3-ethyl-6-fluoro-1-((4-methoxy-3-(piperazin-1-yl)phenyl)sulfonyl)-1H-indole

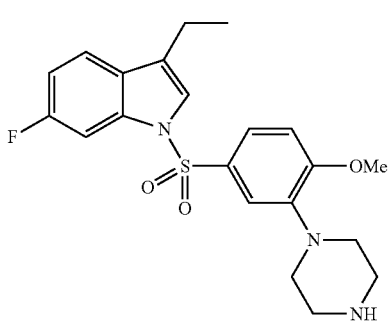 [SMILES: CCc1cn(S(=O)(=O)c2ccc(OC)c(N3CCNCC3)c2)c2cc(F)ccc12]

Step 1) Synthesis of 2,2,2-trichloro-1-(4-(5-((3-ethyl-6-fluoro-1H-indol-1-yl)sulfonyl)-2-methoxyphenyl)piperazin-1-yl)ethanone 6-Fluoro-3-ethyl-1H-indole (196 mg, 1.2 mmol) was reacted with sodium hydride (60 mg, 1.5 mmol, 60%) and 4-methoxy-3-(4-(2,2,2-trichloroacetyl)piperazin-1-yl)benzene-1-sulfonyl chloride (523 mg, 1.2 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a light yellow solid (372 mg, 55%). The compound was characterized by the following spectroscopic data: $^1$H NMR (600 MHz, CDCl$_3$): δ 7.69 (dd, J=10.2, 2.4 Hz, 1H), 7.56 (dd, J=8.4, 1.8 Hz, 1H), 7.38 (dd, J=8.4, 5.4 Hz, 1H), 7.28 (d, J=2.4 Hz, 1H), 7.25 (t, J=1.2 Hz, 1H), 6.98 (td, J=9.0, 2.4 Hz, 1H), 6.86 (d, J=8.4 Hz, 1H), 4.02 (s, 3H), 3.88 (brs, 4H), 3.07 (t, J=4.8 Hz, 4H), 2.64 (qd, J=7.8, 1.2 Hz, 2H), 1.28 (t, J=7.8 Hz, 3H).

Step 2) Synthesis of 3-ethyl-6-fluoro-1-((4-methoxy-3-(piperazin-1-yl)phenyl)sulfonyl)-1H-indole 2,2,2-Trichloro-1-(4-(5-((3-ethyl-6-fluoro-1H-indol-1-yl)sulfonyl)-2-methoxyphenyl)piperazin-1-yl) ethanone (350 mg, 0.62 mmol) was reacted with potassium hydroxide solution (84 mg of potassium hydroxide solid, 1.5 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (176 mg, 68%). The compound was characterized by the following spectroscopic data: MS (ESI, pos. ion) m/z: 418.3 [M+H]$^+$; $^1$H NMR (600 MHz, CDCl$_3$): δ 7.69 (dd, J=10.2, 1.8 Hz, 1H), 7.51 (dd, J=8.4, 1.8 Hz, 1H), 7.37 (dd, J=8.4, 5.4 Hz, 1H), 7.28 (d, J=1.8 Hz, 1H), 7.25 (s, 1H), 6.96 (td, J=9.0, 2.4 Hz, 1H), 6.81 (d, J=9.0 Hz, 1H), 3.85 (s, 3H), 3.01 (t, J=4.8 Hz, 4H), 2.95 (t, J=4.8 Hz, 4H), 2.64 (q, J=7.2 Hz, 2H), 1.27 (t, J=7.8 Hz, 3H); and $^{13}$C NMR (150 MHz, CDCl$_3$): δ 161.0 (d, J=238.5 Hz), 156.6, 142.3, 135.8 (d, J=12.5 Hz), 129.9, 127.5, 125.1, 122.5 (d, J=4.5 Hz), 120.3 (d, J=9.8 Hz), 116.4, 111.3 (d, J=24.1 Hz), 110.9, 101.3 (d, J=28.3 Hz), 56.0, 51.7, 46.2, 18.2, 13.4.

Example 71 Synthesis of 6-chloro-3-ethyl-1-((4-methoxy-3-(piperazin-1-yl)phenyl)sulfonyl)-1H-indole

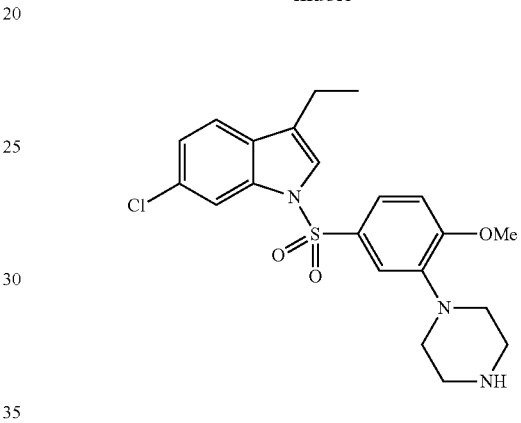

Step 1) Synthesis of 2,2,2-trichloro-1-(4-(5-((6-chloro-3-ethyl-1H-indol-1-yl)sulfonyl)-2-methoxyphenyl)piperazin-1-yl)ethanone 6-Chloro-3-ethyl-1H-indole (215 mg, 1.2 mmol) was reacted with sodium hydride (60 mg, 1.5 mmol, 60%) and 4-methoxy-3-(4-(2,2,2-trichloroacetyl)piperazin-1-yl)benzene-1-sulfonyl chloride (523 mg, 1.2 mmol, dissolved in THF (4 mL)) in THF (12 mL) according to the procedure as described in step 3 of example 1, and the crude product was purified by silica gel chromatography eluted with PE/EtOAc (V/V)=5/1 to give the title compound as a white solid (347 mg, 50%). The compound was characterized by the following spectroscopic data: MS (ESI, pos. ion) m/z: 578.1 [M+H]$^+$; and $^1$H NMR (600 MHz, CDCl$_3$): δ 8.00 (d, J=1.8 Hz, 1H), 7.55 (dd, J=8.4, 2.4 Hz, 1H), 7.37 (d, J=8.4 Hz, 1H), 7.30 (d, J=2.4 Hz, 1H), 7.25 (t, J=1.2 Hz, 1H), 7.20 (dd, J=8.4, 1.8 Hz, 1H), 6.86 (d, J=9.0 Hz, 1H), 4.01 (s, 3H), 3.88 (brs, 4H), J=4.8 Hz, 4H), 2.64 (qd, J=7.8, 1.2 Hz, 2H), 1.27 (t, J=7.2 Hz, 3H).

Step 2) Synthesis of 6-chloro-3-ethyl-1-((4-methoxy-3-(piperazin-1-yl)phenyl)sulfonyl)-1H-indole 2,2,2-Trichloro-1-(4-(5-((6-chloro-3-ethyl-1H-indol-1-yl)sulfonyl)-2-methoxyphenyl)piperazin-1-yl) ethanone (320 mg, 0.55 mmol) was reacted with potassium hydroxide solution (84 mg of potassium hydroxide solid, 1.5 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (143 mg, 60%). The compound was characterized by the following spectroscopic data: MS (ESI, pos. ion) m/z: 434.0 [M+H]$^+$; $^1$H NMR (600 MHz, CDCl$_3$): δ 8.00 (s, 1H), 7.50 (d, J=7.2 Hz, 1H), 7.35 (d, J=8.4 Hz, 1H), 7.31 (s, 1H), 7.25 (s, 1H), 7.18 (d, J=7.8 Hz, 1H), 6.81 (d, J=8.4 Hz, 1H), 3.85 (s, 3H), 3.02 (t, J=4.8 Hz, 4H), 2.96 (t, J=4.8 Hz, 4H), 2.63 (q, J=7.2 Hz, 2H), 1.28 (d, J=7.2 Hz, 3H); and $^{13}$C NMR (150 MHz, DMSO-d$_6$): δ 156.8, 142.3, 135.3, 129.7, 129.5, 128.4, 125.0, 123.9, 123.7, 122.0, 121.6, 115.6, 113.3, 112.2, 56.3, 51.2, 45.7, 17.6, 13.7.

Example 72 Synthesis of 6-bromo-3-ethyl-1-((4-methoxy-3-(piperazin-1-yl)phenyl)sulfonyl)-1H-indole

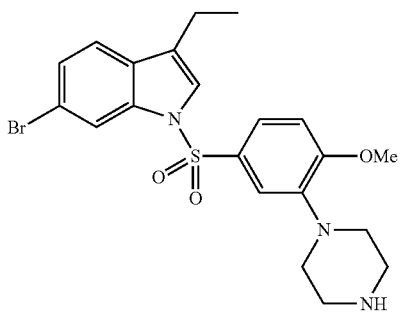 [SMILES: CCc1cn(S(=O)(=O)c2ccc(OC)c(N3CCNCC3)c2)c2cc(Cl)ccc12]

Step 1) Synthesis of 1-(4-(5-((6-bromo-3-ethyl-1H-indol-1-yl)sulfonyl)-2-methoxyphenyl) piperazin-1-yl)-2,2,2-trichloroethanone 6-Bromo-3-ethyl-1H-indole (268 mg, 1.2 mmol) was reacted with sodium hydride (60 mg, 1.5 mmol, 60%) and 4-methoxy-3-(4-(2,2,2-trichloroacetyl)piperazin-1-yl)benzene-1-sulfonyl chloride (523 mg, 1.2 mmol, dissolved in THF (4 mL)) in THF (10 mL) according to the procedure as described in step 3 of example 1, and the crude product was purified by silica gel chromatography eluted with PE/EtOAc (V/V)=5/1 to give the title compound as a white solid (409 mg, 55%). The compound was characterized by the following spectroscopic data: MS (ESI, pos. ion) m/z: 622.0 [M+H]$^+$; and $^1$H NMR (400 MHz, CDCl$_3$): δ 8.16 (s, 1H), 7.55 (dd, J=8.8, 2.4 Hz, 1H), 7.34-7.32 (m, 2H), 7.31 (d, J=2.0 Hz, 1H), 7.24 (s, 1H), 6.86 (d, J=8.8 Hz, 1H), 3.88 (s, 3H), 3.84-3.73 (m, 4H), 3.05 (t, J=4.8 Hz, 4H), 2.64 (qd, J=7.6, 0.8 Hz, 2H), 1.27 (t, J=7.6 Hz, 3H).

Step 2) Synthesis of 6-bromo-3-ethyl-1-((4-methoxy-3-(piperazin-1-yl)phenyl)sulfonyl)-1H-indole 1-(4-(5-((6-Bromo-3-ethyl-1H-indol-1-yl)sulfonyl)-2-methoxyphenyl)piperazin-1-yl)-2,2,2-trichloro ethanone (400 mg, 0.65 mmol) was reacted with potassium hydroxide solution (112 mg of potassium hydroxide solid, 2.0 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (252 mg, 81%). The compound was characterized by the following spectroscopic data: MS (ESI, pos. ion) m/z: 478.0 [M+H]$^+$; $^1$H NMR (600 MHz, CDCl$_3$): δ 8.16 (s, 1H), 7.48 (d, J=9.0 Hz, 1H), 7.34-7.30 (m, 3H), 7.24 (s, 1H), 6.81 (d, J=8.4 Hz, 1H), 3.85 (s, 3H), 3.01 (t, J=4.8 Hz, 4H), 2.95 (t, J=4.8 Hz, 4H), 2.62 (q, J=7.2 Hz, 2H), 1.26 (t, J=7.2 Hz, 3H); and $^{13}$C NMR (150 MHz, CDCl$_3$): δ 156.7, 142.3, 136.3, 130.1, 129.7, 126.3, 125.1, 122.8, 122.3, 120.7, 118.2, 117.1, 116.6, 110.9, 56.0, 51.8, 46.2, 18.2, 13.4.

Example 73 Synthesis of 6-fluoro-1-((4-methoxy-3-(piperazin-1-yl)phenyl)sulfonyl)-3-(methoxymethyl)-1H-indole

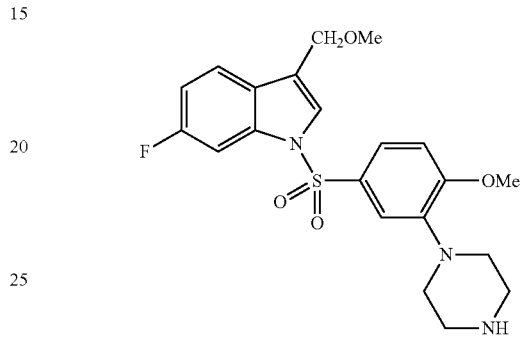

Step 1) Synthesis of tert-butyl 6-fluoro-3-formyl-1H-indole-1-carboxylate

To 15 mL of dichloromethane were added 6-fluoro-1H-indole-3-carbaldehyde (2.32 g, 14.2 mmol) and 4-dimethylaminopyridine (150 mg, 1.23 mmol) in turn. To the mixture was added dropwise di-tert-butyl dicarbonate (4.66 g, 21.3 mmol) at 0° C. in a low temperature bath. After the addition, the mixture was reacted at 25° C. for 24 hours. To the reaction mixture was added 50 mL of dichlormethane, and the resulting mixture was washed with saturated aqueous sodium bicarbonate (40 mL). The organic layer was dried over anhydrous sodium sulfate and filtered. The filtrate was concentrated in vacuo and the residue was purified by silica gel chromatography eluted with PE/EA(V/V)=10/1 to give the title compound as a white solid (3.31 g, 88.4%). The compound was characterized by the following spectroscopic data: $^1$H NMR (600 MHz, CDCl$_3$): δ 10.04 (s, 1H), 8.22-8.17 (m, 2H), 7.84 (d, J=9.6 Hz, 1H), 7.10 (td, J=9.0, 2.4 Hz, 1H), 1.69 (s, 9H).

Step 2) Synthesis of tert-butyl 6-fluoro-3-(hydroxymethyl)-1H-indole-1-carboxylate To a solution of tert-butyl 6-fluoro-3-formyl-1H-indole-1-carboxylate (3.0 g, 11.4 mmol) in tetrahydrofuran (15 mL) was added sodium borohydride (647 mg, 17.1 mmol) slowly at 0° C. in a low temperature bath. After the addition, the mixture was reacted at 25° C. for 4 hours. To the reaction mixture was added 50 mL of dichlormethane, and the resulting mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA(V/V)=5/1 to give the title compound as a white solid (2.35 g, 77.7%). The compound was characterized by the following spectroscopic data: $^1$H NMR (600 MHz, CDCl$_3$): δ 7.82 (s, 1H), 7.53 (dd, J=8.4, 5.4 Hz, 2H), 6.98 (td, J=9.0, 2.4 Hz, 1H), 4.78 (d, J=4.2 Hz, 2H), 2.14 (s, 1H), 1.64 (s, 9H).

Step 3) Synthesis of tert-butyl 3-(acetoxymethyl)-6-fluoro-1H-indole-1-carboxylate To 20 mL of dichloromethane were added tert-butyl 6-fluoro-3-(hydroxymethyl)-1H-indole-1-carboxylate (2.38 g, 8.97 mmol) and triethylamine (2.5 mL, 17.9 mmol) in turn. To the mixture was added dropwise acetyl chloride (1.27 mL, 13.4 mmol) at 0° C. in a low temperature bath. After the addition, the mixture was reacted at 25° C. for 10 hours. To the reaction mixture was added 50 mL of dichloromethane, and the resulting mixture was washed with saturated aqueous sodium bicarbonate (40 mL). The organic layer was dried over anhydrous sodium sulfate and filtered. The filtrate was concentrated in vacuo and the residue was purified by silica gel chromatography eluted with PE/EA (V/V)=20/1 to give the title compound as a white solid (2.76 g, 86.7%). The compound was characterized by the following spectroscopic data: $^1$H NMR (600 MHz, CDCl$_3$): δ 7.85 (s, 1H), 7.60 (s, 1H), 7.50 (dd, J=8.4, 5.4 Hz, 1H), 7.00 (td, J=9.0, 2.4 Hz, 1H), 5.21 (s, 2H), 2.06 (s, 3H), 1.64 (s, 9H).

Step 4) Synthesis of 6-fluoro-3-(methoxymethyl)-1H-indole

To 20 mL of methanol was added tert-butyl 3-(acetoxymethyl)-6-fluoro-1H-indole-1-carboxylate (2.35 g, 7.65 mmol) at 25° C. To the mixture was added dropwise sodium methoxide solution (15 mL, 1 M). After the addition, the mixture was reacted for 10 hours. To the reaction mixture was added 50 mL of ethyl acetate, and the resulting mixture was washed with saturated aqueous sodium chloride (40 mL). The organic layer was dried over anhydrous sodium sulfate and filtered. The filtrate was concentrated in vacuo and the residue was purified by silica gel chromatography eluted with PE/EA(V/V)=10/1 to give the title compound as a pink solid (1.13 g, 82.5%). The compound was characterized by the following spectroscopic data: MS (ESI, pos. ion) m/z: 180.1 [M+H]$^+$; and $^1$H NMR (400 MHz, CDCl$_3$): δ 8.20 (s, 1H), 7.59 (dd, J=8.8, 5.2 Hz, 1H), 7.08 (d, J=2.4 Hz, 1H), 6.98 (dd, J=9.6, 2.0 Hz, 1H), 6.89 (ddd, J=9.6, 8.8, 2.4 Hz, 1H), 4.63 (s, 2H), 3.39 (s, 3H).

Step 5) Synthesis of 2,2,2-trifluoro-1-(4-(5-((6-fluoro-3-(methoxymethyl)-1H-indol-1-yl) sulfonyl)-2-methoxyphenyl)piperazin-1-yl)ethanone 6-Fluoro-3-(methoxymethyl)-1H-indole (580 mg, 3.24 mmol) was reacted with sodium hydride (144 mg, 3.6 mmol, 60%) and 4-methoxy-3-(4-(2,2,2-trifluoroacetyl)piperazin-1-yl)benzene-1-sulfonyl chloride (1.38 g, 3.56 mmol, dissolved in THF (6 mL)) in THF (15 mL) according to the procedure as described in step 3 of example 1, and the crude product was purified by silica gel chromatography eluted with PE/EtOAc(V/V)=5/1 to give the title compound as a brown solid (1.46 g, 85.0%). The compound was characterized by the following spectroscopic data: MS (ESI, pos. ion) m/z: 530.1 [M+H]$^+$; and $^1$H NMR (400 MHz, CDCl$_3$) δ 7.65 (dd, J=9.6, 2.0 Hz, 1H), 7.57 (dd, J=8.8, 2.4 Hz, 1H), 7.49 (dd, J=8.8, 5.6 Hz, 1H), 7.46 (s, 1H), 7.26 (d, J=2.0 Hz, 1H), 6.97 (td, J=9.2, 2.4 Hz, 1H), 6.84 (d, J=8.8 Hz, 1H), 4.51 (d, J=0.8 Hz, 2H), 3.86 (s, 3H), 3.80-3.70 (m, 4H), 3.35 (s, 3H), 3.06-2.98 (m, 4H).

Step 6) Synthesis of 6-fluoro-1-((4-methoxy-3-(piperazin-1-yl)phenyl)sulfonyl)-3-methoxymethyl)-1H-indole 2,2,2-Trifluoro-1-(4-(5-((6-fluoro-3-(methoxymethyl)-1H-indol-1-yl)sulfonyl)-2-methoxyphenyl)piperazin-1-yl)ethanone (600 mg, 1.13 mmol) was reacted with potassium hydroxide solution (112 mg of potassium hydroxide solid, 2.0 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a light yellow solid (304 mg, 61.9%). The compound was characterized by the following spectroscopic data: MS (ESI, pos. ion) m/z: 434.1 [M+H]$^+$; $^1$H NMR (600 MHz, DMSO-d$_6$): δ 7.83 (s, 1H), 7.70 (dd, J=10.2, 2.4 Hz, 1H), 7.64-7.58 (m, 2H), 7.25 (d, J=2.4 Hz, 1H), 7.16 (td, J=9.0, 2.4 Hz, 1H), 7.07 (d, J=8.4 Hz, 1H), 4.52 (s, 2H), 3.80 (s, 3H), 3.22 (s, 3H), 2.81-2.80 (m, 4H), 2.78-2.77 (m, 4H); and $^{13}$C NMR (150 MHz, DMSO-d$_6$): δ 160.7 (d, J=238.3 Hz), 157.1, 142.8, 135.2 (d, J=12.6 Hz), 128.5, 126.8, 126.4, 122.4, 122.1 (d, J=9.9 Hz), 119.8, 115.7, 112.4, 112.1 (d, J=23.8 Hz), 100.8 (d, J=28.2 Hz), 65.3, 57.6, 56.5, 51.5, 46.0.

Example 74 Synthesis of 6-chloro-1-((4-methoxy-3-(piperazin-1-yl)phenyl)sulfonyl)-3-(methoxymethyl)-1H-indole

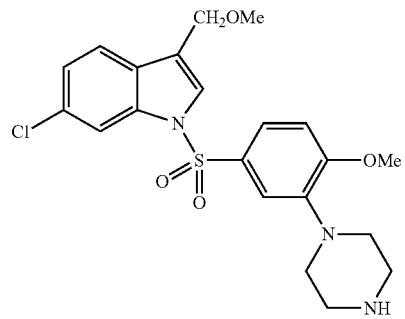

Step 1) Synthesis of 6-chloro-3-(methoxymethyl)-1H-indole

Tert-butyl 3-(acetoxymethyl)-6-chloro-1H-indole-1-carboxylate (0.9 g, 2.78 mmol) was reacted with sodium methoxide solution (5.0 mL, 1 M) in methanol (15 mL) according to the procedure as described in step 4 of example 73, and the crude product was purified by silica gel chromatography eluted with PE/EA(V/V)=10/1 to give the title compound as a yellow solid (0.55 g, 88.6%). The compound was characterized by the following spectroscopic data: MS (ESI, pos. ion) m/z: 196.1 [M+H]$^+$; and $^1$H NMR (600 MHz, CDCl$_3$): δ 8.22 (s, 1H), 7.59 (d, J=8.4 Hz, 1H), 7.27 (s, 1H), 7.09 (d, J=9.0 Hz, 2H), 4.62 (s, 2H), 3.39 (s, 3H).

Step 2) Synthesis of 1-(4-(5-((6-chloro-3-(methoxymethyl)-1H-indol-1-yl)sulfonyl)-2-methoxyphenyl)piperazin-1-yl)-2,2,2-trifluoroethanone 6-Chloro-3-(methoxymethyl)-1H-indole (450 mg, 2.30 mmol) was reacted with sodium hydride (96 mg, 2.4 mmol, 60%) and 4-methoxy-3-(4-(2,2,2-trifluoroacetyl)piperazin-1-yl)benzene-1-sulfonyl chloride (0.98 g, 2.53 mmol, dissolved in THF (6 mL)) in THF (15 mL) according to the procedure as described in step 3 of example 1, and the crude product was purified by silica gel chromatography eluted with PE/EtOAc(V/V)=5/1 to give the title compound as a brown solid (1.26 g, 74.9%). The compound was characterized by the following spectroscopic data: MS (ESI, pos. ion) m/z: 546.1 [M+H]$^+$; and $^1$H NMR (400 MHz, CDCl$_3$): δ 7.97 (d, J=2.0 Hz, 1H), 7.56 (dd, J=8.8, 2.4 Hz, 1H), 7.47 (d, J=8.0 Hz, 2H), 7.30 (d, J=2.0 Hz, 1H), 7.19 (dd, J=8.4, 1.6 Hz, 1H), 6.85 (d, J=8.8 Hz, 1H), 4.51 (s, 2H), 3.86 (s, 3H), 3.81-3.71 (m, 4H), 3.34 (s, 3H), 3.07-3.00 (m, 4H).

Step 3) Synthesis of 6-chloro-1-((4-methoxy-3-(piperazin-1-yl)phenyl)sulfonyl)-3-(methoxymethyl)-1H-indole 1-(4-(5-((6-Chloro-3-(methoxymethyl)-1H-indol-1-yl)sulfonyl)-2-methoxyphenyl)piperazin-1-yl)-2,2,2-trifluoroethanone (900 mg, 1.65 mmol) was reacted with potassium hydroxide solution (168 mg of potassium hydroxide solid, 3.0 mmol, 1 mmol/mL in water) in THF (15 mL) according to the procedure as described in step 4 of example 1, and the crude product was purified by silica gel chromatography eluted with DCM/methanol(V/V)=30/1 to give the title compound as a white solid (556 mg, 74.9%). The compound was characterized by the following spectroscopic data: MS (ESI, pos. ion) m/z: 450.1 [M+H]$^+$; $^1$H NMR (600 MHz, DMSO-d$_6$): δ 7.92 (d, J=1.2 Hz, 1H), 7.86 (s, 1H), 7.61 (d, J=8.4 Hz, 1H), 7.58 (dd, J=9.0, 2.4 Hz, 1H), 7.32 (dd, J=8.4, 1.2 Hz, 1H), 7.26 (d, J=1.8 Hz, 1H), 7.07 (d, J=9.0 Hz, 1H), 4.51 (s, 2H), 3.80 (s, 3H), 3.22 (s, 3H), 2.82-2.81 (m, 4H), 2.78-2.77 (m, 4H); and $^{13}$C NMR (150 MHz, DMSO-d$_6$): δ 156.7, 142.2, 135.0, 129.5, 128.5, 127.9, 126.3, 123.7, 121.9, 121.8, 119.3, 115.3, 112.9, 111.9, 64.7, 57.2, 55.9, 51.0, 45.5.

Example 75 Synthesis of 6-bromo-1-((4-methoxy-3-(piperazin-1-yl)phenyl)sulfonyl)-3-(methoxymethyl)-1H-indole

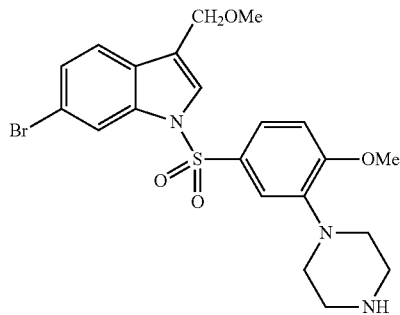

Step 1) Synthesis of 6-bromo-3-(methoxymethyl)-1H-indole

Tert-butyl 3-(acetoxymethyl)-6-bromo-1H-indole-1-carboxylate (0.75 g, 2.04 mmol) was reacted with sodium methoxide solution (4.0 mL, 1 M) in methanol (10 mL) according to the procedure as described in step 4 of example 73, and the crude product was purified by silica gel chromatography eluted with PE/EA(V/V)=10/1 to give the title compound as a light yellow solid (0.43 g, 86.9%). The compound was characterized by the following spectroscopic data: MS (ESI, pos. ion) m/z: 240.0 [M+H]$^+$; and $^1$H NMR (600 MHz, CDCl$_3$): δ 8.23 (s, 1H), 7.54 (d, J=8.4 Hz, 1H), 7.42 (s, 1H), 7.22 (d, J=8.4 Hz, 1H), 7.07 (s, 1H), 4.62 (s, 2H), 3.38 (s, 3H).

Step 2) Synthesis of 1-(4-(5-((6-bromo-3-(methoxymethyl)-1H-indol-1-yl)sulfonyl)-2-methoxyphenyl)piperazin-1-yl)-2,2,2-trifluoroethanone 6-Bromo-3-(methoxymethyl)-1H-indole (400 mg, 1.67 mmol) was reacted with sodium hydride (72 mg, 1.8 mmol, 60%) and 4-methoxy-3-(4-(2,2,2-trifluoroacetyl)piperazin-1-yl)benzene-1-sulfonyl chloride (0.71 g, 1.84 mmol, dissolved in THF (6 mL)) in THF (15 mL) according to the procedure as described in step 3 of example 1, and the crude product was purified by silica gel chromatography eluted with PE/EtOAc(V/V)=5/1 to give the title compound as a brown solid (505 mg, 51.3%). The compound was characterized by the following spectroscopic data: MS (ESI, pos. ion) m/z: 590.1 [M+H]$^+$; and $^1$H NMR (600 MHz, CDCl$_3$): δ 8.13 (s, 1H), 7.54 (d, J=8.4 Hz, 1H), 7.46-7.40 (m, 2H), 7.32 (d, J=12.0 Hz, 2H), 6.84 (d, J=9.0 Hz, 1H), 4.50 (s, 2H), 3.90 (s, 3H), 3.84 (brs, 2H), 3.76 (brs, 2H), 3.34 (s, 3H), 3.04 (brs, 4H).

Step 3) Synthesis of 6-bromo-1-((4-methoxy-3-(piperazin-1-yl)phenyl)sulfonyl)-3-(methoxymethyl)-1H-indole 1-(4-(5-((6-Bromo-3-(methoxymethyl)-1H-indol-1-yl)sulfonyl)-2-methoxyphenyl)piperazin-1-yl)-2,2,2-trifluoroethanone (485 mg, 0.82 mmol) was reacted with potassium hydroxide solution (134 mg of potassium hydroxide solid, 2.4 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (221 mg, 54.4%). The compound was characterized by the following spectroscopic data: MS (ESI, pos. ion) m/z: 494.1 [M+H]$^+$; $^1$H NMR (600 MHz, DMSO-d$_6$): δ 8.06 (d, J=1.2 Hz, 1H), 7.84 (s, 1H), 7.58-7.54 (m, 2H), 7.44 (dd, J=8.4, 1.8 Hz, 1H), 7.26 (d, J=2.4 Hz, 1H), 7.07 (d, J=9.0 Hz, 1H), 4.51 (s, 2H), 3.80 (s, 3H), 3.21 (s, 3H), 2.83-2.82 (m, 4H), 2.78-2.77 (m, 4H); and $^{13}$C NMR (150 MHz, DMSO-d$_6$): δ 156.7, 142.2, 135.3, 128.9, 127.8, 126.3, 126.2, 122.2, 121.8, 119.4, 117.5, 115.8, 115.3, 111.9, 64.7, 57.2, 55.9, 51.1, 45.5.

Example 76 Synthesis of 2,2,2-trifluoro-1-(6-fluoro-1-((4-methoxy-3-(piperazin-1-yl)phenyl) sulfonyl)-1H-indol-3-yl)ethanol

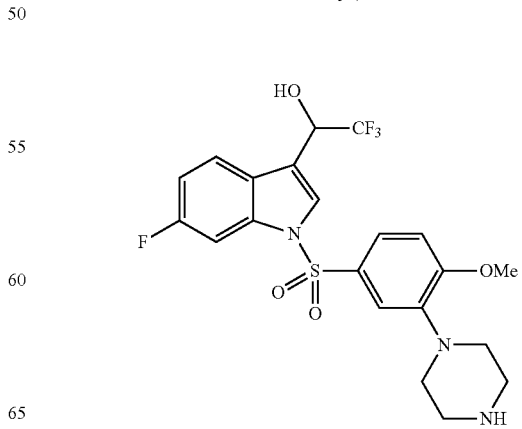

Step 1) Synthesis of 2,2,2-trifluoro-1-(6-fluoro-1H-indol-3-yl)ethanone

To 10 mL of tetrahydrofuran was added 6-fluoroindole (2.0 g, 8.97 mmol) at 0° C. in a low temperature bath, and to the resulting mixture was added dropwise trifluoroacetic anhydride (7.0 mL, 22.2 mmol). After the addition, the mixture was reacted at 25° C. for 4 hours. To the reaction mixture was added 50 mL of water, and the resulting mixture was filtered. The filter cake was dried in vacuo to give the title compound as a brown solid (1.87 g, 90%). The compound was characterized by the following spectroscopic data: MS (ESI, pos. ion) m/z: 232.1 [M+H]$^+$; and $^1$H NMR (400 MHz, DMSO-d$_6$): δ 12.72 (s, 1H), 8.48 (s, 1H), 8.15 (dd, J=8.7, 5.5 Hz, 1H), 7.38 (dd, J=9.3, 1.8 Hz, 1H), 7.18 (td, J=9.8, 2.1 Hz, 1H).

Step 2) Synthesis of 2,2,2-trifluoro-1-(6-fluoro-1-((4-methoxy-3-(4-(2,2,2-trifluoroacetyl) piperazin-1-yl)phenyl)sulfonyl)-1H-indol-3-yl)ethanone 2,2,2-Trifluoro-1-(6-fluoro-1H-indol-3-yl)ethanone (500 mg, 2.1 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (1.0 g, 2.6 mmol, dissolved in THF (6 mL)) in THF (15 mL) according to the procedure as described in step 3 of example 1, and the crude product was purified by silica gel chromatography eluted with PE/EtOAc(V/V)=5/1 to give the title compound as a brown solid (964 mg, 79%). The compound was characterized by the following spectroscopic data: MS (ESI, pos. ion) m/z: 581.6 [M+H]$^+$; and $^1$H NMR (400 MHz, CDCl$_3$): δ 8.38 (d, J=1.5 Hz, 1H), 8.28 (dd, J=8.8, 5.3 Hz, 1H), 7.72-7.66 (m, 2H), 7.36 (d, J=2.3 Hz, 1H), 7.17 (td, J=9.0, 2.3 Hz, 1H), 6.96 (d, J=8.7 Hz, 1H), 3.92 (s, 3H), 3.84 (t, J=4.8 Hz, 2H), 3.76 (t, J=4.2 Hz, 2H), 3.09 (t, J=4.5 Hz, 4H).

Step 3) Synthesis of 2,2,2-trifluoro-1-(6-fluoro-1-((4-methoxy-3-(piperazin-1-yl)phenyl)sulfonyl)-1H-indol-3-yl)ethanol To a solution of 2,2,2-trifluoro-1-(6-fluoro-1-((4-methoxy-3-(4-(2,2,2-trifluoroacetyl) piperazin-1-yl)phenyl)sulfonyl)-1H-indol-3-yl)ethanone (0.3 g, 0.52 mmol) in ethanol (10 mL) was added sodium borohydride (38 mg, 1.0 mmol) in portions slowly at 0° C. in a low temperature bath. After the addition, the mixture was reacted at 25° C. for 1 hour. To the reaction mixture was added 50 mL of water, and the resulting mixture was filtered. The filter cake was dried in vacuo to give the title compound as a white solid (243 mg, 99.7%). The compound was characterized by the following spectroscopic data: MS (ESI, pos. ion) m/z: 488.3 [M+H]$^+$; $^1$H NMR (600 MHz, DMSO-d$_6$): δ 7.95 (s, 1H), 7.75 (dd, J=8.7, 5.5 Hz, 1H), 7.70 (dd, J=9.8, 2.3 Hz, 1H), 7.66 (dd, J=8.7, 2.4 Hz, 1H), 7.20 (d, J=2.3 Hz, 1H), 7.18 (dd, J=9.1, 2.3 Hz, 1H), 7.09 (d, J=8.8 Hz, 1H), 6.96 (d, J=5.4 Hz, 1H), 5.46 (q, J=6.4 Hz, 1H), 3.81 (s, 3H), 2.81 (t, J=3.5 Hz, 4H), 2.78 (t, J=4.0 Hz, 4H); and $^{13}$C NMR (150 MHz, DMSO-d$_6$): δ 160.6 (d, J=240.8 Hz), 157.3, 142.9, 134.9 (d, J=12.6 Hz), 128.2, 127.2, 125.5 (t, J=144.9 Hz), 123.3 (d, J=9.9 Hz), 122.6, 117.8, 115.6, 112.4, 112.3 (d, J=23.8 Hz), 100.6 (d, J=28.2 Hz), 65.8 (q, J=32.3 Hz), 56.5, 51.6, 46.0.

Example 77 Synthesis of 1-(6-chloro-1-((4-methoxy-3-(piperazin-1-yl)phenyl)sulfonyl)-1H-indol-3-yl)-2,2,2-trifluoroethanol

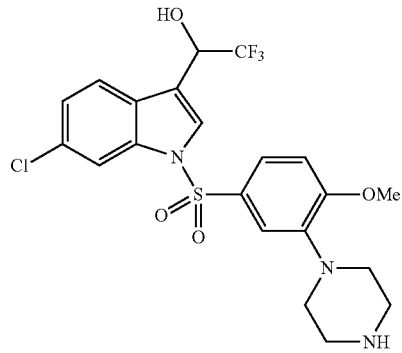

Step 1) Synthesis of 1-(6-chloro-1H-indol-3-yl)-2,2,2-trifluoroethanone

6-Chloroindole (5.0 g, 33.1 mmol) was reacted with trifluoroacetic anhydride (7.0 mL, 49.7 mmol) in THF (20 mL) according to the procedure as described in step 1 of example 76. And after the reaction, the reaction mixture was filtered. The filter cake was dried to give the title compound as a brown solid (7.96 g, 97%). The compound was characterized by the following spectroscopic data: MS (ESI, pos. ion) m/z: 248.1 [M+H]$^+$; and $^1$H NMR (400 MHz, DMSO-d$_6$): δ 12.77 (s, 1H), 8.52 (s, 1H), 8.14 (d, J=8.5 Hz, 1H), 7.63 (s, 1H), 7.34 (d, J=8.5 Hz, 1H).

Step 2) Synthesis of 1-(6-chloro-1-((4-methoxy-3-(4-(2,2,2-trifluoro acetyl)piperazin-1-yl) phenyl)sulfonyl)-1H-indol-3-yl)-2,2,2-trifluoroethanone 1-(6-Chloro-1H-indol-3-yl)-2,2,2-trifluoroethanone (500 mg, 2.0 mmol) was reacted with sodium hydride (96 mg, 2.4 mmol, 60%) and 4-methoxy-3-(4-(2,2,2-trichloroacetyl)piperazin-1-yl)benzene-1-sulfonyl chloride (0.94 g, 2.4 mmol, dissolved in THF (6 mL)) in THF (15 mL) according to the procedure as described in step 3 of example 1, and the crude product was purified by silica gel chromatography eluted with PE/EtOAc(V/V)=5/1 to give the title compound as a white solid (1.01 g, 85%). The compound was characterized by the following spectroscopic data: MS (ESI, pos. ion) m/z: 598.1 [M+H]$^+$; and $^1$H NMR (400 MHz, CDCl$_3$): δ 8.37 (d, J=1.5 Hz, 1H), 8.24 (d, J=8.6 Hz, 1H), 7.99 (d, J=1.6 Hz, 1H), 7.69 (dd, J=8.7, 2.3 Hz, 1H), 7.40-7.38 (m, 2H), 6.96 (d, J=8.7 Hz, 1H), 3.93 (s, 3H), 3.84 (t, J=4.8 Hz, 2H), 3.76 (t, J=4.2 Hz, 2H), 3.10 (t, J=4.6 Hz, 4H).

Step 3) Synthesis of 1-(6-chloro-1-((4-methoxy-3-(piperazin-1-yl)phenyl)sulfonyl)-1H-indol-3-yl)-2,2,2-trifluoroethanol 1-(6-Chloro-1-((4-methoxy-3-(4-(2,2,2-trifluoro acetyl) piperazin-1-yl)phenyl)sulfonyl)-1H-indol-3-yl)-2,2, 2-trifluoroethanone (0.3 g, 0.5 mmol) was reacted with sodium borohydride (38 mg, 1.0 mmol) in ethanol (10 mL) according to the procedure as described in step 3 of example 76. And after the reaction, the reaction mixture was filtered. The filter cake was dried to give the title compound as a white solid (247 mg, 98%). The compound was characterized by the following spectroscopic data: MS (ESI, pos. ion) m/z: 504.2 [M+H]$^+$; $^1$H NMR (400 MHz, DMSO-d$_6$): δ 7.99 (s, 1H), 7.93 (d, J=1.6 Hz, 1H), 7.76 (d, J=8.5 Hz, 1H), 7.63 (dd, J=8.6, 2.2 Hz, 1H), 7.36 (dd, J=8.6, 1.8 Hz, 1H), 7.22 (d, J=2.3 Hz, 1H), 7.11 (d, J=8.8 Hz, 1H), 6.99 (s, 1H), 5.48 (q, J=6.6 Hz, 1H), 3.82 (s, 3H), 2.83-2.82 (m, 4H), 2.79-2.77 (m, 4H); and $^{13}$C NMR (150 MHz, DMSO-d$_6$): δ 157.3, 142.9, 135.1, 130.1, 128.1, 127.7, 127.6, 125.5, 124.3, 123.4, 122.5, 117.8, 115.6, 113.3, 112.4, 65.7 (q, J=32.3 Hz), 56.5, 51.5, 46.0.

Example 78 Synthesis of 1-(6-bromo-1-((4-methoxy-3-(piperazin-1-yl)phenyl)sulfonyl)-1H-indol-3-yl)-2,2,2-trifluoroethanol

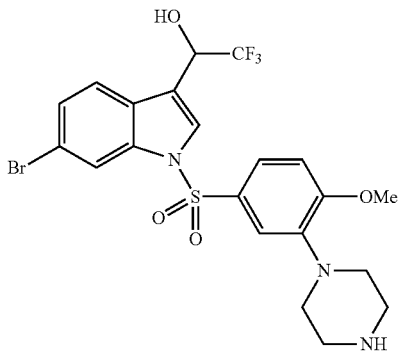 [SMILES: COc1ccc(S(=O)(=O)n2cc(C(O)C(F)(F)F)c3ccc(Cl)cc32)cc1N1CCNCC1]

Step 1) Synthesis of 1-(6-bromo-1H-indol-3-yl)-2,2,2-trifluoroethanone

6-Bromoindole (2.0 g, 10.3 mmol) was reacted with trifluoroacetic anhydride (2.1 mL, 15.4 mmol) in THF (20 mL) according to the procedure as described in step 1 of example 76. And after the reaction, the reaction mixture was filtered. The filter cake was dried to give the title compound as a brown solid (2.76 g, 92%). The compound was characterized by the following spectroscopic data: MS (ESI, pos. ion) m/z: 291.9 [M+H]$^+$; and $^1$H NMR (400 MHz, DMSO-d$_6$): δ 12.76 (s, 1H), 8.50 (s, 1H), 8.09 (d, J=8.2 Hz, 1H), 7.77 (s, 1H), 7.46 (d, J=8.1 Hz, 1H).

Step 2) Synthesis of 1-(6-bromo-1-((4-methoxy-3-(4-(2,2,2-trifluoro acetyl)piperazin-1-yl) phenyl) sulfonyl)-1H-indol-3-yl)-2,2,2-trifluoroethanone 1-(6-Bromo-1H-indol-3-yl)-2,2,2-trifluoroethanone (500 mg, 1.7 mmol) was reacted with sodium hydride (80 mg, 2.0 mmol, 60%) and 4-methoxy-3-(4-(2,2,2-trifluoroacetyl)piperazin-1-yl)benzene-1-sulfonyl chloride (0.80 g, 2.1 mmol, dissolved in THF (6 mL)) in THF (15 mL) according to the procedure as described in step 3 of example 1, and the crude product was purified by silica gel chromatography eluted with PE/EtOAc(V/V)=5/1 to give the title compound as a white solid (589 mg, 54%). The compound was characterized by the following spectroscopic data: MS (ESI, pos. ion) m/z: 642.1 [M+H]$^+$; and $^1$H NMR (400 MHz, CDCl$_3$): δ 8.35 (d, J=1.4 Hz, 1H), 8.19-8.16 (m, 2H), 7.68 (dd, J=8.7, 2.3 Hz, 1H), 7.52 (dd, J=8.5, 1.5 Hz, 1H), 7.41 (d, J=2.3 Hz, 1H), 6.96 (d, J=8.8 Hz, 1H), 3.93 (s, 3H), 3.84 (t, J=4.8 Hz, 2H), 3.76 (t, J=4.3 Hz, 2H), 3.11 (t, J=4.8 Hz, 4H).

Step 3) Synthesis of 1-(6-bromo-1-((4-methoxy-3-(piperazin-1-yl)phenyl)sulfonyl)-1H-indol-3-yl)-2,2,2-trifluoroethanol 1-(6-Bromo-1-((4-methoxy-3-(4-(2,2,2-trifluoro acetyl) piperazin-1-yl)phenyl)sulfonyl)-1H-indol-3-yl)-2,2,2-trifluoroethanone (0.3 g, 0.47 mmol) was reacted with sodium borohydride (36 mg, 0.93 mmol) in ethanol (10 mL) according to the procedure as described in step 3 of example 76. And after the reaction, the reaction mixture was filtered. The filter cake was dried to give the title compound as a white solid (226 mg, 95.3%). The compound was characterized by the following spectroscopic data: MS (ESI, pos. ion) m/z: 548.1 [M+H]$^+$; $^1$H NMR (600 MHz, DMSO-d$_6$): δ 8.06 (d, J=1.6 Hz, 1H), 7.97 (s, 1H), 7.70 (d, J=8.5 Hz, 1H), 7.60 (dd, J=8.7, 2.4 Hz, 1H), 7.47 (dd, J=8.5, 1.7 Hz, 1H), 7.22 (d, J=2.4 Hz, 1H), 7.11 (d, J=8.8 Hz, 1H), 6.98 (s, 1H), 5.48 (q, J=6.8 Hz, 1H), 3.82 (s, 3H), 2.82 (t, J=3.5 Hz, 4H), 2.78 (t, J=4.0 Hz, 4H); and $^{13}$C NMR (150 MHz, DMSO-d$_6$): δ 157.3, 142.8, 135.5, 128.1, 127.5, 127.0, 125.5 (t, J=142.7 Hz), 123.8, 122.5, 118.2, 117.9, 116.2, 115.7, 112.5, 65.7 (q, J=31.6 Hz), 56.5, 51.5, 46.0.

Example 79 Synthesis of 6-fluoro-1-((3-(piperazin-1-yl)-4-(2,2,2-trifluoroethoxy)phenyl) sulfonyl)-1H-indole

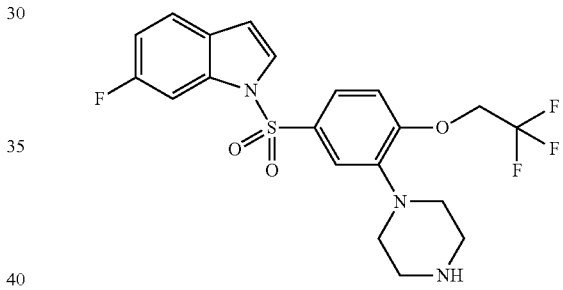

Step 1) Synthesis of 3-(4-(2,2,2-trichloroacetyl) piperazin-1-yl)-4-(2,2,2-trifluoroethoxy)benzene-1-sulfonyl chloride A solution of 2,2,2-trichloro-1-(4-(2-(2,2,2-trifluoroethoxy)phenyl)piperazin-1-yl)ethanone (1 g, 2.46 mmol) in dichloromethane (2 mL) was reacted with chlorosulfonic acid (3 mL) according to the procedure as described in step 2 of example 1. And after the reaction, the reaction mixture was concentrated and dried to give the title compound as a light yellow solid (656 mg, 53%). The compound was characterized by the following spectroscopic data: MS (ESI, pos. ion) m/z: 502.9 [M+H]$^+$; and $^1$H NMR (400 MHz, CDCl$_3$): δ 7.77 (dd, J=8.7, 2.4 Hz, 1H), 7.54 (d, J=2.4 Hz, 1H), 7.01 (d, J=8.7 Hz, 1H), 4.53 (q, J=7.7 Hz, 2H), 4.04 (brs, 4H), 3.31-3.19 (m, 4H).

Step 2) Synthesis of 2,2,2-trichloro-1-(4-(5-((6-fluoro-1H-indol-1-yl)sulfonyl)-2-(2,2,2-trifluoroethoxy)phenyl)piperazin-1-yl)ethanone 6-Fluoroindole (270 mg, 2.0 mmol) was reacted with sodium hydride (80 mg, 2.0 mmol, 60%) and 3-(4-(2,2,2-trichloroacetyl)piperazin-1-yl)-4-(2,2,2-trifluoroethoxy)benzene-1-sulfonyl chloride (1.06 g, 2.1 mmol, dissolved in THF (6 mL)) in THF (15 mL) according to the procedure as described in step 3 of example 1, and the crude product was purified by silica gel chromatography eluted with PE/EtOAc (V/V)=5/1 to give the title compound as a white solid (509 mg, 42.3%). The compound was characterized by the following spectroscopic data: MS (ESI, pos. ion) m/z: 602.1 [M+H]$^+$; and $^1$H NMR (400 MHz, CDCl$_3$): δ 7.69 (dd, J=9.6, 2.0 Hz, 1H), 7.56 (dd, J=8.8, 2.4 Hz, 1H), 7.51 (d, J=3.6 Hz, 1H), 7.46 (dd, J=8.4, 5.2 Hz, 1H), 7.32 (d, J=2.0 Hz, 1H), 7.00 (td, J=9.2, 2.4 Hz, 1H), 6.83 (d, J=8.8 Hz, 1H), 6.64 (dd, J=4.0, 0.8 Hz, 1H), 4.37 (q, J=7.6 Hz, 2H), 3.94 (brs, 4H), 3.10 (t, J=4.8 Hz, 4H).

Step 3) Synthesis of 6-fluoro-1-((3-(piperazin-1-yl)-4-(2,2,2-trifluoroethoxy)phenyl)sulfonyl)-1H-indole 2,2,2-Trichloro-1-(4-(5-((6-fluoro-1H-indol-1-yl)sulfonyl)-2-(2,2,2-trifluoroethoxy)phenyl)piperazin-1-yl) ethanone (500 mg, 0.83 mmol) was reacted with potassium hydroxide solution (134 mg of potassium hydroxide solid, 2.4 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (368 mg, 97%). The compound was characterized by the following spectroscopic data: MS (ESI, pos. ion) m/z: 458.1 [M+H]$^+$; $^1$H NMR (400 MHz, DMSO-d$_6$): δ 7.86 (d, J=3.6 Hz, 1H), 7.73 (dd, J=10.0, 2.0 Hz, 1H), 7.67 (dd, J=8.8, 2.4 Hz, 1H), 7.63 (dd, J=8.8, 5.6 Hz, 1H), 7.33 (d, J=2.4 Hz, 1H), 7.17-7.12 (m, 2H), 6.83 (d, J=3.6 Hz, 1H), 4.82 (q, J=8.8 Hz, 2H), 2.86 (t, J=4.4 Hz, 4H), 2.79 (t, J=4.4 Hz, 4H); and $^{13}$C NMR (100 MHz, DMSO-d$_6$): δ 161.3 (d, J=238.0 Hz), 154.9, 143.7, 135.5 (d, J=12.5 Hz), 131.2, 128.9 (d, J=3.9 Hz), 128.3, 126.4, 124.2 (d, J=9.9 Hz), 122.8, 117.1, 114.9, 113.0 (d, J=23.7 Hz), 110.4, 101.5 (d, J=28.2 Hz), 65.9 (q, J=34.6 Hz), 52.3, 46.7.

Example 80 Synthesis of 6-fluoro-1-((3-(4-methylpiperazin-1-yl)-4-(2,2,2-trifluoroethoxy) phenyl)sulfonyl)-1H-indole

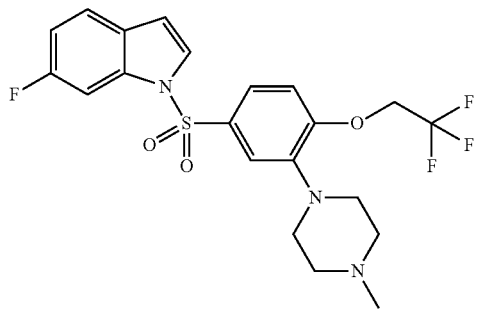 [SMILES: CN1CCN(c2cc(S(=O)(=O)n3ccc4ccc(F)cc43)ccc2OCC(F)(F)F)CC1]

6-Fluoro-1-((3-(piperazin-1-yl)-4-(2,2,2-trifluoroethoxy) phenyl)sulfonyl)-1H-indole (250 mg, 0.55 mmol) was reacted with sodium cyanoborohydride (104 mg, 1.65 mmol) and formaldehyde (40%, 0.11 mL, 1.6 mmol) in methanol (5 mL) according to the procedure as described in example 2, and the crude product was purified by silica gel chromatography eluted with DCM/methanol(V/V)=50/1 to give the title compound as a white solid (218 mg, 84.0%). The compound was characterized by the following spectroscopic data: MS (ESI, pos. ion) m/z: 472.2 [M+H]$^+$; $^1$H NMR (400 MHz, CDCl$_3$): δ 7.69 (dd, J=9.6, 2.0 Hz, 1H), 7.51-7.48 (m, 2H), 7.43 (dd, J=8.4, 5.2 Hz, 1H), 7.32 (d, J=2.4 Hz, 1H), 6.97 (td, J=9.2, 2.4 Hz, 1H), 6.80 (d, J=8.4 Hz, 1H), 6.61 (d, J=3.6 Hz, 1H), 4.34 (q, J=8.0 Hz, 2H), 3.05 (brs, 4H), 2.57 (brs, 4H), 2.35 (s, 3H); and $^{13}$C NMR (100 MHz, CDCl$_3$): δ 160.8 (d, J=240.6 Hz), 153.7, 142.7, 134.9 (d, J=12.4 Hz), 132.2, 126.9 (d, J=1.1 Hz), 126.6 (d, J=4.0 Hz), 122.1 (d, J=9.8 Hz), 121.6, 116.8, 113.7, 111.8 (d, J=24.1 Hz), 108.9, 100.8 (d, J=28.2 Hz), 65.9 (q, J=35.8 Hz), 54.8, 49.8, 45.8.

Example 81 Synthesis of 6-fluoro-1-((3-(piperazin-1-yl)-4-(2,2,3,3-tetrafluoropropoxy) phenyl)sulfonyl)-1H-indole

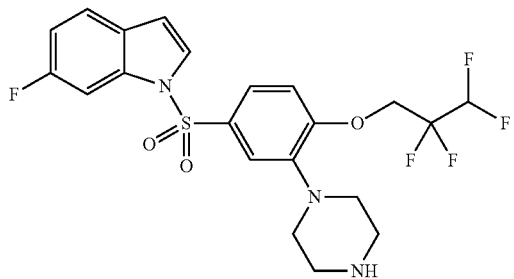 [SMILES: O=S(=O)(c1ccc(OCC(F)(F)C(F)F)c(N2CCNCC2)c1)n1ccc2ccc(F)cc21]

Step 1) Synthesis of 4-(2,2,3,3-tetrafluoropropoxy)-3-(4-(2,2,2-trichloroacetyl)piperazin-1-yl) benzene-1-sulfonyl chloride A solution of 2,2,2-trichloro-1-(4-(2-(2,2,3,3-tetrafluoropropoxy)phenyl)piperazin-1-yl)ethanone (0.8 g, 1.83 mmol) in dichloromethane (2 mL) was reacted with chlorosulfonic acid (3 mL) according to the procedure as described in step 2 of example 1. And after the reaction, the reaction mixture was concentrated and dried to give the title compound as a light yellow solid (911 mg, 93.2%). The compound was characterized by the following spectroscopic data: MS (ESI, pos. ion) m/z: 534.9 [M+H]$^+$; and $^1$H NMR (400 MHz, CDCl$_3$): δ 7.78 (dd, J=8.7, 2.3 Hz, 1H), 7.56 (d, J=2.3 Hz, 1H), 7.04 (d, J=8.7 Hz, 1H), 6.05 (tt, J=53.2, 3.0 Hz, 1H), 4.55 (t, J=12.0 Hz, 2H), 4.02 (brs, 4H), 3.31-3.15 (m, 4H).

Step 2) Synthesis of 2,2,2-trichloro-1-(4-(5-((6-fluoro-1H-indol-1-yl)sulfonyl)-2-(2,2,3,3-tetrafluoropropoxy)phenyl)piperazin-1-yl)ethanone 6-Fluoroindole (270 mg, 2.0 mmol) was reacted with sodium hydride (80 mg, 2.0 mmol, 60%) and 4-(2,2,3,3-tetrafluoropropoxy)-3-(4-(2,2,2-trichloro acetyl)piperazin-1-yl)benzene-1-sulfonyl chloride (1.12 g, 2.1 mmol, dissolved in THF (6 mL)) in THF (15 mL) according to the procedure as described in step 3 of example 1, and the crude product was purified by silica gel chromatography eluted with PE/EA(V/V)=5/1 to give the title compound as a white solid (585 mg, 46.1%). The compound was characterized by the following spectroscopic data: MS (ESI, pos. ion) m/z: 634.1 [M+H]$^+$; and $^1$H NMR (400 MHz, CDCl$_3$): δ 7.69 (dd, J=9.6, 2.0 Hz, 1H), 7.57 (dd, J=8.8, 2.4 Hz, 1H), 7.51 (d, J=3.6 Hz, 1H), 7.45 (dd, J=8.8, 5.6 Hz, 1H), 7.33 (d, J=2.0 Hz, 1H), 6.99 (td, J=8.8, 2.4 Hz, 1H), 6.86 (d, J=8.8 Hz, 1H), 6.64-6.63 (m, 1H), 5.97 (tt, J=53.2, 3.2 Hz, 1H), 4.39 (t, J=12.0 Hz, 2H), 3.93 (brs, 4H), 3.08 (t, J=4.8 Hz, 4H).

Step 3) Synthesis of 6-fluoro-1-((3-(piperazin-1-yl)-4-(2,2,3,3-tetrafluoropropoxy)phenyl) sulfonyl)-1H-indole 2,2,2-Trichloro-1-(4-(5-((6-fluoro-1H-indol-1-yl)sulfonyl)-2-(2,2,3,3-tetrafluoropropoxy)phenyl)piperazin-1-yl)ethanone (500 mg, 0.79 mmol) was reacted with potassium hydroxide solution (134 mg of potassium hydroxide solid, 2.4 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (354 mg, 91.5%). The compound was characterized by the following spectroscopic data: MS (ESI, pos. ion) m/z: 490.1 [M+H]+; 1H NMR (400 MHz, CDCl3): δ 7.69 (dd, J=10.0, 2.4 Hz, 1H), 7.52-7.49 (m, 2H), 7.44 (dd, J=8.4, 5.2 Hz, 1H), 7.33 (d, J=2.0 Hz, 1H), 6.98 (td, J=8.8, 2.4 Hz, 1H), 6.81 (d, J=8.8 Hz, 1H), 6.61 (dd, J=3.6, 0.4 Hz, 1H), 6.00 (tt, J=53.2, 4.0 Hz, 1H), 4.35 (t, J=12.0 Hz, 2H), 2.98 (brs, 4H), 2.94 (brs, 4H); and 13C NMR (100 MHz, CDCl3): δ 160.8 (d, J=240.4 Hz), 154.1, 143.1, 134.9 (d, J=12.6 Hz), 131.9, 126.9, 126.5 (d, J=4.1 Hz), 122.1 (d, J=9.7 Hz), 121.8, 117.0, 113.2, 111.8 (d, J=24.1 Hz), 109.1, 108.9, 100.8 (d, J=28.2 Hz), 65.3 (t, J=29.2 Hz), 51.4, 45.9.

Example 82 Synthesis of 6-fluoro-1-((3-(4-methyl-piperazin-1-yl)-4-(2,2,3,3-tetrafluoropropoxy)phenyl)sulfonyl)-1H-indole

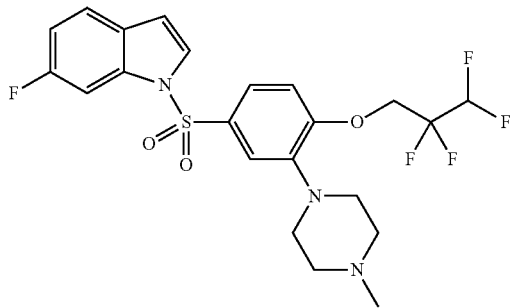 [SMILES: CN1CCN(c2cc(S(=O)(=O)n3ccc4ccc(F)cc43)ccc2OCC(F)(F)C(F)F)CC1]

6-Fluoro-1-((3-(piperazin-1-yl)-4-(2,2,3,3-tetrafluoropropoxy)phenyl)sulfonyl)-1H-indole (250 mg, 0.51 mmol) was reacted with sodium cyanoborohydride (104 mg, 1.65 mmol) and formaldehyde (40%, 0.11 mL, 1.6 mmol) in methanol (5 mL) according to the procedure as described in example 2, and the crude product was purified by silica gel chromatography eluted with DCM/methanol(V/V)=50/1 to give the title compound as a white solid (223 mg, 86.9%). The compound was characterized by the following spectroscopic data: MS (ESI, pos. ion) m/z: 504.2 [M+H]+; 1H NMR (400 MHz, CDCl3): δ 7.69 (dd, J=9.6, 2.0 Hz, 1H), 7.52-7.50 (m, 2H), 7.43 (dd, J=8.8, 5.2 Hz, 1H), 7.33 (d, J=2.4 Hz, 1H), 6.97 (td, J=8.8, 2.0 Hz, 1H), 6.81 (d, J=8.4 Hz, 1H), 6.61 (d, J=3.6 Hz, 1H), 6.00 (tt, J=53.2, 4.0 Hz, 1H), 4.35 (t, J=12.0 Hz, 2H), 3.03 (brs, 4H), 2.55 (brs, 4H), 2.35 (s, 3H); and 13C NMR (100 MHz, CDCl3): δ 160.8 (d, J=240.6 Hz), 154.0, 142.6, 134.9 (d, J=12.5 Hz), 132.0, 126.9, 126.6 (d, J=3.9 Hz), 122.1 (d, J=9.8 Hz), 121.8, 116.9, 113.2, 111.8 (d, J=24.2 Hz), 108.9, 100.8 (d, J=28.3 Hz), 65.3 (t, J=29.3 Hz), 54.9, 50.0, 45.9.

Example 83 Synthesis of 6-chloro-1-((3-(piperazin-1-yl)-4-(2,2,3,3-tetrafluoropropoxy) phenyl)sulfonyl)-1H-indole

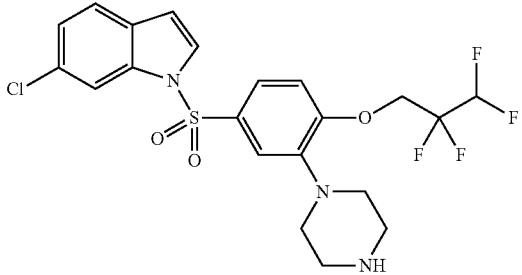 [SMILES: O=S(=O)(c1ccc(OCC(F)(F)C(F)F)c(N2CCNCC2)c1)n1ccc2ccc(Cl)cc21]

Step 1) Synthesis of 2,2,2-trichloro-1-(4-(5-((6-chloro-1H-indol-1-yl)sulfonyl)-2-(2,2,3,3-tetrafluoropropoxy)phenyl)piperazin-1-yl)ethanone 6-Chloroindole (302 mg, 2.0 mmol) was reacted with sodium hydride (80 mg, 2.0 mmol, 60%) and 4-(2,2,3,3-tetrafluoropropoxy)-3-(4-(2,2,2-trichloro acetyl)piperazin-1-yl)benzene-1-sulfonyl chloride (1.12 g, 2.1 mmol, dissolved in THF (6 mL)) in THF (15 mL) according to the procedure as described in step 3 of example 1, and the crude product was purified by silica gel chromatography eluted with PE/EA(V/V)=5/1 to give the title compound as a white solid (667 mg, 51.4%). The compound was characterized by the following spectroscopic data: MS (ESI, pos. ion) m/z: 649.9 [M+H]+; and 1H NMR (400 MHz, CDCl3): δ 8.03-7.95 (m, 1H), 7.57 (dd, J=8.6, 2.3 Hz, 1H), 7.51 (d, J=3.7 Hz, 1H), 7.44 (d, J=8.4 Hz, 1H), 7.36 (d, J=2.3 Hz, 1H), 7.21 (dd, J=8.4, 1.8 Hz, 1H), 6.86 (d, J=8.6 Hz, 1H), 6.63 (dd, J=3.7, 0.7 Hz, 1H), 5.96 (tt, J=53.2, 3.2 Hz, 1H), 4.39 (t, J=12.0 Hz, 2H), 4.01-3.96 (m, 4H), 3.13-3.05 (m, 4H).

Step 2) Synthesis of 6-chloro-1-((3-(piperazin-1-yl)-4-(2,2,3,3-tetrafluoropropoxy)phenyl) sulfonyl)-1H-indole 2,2,2-Trichloro-1-(4-(5-((6-chloro-1H-indol-1-yl)sulfonyl)-2-(2,2,3,3-tetrafluoropropoxy)phenyl)piperazin-1-yl)ethanone (500 mg, 0.77 mmol) was reacted with potassium hydroxide solution (134 mg of potassium hydroxide solid, 2.4 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (331 mg, 85.1%). The compound was characterized by the following spectroscopic data: MS (ESI, pos. ion) m/z: 506.2 [M+H]+; 1H NMR (400 MHz, CDCl3): δ 8.00 (t, J=0.8 Hz, 1H), 7.52-7.49 (m, 2H), 7.43 (d, J=8.4 Hz, 1H), 7.36 (d, J=2.4 Hz, 1H), 7.20 (dd, J=8.0, 1.6 Hz, 1H), 6.82 (d, J=8.8 Hz, 1H), 6.61 (dd, J=4.0, 0.8 Hz, 1H), 6.00 (tt, J=53.2, 4.0 Hz, 1H), 4.36 (t, J=12.0 Hz, 2H), 2.99 (brs, 8H); and 13C NMR (100 MHz, CDCl3): δ 154.1, 143.0, 135.1, 131.8, 130.5, 129.2, 126.9, 124.0, 122.2, 121.8, 117.1, 113.7, 113.2, 109.1, 108.9, 65.3 (t, J=29.1 Hz), 51.4, 45.9.

Example 84 Synthesis of 6-chloro-1-((3-(4-methyl-piperazin-1-yl)-4-(2,2,3,3-tetrafluoropropoxy)phenyl)sulfonyl)-1H-indole

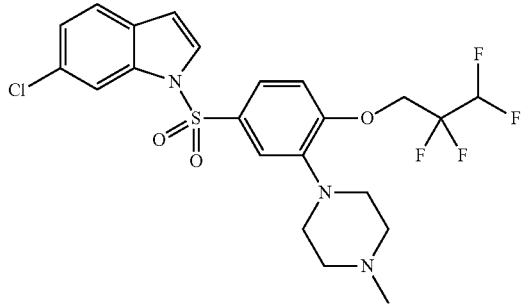 [SMILES: CN1CCN(c2cc(S(=O)(=O)n3ccc4ccc(Cl)cc43)ccc2OCC(F)(F)C(F)F)CC1]

6-Chloro-1-((3-(piperazin-1-yl)-4-(2,2,3,3-tetrafluoropropoxy)phenyl)sulfonyl)-1H-indole (250 mg, 0.49 mmol) was reacted with sodium cyanoborohydride (95 mg, 1.50 mmol) and formaldehyde (40%, 0.11 mL, 1.6 mmol) in methanol (5 mL) according to the procedure as described in example 2, and the crude product was purified by silica gel chromatography eluted with DCM/methanol(V/V)=50/1 to give the title compound as a white solid (223 mg, 87.6%). The compound was characterized by the following spectroscopic data: MS (ESI, pos. ion) m/z: 520.2 [M+H]$^+$; $^1$H NMR (400 MHz, CDCl$_3$): δ 8.00-7.99 (m, 1H), 7.52-7.49 (m, 2H), 7.42 (d, J=8.4 Hz, 1H), 7.35 (d, J=2.4 Hz, 1H), 7.19 (dd, J=8.4, 2.0 Hz, 1H), 6.81 (d, J=8.4 Hz, 1H), 6.61 (dd, J=3.6, 0.4 Hz, 1H), 6.00 (tt, J=53.2, 4.0 Hz, 1H), 4.35 (t, J=12.0 Hz, 2H), 3.04 (brs, 4H), 2.56 (brs, 4H), 2.35 (s, 3H); and $^{13}$C NMR (100 MHz, CDCl$_3$): δ 154.0, 142.6, 135.1, 131.8, 130.6, 129.2, 126.9, 124.0, 122.2, 121.8, 117.0, 113.7, 113.2, 108.9, 65.2 (t, J=29.3 Hz), 54.9, 49.9, 45.8.

Example 85 Synthesis of 3-(difluoromethyl)-6-fluoro-1-((3-(piperazin-1-yl)-4-(2,2,2-trifluoroethoxy)phenyl)sulfonyl)-1H-indole

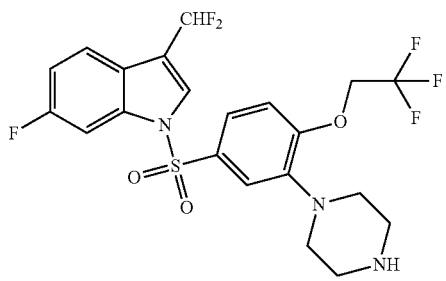 [SMILES: O=S(=O)(c1ccc(OCC(F)(F)F)c(N2CCNCC2)c1)n1cc(C(F)F)c2ccc(F)cc21]

Step 1) Synthesis of 6-fluoro-1-((3-(4-(2,2,2-trichloroacetyl)piperazin-1-yl)-4-(2,2,2-trifluoroethoxy)phenyl)sulfonyl)-1H-indole-3-carbaldehyde 6-Fluoro-1H-indole-3-carbaldehyde (326 mg, 2.0 mmol) was reacted with sodium hydride (80 mg, 2.0 mmol, 60%) and 3-(4-(2,2,2-trichloro acetyl)piperazin-1-yl)-4-(2,2,2-trifluoroethoxy)benzene-1-sulfonyl chloride (1.06 g, 2.1 mmol, dissolved in THF (6 mL)) in THF (15 mL) according to the procedure as described in step 3 of example 1, and the crude product was purified by silica gel chromatography eluted with PE/EA(V/V)=5/1 to give the title compound as a white solid (1.25 g, 99.0%). The compound was characterized by the following spectroscopic data: MS (ESI, pos. ion) m/z: 630.0 [M+H]$^+$; and $^1$H NMR (600 MHz, CDCl$_3$): δ 10.09 (s, 1H), 8.24 (dd, J=9.0, 5.4 Hz, 1H), 8.20 (s, 1H), 7.68 (d, J=2.4 Hz, 1H), 7.67 (s, 1H), 7.43 (d, J=1.8 Hz, 1H), 7.16 (td, J=9.0, 2.4 Hz, 1H), 6.92 (d, J=8.4 Hz, 1H), 4.43 (q, J=7.8 Hz, 2H), 4.00 (brs, 4H), 3.17 (t, J=4.8 Hz, 4H).

Step 2) Synthesis of 2,2,2-trichloro-1-(4-(5-((3-(difluoromethyl)-6-fluoro-1H-indol-1-yl) sulfonyl)-2-(2,2,2-trifluoroethoxy)phenyl)piperazin-1-yl)ethanone 6-Fluoro-1-((3-(4-(2,2,2-trichloro acetyl)piperazin-1-yl)-4-(2,2,2-trifluoroethoxy)phenyl)sulfonyl)-1H-indole-3-carbaldehyde (804 mg, 1.28 mmol) was reacted with diethylaminosulphur trifluoride (335 µL, 2.5 mmol) in DCM (10 mL) according to the procedure as described in step 3 of example 23, and the crude product was purified by silica gel chromatography eluted with PE/EA(V/V)=5/1 to give the title compound as a white solid (616 mg, 73.7%). The compound was characterized by the following spectroscopic data: $^1$H NMR (600 MHz, CDCl$_3$): δ 7.76 (s, 1H), 7.72 (dd, J=9.6, 2.4 Hz, 1H), 7.65 (dd, J=8.4, 5.4 Hz, 1H), 7.62 (dd, J=8.4, 2.4 Hz, 1H), 7.38 (d, J=2.4 Hz, 1H), 7.10 (td, J=9.0, 2.4 Hz, 1H), 6.89 (d, J=9.0 Hz, 1H), 6.86 (t, J=55.2 Hz, 1H), 4.42 (q, J=7.8 Hz, 2H), 4.00 (brs, 4H), 3.15 (t, J=4.8 Hz, 4H).

Step 3) Synthesis of 3-(difluoromethyl)-6-fluoro-1-((3-(piperazin-1-yl)-4-(2,2,2-trifluoroethoxy) phenyl)sulfonyl)-1H-indole 2,2,2-Trichloro-1-(4-(5-((3-(difluoromethyl)-6-fluoro-1H-indol-1-yl)sulfonyl)-2-(2,2,2-trifluoroethoxy) phenyl)piperazin-1-yl)ethanone (613 mg, 0.94 mmol) was reacted with potassium hydroxide solution (158 mg of potassium hydroxide solid, 2.82 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (297 mg, 64.8%). The compound was characterized by the following spectroscopic data: MS (ESI, pos. ion) m/z: 508.1 [M+H]$^+$; $^1$H NMR (600 MHz, CDCl$_3$): δ 7.76 (s, 1H), 7.72 (dd, J=9.6, 1.8 Hz, 1H), 7.64 (dd, J=8.4, 5.4 Hz, 1H), 7.55 (dd, J=8.4, 1.8 Hz, 1H), 7.38 (d, J=1.8 Hz, 1H), 7.08 (td, J=8.4, 2.4 Hz, 1H), 6.86 (d, J=8.4 Hz, 1H), 6.85 (t, J=55.2 Hz, 1H), (q, J=7.8 Hz, 2H), 3.02 (brs, 8H); and $^{13}$C NMR (150 MHz, CDCl$_3$): δ 161.4 (d, J=242.4 Hz), 154.2, 143.6, 135.3 (d, J=12.4 Hz), 131.7, 125.8 (td, J=36.0 Hz), 122.9 (q, J=276.1 Hz), 122.9 (d, J=1.4 Hz), 122.8, 121.5 (d, J=9.0 Hz), 117.0, 116.6 (t, J=26.3 Hz), 114.0, 112.6 (d, J=24.1 Hz), 111.6 (t, J=233.2 Hz), 101.1 (d, J=28.4 Hz), 66.0 (q, J=36.2 Hz), 51.5, 46.0.

Example 86 Synthesis of 3-(difluoromethyl)-6-fluoro-1-((3-(4-methylpiperazin-1-yl)-4-(2,2,2-trifluoroethoxy)phenyl)sulfonyl)-1H-indole

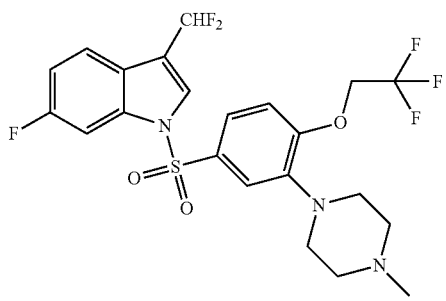 [SMILES: CN1CCN(c2cc(S(=O)(=O)n3cc(C(F)F)c4ccc(F)cc43)ccc2OCC(F)(F)F)CC1]

3-(Difluoromethyl)-6-fluoro-1-((3-(piperazin-1-yl)-4-(2,2,2-trifluoroethoxy)phenyl)sulfonyl)-1H-indole (250 mg, 0.51 mmol) was reacted with sodium cyanoborohydride (95 mg, 1.50 mmol) and formaldehyde (40%, 0.11 mL, 1.6 mmol) in methanol (5 mL) according to the procedure as described in example 2, and the crude product was purified by silica gel chromatography eluted with DCM/methanol (V/V)=50/1 to give the title compound as a white solid (249 mg, 94%). The compound was characterized by the following spectroscopic data: MS (ESI, pos. ion) m/z: 521.9 [M+H]$^+$; $^1$H NMR (600 MHz, DMSO-$d_6$): δ 8.32 (s, 1H), 7.83 (dd, J=9.6, 1.8 Hz, 1H), 7.77 (dd, J=8.4, 1.8 Hz, 1H), 7.71 (dd, J=9.0, 5.4 Hz, 1H), 7.42 (d, J=2.4 Hz, 1H), 7.26 (td, J=9.0, 2.4 Hz, 1H), 7.23 (t, J=55.2 Hz, 1H), 7.19 (d, J=9.0 Hz, 1H), 4.85 (q, J=8.4 Hz, 2H), 2.99 (brs, 4H), 2.42 (brs, 4H), 2.20 (s, 3H); and $^{13}$C NMR (150 MHz, DMSO-$d_6$): δ161.8 (d, J=240.1 Hz), 154.4, 142.5, 134.9 (d, J=12.4 Hz), 129.8, 128.6 (td, J=33.0 Hz), 124.2 (q, J=305.5 Hz), 123.0, 122.5, 122.3 (d, J=10.0 Hz), 116.6, 116.2 (t, J=26.1 Hz), 114.3, 113.1 (d, J=24.0 Hz), 112.5 (t, J=229.3 Hz), 101.2 (d, J=28.4 Hz), 65.3 (q, J=34.5 Hz), 54.9, 50.0, 46.1.

Example 87 Synthesis of 6-chloro-3-(difluoromethyl)-1-((3-(piperazin-1-yl)-4-(2,2,2-trifluoroethoxy)phenyl)sulfonyl)-1H-indole

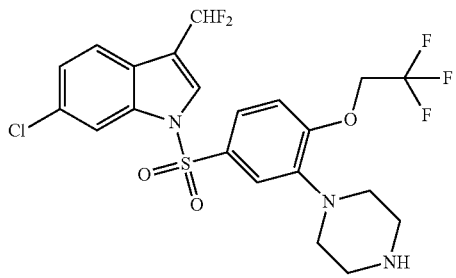 [SMILES: O=S(=O)(c1ccc(OCC(F)(F)F)c(N2CCNCC2)c1)n1cc(C(F)F)c2ccc(Cl)cc21]

Step 1) Synthesis of 6-chloro-1-((3-(4-(2,2,2-trichloroacetyl)piperazin-1-yl)-4-(2,2,2-trifluoroethoxy) phenyl)sulfonyl)-1H-indole-3-carbaldehyde 6-Chloro-1H-indole-3-carbaldehyde (358 mg, 2.0 mmol) was reacted with sodium hydride (80 mg, 2.0 mmol, 60%) and 3-(4-(2,2,2-trichloroacetyl)piperazin-1-yl)-4-(2,2,2-trifluoroethoxy)benzene-1-sulfonyl chloride (1.06 g, 2.1 mmol, dissolved in THF (6 mL)) in THF (15 mL) according to the procedure as described in step 3 of example 1, and the crude product was purified by silica gel chromatography eluted with PE/EA(V/V)=5/1 to give the title compound as a white solid (1.16 g, 89.6%). The compound was characterized by the following spectroscopic data: MS (ESI, pos. ion) m/z: 646.0 [M+H]$^+$; and $^1$H NMR (600 MHz, CDCl$_3$): δ 10.09 (s, 1H), 8.22-8.20 (m, 2H), 7.99 (d, J=1.2 Hz, 1H), 7.67 (dd, J=8.4, 1.8 Hz, 1H), 7.46 (d, J=2.4 Hz, 1H), 7.38 (dd, J=8.4, 1.8 Hz, 1H), 6.92 (d, J=8.4 Hz, 1H), 4.43 (q, J=7.2 Hz, 2H), 3.99 (brs, 4H), 3.18 (t, J=4.8 Hz, 4H).

Step 2) Synthesis of 2,2,2-trichloro-1-(4-(5-((6-chloro-3-(difluoromethyl)-1H-indol-1-yl)sulfonyl)-2-(2,2,2-trifluoroethoxy)phenyl)piperazin-1-yl)ethanone 6-Chloro-1-((3-(4-(2,2,2-trichloro acetyl)piperazin-1-yl)-4-(2,2,2-trifluoroethoxy)phenyl)sulfonyl)-1H-indole-3-carbaldehyde (727 mg, 1.12 mmol) was reacted with diethylaminosulphur trifluoride (335 μL, 2.5 mmol) in DCM (10 mL) according to the procedure as described in step 3 of example 23, and the crude product was purified by silica gel chromatography eluted with PE/EA(V/V)=5/1 to give the title compound as a white solid (603 mg, 80.5%). The compound was characterized by the following spectroscopic data: $^1$H NMR (600 MHz, CDCl$_3$): δ 8.03 (d, J=1.8 Hz, 1H), 7.76 (s, 1H), 7.63-7.61 (m, 2H), 7.41 (d, J=2.4 Hz, 1H), 7.32 (dd, J=8.4, 1.8 Hz, 1H), 6.90 (d, J=8.4 Hz, 1H), 6.85 (t, J=55.8 Hz, 1H), 4.42 (q, J=7.8 Hz, 2H), 3.99 (brs, 4H), 3.16 (t, J=4.8 Hz, 4H).

Step 3) Synthesis of 6-chloro-3-(difluoromethyl)-1-((3-(piperazin-1-yl)-4-(2,2,2-trifluoroethoxy) phenyl)sulfonyl)-1H-indole 2,2,2-Trichloro-1-(4-(5-((6-chloro-3-(difluoromethyl)-1H-indol-1-yl)sulfonyl)-2-(2,2,2-trifluoroethoxy) phenyl)piperazin-1-yl)ethanone (603 mg, 0.90 mmol) was reacted with potassium hydroxide solution (151 mg of potassium hydroxide solid, 2.70 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (266 mg, 56.4%). The compound was characterized by the following spectroscopic data: MS (ESI, pos. ion) m/z: 523.8 [M+H]$^+$; $^1$H NMR (600 MHz, DMSO-$d_6$): δ 7.78 (s, 1H), 7.54 (d, J=8.4 Hz, 1H), 7.50 (s, 1H), 7.47 (dd, J=8.4, 1.2 Hz, 1H), 7.30 (d, J=1.2 Hz, 1H), 7.21 (d, J=7.2 Hz, 1H), 6.91 (d, J=8.4 Hz, 1H), 6.84 (t, J=55.2 Hz, 1H), 4.41 (q, J=7.8 Hz, 2H), 2.96 (brs, 4H), 2.93 (brs, 4H); and $^{13}$C NMR (150 MHz, DMSO-$d_6$+CDCl$_3$): δ 153.8, 142.6, 134.6, 130.9, 130.3, 126.1, 124.6, 124.1 (d, J=11.2 Hz), 123.5 (t, J=275.7 Hz), 121.3, 121.0, 116.26 (d, J=11.1 Hz), 115.9 (t, J=26.2 Hz), 113.4 (d, J=10.0 Hz), 113.15 (d, J=17.1 Hz), 111.1 (t, J=231.3 Hz), 65.3 (q, J=20.5 Hz), 50.6, 45.2.

Example 88 Synthesis of 6-chloro-3-(difluoromethyl)-1-((3-(4-methylpiperazin-1-yl)-4-(2,2,2-trifluoroethoxy)phenyl)sulfonyl)-1H-indole

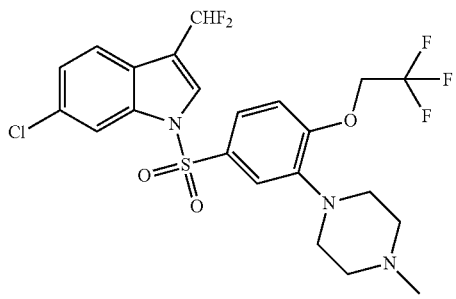 [SMILES: CN1CCN(c2cc(S(=O)(=O)n3cc(C(F)F)c4ccc(Cl)cc43)ccc2OCC(F)(F)F)CC1]

6-Chloro-3-(difluoromethyl)-1-((3-(piperazin-1-yl)-4-(2,2,2-trifluoroethoxy)phenyl)sulfonyl)-1H-indole (250 mg, 0.48 mmol) was reacted with sodium cyanoborohydride (95 mg, 1.50 mmol) and formaldehyde (40%, 0.11 mL, 1.6 mmol) in methanol (5 mL) according to the procedure as described in example 2, and the crude product was purified by silica gel chromatography eluted with DCM/methanol (V/V)=50/1 to give the title compound as a white solid (217 mg, 84.1%). The compound was characterized by the following spectroscopic data: MS (ESI, pos. ion) m/z: 537.8 [M+H]$^+$; $^1$H NMR (600 MHz, DMSO-$d_6$): δ 8.35 (t, J=2.4 Hz, 1H), 8.02 (d, J=1.8 Hz, 1H), 7.73 (dd, J=9.0, 2.4 Hz, 1H), 7.70 (d, J=8.4 Hz, 1H), 7.43-7.41 (m, 2H), 7.23 (t, J=55.2 Hz, 1H), 7.20 (d, J=9.0 Hz, 1H), 4.85 (q, J=8.4 Hz, 2H), 2.99 (brs, 4H), 2.42 (brs, 4H), 2.20 (s, 3H); and $^{13}$C NMR (150 MHz, DMSO-$d_6$): δ 154.5, 142.4, 135.1, 129.7, 128.9 (t, J=10.0 Hz), 127.8, 125.3, 125.1, 125.09 (q, J=316.2 Hz), 122.4, 122.3 116.6, 116.2 (t, J=26.10 Hz), 114.4, 113.7, 112.4 (t, J=190.0 Hz), 65.3 (q, J=34.3 Hz), 54.9, 49.9, 46.1.

Example 89 Synthesis of 6-bromo-3-(difluoromethyl)-1-((3-(piperazin-1-yl)-4-(2,2,2-trifluoroethoxy)phenyl)sulfonyl)-1H-indole

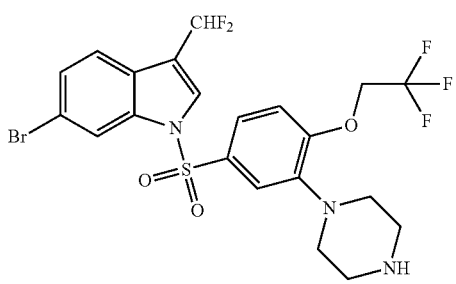

Step 1) Synthesis of 6-bromo-1-((3-(4-(2,2,2-trichloroacetyl)piperazin-1-yl)-4-(2,2,2-trifluoroethoxy) phenyl)sulfonyl)-1H-indole-3-carbaldehyde 6-Bromo-1H-indole-3-carbaldehyde (448 mg, 2.0 mmol) was reacted with sodium hydride (80 mg, 2.0 mmol, 60%) and 3-(4-(2,2,2-trichloroacetyl)piperazin-1-yl)-4-(2,2,2-trifluoroethoxy)benzene-1-sulfonyl chloride (1.06 g, 2.1 mmol, dissolved in THF (6 mL)) in THF (15 mL) according to the procedure as described in step 3 of example 1, and the crude product was purified by silica gel chromatography eluted with PE/EA(V/V)=5/1 to give the title compound as a white solid (1.34 g, 96.9%). The compound was characterized by the following spectroscopic data: MS (ESI, pos. ion) m/z: 689.9 [M+H]$^+$; and $^1$H NMR (600 MHz, CDCl$_3$): δ 10.09 (s, 1H), 8.18-8.15 (m, 3H), 7.66 (dd, J=8.4, 2.4 Hz, 1H), 7.52 (dd, J=8.4, 1.8 Hz, 1H), 7.48 (d, J=2.4 Hz, 1H), 6.92 (d, J=9.0 Hz, 1H), 4.43 (q, J=7.8 Hz, 2H), 4.00 (brs, 4H), 3.16 (t, J=4.8 Hz, 4H).

Step 2) Synthesis of 1-(4-(5-(((6-bromo-3-(difluoromethyl)-1H-indol-1-yl)sulfonyl)-2-(2,2,2-trifluoroethoxy)phenyl)piperazin-1-yl)-2,2,2-trichloroethanone 6-Bromo-1-((3-(4-(2,2,2-trichloro acetyl)piperazin-1-yl)-4-(2,2,2-trifluoroethoxy)phenyl)sulfonyl)-1H-indole-3-carbaldehyde (710 mg, 1.03 mmol) was reacted with diethylaminosulphur trifluoride (335 µL, 2.5 mmol) in DCM (10 mL) according to the procedure as described in step 3 of example 23, and the crude product was purified by silica gel chromatography eluted with PE/EA(V/V)=5/1 to give the title compound as a white solid (644 mg, 87.6%). The compound was characterized by the following spectroscopic data: $^1$H NMR (600 MHz, CDCl$_3$): δ 8.20 (s, 1H), 7.74 (s, 1H), 7.61 (dd, J=8.4, 2.4 Hz, 1H), 7.57 (d, J=8.4 Hz, 1H), 7.46 (dd, J=6.6, 1.8 Hz, 1H), 7.43 (d, J=2.2 Hz, 1H), 6.89 (d, J=8.4 Hz, 1H), 6.85 (t, J=55.2 Hz, 1H), 4.42 (q, J=7.2 Hz, 2H), 4.00 (brs, 4H), 3.6 (t, J=4.8 Hz, 4H).

Step 3) Synthesis of 6-bromo-3-(difluoromethyl)-1-((3-(piperazin-1-yl)-4-(2,2,2-trifluoroethoxy) phenyl)sulfonyl)-1H-indole 1-(4-(5-(((6-Bromo-3-(difluoromethyl)-1H-indol-1-yl)sulfonyl)-2-(2,2,2-trifluoroethoxy)phenyl)piperazin-1-yl)-2,2,2-trichloroethanone (640 mg, 0.89 mmol) was reacted with potassium hydroxide solution (151 mg of potassium hydroxide solid, 2.70 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (270 mg, 53.4%). The compound was characterized by the following spectroscopic data: MS (ESI, pos. ion) m/z: 568.0 [M+H]$^+$; $^1$H NMR (600 MHz, DMSO-$d_6$): δ 8.33 (s, 1H), 8.15 (d, J=1.8 Hz, 1H), 7.70 (dd, J=8.4, 2.4 Hz, 1H), 7.65 (d, J=8.4 Hz, 1H), 7.54 (dd, J=8.4, 1.8 Hz, 1H), 7.40 (d, J=2.4 Hz, 1H), 7.23 (t, J=55.2 Hz, 1H), 7.19 (d, J=8.4 Hz, 1H), 4.84 (q, J=8.4 Hz, 2H), 2.90-2.89 (m, 4H), 2.81-2.79 (m, 4H); and $^{13}$C NMR (150 MHz, DMSO-$d_6$): δ 154.6, 143.0, 135.3, 129.7, 128.8 (t, J=10.2 Hz), 127.8, 125.6, 124.2 (q, J=275.8 Hz), 122.7, 122.2, 118.9, 116.6, 116.5, 116.3 (t, J=26.2 Hz), 114.4, 112.4 (t, J=229.6 Hz), 65.3 (q, J=34.4 Hz), 51.4, 45.9.

Example 90 Synthesis of 6-bromo-3-(difluoromethyl)-1-((3-(4-methylpiperazin-1-yl)-4-(2,2,2-trifluoroethoxy)phenyl)sulfonyl)-1H-indole

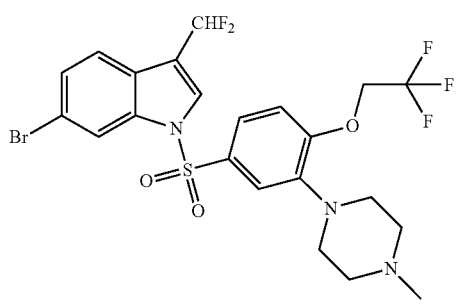

6-Bromo-3-(difluoromethyl)-1-((3-(piperazin-1-yl)-4-(2,2,2-trifluoroethoxy)phenyl)sulfonyl)-1H-indole (250 mg, 0.44 mmol) was reacted with sodium cyanoborohydride (95 mg, 1.50 mmol) and formaldehyde (40%, 0.11 mL, 1.6 mmol) in methanol (5 mL) according to the procedure as described in example 2, and the crude product was purified by silica gel chromatography eluted with DCM/methanol (V/V)=50/1 to give the title compound as a white solid (231 mg, 90.4%). The compound was characterized by the following spectroscopic data: MS (ESI, pos. ion) m/z: 581.8 [M+H]$^+$; $^1$H NMR (600 MHz, DMSO-d$_6$): δ 8.33 (s, 1H), 8.16 (d, J=1.2 Hz, 1H), 7.71 (dd, J=9.0, 2.4 Hz, 1H), 7.65 (d, J=8.4 Hz, 1H), 7.54 (dd, J=8.4, 1.8 Hz, 1H), 7.43 (d, J=2.4 Hz, 1H), 7.23 (t, J=54.2 Hz, 1H), 7.20 (d, J=9.0 Hz, 1H), 4.85 (q, J=8.4 Hz, 2H), 3.00 (brs, 4H), 2.43 (brs, 4H), 2.21 (s, 3H); and $^{13}$C NMR (150 MHz, DMSO-d$_6$): δ 154.5, 142.4, 135.3, 129.6, 128.8 (t, J=10.0 Hz), 127.8, 125.6, 124.4 (q, J=275.7 Hz), 122.7, 122.3, 118.9, 116.7, 116.5, 116.3 (t, J=26.2 Hz), 114.4, 112.4 (t, J=232.2 Hz), 65.3 (q, J=34.5 Hz), 54.9, 49.9, 46.1.

Example 91 Synthesis of 6-fluoro-1-((4-methoxy-3-(piperazin-1-yl)naphthalen-1-yl) sulfonyl)-3-methyl-1H-indole

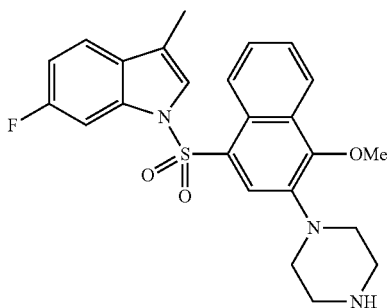 [SMILES: COc1c(N2CCNCC2)cc(S(=O)(=O)n2cc(C)c3ccc(F)cc32)c2ccccc12]

Step 1) Synthesis of 2,2,2-trichloro-1-(4-(1-methoxynaphthalen-2-yl)piperazin-1-yl)ethanone To a solution of 1-(1-methoxynaphthalen-2-yl)piperazine (680 mg, 2.81 mmol) and triethylamine (1.12 mL, 8.42 mmol) in dichloromethane (15 mL) was added dropwise trichloroacetyl chloride (0.47 mL, 4.21 mmol) at 0° C. in a low temperature bath. At the end of the addition, the mixture was reacted at 25° C. for 24 hours. To the reaction mixture was added 50 mL of dichloromethane, and the mixture was washed with 40 mL of saturated sodium bicarbonate. The organic layer was dried over anhydrous sodium sulfate and filtered. The filtrate was concentrated in vacuo and the residue was purified by silica gel chromatography eluted with PE/EtOAc(V/V)=20/1 to give the title compound as a light yellow solid (788 mg, 72.3%). The compound was characterized by the following spectroscopic data: MS (ESI, pos. ion) m/z: 387.9 [M+H]$^+$; $^1$H NMR (600 MHz, CDCl$_3$): δ 8.14 (d, J=8.5 Hz, 1H), 7.81 (d, J=8.2 Hz, 1H), 7.63 (d, J=8.8 Hz, 1H), 7.51 (t, J=7.5 Hz, 1H), 7.42 (t, J=7.4 Hz, 1H), 7.28 (d, J=8.5 Hz, 1H), 4.13-3.89 (m, 7H), 3.39-3.33 (m, 4H).

Step 2) Synthesis of 4-methoxy-3-(4-(2,2,2-trichloroacetyl)piperazin-1-yl)naphthalene-1-sulfonyl chloride To a solution of 2,2,2-trichloro-1-(4-(1-methoxynaphthalen-2-yl)piperazin-1-yl)ethanone (782 mg, 2.02 mmol) in dichloromethane (5 mL) was added dropwise chlorosulfonic acid (352.9 mg, 3.03 mmol) at 0° C. in a low temperature bath. After the addition, the mixture was reacted at 25° C. for 24 hours. Then phosphorus pentachloride (624 mg, 3.0 mmol) was added to the reaction mixture and the resulting mixture was reacted for an additional 5 hours. The reaction mixture was poured into a mixture of ice water (30 mL) and dichromethane (50 mL), then the mixture was stirred vigorously and separated. The organic layer was dried over anhydrous magnesium sulfate and filtered. The filtrate was concentrated in vacuo to give the title compound as a light yellow solid (595 mg, 60.7%). The compound was characterized by the following spectroscopic data: MS (ESI, pos. ion) m/z: 486.9 [M+H]$^+$; and $^1$H NMR (600 MHz, CDCl$_3$): δ 8.69 (d, J=8.5 Hz, 1H), 8.30 (d, J=8.2 Hz, 1H), 8.13 (s, 1H), 7.73-7.64 (m, 2H), 4.10 (brs, 7H), 3.38-3.32 (m, 4H).

Step 3) Synthesis of 2,2,2-trichloro-1-(4-(4-((6-fluoro-3-methyl-1H-indol-1-yl)sulfonyl)-1-methoxynaphthalen-2-yl)piperazin-1-yl)ethanone 6-Fluoro-3-methyl-1H-indole (298 mg, 2.0 mmol) was reacted with sodium hydride (80 mg, 2.0 mmol, 60%) and 4-methoxy-3-(4-(2,2,2-trichloroacetyl)piperazin-1-yl)naphthalene-1-sulfonyl chloride (1.02 g, 2.1 mmol, dissolved in THF (6 mL)) in THF (15 mL) according to the procedure as described in step 3 of example 1, and the crude product was purified by silica gel chromatography eluted with PE/EA (V/V)=10/1 to give the title compound as a white solid (361 mg, 30.2%). The compound was characterized by the following spectroscopic data: MS (ESI, pos. ion) m/z: 598.0 [M+H]$^+$; and $^1$H NMR (400 MHz, CDCl$_3$): δ 8.60-8.54 (m, 1H), 8.18-8.12 (m, 1H), 7.77 (s, 1H), 7.56-7.49 (m, 3H), 7.41 (d, J=1.2 Hz, 1H), 7.35 (dd, J=8.6, 5.3 Hz, 1H), 6.99-6.91 (m, 1H), 4.01 (brs, 4H), 3.97 (s, 3H), 3.26-3.13 (m, 4H), 2.20 (s, 3H).

Step 4) Synthesis of 6-fluoro-1-((4-methoxy-3-(piperazin-1-yl)naphthalen-1-yl)sulfonyl)-3-methyl-1H-indole 2,2,2-Trichloro-1-(4-(4-((6-fluoro-3-methyl-1H-indol-1-yl)sulfonyl)-1-methoxynaphthalen-2-yl)piperazin-1-yl)ethanone (379 mg, 0.63 mmol) was reacted with potassium hydroxide solution (106 mg of potassium hydroxide solid, 1.9 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a white solid (278 mg, 97.3%). The compound was characterized by the following spectroscopic data: MS (ESI, pos. ion) m/z: 454.2 [M+H]$^+$; $^1$H NMR (600 MHz, CDCl$_3$): δ 8.58-8.52 (m, 1H), 8.18-8.12 (m, 1H), 7.87 (s, 1H), 7.54 (dd, J=9.8, 2.1 Hz, 1H), 7.50-7.45 (m, 2H), 7.43 (s, 1H), 7.34 (dd, J=8.6, 5.2 Hz, 1H), 6.94 (td, J=9.0, 2.2 Hz, 1H), 3.98 (s, 3H), 3.08 (brs, 4H), 3.07 (brs, 4H), 2.20 (s, 3H); and $^{13}$C NMR (150 MHz, CDCl$_3$): δ 161.1 (d, J=240.2 Hz), 151.8, 138.5, 135.3 (d, J=12.4 Hz), 130.2, 128.8, 127.7, 127.0 (d, J=4.9 Hz), 125.7, 123.7, 123.6, 123.5, 122.6, 120.3 (d, J=9.9 Hz), 117.3, 111.2 (d, J=24.0 Hz), 100.8 (d, J=28.4 Hz), 59.2, 51.3, 46.4, 9.7.

Example 92 Synthesis of 6-fluoro-1-((4-methoxy-3-(4-methylpiperazin-1-yl)naphthalen-1-yl) sulfonyl)-3-methyl-1H-indole

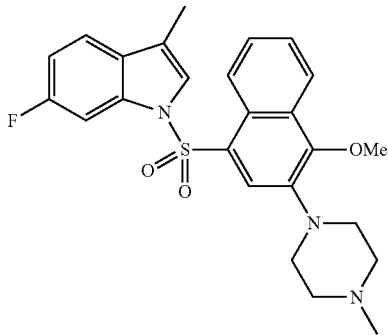 [SMILES: COc1c(N2CCN(C)CC2)cc(S(=O)(=O)n2cc(C)c3ccc(F)cc32)c2ccccc12]

6-Fluoro-1-((4-methoxy-3-(piperazin-1-yl)naphthalen-1-yl)sulfonyl)-3-methyl-1H-indole (151 mg, 0.33 mmol) was reacted with sodium cyanoborohydride (63 mg, 1.0 mmol) and formaldehyde (40%, 0.07 mL, 1.0 mmol) in methanol (5 mL) according to the procedure as described in example 2, and the crude product was purified by silica gel chromatography eluted with DCM/methanol(V/V)=50/1 to give the title compound as a light yellow solid (148 mg, 95.9%). The compound was characterized by the following spectroscopic data: MS (ESI, pos. ion) m/z: 468.2 [M+H]$^+$; $^1$H NMR (600 MHz, CDCl$_3$): δ 8.55 (dd, J=6.6, 3.6 Hz, 1H), 8.14 (dd, J=6.0, 3.0 Hz, 1H), 7.80 (s, 1H), 7.55 (dd, J=9.6, 1.8 Hz, 1H), 7.50-7.45 (m, 2H), 7.43 (s, 1H), 7.34 (dd, J=8.4, 4.8 Hz, 1H), 6.98-6.91 m, 1H), 3.95 (s, 3H), 3.15 (brs, 4H), 2.59 (brs, 4H), 2.36 (s, 3H), 2.21 (s, 3H); and $^{13}$C NMR (150 MHz, CDCl$_3$): δ 160.8 (d, J=240.2 Hz), 151.5, 138.1, 135.3 (d, J=12.4 Hz), 130.2, 128.9, 127.7, 126.9 (d, J=8.1 Hz), 125.6, 123.7, 123.6, 123.2, 122.6, 120.3 (d, J=9.9 Hz), 117.3, 111.3 (d, J=24.0 Hz), 100.8 (d, J=28.4 Hz), 59.1, 55.4, 49.8, 46.2, 9.7.

Example 93 Synthesis of 6-chloro-1-((4-methoxy-3-(piperazin-1-yl)naphthalen-1-yl)sulfonyl)-3-methyl-1H-indole

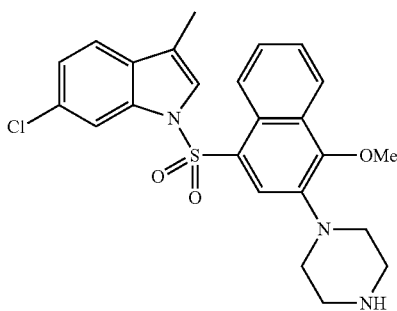

Step 1) Synthesis of 2,2,2-trichloro-1-(4-(4-((6-chloro-3-methyl-1H-indol-1-yl)sulfonyl)-1-methoxynaphthalen-2-yl)piperazin-1-yl)ethanone 6-Chloro-3-methyl-1H-indole (330 mg, 2.0 mmol) was reacted with sodium hydride (80 mg, 2.0 mmol, 60%) and 4-methoxy-3-(4-(2,2,2-trichloroacetyl)piperazin-1-yl)naphthalene-1-sulfonyl chloride (1.02 g, 2.1 mmol, dissolved in THF (6 mL)) in THF (15 mL) according to the procedure as described in step 3 of example 1, and the crude product was purified by silica gel chromatography eluted with PE/EA (V/V)=10/1 to give the title compound as a white solid (299 mg, 24.4%). The compound was characterized by the following spectroscopic data: $^1$H NMR (400 MHz, CDCl$_3$): δ 8.62-8.55 (m, 1H), 8.18-8.12 (m, 1H), 7.90 (s, 1H), 7.83 (d, J=1.6 Hz, 1H), 7.55-7.48 (m, 2H), 7.43 (d, J=1.2 Hz, 1H), 7.32 (d, J=8.4 Hz, 1H), 7.16 (dd, J=8.4, 1.7 Hz, 1H), 4.00 (brs, 7H), 3.28-3.16 (m, 4H), 2.19 (s, 3H).

Step 2) Synthesis of 6-chloro-1-((4-methoxy-3-(piperazin-1-yl)naphthalen-1-yl)sulfonyl)-3-methyl-1H-indole 2,2,2-Trichloro-1-(4-(4-((6-chloro-3-methyl-1H-indol-1-yl)sulfonyl)-1-methoxynaphthalen-2-yl)piperazin-1-yl)ethanone (470 mg, 0.76 mmol) was reacted with potassium hydroxide solution (129 mg of potassium hydroxide solid, 2.30 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (293 mg, 82.1%). The compound was characterized by the following spectroscopic data: MS (ESI, pos. ion) m/z: 470.1 [M+H]$^+$; $^1$H NMR (600 MHz, CDCl$_3$): δ 8.58-8.53 (m, 1H), 8.17-8.12 (m, 1H), 7.97 (s, 1H), 7.84 (d, J=1.8 Hz, 1H), 7.51-7.43 (m, 3H), 7.31 (d, J=8.4 Hz, 1H), 7.15 (dd, J=8.4, 1.8 Hz, 1H), 3.98 (s, 3H), 3.15-3.14 (m, 4H), 3.12-3.11 (m, 4H), 2.19 (s, 3H); and $^{13}$C NMR (150 MHz, CDCl$_3$): δ 152.2, 138.7, 135.5, 130.5, 130.4, 130.2, 128.6, 127.2, 127.1, 125.8, 124.2, 123.8, 123.6, 122.8, 120.5, 117.4, 113.9, 59.4, 51.7, 46.6, 9.8.

Example 94 Synthesis of 6-chloro-1-((4-methoxy-3-(4-methylpiperazin-1-yl)naphthalene-1-yl)sulfonyl)-3-methyl-1H-indole

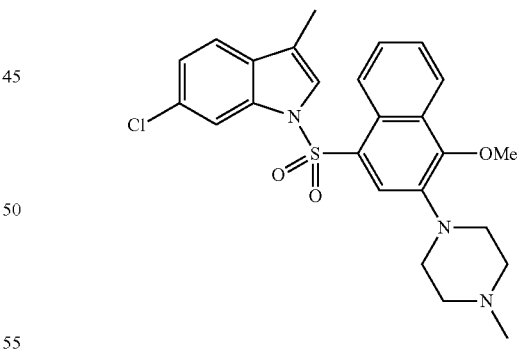

6-Chloro-1-((4-methoxy-3-(piperazin-1-yl)naphthalen-1-yl)sulfonyl)-3-methyl-1H-indole (166 mg, 0.35 mmol) was reacted with sodium cyanoborohydride (67 mg, 1.1 mmol) and formaldehyde (40%, 0.07 mL, 1.0 mmol) in methanol (5 mL) according to the procedure as described in example 2, and the crude product was purified by silica gel chromatography eluted with DCM/methanol(V/V)=50/1 to give the title compound as a white solid (167 mg, 98.2%). The compound was characterized by the following spectroscopic data: MS (ESI, pos. ion) m/z: 484.1 [M+H]$^+$; $^1$H NMR (600 MHz, CDCl$_3$): δ 8.57-8.53 (m, 1H), 8.16-8.11 (m, 1H), 7.88

(s, 1H), 7.84 (s, 1H), 7.50-7.45 (m, 2H), 7.44 (s, 1H), 7.32 (d, J=8.4 Hz, 1H), 7.15 (d, J=8.4 Hz, 1H), 3.95 (s, 3H), 3.18 (brs, 4H), 2.61 (brs, 4H), 2.37 (s, 3H), 2.20 (s, 3H); and $^{13}$C NMR (150 MHz, CDCl$_3$): δ 151.7, 138.0, 135.4, 130.4, 130.2, 129.9, 128.6, 127.0, 125.6, 124.0, 123.7, 123.6, 123.4, 122.6, 120.3, 117.3, 113.7, 59.2, 55.4, 49.8, 46.1, 29.7.

Example 95 Synthesis of 6-bromo-1-((4-methoxy-3-(piperazin-1-yl)naphthalen-1-yl) sulfonyl)-3-methyl-1H-indole

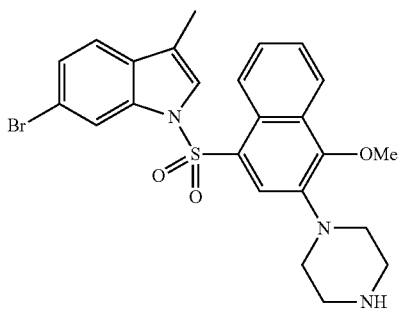 [SMILES: COc1c(N2CCNCC2)cc(S(=O)(=O)n2cc(C)c3ccc(Cl)cc32)c2ccccc12]

Step 1) Synthesis of 1-(4-(4-(((6-bromo-3-methyl-1H-indol-1-yl)sulfonyl)-1-methoxynaphthalen-2-yl)piperazin-1-yl)-2,2,2-trichloroethanone 6-Bromo-3-methyl-1H-indole (420 mg, 2.0 mmol) was reacted with sodium hydride (80 mg, 2.0 mmol, 60%) and 4-methoxy-3-(4-(2,2,2-trichloroacetyl)piperazin-1-yl)naphthalene-1-sulfonyl chloride (1.02 g, 2.1 mmol, dissolved in THF (6 mL)) in THF (15 mL) according to the procedure as described in step 3 of example 1, and the crude product was purified by silica gel chromatography eluted with PE/EA (V/V)=10/1 to give the title compound as a white solid (339 mg, 25.7%). The compound was characterized by the following spectroscopic data: $^1$H NMR (400 MHz, CDCl$_3$): δ 8.62-8.56 (m, 1H), 8.18-8.12 (m, 1H), 8.00 (d, J=6.4 Hz, 1H), 7.96-7.92 (m, 1H), 7.56-7.48 (m, 2H), 7.43 (s, 1H), 7.32-7.24 (m, 2H), 4.10-3.92 (m, 7H), 3.30-3.20 (m, 4H), 2.19 (s, 3H).

Step 2) Synthesis of 6-bromo-1-((4-methoxy-3-(piperazin-1-yl)naphthalen-1-yl)sulfonyl)-3-methyl-1H-indole 1-(4-(4-((6-Bromo-3-methyl-1H-indol-1-yl)sulfonyl)-1-methoxynaphthalen-2-yl)piperazin-1-yl)-2,2,2-trichloroethanone (472 mg, 0.72 mmol) was reacted with potassium hydroxide solution (120 mg of potassium hydroxide solid, 2.15 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (273 mg, 73.8%). The compound was characterized by the following spectroscopic data: MS (ESI, pos. ion) m/z: 514.1 [M+H]$^+$; $^1$H NMR (600 MHz, CDCl$_3$): δ 8.58-8.53 (m, 1H), 8.17-8.12 (m, 1H), 8.00 (s, 2H), 7.50-7.45 (m, 2H), 7.44 (s, 1H), 7.29-7.25 (m, 2H), 3.98 (s, 3H), 3.16-3.04 (m, 8H), 2.19 (s, 3H); and $^{13}$C NMR (150 MHz, CDCl$_3$): δ (ppm) 152.2, 138.7, 135.7, 130.6, 130.4, 128.4, 127.2, 127.1, 126.2, 125.8, 124.3, 124.1, 123.8, 122.9, 120.9, 118.2, 117.4, 116.7, 59.4, 51.7, 46.6, 9.8.

Example 96 Synthesis of 6-bromo-1-((4-methoxy-3-(4-methylpiperazin-1-yl)naphthalene-1-yl)sulfonyl)-3-methyl-1H-indole

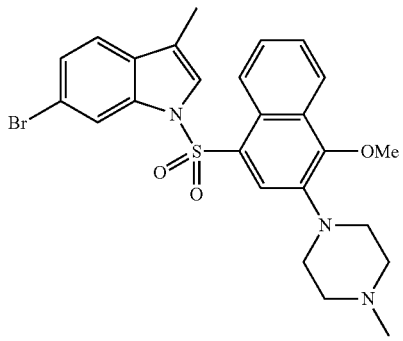 [SMILES: COc1c(N2CCN(C)CC2)cc(S(=O)(=O)n2cc(C)c3ccc(Cl)cc32)c2ccccc12]

6-Bromo-1-((4-methoxy-3-(piperazin-1-yl)naphthalen-1-yl)sulfonyl)-3-methyl-1H-indole (152 mg, 0.30 mmol) was reacted with sodium cyanoborohydride (67 mg, 1.1 mmol) and formaldehyde (40%, 0.07 mL, 1.0 mmol) in methanol (5 mL) according to the procedure as described in example 2, and the crude product was purified by silica gel chromatography eluted with DCM/methanol(V/V)=50/1 to give the title compound as a white solid (150 mg, 94.7%). The compound was characterized by the following spectroscopic data: MS (ESI, pos. ion) m/z: 528.1 [M+H]$^+$; $^1$H NMR (600 MHz, CDCl$_3$): δ 8.57-8.53 (m, 1H), 8.16-8.11 (m, 1H), 8.00 (s, 1H), 7.91 (s, 1H), 7.50-7.45 (m, 2H), 7.43 (s, 1H), 7.30-7.25 (m, 2H), 3.95 (s, 3H), 3.19 (brs, 4H), 2.61 (brs, 4H), 2.37 (s, 3H), 2.19 (s, 3H); and $^{13}$C NMR (150 MHz, CDCl$_3$): δ 151.9, 138.2, 135.8, 130.5, 130.4, 128.7, 127.1, 126.3, 125.8, 124.1, 123.9, 123.8, 122.8, 120.9, 118.2, 117.4, 116.8, 59.4, 55.6, 50.0, 46.3, 9.8.

Example 97 Synthesis of 5-chloro-3-(difluoromethyl)-1-((4-methoxy-3-(piperazin-1-yl) naphthalen-1-yl)sulfonyl)-1H-indole

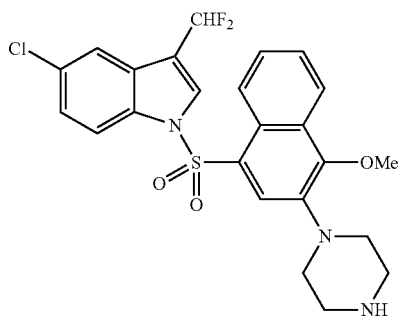 [SMILES: COc1c(N2CCNCC2)cc(S(=O)(=O)n2cc(C(F)F)c3cc(Cl)ccc32)c2ccccc12]

Step 1) Synthesis of 5-chloro-1-((4-methoxy-3-(4-(2,2,2-trichloro acetyl)piperazin-1-yl) naphthalen-1-yl)sulfonyl)-1H-indole-3-carbaldehyde 5-Chloro-1H-indole-3-carbaldehyde (358 mg, 2.0 mmol) was reacted with sodium hydride (80 mg, 2.0 mmol, 60%) and 4-methoxy-3-(4-(2,2,2-trichloroacetyl)piperazin-1-yl) naphthalene-1-sulfonyl chloride (1.17 g, 2.4 mmol, dissolved in THF (6 mL)) in THF (15 mL) according to the procedure as described in step 3 of example 1, and the crude product was purified by silica gel chromatography eluted with PE/EA(V/V)=10/1 to give the title compound as a white solid (462 mg, 51%). The compound was characterized by the following spectroscopic data: $^1$H NMR (600 MHz, CDCl$_3$): δ 10.07 (s, 1H), 8.49-8.46 (m, 1H), 8.40 (s, 1H), 8.27 (s, 1H), 8.23 (d, J=2.0 Hz, 1H), 8.23-8.20 (m, 1H), 7.70 (d, J=8.9 Hz, 1H), 7.60-7.53 (m, 2H), 7.32 (dd, J=8.9, 2.1 Hz, 1H), 4.18-4.02 (m, 7H), 3.33 (t, J=5.0 Hz, 4H).

Step 2) Synthesis of 2,2,2-trichloro-1-(4-(4-((5-chloro-3-(difluoromethyl)-1H-indol-1-yl)sulfonyl)-1-methoxynaphthalen-2-yl)piperazin-1-yl)ethanone 5-Chloro-1-((4-methoxy-3-(4-(2,2,2-trichloro acetyl)piperazin-1-yl)naphthalen-1-yl)sulfonyl)-1H-indole-3-carbaldehyde (630 mg, 1.0 mmol) was reacted with diethylaminosulphur trifluoride (390 μL, 3.0 mmol) in DCM (12 mL) according to the procedure as described in step 3 of example 23, and the crude product was purified by silica gel chromatography eluted with PE/EA(V/V)=5/1 to give the title compound as a white solid (385 mg, 59%). The compound was characterized by the following spectroscopic data: $^1$H NMR (600 MHz, CDCl$_3$): δ 8.51-8.47 (m, 1H), 8.22-8.17 (m, 1H), 8.02 (s, 1H), 7.96 (t, J=2.2 Hz, 1H), 7.77 (d, J=9.0 Hz, 1H), 7.65 (d, J=1.7 Hz, 1H), 7.58-7.53 (m, 2H), 7.30 (dd, J=8.9, 2.0 Hz, 1H), 6.83 (t, J=55.4 Hz, 1H), 4.20-3.92 (m, 7H), 3.27 (t, J=4.9 Hz, 4H).

Step 3) Synthesis of 5-chloro-3-(difluoromethyl)-1-((4-methoxy-3-(piperazin-1-yl)naphthalen-1-yl)sulfonyl)-1H-indole 2,2,2-Trichloro-1-(4-(4-((5-chloro-3-(difluoromethyl)-1H-indol-1-yl)sulfonyl)-1-methoxynaphthalen-2-yl) piperazin-1-yl)ethanone (365 mg, 0.56 mmol) was reacted with potassium hydroxide solution (94 mg of potassium hydroxide solid, 1.68 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (237 mg, 84%). The compound was characterized by the following spectroscopic data: MS (ESI, pos. ion) m/z: 506.1 [M+H]$^+$; $^1$H NMR (600 MHz, CDCl$_3$): δ 8.52-8.42 (m, 1H), 8.23-8.16 (m, 1H), 8.14 (s, 1H), 7.97 (s, 1H), 7.77 (d, J=8.9 Hz, 1H), 7.63 (s, 1H), 7.52-7.51 (m, 2H), 7.30 (d, J=8.9 Hz, 1H), 6.82 (t, J=55.4 Hz, 1H), 4.01 (s, 3H), 3.26 (brs, 4H), 3.24 (brs, 4H); and $^{13}$C NMR (150 MHz, CDCl$_3$): δ 152.9, 138.2, 133.3, 130.3, 129.8, 127.7, 127.6, 127.5, 127.3, 127.1 (t, J=12.2 Hz), 125.8, 125.7, 124.4, 123.1, 123.0, 120.2, 114.4, 111.4 (t, J=235.3 Hz), 59.5, 50.5, 45.8.

Example 98 Synthesis of 5-chloro-3-(difluoromethyl)-1-((4-methoxy-3-(4-methylpiperazin-1-yl) naphthalen-1-yl)sulfonyl)-1H-indole

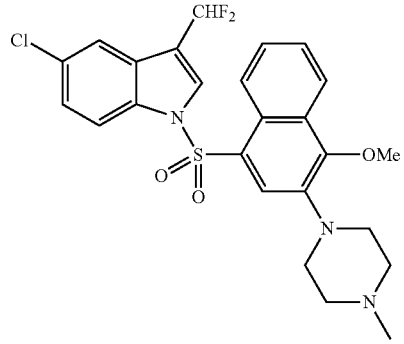 [SMILES: COc1c(N2CCN(C)CC2)cc(S(=O)(=O)n2cc(C(F)F)c3cc(Cl)ccc32)c2ccccc12]

5-Chloro-3-(difluoromethyl)-1-((4-methoxy-3-(piperazin-1-yl)naphthalen-1-yl)sulfonyl)-1H-indole (109 mg, 0.21 mmol) was reacted with sodium cyanoborohydride (40 mg, 0.63 mmol) and formaldehyde (40%, 0.05 mL, 0.63 mmol) in methanol (5 mL) according to the procedure as described in example 2, and the crude product was purified by silica gel chromatography eluted with DCM/methanol (V/V)=50/1 to give the title compound as a yellow solid (80 mg, 72%). The compound was characterized by the following spectroscopic data: MS (ESI, pos. ion) m/z: 520.2 [M+H]$^+$; $^1$H NMR (600 MHz, CDCl$_3$): δ 8.50-8.46 (m, 1H), 8.21-8.17 (m, 1H), 8.09 (s, 1H), 7.97 (s, 1H), 7.76 (d, J=8.9 Hz, 1H), 7.64 (d, J=1.3 Hz, 1H), 7.53-7.50 (m, 2H), 7.28 (dd, J=8.9, 1.9 Hz, 1H), 6.82 (t, J=55.4 Hz, 1H), 4.00 (s, 3H), 3.22 (brs, 4H), 2.65 (brs, 4H), 2.40 (s, 3H); and $^{13}$C NMR (100 MHz, CDCl$_3$): δ 152.5, 138.2, 133.3, 130.3, 129.8, 127.5, 127.4, 127.2, 127.1 (t, J=9.1 Hz), 125.8, 125.6, 124.4, 123.1, 122.9, 120.3, 115.2 (t, J=27.3 Hz), 114.5, 111.5 (t, J=235.3 Hz), 59.2, 55.4, 50.0, 46.1.

Example 99 Synthesis of 5-bromo-3-(difluoromethyl)-1-((4-methoxy-3-(piperazin-1-yl) naphthalen-1-yl)sulfonyl)-1H-indole

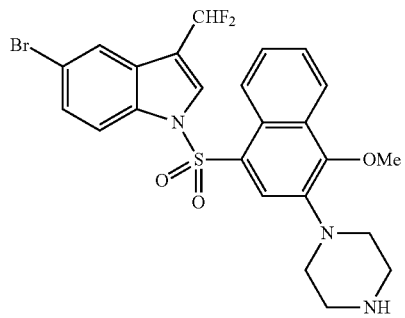

Step 1) Synthesis of 5-bromo-1-((4-methoxy-3-(4-(2,2,2-trichloroacetyl)piperazin-1-yl) naphthalen-1-yl)sulfonyl)-1H-indole-3-carbaldehyde 5-Bromo-1H-indole-3-carbaldehyde (448 mg, 2.0 mmol) was reacted with sodium hydride (80 mg, 2.0 mmol, 60%) and 4-methoxy-3-(4-(2,2,2-trichloroacetyl)piperazin-1-yl) naphthalene-1-sulfonyl chloride (1.17 g, 2.4 mmol, dissolved in THF (6 mL)) in THF (15 mL) according to the procedure as described in step 3 of example 1, and the crude product was purified by silica gel chromatography eluted with PE/EA(V/V)=10/1 to give the title compound as a white solid (737 mg, 51%). The compound was characterized by the following spectroscopic data: $^1$H NMR (600 MHz, CDCl$_3$): δ 10.06 (s, 1H), 8.48-8.45 (m, 1H), 8.40 (d, J=1.8 Hz, 1H), 8.39 (s, 1H), 8.27 (s, 1H), 8.23-8.20 (m, 1H), 7.64 (d, J=8.9 Hz, 1H), 7.59-7.54 (m, 2H), 7.46 (dd, J=8.9, 1.9 Hz, 1H), 4.19-4.02 (m, 7H), 3.33 (t, J=4.9 Hz, 4H).

Step 2) Synthesis of 1-(4-(4-((5-bromo-3-(difluoromethyl)-1H-indol-1-yl)sulfonyl)-1-methoxynaphthalen-2-yl)piperazin-1-yl)-2,2,2-trichloroethanone 5-Bromo-1-((4-methoxy-3-(4-(2,2,2-trichloro acetyl)piperazin-1-yl)naphthalen-1-yl)sulfonyl)-1H-indole-3-carbaldehyde (671 mg, 1.0 mmol) was reacted with diethylaminosulphur trifluoride (390 μL, 3.0 mmol) in DCM (10 mL) according to the procedure as described in step 3 of example 23, and the crude product was purified by silica gel chromatography eluted with PE/EA(V/V)=5/1 to give the title compound as a yellow solid (222 mg, 32%). The compound was characterized by the following spectroscopic data: $^1$H NMR (600 MHz, CDCl$_3$): δ 8.51-8.46 (m, 1H), 8.20 (dd, J=6.7, 3.0 Hz, 1H), 8.03 (s, 1H), 7.94 (t, J=2.2 Hz, 1H), 7.81 (d, J=1.4 Hz, 1H), 7.71 (d, J=8.9 Hz, 1H), 7.57-7.54 (m, 2H), 7.44 (dd, J=8.9, 1.9 Hz, 1H), 6.82 (t, J=55.4 Hz, 1H), 4.17-3.94 (m, 7H), 3.28 (t, J=4.8 Hz, 4H).

Step 3) Synthesis of 5-bromo-3-(difluoromethyl)-1-((4-methoxy-3-(piperazin-1-yl)naphthalen-1-yl)sulfonyl)-1H-indole 1-(4-(4-((5-Bromo-3-(difluoromethyl)-1H-indol-1-yl)sulfonyl)-1-methoxynaphthalen-2-yl)piperazin-1-yl)-2,2,2-trichloroethanone (210 mg, 0.3 mmol) was reacted with potassium hydroxide solution (50 mg of potassium hydroxide solid, 0.89 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (119 mg, 72%). The compound was characterized by the following spectroscopic data: MS (ESI, pos. ion) m/z: 550.1 [M+H]$^+$; $^1$H NMR (600 MHz, CDCl$_3$): δ 8.50-8.44 (m, 1H), 8.20-8.18 (m, 1H), 8.13 (s, 1H), 7.96 (t, J=2.1 Hz, 1H), 7.81 (d, J=1.2 Hz, 1H), 7.71 (d, J=8.9 Hz, 1H), 7.53-7.50 (m, 2H), 7.42 (dd, J=8.9, 1.8 Hz, 1H), 6.82 (t, J=55.4 Hz, 1H), 4.03 (s, 3H), 3.16 (t, J=5.1 Hz, 4H), 3.12 (t, J=5.0 Hz, 4H); and $^{13}$C NMR (150 MHz, CDCl$_3$): δ 152.7, 138.6, 133.6, 130.3, 128.4, 128.0 (t, J=1.5 Hz), 127.5, 127.4, 127.2, 127.0 (t, J=9.1 Hz), 125.6, 124.5, 123.3, 123.0, 117.3, 115.1 (t, J=27.2 Hz), 114.8, 111.4 (t, J=235.6 Hz), 59.3, 51.4, 46.3.

Example 100 Synthesis of 5-bromo-3-(difluoromethyl)-1-((4-methoxy-3-(4-methylpiperazin-1-yl) naphthalen-1-yl)sulfonyl)-1H-indole

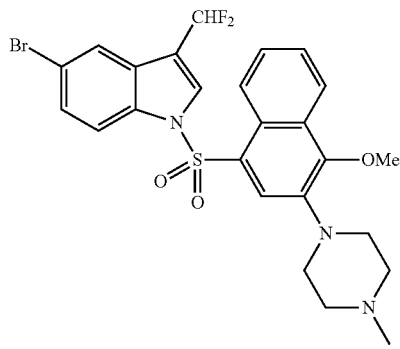

5-Bromo-3-(difluoromethyl)-1-((4-methoxy-3-(piperazin-1-yl)naphthalen-1-yl)sulfonyl)-1H-indole (55 mg, 0.1 mmol) was reacted with sodium cyanoborohydride (20 mg, 0.32 mmol) and formaldehyde (40%, 0.03 mL, 0.39 mmol) in methanol (5 mL) according to the procedure as described in example 2, and the crude product was purified by silica gel chromatography eluted with DCM/methanol(V/V)=50/1 to give the title compound as a yellow solid (54 mg, 98%). The compound was characterized by the following spectroscopic data: MS (ESI, pos. ion) m/z: 564.0 [M+H]$^+$; $^1$H NMR (600 MHz, CDCl$_3$): δ 8.49-8.47 (m, 1H), 8.19-8.18 (m, 1H), 8.11 (s, 1H), 7.96 (s, 1H), 7.80 (s, 1H), 7.71 (d, J=8.9 Hz, 1H), 7.54-7.48 (m, 2H), 7.42 (d, J=8.9 Hz, 1H), 6.82 (t, J=55.4 Hz, 1H), 4.01 (s, 3H), 3.23 (brs, 4H), 2.67 (brs, 4H), 2.41 (s, 3H); and $^{13}$C NMR (150 MHz, CDCl$_3$): δ 152.5, 138.1, 133.7, 130.3, 128.4, 128.0, 127.5, 127.2, 126.9 (t, J=9.5 Hz), 125.5, 124.4, 123.3, 123.0, 122.9, 117.4, 115.1 (t, J=26.3 Hz), 114.8, 111.4 (t, J=235.1 Hz), 59.2, 55.3, 49.9, 46.0.

Example 101 Synthesis of 3-(difluoromethyl)-6-fluoro-1-((4-methoxy-3-(piperazin-1-yl) naphthalen-1-yl)sulfonyl)-1H-indole

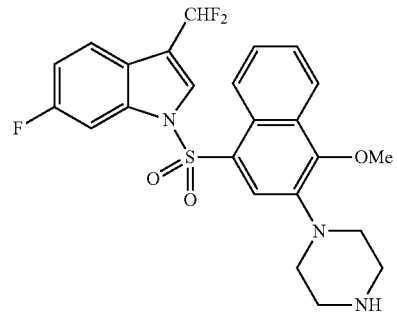 [SMILES: COc1c(N2CCNCC2)cc(S(=O)(=O)n2cc(C(F)F)c3ccc(F)cc32)c2ccccc12]

Step 1) Synthesis of 6-fluoro-1-((4-methoxy-3-(4-(2,2,2-trichloroacetyl)piperazin-1-yl)naphthalen-1-yl)sulfonyl)-1H-indole-3-carbaldehyde 6-Fluoro-1H-indole-3-carbaldehyde (326 mg, 2.0 mmol) was reacted with sodium hydride (80 mg, 2.0 mmol, 60%) and 4-methoxy-3-(4-(2,2,2-trichloroacetyl)piperazin-1-yl) naphthalene-1-sulfonyl chloride (1.17 g, 2.4 mmol, dissolved in THF (6 mL)) in THF (15 mL) according to the procedure as described in step 3 of example 1, and the crude product was purified by silica gel chromatography eluted with PE/EA(V/V)=10/1 to give the title compound as a white solid (649 mg, 53%). The compound was characterized by the following spectroscopic data: $^1$H NMR (600 MHz, CDCl$_3$): δ 10.09 (s, 1H), 8.52 (dd, J=6.7, 2.8 Hz, 1H), 8.41 (s, 1H), 8.32 (s, 1H), 8.27-8.23 (m, 1H), 8.20 (dd, J=8.7, 5.4 Hz, 1H), 7.63-7.56 (m, 2H), 7.50 (dd, J=9.4, 2.2 Hz, 1H), 7.10 (td, J=9.0, 2.3 Hz, 1H), 4.08 (brs, 7H), 3.39-3.32 (m, 4H).

Step 2) Synthesis of 2,2,2-trichloro-1-(4-(4-((3-(difluoromethyl)-6-fluoro-1H-indol-1-yl) sulfonyl)-1-methoxynaphthalen-2-yl)piperazin-1-yl)ethanone 6-Fluoro-1-((4-methoxy-3-(4-(2,2,2-trichloro acetyl)piperazin-1-yl)naphthalen-1-yl)sulfonyl)-1H-indole-3-carbaldehyde (613 mg, 1.0 mmol) was reacted with diethylaminosulphur trifluoride (390 μL, 3.0 mmol) in DCM (10 mL) according to the procedure as described in step 3 of example 23, and the crude product was purified with silica gel chromatography eluted with PE/EA(V/V)=5/1 to give the title compound as a yellow solid (298 mg, 47%). The compound was characterized by the following spectroscopic data: MS (ESI, pos. ion) m/z: 634.0 [M+H]$^+$; and $^1$H NMR (600 MHz, CDCl$_3$): δ 8.53 (dd, J=6.1, 3.4 Hz, 1H), 8.25-8.21 (m, 1H), 8.02 (s, 1H), 7.95 (t, J=2.3 Hz, 1H), 7.64 (dd, J=8.7, 5.2 Hz, 1H), 7.62-7.54 (m, 3H), 7.07 (td, J=8.9, 2.2 Hz, 1H), 6.86 (t, J=55.4 Hz, 1H), 4.06 (brs, 7H), 3.34-3.22 (m, 4H).

Step 3) Synthesis of 3-(difluoromethyl)-6-fluoro-1-((4-methoxy-3-(piperazin-1-yl)naphthalen-1-yl)sulfonyl)-1H-indole 2,2,2-Trichloro-1-(4-(4-((3-(difluoromethyl)-6-fluoro-1H-indol-1-yl)sulfonyl)-1-methoxynaphthalen-2-yl) piperazin-1-yl)ethanone (240 mg, 0.38 mmol) was reacted with potassium hydroxide solution (67 mg of potassium hydroxide solid, 1.2 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (151 mg, 81%). The compound was characterized by the following spectroscopic data: MS (ESI, pos. ion) m/z: 490.2 [M+H]$^+$; $^1$H NMR (600 MHz, CDCl$_3$): δ 8.54-8.48 (m, 1H), 8.22 (dd, J=6.7, 3.1 Hz, 1H), 8.12 (s, 1H), 7.97 (s, 1H), 7.63 (dd, J=8.6, 5.2 Hz, 1H), 7.60-7.51 (m, 3H), 7.04 (td, J=8.9, 2.2 Hz, 1H), 6.86 (t, J=55.4 Hz, 1H), 4.05 (s, 3H), 3.20-3.19 (m, 4H), 3.16-3.15 (m, 4H); and $^{13}$C NMR (150 MHz, CDCl$_3$): δ 161.1 (d, J=242.4 Hz), 152.7, 138.5, 135.2 (d, J=12.3 Hz), 130.3, 127.5, 127.4, 127.2, 126.2 (td, J=9.8, 3.6 Hz), 125.6, 124.5, 123.1, 123.0, 122.7, 121.6 (d, J=9.9 Hz), 115.6 (t, J=26.3 Hz), 112.5 (d, J=24.1 Hz), 111.6 (t, J=233.2 Hz), 100.9 (d, J=28.4 Hz), 59.3, 51.2, 46.3.

Example 102 Synthesis of 3-(difluoromethyl)-6-fluoro-1-((4-methoxy-3-(4-methylpiperazin-1-yl) naphthalen-1-yl)sulfonyl)-1H-indole

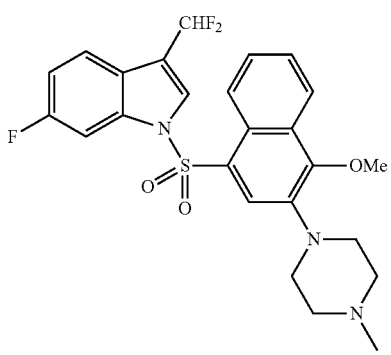 [SMILES: COc1c(N2CCN(C)CC2)cc(S(=O)(=O)n2cc(C(F)F)c3ccc(F)cc32)c2ccccc12]

3-(Difluoromethyl)-6-fluoro-1-((4-methoxy-3-(piperazin-1-yl)naphthalen-1-yl)sulfonyl)-1H-indole (49 mg, 0.1 mmol) was reacted with sodium cyanoborohydride (20 mg, 0.32 mmol) and formaldehyde (40%, 0.03 mL, 0.39 mmol) in methanol (5 mL) according to the procedure as described in example 2, and the crude product was purified by silica gel chromatography eluted with DCM/methanol(V/V)=50/1 to give the title compound as a yellow solid (46 mg, 91%). The compound was characterized by the following spectroscopic data: MS (ESI, pos. ion) m/z: 504.1 [M+H]$^+$; $^1$H NMR (400 MHz, CDCl$_3$): δ 8.55-8.49 (m, 1H), 8.24-8.17 (m, 1H), 8.07 (s, 1H), 7.96 (t, J=2.4 Hz, 1H), 7.63 (dd, J=8.7, 5.2 Hz, 1H), 7.59-7.52 (m, 3H), 7.04 (td, J=8.9, 2.3 Hz, 1H), 6.86 (t, J=55.4 Hz, 1H), 4.02 (s, 3H), 3.35-3.21 (m, 4H), 2.71 (brs, 4H), 2.45 (s, 3H); and $^{13}$C NMR (100 MHz, CDCl$_3$): δ 161.1 (d, J=242.5 Hz), 152.5, 138.1, 135.3 (d, J=12.5 Hz), 130.3, 127.6, 127.4, 127.2, 126.1 (td, J=13.7, 4.1 Hz), 125.6, 124.3, 123.1, 122.9, 122.7, 121.6 (d, J=9.9 Hz), 115.5 (t, J=26.5 Hz), 112.4 (d, J=24.1 Hz), 111.6 (t, J=233.4 Hz), 100.9 (d, J=28.5 Hz), 59.3, 55.2, 49.7, 45.9.

Example 103 Synthesis of 6-chloro-3-(difluoromethyl)-1-((4-methoxy-3-(piperazin-1-yl) naphthalen-1-yl)sulfonyl)-1H-indole

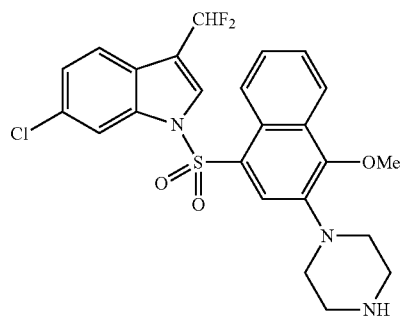 [SMILES: COc1c(N2CCNCC2)cc(S(=O)(=O)n2cc(C(F)F)c3ccc(Cl)cc32)c2ccccc12]

Step 1) Synthesis of 6-chloro-1-((4-methoxy-3-(4-(2,2,2-trichloroacetyl)piperazin-1-yl) naphthalen-1-yl)sulfonyl)-1H-indole-3-carbaldehyde 6-Chloro-1H-indole-3-carbaldehyde (358 mg, 2.0 mmol) was reacted with sodium hydride (80 mg, 2.0 mmol, 60%) and 4-methoxy-3-(4-(2,2,2-trichloroacetyl)piperazin-1-yl) naphthalene-1-sulfonyl chloride (1.17 g, 2.4 mmol, dissolved in THF (6 mL)) in THF (15 mL) according to the procedure as described in step 3 of example 1, and the crude product was purified by silica gel chromatography eluted with PE/EA(V/V)=10/1 to give the title compound as a white solid (616 mg, 49%). The compound was characterized by the following spectroscopic data: $^1$H NMR (600 MHz, DMSO-d$_6$): δ 10.05 (s, 1H), 9.26 (s, 1H), 8.53-8.43 (m, 2H), 8.24-8.18 (m, 1H), 8.05 (d, J=8.5 Hz, 1H), 7.88 (d, J=1.7 Hz, 1H), 7.69-7.60 (m, 2H), 7.41 (dd, J=8.5, 1.8 Hz, 1H), 4.07 (brs, 7H), 3.4 (brs, 4H).

Step 2) Synthesis of 2,2,2-trichloro-1-(4-(4-((6-chloro-3-(difluoromethyl)-1H-indol-1-yl) sulfonyl)-1-methoxynaphthalen-2-yl)piperazin-1-yl)ethanone 6-Chloro-1-((4-methoxy-3-(4-(2,2,2-trichloro acetyl)piperazin-1-yl)naphthalen-1-yl)sulfonyl)-1H-indole-3-carbaldehyde (610 mg, 0.97 mmol) was reacted with diethylaminosulphur trifluoride (390 μL, 3.0 mmol) in DCM (10 mL) according to the procedure as described in step 3 of example 23, and the crude product was purified by silica gel chromatography eluted with PE/EA(V/V)=5/1 to give the title compound as a yellow solid (298 mg, 47%). The compound was characterized by the following spectroscopic data: $^1$H NMR (400 MHz, CDCl$_3$): δ 8.55 (dd, J=6.3, 3.1 Hz, 1H), 8.28-8.19 (m, 1H), 8.12 (s, 1H), 7.96 (s, 1H), 7.87 (s, 1H), 7.61-7.58 (m, 3H), 7.28 (s, 1H), 6.85 (t, J=55.4 Hz, 1H), 4.07 (brs, 7H), 3.39-3.24 (m, 4H).

Step 3) Synthesis of 6-chloro-3-(difluoromethyl)-1-((4-methoxy-3-(piperazin-1-yl)naphthalen-1-yl)sulfonyl)-1H-indole 2,2,2-Trichloro-1-(4-(4-((6-chloro-3-(difluoromethyl)-1H-indol-1-yl)sulfonyl)-1-methoxynaphthalen-2-yl) piperazin-1-yl)ethanone (250 mg, 0.38 mmol) was reacted with potassium hydroxide solution (67 mg of potassium hydroxide solid, 1.2 mmol, 1 mmol/mL in water) in THF (10 mL) according to the procedure as described in step 4 of example 1, and the crude product was purified by silica gel chromatography eluted with DCM/methanol(V/V)=30/1 to give the title compound as a light yellow solid (140 mg, 73%). The compound was characterized by the following spectroscopic data: MS (ESI, pos. ion) m/z: 506.1 [M+H]$^+$; $^1$H NMR (600 MHz, CDCl$_3$): δ 8.53 (dd, J=6.5, 3.1 Hz, 1H), 8.24-8.17 (m, 2H), 7.97 (d, J=2.1 Hz, 1H), 7.88 (d, J=1.5 Hz, 1H), 7.61-7.53 (m, 3H), 7.25 (dd, J=8.5, 1.6 Hz, 1H), 6.86 (t, J=55.4 Hz, 1H), 4.05 (s, 3H), 3.32 (brs, 4H), 3.26 (brs, 4H); and $^{13}$C NMR (150 MHz, CDCl$_3$): δ 153.0, 138.2, 135.1, 131.52, 130.3, 127.8, 127.3, 127.2, 126.4, 125.8, 124.8, 124.5, 123.1, 123.0, 121.4, 115.6 (t, J=26.3 Hz), 113.8, 111.5 (t, J=23.4 Hz), 59.6, 50.5, 45.7.

Example 104 Synthesis of 6-chloro-3-(difluoromethyl)-1-((4-methoxy-3-(4-methylpiperazin-1-yl)naphthalen-1-yl)sulfonyl)-1H-indole

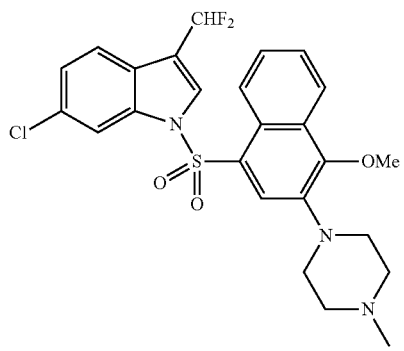 [SMILES: COc1c(N2CCN(C)CC2)cc(S(=O)(=O)n2cc(C(F)F)c3ccc(Cl)cc32)c2ccccc12]

6-Chloro-3-(difluoromethyl)-1-((4-methoxy-3-(piperazin-1-yl)naphthalen-1-yl)sulfonyl)-1H-indole (51 mg, 0.1 mmol) was reacted with sodium cyanoborohydride (20 mg, 0.32 mmol) and formaldehyde (40%, 0.03 mL, 0.39 mmol) in methanol (5 mL) according to the procedure as described in example 2, and the crude product was purified by silica gel chromatography eluted with DCM/methanol(V/V)=50/1 to give the title compound as a yellow solid (46 mg, 91%). The compound was characterized by the following spectroscopic data: MS (ESI, pos. ion) m/z: 520.1 [M+H]$^+$; $^1$H NMR (600 MHz, CDCl$_3$): δ 8.52 (dd, J=6.5, 3.0 Hz, 1H), 8.24-8.18 (m, 2H), 7.98 (d, J=2.2 Hz, 1H), 7.88 (d, J=1.5 Hz, 1H), 7.60-7.53 (m, 3H), 7.27 (dd, J=8.4, 1.5 Hz, 1H), 6.85 (t, J=55.4 Hz, 1H), 4.03 (s, 3H), 3.28 (brs, 4H), 2.71 (brs, 4H), 2.47 (s, 3H); and $^{13}$C NMR (150 MHz, CDCl$_3$): δ 153.1, 138.2, 135.0, 131.52, 130.3, 127.8, 127.3, 127.2, 126.3, 125.7, 124.8, 124.5, 123.1, 123.0, 121.3, 115.6 (t, J=26.4 Hz), 113.7, 111.4 (t, J=23.3 Hz), 59.4, 55.5, 49.8, 45.5.

BIOLOGICAL ASSAYS

The invention provides the following methods for measuring biological activity of the compounds of this invention:

(A). The binding affinity of the compound of this invention to human 5-HT$_6$ receptor expressed in CHO cell was evaluated by radioligand binding assay as follows.

32 μg membrane proteins of CHO cell expressing human 5-HT$_6$ receptor, 2 nM of radioactive marker [3H]LSD, the compound of the present invention having different test concentrations and a buffer solution were mixed uniformly, and the resulting mixture was incubated at 37° C. for 120 mins, in which the buffer solution was comprised of 50 mM Tris-HCl (pH 7.4), 10 mM MgCl$_2$, 0.5 mM EDTA, 10 μM pargyline and 20 mg/L protease inhibitor.

100 μM of 5-HT was added to the mixture to eliminate nonspecific binding sites. After incubation, the resulting mixture was filtered with glassfabricfilter in vacuo, and the glassfabricfilter should be preimpregnated with 0.3% PEI before filtering and washed with 50 mM of Tris-HCl several times after filtering. After the filter was dried, the radioactivity of the scintillation mixture was determined by liquid scintillation counting with a scintillometer. The reference standard was 5-HT, and IC$_{50}$ values were calculated from plots of competitive inhibition curves formed based on several inhibition ratios and the corresponding compound concentrations.

The binding affinity of the compound described in the examples to human 5-HT$_6$ receptor expressed in CHO cell was evaluated by the radioligand binding assay described above. And the results were shown in table 2:

TABLE 2

Results of the affinity binding assays

| Example. No | IC$_{50}$ (nM) |
|---|---|
| Example 1 | 1.7 |
| Example 2 | 0.59 |
| Example 3 | 0.96 |
| Example 4 | 0.87 |
| Example 5 | 1.1 |
| Example 6 | 0.43 |
| Example 7 | 3.7 |
| Example 8 | 2.0 |
| Example 9 | 3.5 |
| Example 10 | 2.1 |
| Example 11 | 1.4 |
| Example 12 | 1.1 |
| Example 13 | 2.1 |
| Example 14 | 1.5 |
| Example 15 | 3.2 |
| Example 16 | 4.2 |
| Example 17 | 1.3 |
| Example 18 | 0.67 |
| Example 19 | 0.21 |
| Example 20 | 0.14 |
| Example 21 | 0.17 |
| Example 22 | 0.57 |
| Example 23 | 0.46 |
| Example 24 | 0.074 |
| Example 25 | 0.64 |
| Example 26 | 0.22 |
| Example 27 | 0.55 |
| Example 28 | 0.2 |
| Example 29 | 0.26 |
| Example 30 | 0.066 |
| Example 31 | 0.085 |
| Example 32 | 0.1 |
| Example 33 | 0.33 |
| Example 34 | 0.09 |
| Example 37 | 0.13 |

TABLE 2-continued

Results of the affinity binding assays

| Example. No | $IC_{50}$ (nM) |
| --- | --- |
| Example 39 | 0.092 |
| Example 40 | 0.09 |
| Example 41 | 0.5 |
| Example 44 | 0.4 |
| Example 45 | 0.14 |
| Example 46 | 0.25 |
| Example 47 | 0.4 |
| Example 48 | 1.4 |
| Example 49 | 0.54 |
| Example 55 | 3.5 |
| Example 56 | 1.1 |
| Example 57 | 0.58 |
| Example 58 | 0.43 |
| Example 60 | 0.67 |
| Example 62 | 0.87 |
| Example 70 | 0.63 |
| Example 71 | 0.45 |
| Example 72 | 0.60 |
| — | — |

It was shown in table 2 that, the compounds of this invention generally showed good activities in the test of binding affinity to human 5-HT$_6$ receptor expressed in CHO cell evaluated by a radioligand binding assay.

(B). Evaluation of metabolic stabilities of the compounds in human liver microsomes.

The compound of the present invention and human liver microsomes were added into 0.1M potassium phosphate buffer (1.0 mM EDTA was added, pH=7.4) and the mixture was incubated at 37° C. The concentrations of the compound in different incubation time were determined, and the value of half-life of the compound was calculated by using Graph-Pad Prism5.01 from a relevant curve formed by plotting the relative concentration of the compound against the incubation time. And then the intrinsic clearance was calculated. The testing system was shown in table 3:

TABLE 3

Testing system

| | |
| --- | --- |
| Tested compounds | The compounds of the invention (dissolved in DMSO and diluted with acetonitrile) |
| Human liver microsome | Mixed sample with a final concentration of 0.5 mg/mL |
| Buffers | 0.1M potassium phosphate (containing 1.0 mM EDTA, pH = 7.4) |
| Final concentration of tested compound | 1 µM |
| Final content of organic solvent | 0.2% |
| Final reaction system | 30 µL of buffer solution containing human liver microsomes and tested compound; 15 µL NADPH buffer solution (6 mM) |
| Testing conditions | Time points: 0 min, 15 min, 30 min, 60 min; Temperature: 37° C.; pH: 7.4 |
| Numbers of duplicate sample | 2 |
| Analytical methods | LC/MS/MS, propranolol as internal standard |

The samples were analyzed by LC/MS/MS equipped with waters xbridge C18 EB-A-1420 chromatographic column and ESI radioactive source. The mobile phase was comprised of mobile phase A (0.1% formic acid and 2 mM ammonium formate in H$_2$O) and mobile phase B (0.1% formic acid and 2 mM ammonium formate in methanol); the flow rate was 0.4 mL/min; and the temperature of the column was kept at 40° C. The ratio of peak area between testing sample and internal standard was obtained by LC/MS/MS analysis, the relative content of the compound at each time point was calculated based on the peak area ratio and the content of the compound at 0 min time point (100%). The value of half-life of the compound was calculated on the basis of the relevant curve chart, which was made by plotting the relative content of test compound against the incubation time. And then the intrinsic clearance was calculated. The testing results of half-life and intrinsic clearance of the compound of this invention were shown in table 4.

TABLE 4

Testing results of half life and intrinsic clearance of the compound of this invention

| Example. No | Half-life (min) | intrinsic clearance (mL/min/kg) |
| --- | --- | --- |
| Example 31 | 118.9 | 14.62 |
| Example 33 | 132.30 | 13.14 |
| Example 68 | 69.47 | 25.02 |

It was shown in table 4 that, the compounds of this invention had good stabilities in human liver microsomes.

Reference throughout this specification to "one embodiment", "an embodiment", "some embodiments", "explanatory embodiment", "an example", "a specific example" or "some examples", means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples", or "in some examples" in various places throughout this specification are not necessarily referring to the same embodiment or example of the present disclosure. Furthermore, the particular features, structures, materials or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:
1. A compound having Formula (I)

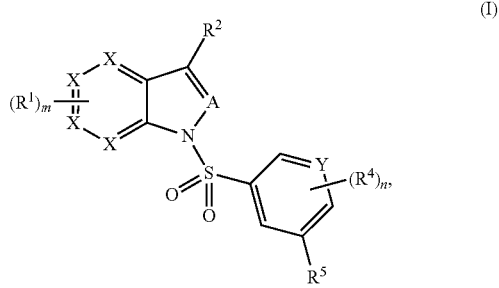

or a stereoisomer, a geometric isomer, a tautomer, an N-oxide, a hydrate, a solvate, or a pharmaceutically acceptable salt thereof, wherein:

m is 0, 1, 2 or 3;
n is 1, 2 or 3;
R¹ is F, Cl, Br or CF₃; R² is C₁₋₆ haloalkyl; R⁴ is C₁₋₆ alkoxy; R⁵ is

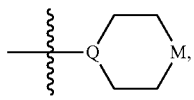

and wherein Q is N or CH and M is —NR⁷, and wherein R⁷ is H, C₁₋₆ alkyl, C₃₋₆ cycloalkyl or oxetanyl; and each of A, X and Y is CH.

2. The compound according to claim 1 having Formula (II)

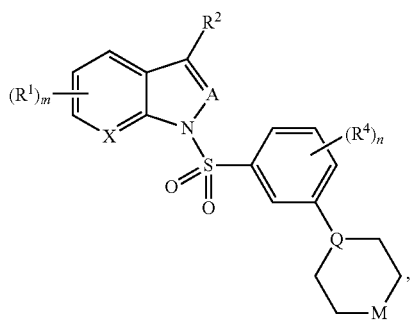

or a stereoisomer, a geometric isomer, a tautomer, an N-oxide, a hydrate, a solvate, or a pharmaceutically acceptable salt thereof, wherein:

m is 1, 2 or 3; and
n is 1.

3. The compound according to claim 1, wherein R² is —CHF₂, —CF₃, —CH₂CF₃, —CF₂CHF₂, —CHFCF₃, —CF₂CF₃, —CH₂CF₂CF₃, or —CH₂CF₂CHF₂.

4. The compound according to claim 1, wherein each R⁴ is independently methoxy, ethoxy, n-propoxy, iso-propoxy, n-butoxy, iso-butoxy, or tert-butoxy.

5. The compound according to claim 2, wherein R⁷ is H, methyl, ethyl, n-propyl, iso-propyl, n-butyl, iso-butyl, tert-butyl, —CH₂CH₂CH(CH₃)₂, —CH₂C(CH₃)₃, cyclopropyl, cyclobutyl, cyclopentyl, or oxetanyl.

6. The compound according to claim 1 having one of the following structures:

(23)

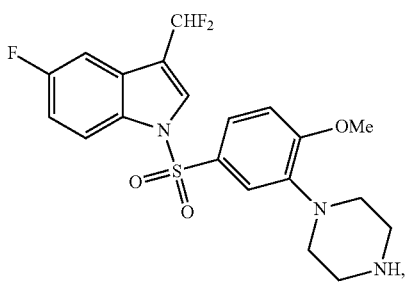

(24)

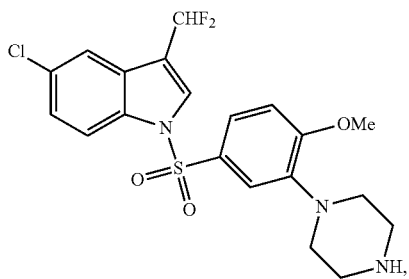

(25)

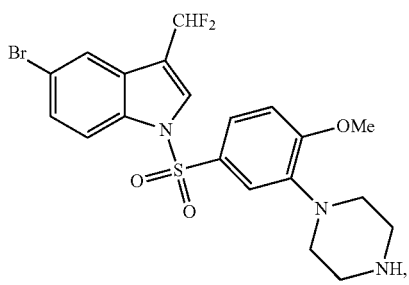

(26)

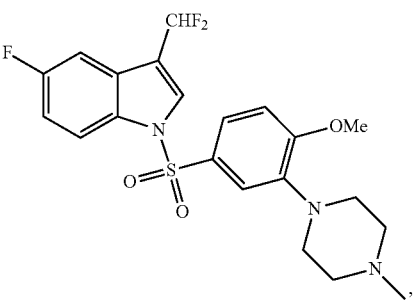

(27)

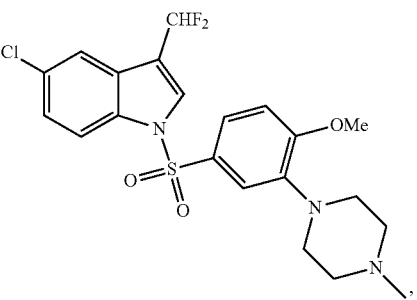

(28)

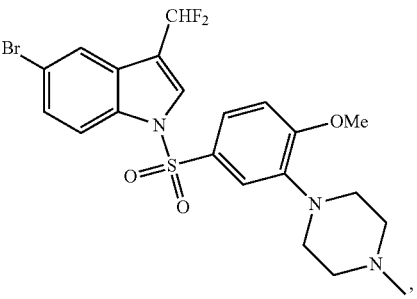

-continued
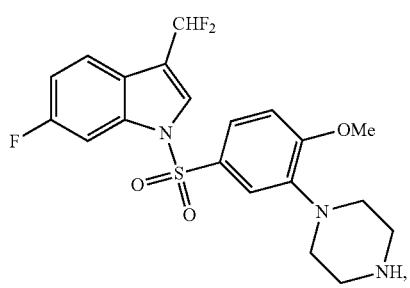
(29)
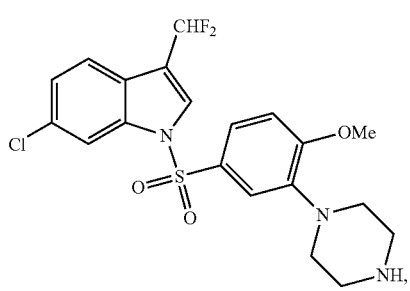
(30)
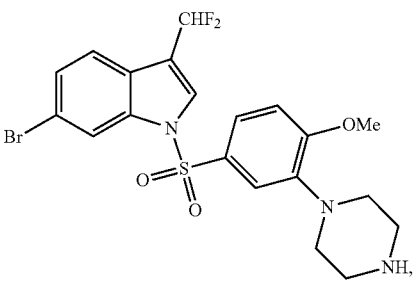
(31)
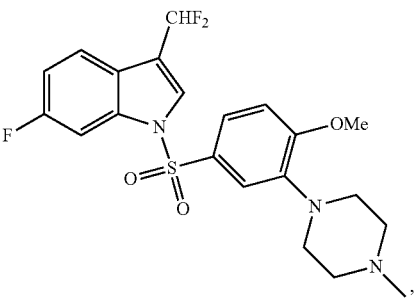
(32)
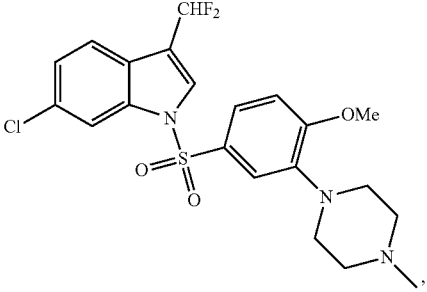
(33)
-continued
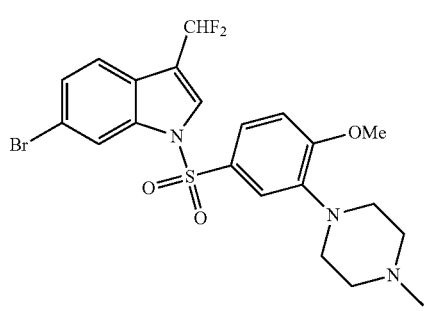
(34)
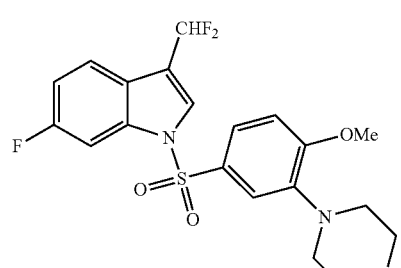
(35)
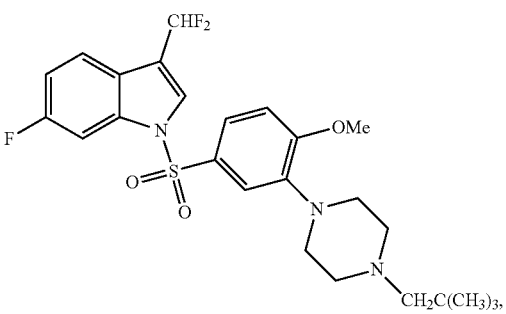
(36)
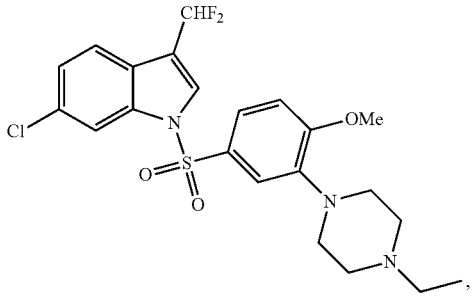
(37)
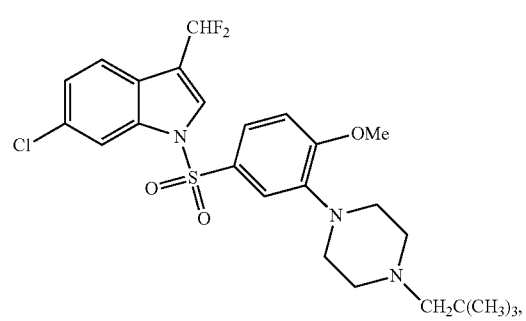
(38)

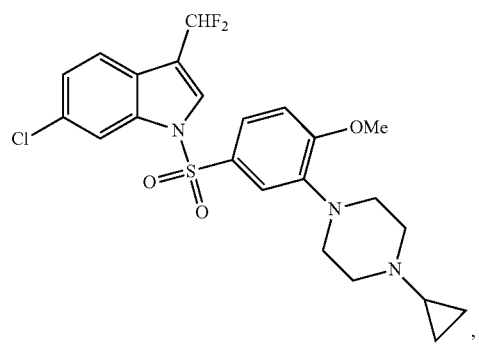
(39)
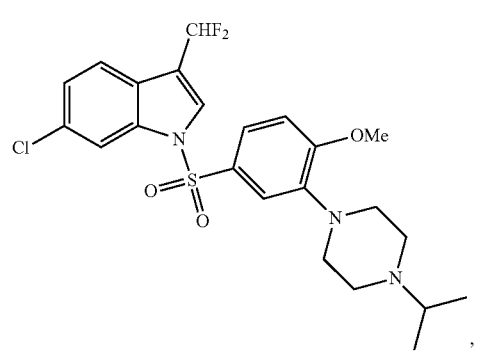
(40)
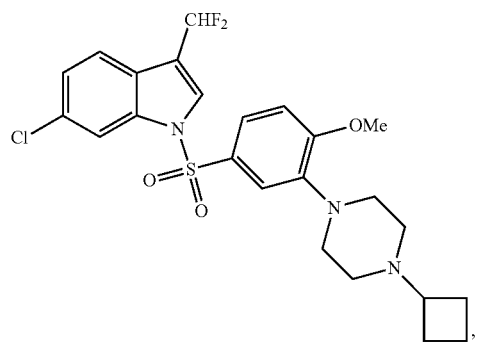
(41)
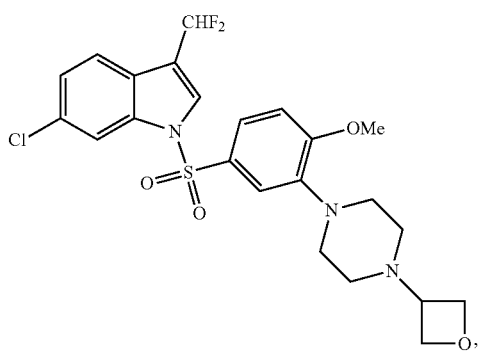
(42)
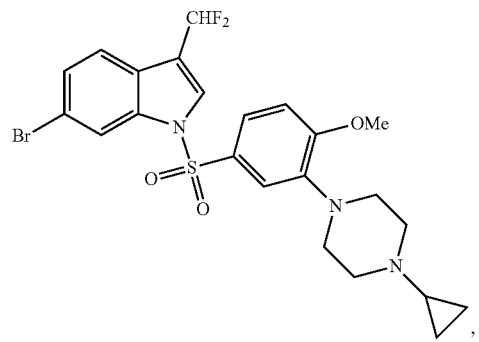
(43)
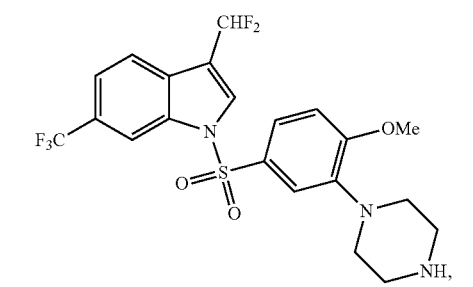
(44)
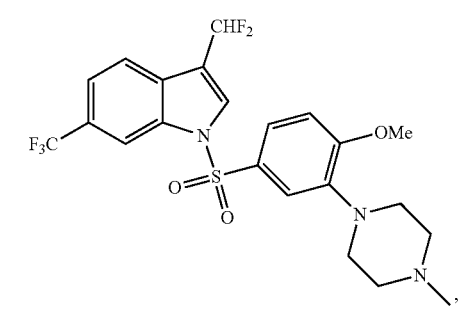
(45)
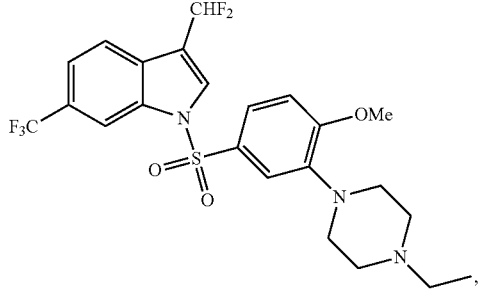
(46)
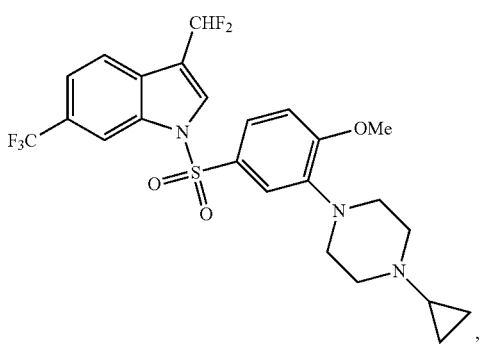
(47)

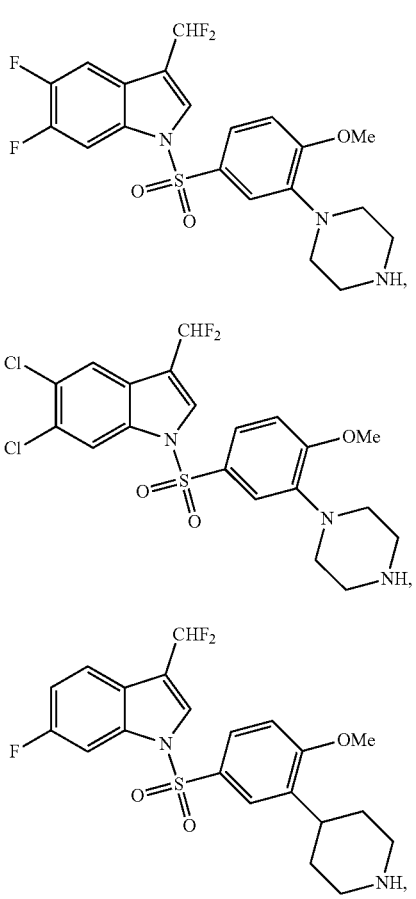
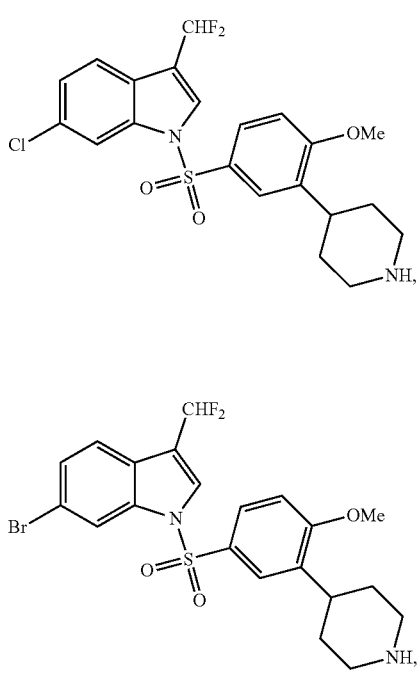
or a stereoisomer, a geometric isomer, a tautomer, an N-oxide, a hydrate, a solvate, or a pharmaceutically acceptable salt thereof.
7. A pharmaceutical composition comprising the compound according to claim 1, and a pharmaceutically acceptable carrier, excipient, diluent, adjuvant, vehicle or a combination thereof.
* * * * *